(12) United States Patent
Du Prez et al.

(10) Patent No.: US 9,586,935 B2
(45) Date of Patent: Mar. 7, 2017

(54) URAZOLE COMPOUNDS

(71) Applicant: UNIVERSITEIT GENT, Ghent (BE)

(72) Inventors: Filip Du Prez, Ghent (BE); Johan Winne, Melle (BE); Stijn Billiet, Deinze (BE); Kevin De Bruycker, Wichelen (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 14/910,058

(22) PCT Filed: Aug. 8, 2014

(86) PCT No.: PCT/EP2014/067074
§ 371 (c)(1),
(2) Date: Feb. 4, 2016

(87) PCT Pub. No.: WO2015/018928
PCT Pub. Date: Feb. 12, 2015

(65) Prior Publication Data
US 2016/0200707 A1    Jul. 14, 2016

(30) Foreign Application Priority Data
Aug. 9, 2013  (EP) .................................... 13179971

(51) Int. Cl.
*C07D 403/04* (2006.01)
*C08F 112/08* (2006.01)
(Continued)

(52) U.S. Cl.
CPC ............. *C07D 403/04* (2013.01); *C08F 12/08* (2013.01); *C08F 112/08* (2013.01);
(Continued)

(58) Field of Classification Search
CPC .................................................. C07D 403/04
See application file for complete search history.

(56) References Cited

FOREIGN PATENT DOCUMENTS

WO     2004003044 A2    1/2004

OTHER PUBLICATIONS

Baran et al., Organic Letters, 2003, 5(11), 1999-2001.*
(Continued)

*Primary Examiner* — Vu A Nguyen
(74) *Attorney, Agent, or Firm* — Amster, Rothstein & Ebenstein LLP

(57) ABSTRACT

The present invention relates to a compound of formula (I) or a stereoisomer, enantiomer, racemic, or tautomer thereof, (I) wherein $R^1$, $R^2$, $R^3$, $R^4$, $R^5$, $R^6$, $R^7$, $L^1$ and $Q^1$ have the meaning defined in the claims and the description. The present invention also relates to a process for the preparation of the compound of formula (I). The present invention also relates to the use of a compound of formula (I) as an in situ precursor of a triazolinedione reagent for the functionalization of enes, dienes, aryl and heteroaryl systems via the ene reactions, Diels-Alder reactions, and electrophilic aromatic substitution reactions of said reagent. The present invention also relates to the use of a compound of formula (I) in polymers, membranes, adhesives, foams, sealants, molded articles, films, extruded articles, fibers, elastomers, polymer based additives, pharmaceutical and biomedical products, varnishes, paints, coatings, inks, composite material, organic LEDs, organic semiconductors, conducting organic polymers, or 3D printed articles. The present invention also
(Continued)

relates to article comprising said compound of formula (I) and to a process for reshaping and/or repairing said article.

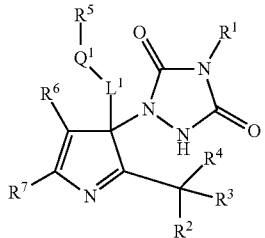

(I)

15 Claims, 22 Drawing Sheets

(51) Int. Cl.
| | |
|---|---|
| *C08F 120/68* | (2006.01) |
| *C08F 120/14* | (2006.01) |
| *C08G 18/66* | (2006.01) |
| *C08G 18/73* | (2006.01) |
| *C08G 18/38* | (2006.01) |
| *C08F 12/08* | (2006.01) |

(52) U.S. Cl.
CPC .......... *C08F 120/14* (2013.01); *C08F 120/68* (2013.01); *C08G 18/3844* (2013.01); *C08G 18/6666* (2013.01); *C08G 18/73* (2013.01); *C08G 2261/46* (2013.01)

(56) References Cited

OTHER PUBLICATIONS

SciFinder Sub-structure Search Results, Nov. 22, 2016.*
PCT Notification Concerning Transmittal of International Preliminary Report on Patentability and Written Opinion of the International Searching Authority, date of issuance Feb. 9, 2016 in connection with PCT International Patent Application No. PCT/EP2014/067074, 6 pages.
PCT International Search Report and Written Opinion dated Aug. 10, 2014 for PCT International Patent Application No. PCT/EP2014/067074, 8 pages.
Wilson R M et al., entitled "Nucleophilic additions to triazolinedione ylides, extremely reactive carbonyl equivalents: a new class of condensation reactions," The Journal of Organic Chemistry, vol. 52, No. 13, Jun. 1, 1987, pp. 2699-2707.
Wilson R M et al., entitled "The chemistry of an azomethine imine derived from 2,3-dimethylindole and n-phenyl triazolinedione: A new and facile condensation method," Tetrahedron Letters, vol. 26, No. 31, Jan. 1, 1985, pp. 3673-3676.

* cited by examiner (a) Short side  (b) Long side

URAZOLE COMPOUNDS

CROSS-REFERENCE TO RELATED APPLICATIONS

This application is a U.S. national stage entry under 35 U.S.C. §371 of PCT International Patent Application No. PCT/EP2014/067074, filed Aug. 8, 2014, which claims priority to European Patent Application No. 13179971.0, filed Aug. 9, 2013, the contents of which are incorporated herein by reference in their entirety.

FIELD OF THE INVENTION

The invention pertains to urazole compounds and polymers functionalized with urazole compounds and the use thereof in polymers, membranes, adhesives, foams, sealants, molded articles, films, extruded articles, fibers, elastomers, polymer based additives, pharmaceutical and biomedical products, varnishes, paints, coatings, inks; or composite material.

BACKGROUND OF THE INVENTION

Among a large variety of nitrogen-containing heterocyclic compounds, heterocycles containing an urazole (1,2,4-triazolidine-3,5-dione) moiety are of interest because they constitute an important class of natural and non-natural products, many of which exhibit useful industrial applications. Industrially urazole is used in the manufacture of automobile air bags, as blowing agent in plastics, in the production of herbicides, and antifungal compounds and in polymeric materials.

Urazole can be obtained from 1,2,4-triazoline-3,5-dione (TAD). 1,2,4-triazoline-3,5-dione are known to be enophile and dienophile and readily undergoes cycloaddition reactions such as Diels-Alder (DA) reaction in the presence of suitable DA or ene reactions in the presence of suitable ene reaction partners.

Since its first description in the literature in 1928, the Diels-Alder (DA) reaction has become one of the most known reactions in organic synthesis. The reaction comprises a [4+2] cycloaddition reaction between an electron-rich diene and an electron-poor dienofile (for example an alkene), resulting in the net rupture of two π bonds, and the formation of two σ bonds. The furan-maleimide system (Scheme 1) is the most studied DA system with applications in polymer chemistry. This system however has several drawbacks namely, that the adduct produced from the furan and maleimide DA reaction is prone to hydrolysis. Moreover, the DA-reaction is often slow and requires the use of metal-based catalysts, which present environmental concerns. Another problem that this system presents is that the reactivity of maleimide limits the array of adducts produced. Moreover, as shown in Scheme A, the DA-reaction between furan and maleimide does not proceed at room temperature.

Scheme A

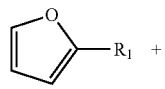

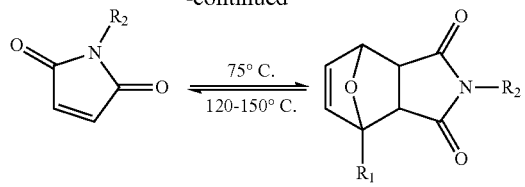

Compounds containing urazole moiety have attracted much interest in recent years. Despite the available synthetic methods, there still exists a need for developing more efficient procedures, which would allow the ready synthesis of new urazole compounds.

It is an object of the present invention to provide new molecules comprising specific urazole moiety and new process for preparing them.

SUMMARY OF THE INVENTION

According to a first aspect of the present invention, a compound of formula (I) is provided or a stereoisomer, enantiomer, racemic, or tautomer thereof, (I)

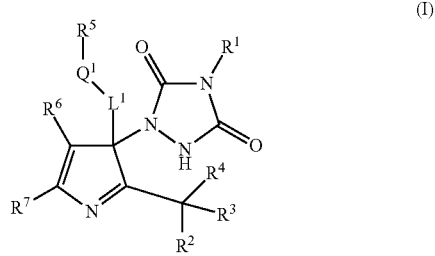

wherein,
$L^1$ is selected from $C_{1-10}$alkylene; $C_{2-10}$alkenylene; or $C_{2-10}$alkynylene; or $L^1$ and $R^2$ together with the carbon atoms to which they are attached form a saturated or unsaturated 4-, 5-, 6-, 7- or 8-membered ring; wherein said $C_{1-10}$alkylene; $C_{2-10}$alkenylene; $C_{2-10}$alkynylene, or saturated or unsaturated 4-, 5-, 6-, 7- or 8-membered ring, optionally comprises one or more heteroatoms in the alkylene, alkenylene, alkynylene, or saturated or unsaturated 4-, 5-, 6-, 7- or 8-membered ring moiety, said heteroatoms being each independently selected from O, S and N; and wherein said $C_{1-10}$alkylene; $C_{2-10}$alkenylene; $C_{2-10}$alkynylene, or saturated or unsaturated 4-, 5-, 6-, 7- or 8-membered ring, can be unsubstituted or substituted with one or more $Z^1$;
$Q^1$ is a single bond or is selected from the group consisting of —OC(O)—; —NH—C(O)—; —OS(O)—; —OS(O)$_2$—; —NH—S(O)—; —NH—S(O)$_2$—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; wherein each left side of said groups is attached to $L^1$ and the right side thereof is attached to $R^5$; and wherein,
q is an integer selected from 1; 2 or 3;
p is an integer selected from 0; 1 or 2;
$L^4$ is a single bond or is selected from the group consisting of $C_{1-10}$alkylene; $C_{2-10}$alkenylene; and $C_{2-10}$alkynylene;
wherein said $C_{1-10}$alkylene; $C_{2-10}$alkenylene; and $C_{2-10}$alkynylene, optionally comprises one or more heteroatoms in the alkylene, alkenylene, alkynylene moiety, said heteroatoms being each independently selected from O, S and N;

and wherein said $C_{1-10}$alkylene; $C_{2-10}$alkenylene; $C_{2-10}$alkynylene, can be unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

wherein said $C_{2-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; heteroaryl$C_{1-6}$alkyl, optionally comprises one or more heteroatoms in the alkyl moiety, said heteroatoms being each independently selected from O, S or N;

wherein at least one carbon atom or heteroatom of said $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; and heteroaryl $C_{1-6}$alkyl, can be oxidized to form at least one C=O, C=S, N=O, N=S, S=O or $S(O)_2$;

wherein said $C_{2-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-6}$aryl, heterocyclyl; heteroaryl; heterocyclyl$C_{1-6}$alkyl; and heteroaryl$C_{1-6}$alkyl, can be unsubstituted or substituted with one or more $Z^3$;

and wherein said polymeric group is selected from the group comprising polyethylene oxide; polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

or $R^1$ is a group of formula (i);

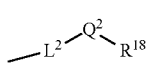

(i)

wherein, $L^2$ is a single bond or is selected from the group consisting of $C_{1-10}$alkylene; $C_{2-10}$alkenylene; $C_{2-10}$alkynylene; and $C_{6-12}$arylene;

wherein said $C_{1-10}$alkylene; $C_{2-10}$alkenylene; $C_{2-10}$alkynylene, or $C_{6-12}$arylene, optionally comprises one or more heteroatoms in the alkylene, alkenylene, alkynylene, or arylene moiety, said heteroatoms being each independently selected from O, S and N;

and wherein said $C_{1-10}$alkylene; $C_{2-10}$alkenylene; $C_{2-10}$alkynylene, or $C_{6-12}$arylene, can be unsubstituted or substituted with one or more $Z^4$;

$Q^2$ is selected from the group consisting of $C_{1-10}$alkylene; $C_{3-6}$cycloalkylene; —OC(O)—; —NH—C(O)—; —NH—C(O)—[CR$^{13}$R$^{14}$]$_q$—; —OS(O)—; —OS(O)$_2$—; —NH—S(O)—; and —NH—S(O)$_2$; wherein each left side of said groups is attached to $L^2$ and the right side thereof is attached to $R^{18}$;

wherein said $C_{1-10}$alkylene, optionally comprises one or more heteroatoms, said heteroatoms being each independently selected from O, S and N;

and wherein said $C_{1-10}$alkylene and said $C_{3-6}$cycloalkylene can be unsubstituted or substituted with one or more $Z^5$;

or $Q^2$ is a group of formula (ii);

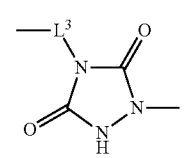

(ii)

wherein the left side of the group formula (ii) is attached to $L^2$ and the right side thereof is attached to $R^{18}$; and wherein, or $Q^2$-$R^{18}$ is a group of formula (iii);

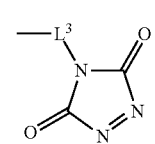

(iii)

wherein the left side of the group formula (ii) is attached to $L^2$ and the right side thereof is attached to $R^{18}$; and wherein, $L^3$ is a single bond or is selected from the group consisting of $C_{1-10}$alkylene; $C_{2-10}$alkenylene; $C_{2-10}$alkynylene; and $C_{6-12}$aryl;

wherein said $C_{1-10}$alkylene; $C_{2-10}$alkenylene; $C_{2-10}$alkynylene, or $C_{6-12}$aryl, optionally comprises one or more heteroatoms in the alkylene, alkenylene, alkynylene, or aryl moiety, said heteroatoms being each independently selected from O, S and N;

and wherein said $C_{1-10}$alkylene; $C_{2-10}$alkenylene; $C_{2-10}$alkynylene, or $C_{6-12}$aryl can be unsubstituted or substituted with one or more $Z^6$;

$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

$R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

or $R^2$ and $R^3$ and $R^4$ together with the carbon atom to which they are attached can form a saturated or unsaturated 4-, 5-, 6-, 7- or 8-membered ring;

or $R^2$ and $L^1$ together with the carbon atom to which they are attached can form a saturated or unsaturated 4-, 5-, 6-, 7- or 8-membered ring;

wherein for $R^2$, $R^3$ and $R^4$, each independently; said $C_{1-20}$alkyl, $C_{2-20}$alkenyl, $C_{2-20}$alkynyl, $C_{6-12}$aryl $C_{1-6}$alkyl, heterocyclyl$C_{1-6}$alkyl; heteroaryl$C_{1-6}$alkyl, or saturated or unsaturated 4-, 5-, 6-, 7- or 8-membered ring, optionally comprises one or more heteroatoms in the alkyl, alkenyl, alkynyl, or unsaturated 4-, 5-, 6-, 7- or 8-membered ring moiety, said heteroatoms being each independently selected from O, S and N;

wherein for $R^2$, $R^3$ and $R^4$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl, heteroaryl$C_{1-6}$alkyl, or saturated or unsaturated 4-, 5-, 6-, 7- or 8-membered ring can be unsubstituted or substituted with one or more $Z^7$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^5$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; and a pharmaceutically active moiety;

wherein said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl$C_{1-6}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; heteroaryl$C_{1-6}$alkyl; and polymeric group, can be unsubstituted or substituted with one or more $Z^8$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); olyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^6$ is selected from the group consisting of $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; and a pharmaceutically active moiety;

$R^7$ is selected from the group consisting of $C_{1-20}$alkyl; $C_{2-20}$alkenyl; $C_{2-20}$alkynyle; $C_{6-12}$aryl; $C_{3-8}$cycloalkyle; $C_{6-12}$aryl$C_{1-6}$alkyl; heterocyclyl; heteroaryl; heterocyclyl$C_{1-6}$alkyl; heteroaryl$C_{1-6}$alkyl; or a polymeric group; and a polymeric group; and a pharmaceutically active moiety;

or $R^6$ and $R^7$ together with the carbon atoms to which they are attached form an unsaturated 4-, 5-, 6-, 7- or 8-membered ring;

wherein for $R^6$ and $R^7$, each independently; said $C_{1-20}$alkyl, $C_{2-20}$alkenyl, $C_{2-20}$alkynyl, $C_{6-12}$aryl $C_{1-6}$alkyl, heterocyclyl$C_{1-6}$alkyl, heteroaryl $C_{1-6}$alkyl or unsaturated 4-, 5-, 6-, 7- or 8-membered ring, optionally comprises one or more heteroatoms in the alkyl, alkenyl, alkynyl, or unsaturated 4-, 5-, 6-, 7- or 8-membered ring moiety, said heteroatoms being each independently selected from O, S and N;

wherein for $R^6$ and $R^7$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, polymeric group, or saturated or unsaturated 4-, 5-, 6-, 7- or 8-membered ring can be unsubstituted or substituted with one or more $Z^9$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^9$ is independently selected from hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl; can be oxidized to form at least one C=O, C=S, N=, N=S, S=O or $S(O)_2$;

each $R^{10}$ is independently selected from hydrogen, $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N; and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

or wherein $R^{11}$ and $R^{12}$ together with the atom to which they are attached form a 5-, 6-, or 7-membered heterocycle.

each $R^{13}$ and $R^{14}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

or wherein $R^{13}$ and $R^{14}$ together with the atom to which they are attached form a 5-, 6-, or 7-membered heterocycle;

$R^{15}$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; and a pharmaceutically active moiety;

wherein said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl$C_{1-6}$alkyl, optionally comprises one or more heteroatoms in the alkyl, alkenyl, and alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; heteroaryl$C_{1-6}$alkyl; and polymeric group, can be unsubstituted or substituted with one or more $Z^{10}$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^{16}$ and $R^{17}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl$C_{1-6}$alkyl, optionally comprise one or more heteroatoms in the alkyl, alkenyl or alkynyl moiety, said heteroatoms being each independently selected from O, S and N; and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

or wherein $R^{16}$ and $R^{17}$ together with the atom to which they are attached form a 5-, 6-, or 7-membered heterocycle;

$R^{18}$ is selected from the group consisting of hydrogen, $C_{1-10}$alkyl; $C_{3-8}$cycloalkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

wherein said $C_{1-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; and heteroaryl$C_{1-6}$alkyl, optionally comprises one or more heteroatoms in the alkyl moiety, said heteroatoms being each independently selected from O, S or N;

wherein said $C_{1-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, heterocyclyl; heteroaryl; heterocyclyl$C_{1-6}$alkyl; and heteroaryl$C_{1-6}$alkyl, can be unsubstituted or substituted with one or more $Z^{11}$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

The present invention therefore provides new molecules including macromolecules, polymers, polymer networks, organic materials, and composites materials of formula (I), which show the quite remarkable ability to generate highly reactive molecules/polymer-bound triazolinedione groups under thermal conditions, which can be controlled to react in a highly specific manner.

This surprising reactivity allows network malleability, site-specific post-polymerization functionalization and generally responsive and/or adaptable materials. The reaction advantageously proceeds in a highly specific manner, with no side reactions (even after several heating/cooling cycles).

According to a second aspect of the present invention, a process for preparing a compound according to the first aspect of the invention is provided. The process comprises the step of contacting at least one compound of formula (II) with at least one compound of formula (III), thereby obtaining a compound of formula (I), wherein R$^1$, R$^2$, R$^3$, R$^4$, R$^5$, L$^1$, Q$^1$, Z$^9$ have the same meaning as defined herein,

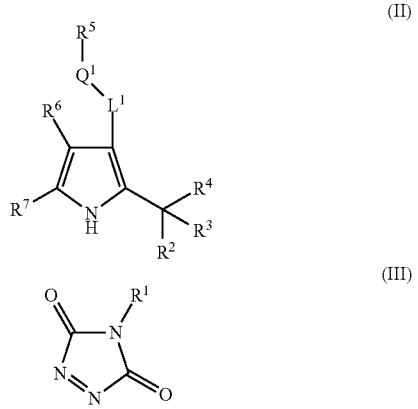

(II)

(III)

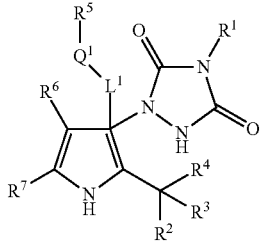

(I)

The present invention also encompasses a compound of formula (I) according to the first aspect of the invention obtainable by contacting a compound of formula (II) with a compound of formula (III).

The present inventors have shown that this process enables the chemical synthesis of a wide range of products of formula (I) and in particular of remendable compounds of formula (I).

The present process allows macromolecular functionalization, polymer-polymer linking and polymer cross-linking under ambient conditions without the need for a catalyst, using scalable and robust building blocks. Surprisingly, the triazolinediones compound of formula (III) can be used to introduce reversible links into materials, giving rise to advantageous material properties such as self-healing, recycling and network malleability.

The triazolinediones compound of formula (III) offer a wide range of selective covalent bond forming reactions, most of which occur very rapidly under ambient and equimolar conditions, without the need for a catalyst, giving functionalized polymers, block-copolymers and cross-linked polymers.

The triazolinedione compound of formula (III) in contact with pyrrole of formula (II) allows a reversible adduct-formation with a very useful temperature range for self-healing applications.

The present inventors have surprisingly found that the ene-type reaction between triazolinedione compound of formula (III) and a pyrrole of formula (II) can be used to prepare polymer networks that can be healed, reshaped and recycled under thermal conditions, effected by the reversible triazolidinedione-pyrrole click reaction, without apparent thermal degradation of the triazoline dione moieties, which is known to occur when TADs are heated in condensed phases or exposed to moisture or hydroxyl moieties for prolonged periods even under ambient conditions. Thus, the TAD-pyrrole conjugation does not only serve as a masked TAD reagent, but it also prolongs its useful shelf life and protects it from the most common degradation processes associated with TADs (dimerization, hydrolysis and alcoholysis).

The present process provides a range of selective reversible covalent linking reactions that are high yielding at low temperature (<20° C.), without the need for a catalyst. An additional feature of this process is the intense color of triazolinediones compounds, providing a very useful visual feedback system, as most of the corresponding urazoles are colorless.

The present invention therefore also encompasses a process for reversible formation of a compound according to the first aspect of the invention, the process comprising the steps of contacting a compound of formula (II) with a compound of formula (III) at a temperature of at most 29° C., thereby forming a compound of formula (I), and subsequently releasing at least part of said of compound of formula (III) and at least part of said compound of formula (II) by submitting said compound of formula (I) to a temperature of at least 30° C., preferably of at least 40° C., for example of at least 60° C., preferably of at least 80° C., preferably of at most 150° C., for example of at most 145° C., for example of at most 140° C.

The present invention also encompasses a process for repairing an article comprising a compound according to the first aspect of the invention, comprising the step of thermally treating the compound of formula (I) at a temperature of at least 30° C., preferably at least 40° C., for example at least 60° C., preferably at least 80° C., preferably at most 150° C., for example at most 145° C., for example at most 140° C. In some embodiment this process for repairing comprises the steps of cooling said article thereby repairing said article.

In some embodiments, the present inventors have shown that the present compounds of formula (I) can be successfully used as precursor of 1,2,4-triazoline-3,5-dione in condensed phases, since the compound of formula (I) can reversibly transform to 1,2,4-triazoline-3,5-dione of formula (III) and pyrrole compound of formula (II). The present invention allows therefore the stage storage of compound of formula (III) under the form of compounds of formula (I), and reverting to the compound of formula (III) by thermally treating compound of formula (I).

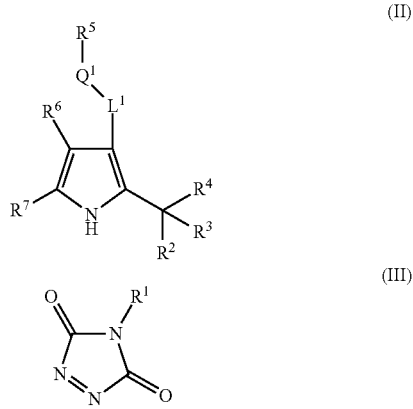

The present invention also encompasses the use of a compound of formula (I) as precursor for a compound of formula (III).

In addition, the compounds of formula (I) are functional materials that can recover mechanical properties, by self healing and mending using this reversible process. The reversible nature of the linkage allows for network remodeling at the damage site.

The present invention also encompasses remendable materials comprising a compound of formula (I). Said materials offer increased durability, safety, and cost efficiency for many applications.

The present invention also encompasses polyurethane obtained by contacting a compound of formula (I) with at least one isocyanate and with at least one polyol.

The present invention also encompasses a polymer having structural formula (I), wherein at least one of $R^1$, $R^2$, $R^3$, $R^4$, $R^5$, $R^6$ or $R^7$ is a polymeric group, said polymeric group being selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

The present invention also encompasses a polymer of (meth)acrylate, having structural formula (I), wherein at least one of $R^1$, $R^2$, $R^3$, $R^4$, $R^5$, $R^6$ or $R^7$ is a polymeric group, selected from the group comprising poly(methyl methacrylate); polyacrylate; polymethacrylate; copolymer of acrylate, methacrylate and/or styrene; poly(isobornyl acrylate); polyacrylonitrile; and/or block, comb and/or star copolymers of the polymeric group.

The present invention also encompasses a polymer of styrene having structural formula (I), wherein at least one of $R^1$, $R^2$, $R^3$, $R^4$, $R^5$, $R^6$ or $R^7$ is a polymeric group, said polymeric group being selected from the group comprising polystyrene; copolymer of acrylate, methacrylate and/or styrene; acrylonitrile butadiene styrene (ABS); styrene-butadiene rubber (SBR); and/or block, comb and/or star copolymers of the polymeric group.

The present invention also encompasses a polymer of isobornyl acrylate, having structural formula (I), wherein at least one of $R^1$, $R^2$, $R^3$, $R^4$, $R^5$, $R^6$ or $R^7$ is a polymeric group selected from poly(isobornyl acrylate); and/or block, comb and/or star copolymers of the polymeric group.

The present invention also encompasses a polymer of urethane, having structural formula (I), wherein at least one of $R^1$, $R^2$, $R^3$, $R^4$, $R^5$, $R^6$ or $R^7$ is a polyurethane.

The present invention also encompasses the use of a compound according to the first aspect of the invention as an in situ precursor of triazolinedione, preferably the invention encompasses the use of a compound according to the first aspect of the invention as an in situ precursor of a triazolinedione for the functionalization of enes, dienes, aryl and heteroaryl systems via the ene reactions, Diels-Alder reactions, and electrophilic aromatic substitution reactions of said triazolinedione. The present compounds of formula (I) according to the first aspect of the invention are particularly useful to generate reactive triazoline dione reagents to perform thermally induced click-type covalent linking.

The present invention also encompasses the use of a compound according to the first aspect of the invention in polymers, membranes, adhesives, foams, sealants, molded articles, films, extruded articles, fibers, elastomers, polymer based additives, pharmaceutical and biomedical products, varnishes, paints, coatings, inks, composite material, organic LEDs, organic semiconductors, conducting organic polymers, and 3D printed articles.

The present invention also encompasses an article comprising a compound according to the first aspect of the invention.

The present invention also encompasses a self-healing material comprising a compound according to the first aspect of the invention.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The independent and dependent claims set out particular and preferred features of the invention. Features from the dependent claims may be combined with features of the independent or other dependent claims as appropriate.

DETAILED DESCRIPTION OF THE INVENTION

Figure 1A:
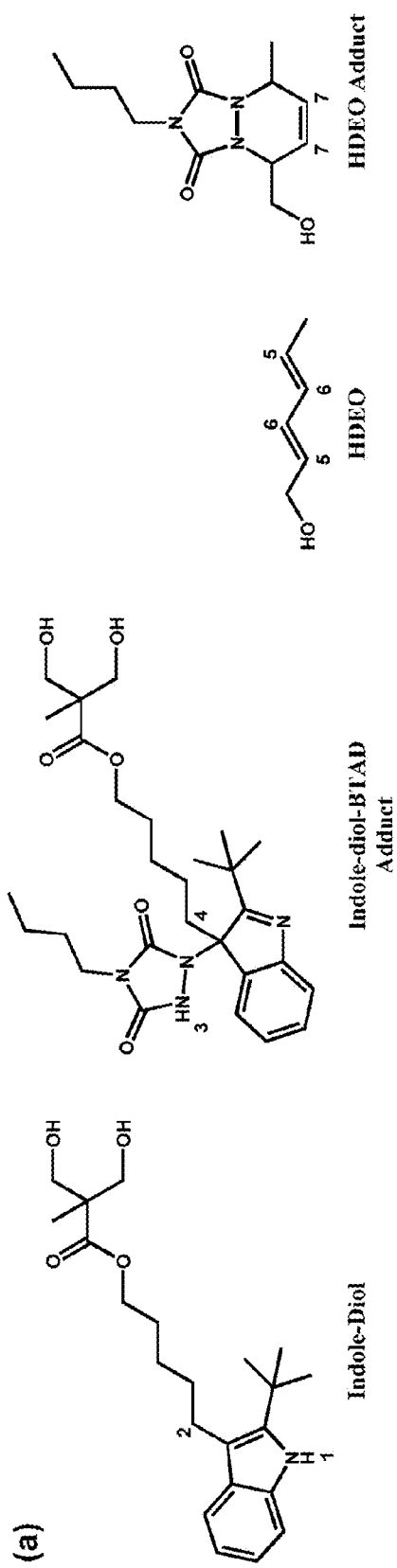
FIG. 1. Section (a) represents the structures of the reactants and the adducts produced in Example 40. Section (b) represents the $^1$H NMR spectra of the different reactants and the adducts used in Example 40. Section (c) represents the evolution of the $^1$H NMR spectra of the indole-diol-BTAD adduct+HDEO at different temperatures.

Before the present invention is described, it is to be understood that this invention is not limited to particular processes, methods, and compounds described, as such processes, methods, and compounds may, of course, vary. It is also to be understood that the terminology used herein is not intended to be limiting, since the scope of the present invention will be limited only by the appended claims.

When describing the compounds and processes of the invention, the terms used are to be construed in accordance with the following definitions, unless a context dictates otherwise.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

As used herein, the term "and/or," when used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

The recitation of numerical ranges by endpoints includes all numbers and fractions subsumed within the respective ranges, as well as the recited endpoints.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

When describing the present invention, the terms used are to be construed in accordance with the following definitions, unless a context dictates otherwise.

Whenever the term "substituted" is used herein, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation from a reaction mixture.

Where groups can be substituted, such groups may be substituted with one or more, and preferably one, two or three substituents. Substituents may be selected from but not limited to, for example, the group comprising halogen; $C_{1-6}$alkyl; halo$C_{1-6}$alkyl; halo$C_{1-6}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; or a polymeric group; and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

The terminology "optionally comprises one or more heteroatoms, said heteroatoms being selected from the atoms O, S, or N" as used herein, refers to a group where one or more carbon atoms are replaced by at least one oxygen, nitrogen or sulfur atom and thus includes, depending on the group to which is referred, heteroalkyl, heteroalkenyl, heteroalkynyl, heteroalkylene, heteroalkenylene, heteroalkynylene, cycloheteroalkyl, cycloheteroalkenyl, cycloheteroalkynyl, heteroaryl, arylheteroalkyl(ene), heteroarylalkyl(ene), heteroarylheteroalkyl(ene), arylheteroalkenyl(ene), heteroarylalkenyl(ene), heteroarylheteroalkenyl(ene), heteroarylheteroalkenyl(ene), arylheteroalkynyl(ene), heteroarylalkynyl(ene), heteroarylheteroalkynyl(ene), among others. This term therefore comprises, depending on the group to which is referred, as an example "heteroalkyl" such as alkoxy, alkoxyalkyl, mono- or di-alkylamino, mono- or di-alkylaminoalkyl, alkylthio, alkylthioalkyl; "heteroalkenyl" such as alkenyloxy, alkenyloxyalkenyl, mono- or di-alkenylamino, mono- or di-alkenylaminoalkenyl, alkenylthio, alkenylthioalkenyl, and "heteroalkynyl" such as alkynyloxy, alkynyloxyalkynyl, mono- or di-alkynylamino, mono- or di-alkynylaminoalkynyl, alkynylthio, alkynylthio-alkynyl. As an example, the terminology "alkyl optionally comprises one or more heteroatoms, said heteroatoms being selected from the atoms of O, S, or N" therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain. Examples of heteroalkyl include alkoxy, alkoxyalkyl, alkylamino, alkylaminoalkyl, alkylthio, alkylthioalkyl, such as methoxy, methylthio, ethoxy, propoxy, $CH_3$—O—$CH_2$—, $CH_3$—S—$CH_2$—, $CH_3$—$CH_2$—O—$CH_2$—, $CH_3NH$—, $(CH_3)_2N$—, $(CH_3)_2$—$CH_2$—$NHCH_2$—$CH_2$—, among many other examples. As an example, the terminology "arylalkyl optionally comprises one or more heteroatoms in the alkyl chain, said heteroatoms being selected from the atoms O, S, or N" therefore refers to aryl-heteroalkyl, meaning an arylalkyl which comprises one or more heteroatoms in the hydrocarbon chain, whereas the heteroatoms may be positioned at the beginning of the hydrocarbon chain, in the hydrocarbon chain or at the end of the hydrocarbon chain. "Aryl-heteroalkyl" thus includes aryloxy, arylalkoxy, aryl-alkyl-NH— and the like and examples are phenyloxy, benzyloxy, aryl-$CH_2$—S—$CH_2$—, aryl-$CH_2$—O—$CH_2$—, aryl-NH—$CH_2$— among many other examples.

The terminology regarding a chemical group "wherein at least one carbon atom or heteroatom of said group can be oxidized to form at least one C=O, C=S, N=O, N=S, S=O or $S(O)_2$" as used herein, refers to a group where two or more hydrogen atoms on a carbon atom or heteroatom of said group are taken together to form C=O, C=S, N=O, N=S, S=O or $S(O)_2$. As an example, the terminology refers to "an alkyl wherein a carbon atom or heteroatom of said alkyl can oxidized to form a C=O, C=S, N=O, N=S, S=O or $S(O)_2$", includes among other examples $CH_3$—C(O)—$CH_2$—, $CH_3$—C(O)—, $CH_3$—C(S)—$CH_2$— and $(CH_3)_2$—$CH_2$—C(O)—$CH_2$—$CH_2$—.

The combination for a group "optionally comprises one or more heteroatoms, said heteroatoms being selected from the atoms O, S, or N" and "wherein a carbon atom or heteroatom of said group can be oxidized to form a C=O, C=S, N=O, N=S, S=O or $S(O)_2$," can combine the two aspects described herein above and includes, if the group referred to is alkyl, among other examples $CH_3$—COO—, $CH_3$—COO—$CH_2$—, $CH_3$—NH—CO—, $CH_3$—NH—CO—$CH_2$—, $CH_3$—NH—CS—$CH_2$—, $CH_3$—NH—CS—NH—$CH_2$—, $CH_3$—NH—$S(O)_2$— and $CH_3$—NH—$S(O)_2$—NH—$CH_2$—.

The term "halo" or "halogen" as a group or part of a group is generic for fluoro, chloro, bromo, iodo.

The term "oxo" as used herein refers to the group =O.

The term "amino" refers to the group —$NH_2$.

The term "hydroxyl" or "hydroxy" as used herein refers to the group —OH.

The term "nitro" as used herein refers to the group —$NO_2$.

The term "cyano" as used herein refers to the group —CN.

The term "carboxy" or "carboxyl" or "hydroxycarbonyl" as used herein refers to the group —$CO_2H$.

The term "alkyl", as a group or part of a group, refers to a hydrocarbyl group of Formula $C_nH_{2n+1}$ wherein n is a number of at least 1. Alkyl groups may be linear, or branched and may be substituted as indicated herein. Generally, the alkyl groups comprise from 1 to 20 carbon atoms, preferably from 1 to 12 carbon atoms, preferably from 1 to 10 carbon atoms, preferably from 1 to 6 carbon atoms, more preferably 1, 2, 3, 4, 5, 6 carbon atoms. When a subscript is used herein following a carbon atom, the subscript refers to the number of carbon atoms that the named group may contain. For example, the term "$C_{1-20}$alkyl", as a group or part of a group, refers to a hydrocarbyl group of Formula $C_nH_{2n+1}$ wherein n is a number ranging from 1 to 20. Thus, for example, $C_{1-20}$alkyl groups include all linear, or branched alkyl groups having 1 to 20 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers, undecyl and its isomers, dodecyl and its isomers, tridecyl and its isomers, tetradecyl and its isomers, pentadecyl and its isomers, hexadecyl and its isomers, heptadecyl and its isomers, octadecyl and its isomers, nonadecyl and its isomers, icosyl and its isomers, and the like. For example, $C_{1-10}$alkyl includes all linear, or branched alkyl groups having 1 to 10 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers and the like. For example, $C_{1-6}$alkyl includes all linear, or branched alkyl groups having 1 to 6 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers. When the suffix "ene" is used in conjunction with an alkyl group, i.e. "alkylene", this is intended to mean the alkyl group as defined herein having two single bonds as points of attachment to other groups. Non-limiting examples of alkylene groups includes methylene, ethylene, methylmethylene, propylene, ethylethylene, and 1,2-dimethylethylene. Similarly, where alkenyl groups as defined herein and alkynyl groups as defined herein, respectively, are divalent groups having single bonds for attachment to two other groups, they are termed "alkenylene" and "alkynylene" respectively.

The term "$C_{2-20}$alkenyl" as a group or part of a group, to an unsaturated hydrocarbyl group, which may be linear, branched or cyclic, comprising one or more carbon-carbon double bonds. Alkenyl groups thus preferably comprise between 2 and 20 carbon atoms, preferably between 2 and 10 carbon atoms, still more preferably between 2 and 6 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "$C_{2-20}$alkynyl" as a group or part of a group, refers to a class of monovalent unsaturated hydrocarbyl groups, wherein the unsaturation arises from the presence of one or more carbon-carbon triple bonds. Alkynyl groups thus preferably comprise between 2 and 20 carbon atoms, preferably between 2 and 10 carbon atoms, still more preferably between 2 and 6 carbon atoms. Non limiting examples of alkynyl groups are ethynyl, 2-propynyl, 2-butynyl, 3-butynyl, 2-pentynyl and its isomers, 2-hexynyl and its isomers—and the like.

The term "cycloalkyl", as a group or part of a group, refers to a cyclic alkyl group, that is a monovalent, saturated, hydrocarbyl group having 1 or more cyclic structure, and comprising from 3 to 12 carbon atoms, more preferably from 3 to 9 carbon atoms, more preferably from 3 to 6 carbon atoms, still more preferably from 5 to 6 carbon atoms. Cycloalkyl includes all saturated hydrocarbon groups containing 1 or more rings, including monocyclic or bicyclic groups. The further rings of multi-ring cycloalkyls may be either fused, bridged and/or joined through one or more spiro atoms. The term "$C_{3-6}$cycloalkyl", a cyclic alkyl group comprising from 3 to 6 carbon atoms, more preferably from 5 to 6 carbon atoms. Examples of $C_{3-6}$cycloalkyl groups include but are not limited to cyclopropyl, cyclobutyl, cyclopentyl, cyclohexyl. Cycloalkyl groups may also be considered to be a subset of homocyclic rings discussed hereinafter. When the suffix "ene" is used in conjunction with a cycloalkyl group, i.e. cycloalkylene, this is intended to mean the cycloalkyl group as defined herein having two single bonds as points of attachment to other groups.

The term "homocyclic ring" as a group or part of a group, refers to a ring wherein the ring atoms comprise only carbon atoms. Non limiting examples of homocyclic rings include cycloalkyl, cycloalkenyl, with cycloalkyl being preferred. Where a ring carbon atom is replaced with a heteroatom, preferably nitrogen, oxygen of sulfur, the heteroatom-containing ring resultant from such a replacement is referred to herein as a heterocyclic ring. More than one carbon atom in a ring may be replaced so forming heterocyclic ring having a plurality of heteroatoms.

The term "halo$C_{1-6}$alkyl" as a group or part of a group, refers to a $C_{1-6}$alkyl group having the meaning as defined above wherein one or more hydrogens are replaced with one or more halogen as defined above. Non-limiting examples of such haloalkyl groups include chloromethyl, 1-bromoethyl, fluoromethyl, difluoromethyl, trifluoromethyl, 1,1,1-trifluoroethyl and the like.

The term "$C_{1-6}$alkoxy" or "$C_{1-6}$alkyloxy", as a group or part of a group, refers to a group having the Formula —$OR^a$ wherein $R^a$ is $C_{1-6}$alkyl as defined herein above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy.

The term "$C_{1-6}$alkoxy$C_{1-6}$alkyl" or "$C_{1-6}$alkyloxy$C_{1-6}$alkyl", as a group or part of a group, refers to a group having the Formula —$R^e$—O—$R^a$ wherein $R^a$ is $C_{1-6}$alkyl as defined herein, and $R^e$ is $C_{1-6}$alkylene.

The term "$C_{1-6}$alkylthio", as a group or part of a group, refers to a group having the Formula —S—$R^a$ wherein $R^a$ is $C_{1-6}$alkyl as defined herein above. Non-limiting examples of $C_{1-6}$alkylthio groups include methylthio (—$SCH_3$), ethylthio (—$SCH_2CH_3$), n-propylthio, isopropylthio, n-butylthio, isobutylthio, sec-butylthio, tert-butylthio, and the like.

The term "$C_{1-6}$alkylthio$C_{1-6}$alkyl", as a group or part of a group, refers to a group having the Formula —$R^e$—S—$R^a$ wherein $R^a$ is $C_{1-6}$alkyl as defined herein, and $R^e$ is $C_{1-6}$alkylene.

The term "halo$C_{1-6}$alkoxy", as a group or part of a group, refers to a group of Formula —O—$R^b$ wherein $R^b$ is halo $C_{1-6}$alkyl as defined herein. Non-limiting examples of suitable halo$C_{1-6}$alkoxy include fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy, 2,2,2-trichloroethoxy, trichloromethoxy, 2-bromoethoxy, pentafluoroethyl, 3,3,3-trichloropropoxy, 4,4,4-trichlorobutoxy.

The terms "mono- or di-$C_{1-6}$alkylamino" or "$C_{1-6}$alkylamino", as a group or part of a group, refers to a group of formula $N(R^c)(R^d)$ wherein $R^c$ and $R^d$ are each independently selected from hydrogen, or $C_{1-6}$alkyl, wherein at least one of $R^c$ or $R^d$ is $C_{1-6}$alkyl. Thus, alkylamino include mono-alkyl amino group (e.g. mono-$C_{1-6}$alkylamino group such as methylamino and ethylamino), and di-alkylamino group (e.g. di-$C_{1-6}$alkylamino group such as dimethylamino and diethylamino). Non-limiting examples of suitable alkylamino groups include n-propylamino, isopropylamino, n-butylamino, i-butylamino, sec-butylamino, t-butylamino, pentylamino, n-hexylamino, di-n-propylamino, di-i-propylamino, ethylmethylamino, methyl-n-propylamino, methyl-i-propylamino, n-butylmethylamino, i-butylmethylamino, t-butylmethylamino, ethyl-n-propylamino, ethyl-i-propylamino, n-butylethylamino, i-butylethylamino, t-butylethylamino, di-n-butylamino, di-i-butylamino, methylpentylamino, methylhexylamino, ethylpentylamino, ethylhexylamino, propylpentylamino, propylhexylamino, and the like.

The terms "mono- or di-$C_{1-6}$alkylamino$C_{1-6}$alkyl" or "$C_{1-6}$alkylamino$C_{1-6}$alkyl", as a group or part of a group, refers to a group of formula —$R^e$—N($R^c$)($R^d$) wherein $R^c$ and $R^d$ are each independently selected from hydrogen, or $C_{1-6}$alkyl, wherein at least one of $R^c$ or $R^d$ is $C_{1-6}$alkyl and $R^e$ is $C_{1-6}$alkylene.

The term "$C_{1-6}$alkoxycarbonyl", as a group or part of a group, refers to a group of formula C(=O)O$R^a$, wherein $R^a$ is as defined above for $C_{1-6}$alkyl.

The term "$C_{1-6}$alkylcarbonyloxy", as a group or part of a group, refers to a group of Formula 0-C(=O)$R^a$ wherein $R^a$ is as defined above for $C_{1-6}$alkyl.

The term "$C_{6-12}$aryl", as a group or part of a group, refers to a polyunsaturated, aromatic hydrocarbyl group having a single ring (i.e. phenyl) or multiple aromatic rings fused together (e.g. naphthalene), or linked covalently, typically containing 6 to 12 atoms; wherein at least one ring is aromatic. The aromatic ring may optionally include one to two additional rings (either cycloalkyl, heterocyclyl or heteroaryl) fused thereto. Examples of suitable aryl include $C_{6-10}$aryl, more preferably $C_{6-8}$aryl. Non-limiting examples of $C_{6-12}$aryl comprise phenyl, biphenylyl, biphenylenyl, or 1- or 2-naphthanelyl; 5- or 6-tetralinyl, 1-, 2-, 3-, 4-, 5-, 6-, 7- or 8-azulenyl, 4-, 5-, 6 or 7-indenyl, 4- or 5-indanyl, 5-, 6-, 7- or 8-tetrahydronaphthyl, 1,2,3,4-tetrahydronaphthyl, and 1,4-dihydronaphthyl. When the suffix "ene" is used in conjunction with an aryl group, this is intended to mean the aryl group as defined herein having two single bonds as points of attachment to other groups, such as phenylene, biphenylylene, naphthylene, indenylene, and the like. Where a carbon atom in an aryl group is replaced with a heteroatom, the resultant ring is referred to herein as a heteroaryl ring.

The term "$C_{6-12}$aryl$C_{1-12}$alkyl", as a group or part of a group, means a $C_{1-6}$alkyl as defined herein, wherein at least one hydrogen atom is replaced by at least one $C_{6-12}$aryl as defined herein. Non-limiting examples of $C_{6-12}$aryl$C_{1-6}$alkyl group include benzyl, phenethyl, dibenzylmethyl, methylphenylmethyl, 3-(2-naphthyl)-butyl, and the like.

The term "$C_{6-12}$aryl$C_{1-12}$alkyl$C_{6-12}$aryl", as a group or part of a group, means a $C_{6-12}$aryl, wherein at least one hydrogen atom is replaced by at least one $C_{6-12}$aryl $C_{1-12}$alkyl as defined herein.

The terms "heterocyclyl" or "heterocyclo", as a group or part of a group, refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from N, O and/or S, where the N and S heteroatoms may optionally be oxidized and the N heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms.

Non limiting exemplary heterocyclic groups include aziridinyl, oxiranyl, thiiranyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, pyrrolidinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl.

The term "heteroaryl" as a group or part of a group, refers but is not limited to 5 to 12 atom aromatic rings or ring systems containing 1 to 2 rings which are fused together or linked covalently, typically containing 5 to 12 atoms; at least one of which is aromatic in which one or more carbon atoms in one or more of these rings can be replaced by N, O and/or S atoms where the N and S heteroatoms may optionally be oxidized and the N heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxopyridazin-1(6H)-yl, 2-oxopyridin-1(2H)-yl, 6-oxopyridazin-1(6H)-yl, 2-oxopyridin-1(2H)-yl, 1,3-benzodioxolyl, quinolinyl, isoquinolinyl, cinnolinyl, quinazolinyl, quinoxalinyl, The term "pyrrolyl" (also called azolyl) as used herein includes pyrrol-1-yl, pyrrol-2-yl and pyrrol-3-yl. The term "furanyl" (also called "furyl") as used herein includes furan-2-yl and furan-3-yl (also called furan-2-yl and furan-3-yl). The term "thiophenyl" (also called "thienyl") as used herein includes thiophen-2-yl and thiophen-3-yl (also called thien-2-yl and thien-3-yl). The term "pyrazolyl" (also called 1H-pyrazolyl and 1,2-diazolyl) as used herein includes pyrazol-1-yl, pyrazol-3-yl, pyrazol-4-yl and pyrazol-5-yl. The term "imidazolyl" as used herein includes imidazol-1-yl, imidazol-2-yl, imidazol-4-yl and imidazol-5-yl. The term "oxazolyl" (also called 1,3-oxazolyl) as used herein includes oxazol-2-yl; oxazol-4-yl and oxazol-5-yl. The term "isoxazolyl" (also called 1,2-oxazolyl), as used herein includes isoxazol-3-yl, isoxazol-4-yl, and isoxazol-5-yl. The term "thiazolyl" (also called 1,3-thiazolyl), as used herein includes thiazol-2-yl, thiazol-4-yl and thiazol-5-yl (also called 2-thiazolyl, 4-thiazolyl and 5-thiazolyl). The term "isothiazolyl" (also called 1,2-thiazolyl) as used herein includes isothiazol-3-yl, isothiazol-4-yl, and isothiazol-5-yl. The term "triazolyl" as used herein includes 1H-triazolyl and 4H-1,2,4-triazolyl, "1H-triazolyl" includes 1H-1,2,3-triazol-1-yl, 1H-1,2,3-triazol-4-yl, 1H-1,2,3-triazol-5-yl, 1H-1,2,4-triazol-1-yl, 1H-1,2,4-triazol-3-yl and 1H-1,2,4-triazol-5-yl. "4H-1,2,4-triazolyl" includes 4H-1,2,4-triazol-4-yl, and 4H-1,2,4-triazol-3-yl. The term "oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl. The term "thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl. The term "tetrazolyl" as used herein includes 1H-tetrazol-1-yl, 1H-tetrazol-5-yl, 2H-tetrazol-2-yl, and 2H-tetrazol-5-yl. The term "oxatriazolyl" as used herein includes 1,2,3,4-oxatriazol-5-yl and 1,2,3,5-oxatriazol-4-yl. The term "thiatriazolyl" as used herein includes 1,2,3,4-thiatriazol-5-yl and 1,2,3,5-thiatriazol-4-yl. The term "pyridinyl" (also called "pyridyl") as used herein includes pyridin-2-yl, pyridin-3-yl and pyridin-4-yl (also called 2-pyridyl, 3-pyridyl and 4-pyridyl). The term "pyrimidyl" as used herein includes pyrimid-2-yl, pyrimid-4-yl, pyrimid-5-yl and pyrimid-6-yl. The term "pyrazinyl" as used herein includes pyrazin-2-yl and pyrazin-3-yl. The term "pyridazinyl as used herein includes pyridazin-3-yl and pyridazin-4-yl. The term "oxazinyl" (also called "1,4-oxazinyl") as used herein includes 1,4-oxazin-4-yl and 1,4-oxazin-5-yl. The term "dioxinyl" (also called "1,4-dioxinyl") as used herein includes 1,4-dioxin-2-yl and 1,4-dioxin-3-yl. The term "thiazinyl" (also called "1,4-thiazinyl") as used herein includes 1,4-thiazin-2-yl, 1,4-thiazin-3-yl, 1,4-thiazin-4-yl, 1,4-thiazin-5-yl and 1,4-thiazin-6-yl. The term "triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl. The term "imidazo[2,1-b][1,3]thiazolyl" as used herein includes imidazo[2,1-b][1,3]thiazoi-2-yl, imidazo[2,1-b][1,3]thiazol-3-yl, imidazo[2,1-b][1,3]thiazol-5-yl and imidazo[2,1-b][1,3]thiazol-6-yl. The term "thieno[3,2-b]furanyl" as used herein includes thieno[3,2-b]furan-2-yl, thieno[3,2-b]furan-3-yl, thieno[3,2-b]furan-4-yl, and thieno[3,2-b]furan-5-yl. The term "thieno[3,2-b]thiophenyl" as used herein includes thieno[3,2-b]thien-2-yl, thieno[3,2-b]thien-3-yl, thieno[3,2-b]thien-5-yl and thieno[3,2-b]thien-6-yl. The term "thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl. The term "thieno[2,3-d]imidazolyl" as used herein includes thieno[2,3-d]imidazol-2-yl, thieno[2,3-d]imidazol-4-yl and thieno[2,3-d]imidazol-5-yl. The term "tetrazolo[1,5-a]pyridinyl" as used herein includes tetrazolo[1,5-a]pyridine-5-yl, tetrazolo[1,5-a]pyridine-6-yl, tetrazolo[1,5-a]pyridine-7-yl, and tetrazolo[1,5-a]pyridine-8-yl. The term "indolyl" as used herein includes indol-1-yl, indol-2-yl, indol-3-yl, -indol-4-yl, indol-5-yl, indol-6-yl and indol-7-yl. The term "indolizinyl" as used herein includes indolizin-1-yl, indolizin-2-yl, indolizin-3-yl, indolizin-5-yl, indolizin-6-yl, indolizin-7-yl, and indolizin-8-yl. The term "isoindolyl" as used herein includes isoindol-1-yl, isoindol-2-yl, isoindol-3-yl, isoindol-4-yl, isoindol-5-yl, isoindol-6-yl and isoindol-7-yl. The term "benzofuranyl" (also called benzo[b]furanyl) as used herein includes benzofuran-2-yl, benzofuran-3-yl, benzofuran-4-yl, benzofuran-5-yl, benzofuran-6-yl and benzofuran-7-yl. The term "isobenzofuranyl" (also called benzo[c]furanyl) as used herein includes isobenzofuran-1-yl, isobenzofuran-3-yl, isobenzofuran-4-yl, isobenzofuran-5-yl, isobenzofuran-6-yl and isobenzofuran-7-yl. The term "benzothiophenyl" (also called benzo[b]thienyl) as used herein includes 2-benzo[b]thiophenyl, 3-benzo[b]thiophenyl, 4-benzo[b]thiophenyl, 5-benzo[b]thiophenyl, 6-benzo[b]thiophenyl and -7-benzo[b]thiophenyl (also called benzothien-2-yl, benzothien-3-yl, benzothien-4-yl, benzothien-5-yl, benzothien-6-yl and benzothien-7-yl). The term "isobenzothiophenyl" (also called benzo[c]thienyl) as used herein includes isobenzothien-1-yl, isobenzothien-3-yl, isobenzothien-4-yl, isobenzothien-5-yl, isobenzothien-6-yl and isobenzothien-7-yl. The term "indazolyl" (also called 1H-indazolyl or 2-azaindolyl) as used herein includes 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, and 2H-indazol-7-yl. The term "benzimidazolyl" as used herein includes benzimidazol-1-yl, benzimidazol-2-yl, benzimidazol-4-yl, benzimidazol-5-yl, benzimidazol-6-yl and benzimidazol-7-yl. The term "1,3-benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl. The term "1,2-benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl. The term "2,1-benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl. The term "1,3-benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl. The term "1,2-benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl. The term "2,1-benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl. The term "benzotriazolyl" as used herein includes benzotriazol-1-yl, benzotriazol4-yl, benzotriazol-5-yl, benzotriazol-6-yl and benzotriazol-7-yl. The term "1,2,3-benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl. The term "2,1,3-benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl. The term "1,2,3-benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl. The term "2,1,3-benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl. The term "thienopyridinyl" as used herein includes thieno[2,3-b]pyridinyl, thieno[2,3-c]pyridinyl, thieno[3,2-c]pyridinyl and thieno[3,2-b]pyridinyl. The term "purinyl" as used herein includes purin-2-yl, purin-6-yl, purin-7-yl and purin-8-yl. The term "imidazo[1,2-a]pyridinyl", as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl. The term "1,3-benzodioxolyl", as used herein includes 1,3-benzodioxol-4-yl, 1,3-benzodioxol-5-yl, 1,3-benzodioxol-6-yl, and 1,3-benzodioxol-7-yl. The term "quinolinyl" as used herein includes quinolin-2-yl, quinolin-3-yl, quinolin-4-yl, quinolin-5-yl, quinolin-6-yl, quinolin-7-yl and quinolin-8-yl. The term "isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl. The term "cinnolinyl" as used herein includes cinnolin-3-yl, cinnolin-4-yl, cinnolin-5-yl, cinnolin-6-yl, cinnolin-7-yl and cinnolin-8-yl. The term "quinazolinyl" as used herein includes quinazolin-2-yl, quiriazolin-4-yl, quinazolin-5-yl, quinazolin-6-yl, quinazolin-7-yl and quinazolin-8-yl. The term "quinoxalinyl", as used herein includes quinoxalin-2-yl, quinoxalin-5-yl, and quinoxalin-6-yl.

The term "heteroalkyl", as a group or part of a group, also encompasses groups of Formula —X—$R^f$ or —$R^e$—X—$R^f$, and alkyl substituted with one or more groups of formula —X—R$^f$ or —R$^e$—X—R$^f$, wherein R$^e$ is as defined above for C$_{1-6}$alkylene and X is NR$^c$, S or O, and R$^c$ is selected from hydrogen, or C$_{1-6}$alkyl, and R$^f$ is hydrogen, C$_{1-6}$acyl, C$_{1-6}$alkyl, C$_{3-6}$cycloalky; Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, and the like.

The term "heterocyclylC$_{1-6}$alkyl", as a group or part of a group, refers to a group or formula —R$^e$—R$^g$ wherein R$^e$ is C$_{1-6}$alkylene and R$^g$ is a heterocyclyl group as defined herein.

The term "heterocyclyloxycarbonyl" as a group or part of a group, refers to a group of Formula —C(=O)—O—R$^g$ wherein R$^g$ is heterocyclyl as defined herein.

The term "heteroaryloxycarbonyl" as a group or part of a group, refers to a group of Formula —C(=O)—O—R$^i$ wherein R$^i$ is heteroaryl as defined herein.

The term "C$_{6-12}$aryloxycarbonyl" as a group or part of a group, refers to a group of Formula —C(=O)—O—R$^h$ wherein R$^h$ is C$_{6-12}$aryl as defined herein.

The term "heterocyclylcarbonyloxy" as a group or part of a group, refers to a group of Formula —O—C(=O)—R$^g$ wherein R$^g$ is heterocyclyl as defined herein.

The term "arylcarbonyloxy" as a group or part of a group, refers to refers to a group of Formula —O—C(=O)—R$^h$ wherein R$^h$ is aryl as defined herein.

The term "heteroarylcarbonyloxy" as a group or part of a group, refers to refers to a group of Formula —O—C(=O)—R$^h$ wherein R$^h$ is heteroaryl as defined herein.

The term "C$_{1-6}$alkylcarbonylamino" as a group or part of a group, refers to a group of Formula —NH(C=O)R$^a$ or —NR$^a$(C=O)R$^a$, wherein R$^a$ is C$_{1-6}$alkyl.

The term "haloC$_{1-6}$alkylcarbonylamino" as a group or part of a group, refers to a group of Formula —NH(C=O)R$^k$ or —NR$^a$(C=O)R$^k$, wherein R$^o$ is C$_{1-6}$alkyl as defined herein and R$^k$ is haloC$_{1-6}$alkyl as defined herein.

The term "heterocyclylcarbonylamino" as a group or part of a group, refers to a group of Formula —NH(C=O)R$^g$ or —NR$^a$(C=O)R$^g$, wherein R$^a$ is C$_{1-6}$alkyl as defined herein and R$^g$ is heterocyclyl as defined herein The term "C$_{6-12}$arylcarbonylamino" as a group or part of a group, refers to a group of Formula —NH(C=O)R$^h$ or —NR$^a$(C=O)R$^h$, wherein R$^a$ is C$_{1-6}$alkyl as defined herein and R$^h$ is C$_{6-12}$aryl as defined herein.

The term "heteroarylcarbonylamino" as a group or part of a group, refers to a group of Formula —NH(C=O)R$^i$ or —NR$^a$(C=O)R$^i$, wherein R$^a$ is C$_{1-6}$alkyl as defined herein and R$^i$ is heteroaryl as defined herein.

The term "carbamoyl" (aminocarbony) as a group or part of a group, refers to the group —(C=O)—NH$_2$.

The term "polymeric group" as used herein also encompasses oligomeric groups, and refers to a compound containing more than 8 repeat units, preferably more than 10, preferably more than 20, preferably more than 50, preferably more than 100 repeat units. The polymeric group may be any polymer in which the monomer reactive groups include epoxies, amines, vinyl groups, methacrylates, isobornyl acrylates; alcohols, carboxyl groups, aldehydes, or isocyanates, and the like. In some embodiments, the polymer group may include a polyacrylate such as polymethylacrylate, or poly(ethyl acrylate); a poly(alkylacrylate) such as poly(methyl methacrylate); a polyurethane; a poly(isobornyl acrylate); a polyamide such as nylon; a polyester such as poly(ethylene terephthalate) and polycaprolactone; a polycarbonate; a polyether; an epoxy polymer; a vinyl ester polymer; a polyimide such as polypyromellitimide (for example KAPTAN); a phenol-formaldehyde polymer such as BAKELITE; an amine-formaldehyde polymer such as a melamine polymer; a polysulfone; a poly(acrylonitrile-butadiene-styrene) (ABS); a polyolefin such as polyethylene, polystyrene, polyacrylonitrile, a polyvinyl, polyvinyl chloride and poly(DCPD); a polysilane such as poly(carboranesiloxane); and a polyphosphazene.

The term "leaving group" as used herein means a chemical group which is susceptible to be displaced by a nucleophile or cleaved off or hydrolyzed in basic or acidic conditions. In a particular embodiment, a leaving group is selected from a halogen atom (e.g., Cl, Br, I) or a sulfonate (e.g., mesylate, tosylate, triflate).

Whenever used in the present invention the term "compounds of the invention" or a similar term is meant to include the compounds of general Formula I and any subgroup thereof. This term also encompasses N-oxides form thereof, as well as quaternized nitrogen analogues. The N-oxide forms of said compounds are meant to comprise compounds wherein one or several nitrogen atoms are oxidized to the so-called N-oxide.

The term "pharmaceutically active moiety" refers to an active chemical moiety used in the manufacturing of drugs. The pharmaceutically active moiety can be a therapeutic, a prophylactic, or a diagnostic agent, with beneficial pharmaceutical, therapeutic, nutritional, or cosmetic effects. In some embodiments, the pharmaceutically active moiety is derived from one of the group comprising synthetic organic molecules, naturally occurring organic molecules, nucleic acid molecules, saccharides and oligosaccharides, biosynthetic proteins or peptides, naturally occurring peptides or proteins, and modified naturally occurring peptides or proteins, and the like.

The terms described above and others used in the specification are well understood to those in the art.

Preferred statements (features), and embodiments of the compounds and processes of this invention are now set forth, Each statements and embodiments of the invention so defined may be combined with any other statement and/or embodiments unless clearly indicated to the contrary. In particular, any feature indicated as being preferred or advantageous may be combined with any other feature or features indicated as being preferred or advantageous.

Numbered statements of this invention are:
1. A compound of formula (I),

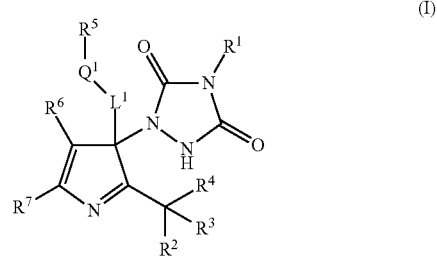

wherein,
L$^1$ is selected from C$_{1-10}$alkylene; C$_{6-12}$arylene, C$_{2-10}$alkenylene; or C$_{2-10}$alkynylene; or L$^1$ and R$^2$ together with the carbon atoms to which they are attached form a saturated or unsaturated 4-, 5-, 6-, 7- or 8-membered ring;

wherein said $C_{1-10}$alkylene; $C_{2-10}$alkenylene; $C_{2-10}$alkynylene, or saturated or unsaturated 4-, 5-, 6-, 7- or 8-membered ring, optionally comprises one or more heteroatoms in the alkylene, alkenylene, alkynylene, or saturated or unsaturated 4-, 5-, 6-, 7- or 8-membered ring moiety, said heteroatoms being each independently selected from O, S and N;
and wherein said $C_{1-10}$alkylene; $C_{2-10}$alkenylene; $C_{2-10}$alkynylene, or saturated or unsaturated 4-, 5-, 6-, 7- or 8-membered ring, can be unsubstituted or substituted with one or more $Z^1$;
$Q^1$ is a single bond or is selected from the group consisting of —OC(O)—; —NH—C(O)—; —OS(O)—; —OS(O)$_2$—; —NH—S(O)—; —NH—S(O)$_2$—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; wherein each left side of said groups is attached to L$^1$ and the right side thereof is attached to R$^5$; and wherein,
q is an integer selected from 1; 2 or 3;
p is an integer selected from 0; 1 or 2;
$L^4$ is a single bond or is selected from the group consisting of $C_{1-10}$alkylene; $C_{2-10}$alkenylene; and $C_{2-10}$alkynylene;
wherein said $C_{1-10}$alkylene; $C_{2-10}$alkenylene; and $C_{2-10}$alkynylene, optionally comprises one or more heteroatoms in the alkylene, alkenylene, alkynylene moiety, said heteroatoms being each independently selected from O, S and N;
and wherein said $C_{1-10}$alkylene; $C_{2-10}$alkenylene; $C_{2-10}$alkynylene, can be unsubstituted or substituted with one or more $Z^2$;
$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;
wherein said $C_{2-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; heteroaryl$C_{1-6}$alkyl, optionally comprises one or more heteroatoms in the alkyl moiety, said heteroatoms being each independently selected from O, S or N;
wherein at least one carbon atom or heteroatom of said $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; and heteroaryl$C_{1-6}$alkyl, can be oxidized to form at least one C=O, C=S, N=O, N=S, S=O or S(O)$_2$;
wherein said $C_{2-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, heterocyclyl; heteroaryl; heterocyclyl$C_{1-6}$alkyl; and heteroaryl$C_{1-6}$alkyl, can be unsubstituted or substituted with one or more $Z^3$;
and wherein said polymeric group is selected from the group comprising polyethylene oxide; polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;
or $R^1$ is a group of formula (i);

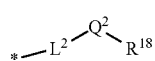

(i)

wherein, the asterisk show the point of attachment to compound of formula (I)
$L^2$ is a single bond or is selected from the group consisting of $C_{1-10}$alkylene; $C_{2-10}$alkenylene; $C_{2-10}$alkynylene; and $C_{6-12}$arylene;
wherein said $C_{1-10}$alkylene; $C_{2-10}$alkenylene; $C_{2-10}$alkynylene, or $C_{6-12}$arylene, optionally comprises one or more heteroatoms in the alkylene, alkenylene, alkynylene, or arylene moiety, said heteroatoms being each independently selected from O, S and N;
and wherein said $C_{1-10}$alkylene; $C_{2-10}$alkenylene; $C_{2-10}$alkynylene, or $C_{6-12}$arylene can be unsubstituted or substituted with one or more $Z^4$;
$Q^2$ is selected from the group consisting of $C_{1-10}$alkylene; $C_{3-6}$cycloalkylene; —OC(O)—; —NH—C(O)—; —NH—C(O)—[CR$^{13}$R$^{14}$]$_q$—; —OS(O)—; —OS(O)$_2$—; —NH—S(O)—; and —NH—S(O)$_2$; wherein each left side of said groups is attached to L$^2$ and the right side thereof is attached to R$^{18}$;
wherein said $C_{1-10}$alkylene, optionally comprises one or more heteroatoms, said heteroatoms being each independently selected from O, S and N;
and wherein said $C_{1-10}$alkylene and said $C_{3-6}$cycloalkylene can be unsubstituted or substituted with one or more $Z^5$;
or $Q^2$ is a group of formula (ii);

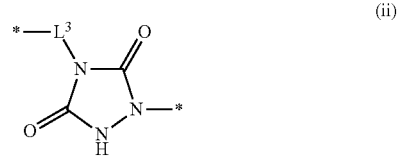

(ii)

wherein the left side of the group formula (ii) with the asterisk is attached to L$^2$ and the right side thereof is attached to R$^{18}$; and wherein,
or $Q^2$-R$^{18}$ is a group of formula (iii);

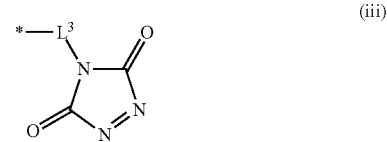

(iii)

wherein the left side of the group formula (ii) is attached to L$^2$ and the right side thereof is attached to R$^{18}$; and wherein,
L$^3$ is a single bond or is selected from the group consisting of $C_{1-10}$alkylene; $C_{2-10}$alkenylene; $C_{2-10}$alkynylene; and $C_{6-12}$aryl;
wherein said $C_{1-10}$alkylene; $C_{2-10}$alkenylene; $C_{2-10}$alkynylene, or $C_{6-12}$aryl, optionally comprises one or more heteroatoms in the alkylene, alkenylene, alkynylene, or aryl moiety, said heteroatoms being each independently selected from O, S and N;
and wherein said $C_{1-10}$alkylene; $C_{2-10}$alkenylene; $C_{2-10}$alkynylene, or $C_{6-12}$aryl, can be unsubstituted or substituted with one or more $Z^6$;
$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{6-12}$alkyl; $C_{6-12}$aryl$C_{1-6}$alkyl $C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

$R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl $C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl $C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

or $R^2$ and $R^3$ and $R^4$ together with the carbon atom to which they are attached can form a saturated or unsaturated 4-, 5-, 6-, 7- or 8-membered ring;

or $R^2$ and $L^1$ together with the carbon atom to which they are attached can form a saturated or unsaturated 4-, 5-, 6-, 7- or 8-membered ring;

wherein for $R^2$, $R^3$ and $R^4$, each independently; said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, or saturated or unsaturated 4-, 5-, 6-, 7- or 8-membered ring, optionally comprises one or more heteroatoms in the alkyl, alkenyl, alkynyl, or unsaturated 4-, 5-, 6-, 7- or 8-membered ring moiety, said heteroatoms being each independently selected from O, S and N;

wherein for $R^2$, $R^3$ and $R^4$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl, heteroaryl$C_{1-6}$alkyl, or saturated or unsaturated 4-, 5-, 6-, 7- or 8-membered ring can be unsubstituted or substituted with one or more $Z^7$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^5$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; and a pharmaceutically active moiety;

wherein said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl $C_{1-6}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one $C=O$, $C=S$, $N=O$, $N=S$, $S=O$ or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; heteroaryl$C_{1-6}$alkyl; and polymeric group, can be unsubstituted or substituted with one or more $Z^8$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^6$ is selected from the group consisting of $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; and a pharmaceutically active moiety;

$R^7$ is selected from the group consisting of $C_{1-20}$alkyl; $C_{2-20}$alkenyl; $C_{2-20}$alkynyle; $C_{6-12}$aryl; $C_{3-8}$cycloalkyle; $C_{6-12}$aryl$C_{1-6}$alkyl; heterocyclyl; heteroaryl; heterocyclyl$C_{1-6}$alkyl; heteroaryl$C_{1-6}$alkyl; or a polymeric group; and a polymeric group; and a pharmaceutically active moiety;

or $R^6$ and $R^7$ together with the carbon atoms to which they are attached form an unsaturated 4-, 5-, 6-, 7- or 8-membered ring;

wherein for $R^6$ and $R^7$, each independently; said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl, heteroaryl$C_{1-6}$alkyl or unsaturated 4-, 5-, 6-, 7- or 8-membered ring, optionally comprises one or more heteroatoms in the alkyl, alkenyl, alkynyl, or unsaturated 4-, 5-, 6-, 7- or 8-membered ring moiety, said heteroatoms being each independently selected from O, S and N;

wherein for $R^6$ and $R^7$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl, heteroaryl, heterocyclyl $C_{1-6}$alkyl, heteroaryl$C_{1-6}$alkyl, polymeric group, or saturated or unsaturated 4-, 5-, 6-, 7- or 8-membered ring, can be unsubstituted or substituted with one or more $Z^9$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^9$ is independently selected from hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one $C=O$, $C=S$, $N=O$, $N=S$, $S=O$ or $S(O)_2$;

each $R^{10}$ is independently selected from hydrogen, $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

or wherein $R^{11}$ and $R^{12}$ together with the atom to which they are attached form a 5-, 6-, or 7-membered heterocycle.

each $R^{13}$ and $R^{14}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

or wherein $R^{13}$ and $R^{14}$ together with the atom to which they are attached form a 5-, 6-, or 7-membered heterocycle;

$R^{15}$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; and a pharmaceutically active moiety;

wherein said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl $C_{1-6}$alkyl, optionally comprises one or more heteroatoms in the alkyl, alkenyl, and alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; heteroaryl$C_{1-6}$alkyl; and polymeric group, can be unsubstituted or substituted with one or more $Z^{10}$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^{16}$ and $R^{17}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl $C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

or wherein $R^{16}$ and $R^{17}$ together with the atom to which they are attached form a 5-, 6-, or 7-membered heterocycle;

$R^{18}$ is selected from the group consisting of hydrogen, $C_{1-10}$alkyl; $C_{3-8}$cycloalkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

wherein said $C_{1-10}$alkyl, $C_{6-12}$aryl$C_{1-6}$alkyl, $C_{6-12}$aryl $C_{1-6}$alkyl$C_{6-12}$aryl, heterocyclyl$C_{1-6}$alkyl; and heteroaryl $C_{1-6}$alkyl, optionally comprises one or more heteroatoms in the alkyl moiety, said heteroatoms being each independently selected from O, S or N;

wherein said $C_{1-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, heterocyclyl; heteroaryl; heterocyclyl$C_{1-6}$alkyl; and heteroaryl$C_{1-6}$alkyl, can be unsubstituted or substituted with one or more $Z^{11}$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; $C_{6-12}$aryl; halo$C_{1-6}$alkyl; halo$C_{1-6}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O) NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

2. A compound of formula (I),

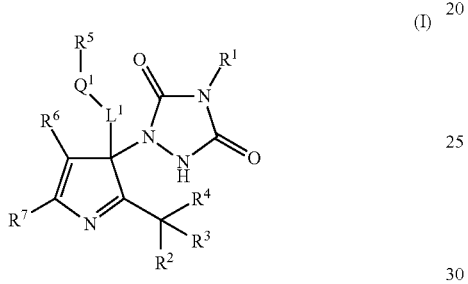

(I)

wherein,

L$^1$ is selected from $C_{1-10}$alkylene; $C_{2-10}$alkenylene; or $C_{2-10}$alkynylene; or L$^1$ and R$^2$ together with the carbon atoms to which they are attached form a saturated or unsaturated 4-, 5-, 6-, 7- or 8-membered ring;
wherein said $C_{1-10}$alkylene; $C_{2-10}$alkenylene; $C_{2-10}$alkynylene, or saturated or unsaturated 4-, 5-, 6-, 7- or 8-membered ring, optionally comprises one or more heteroatoms in the alkylene, alkenylene, alkynylene, or saturated or unsaturated 4-, 5-, 6-, 7- or 8-membered ring moiety, said heteroatoms being each independently selected from O, S and N;
and wherein said $C_{1-10}$alkylene; $C_{2-10}$alkenylene; $C_{2-10}$alkynylene, or saturated or unsaturated 4-, 5-, 6-, 7- or 8-membered ring, can be unsubstituted or substituted with one or more Z$^1$;

Q$^1$ is a single bond or is selected from the group consisting of —OC(O)—; —NH—C(O)—; —OS(O)—; —OS(O)$_2$—; —NH—S(O)—; —NH—S(O)$_2$—; —OC(O)—[CR$^{13}$R$^{14}$]$_q$—; and —OC(O)—[C(R$^{13}$) (L$^4$-O—R$^{15}$)]$_q$—[CR$^{16}$R$^{17}$]$_p$—O—; wherein each left side of said groups is attached to L$^1$ and the right side thereof is attached to R$^5$; and wherein,
q is an integer selected from 1; 2 or 3;
p is an integer selected from 0; 1 or 2;
L$^4$ is a single bond or is selected from the group consisting of $C_{1-10}$alkylene; $C_{2-10}$alkenylene; and $C_{2-10}$alkynylene;
wherein said $C_{1-10}$alkylene; $C_{2-10}$alkenylene; and $C_{2-10}$alkynylene, optionally comprises one or more heteroatoms in the alkylene, alkenylene, alkynylene moiety, said heteroatoms being each independently selected from O, S and N;
and wherein said $C_{1-10}$alkylene; $C_{2-10}$alkenylene; $C_{2-10}$alkynylene, can be unsubstituted or substituted with one or more Z$^2$;

R$^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;
wherein said $C_{2-10}$alkyl, $C_{6-12}$aryl$C_{1-6}$alkyl, $C_{6-12}$aryl$C_{1-6}$alkyl$C_{6-12}$aryl, heterocyclyl$C_{1-6}$ alkyl; heteroaryl$C_{1-6}$alkyl, optionally comprises one or more heteroatoms in the alkyl moiety, said heteroatoms being each independently selected from O, S or N;
wherein at least one carbon atom or heteroatom of said $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; and heteroaryl $C_{1-6}$alkyl, can be oxidized to form at least one C=O, C=S, N=O, N=S, S=O or S(O)$_2$;
wherein said $C_{2-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, heterocyclyl; heteroaryl; heterocyclyl$C_{1-6}$alkyl; and heteroaryl$C_{1-6}$alkyl, can be unsubstituted or substituted with one or more Z$^3$;
and wherein said polymeric group is selected from the group comprising polyethylene oxide; polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;
or R$^1$ is a group of formula (i);

(i)

wherein, the asterisk show the point of attachment to compound of formula (I)
L$^2$ is a single bond or is selected from the group consisting of $C_{1-10}$alkylene; $C_{2-10}$alkenylene; $C_{2-10}$alkynylene; and $C_{6-12}$arylene;
wherein said $C_{1-10}$alkylene; $C_{2-10}$alkenylene; $C_{2-10}$alkynylene, or $C_{6-12}$arylene, optionally comprises one or more heteroatoms in the alkylene, alkenylene, alkynylene, or arylene moiety, said heteroatoms being each independently selected from O, S and N;
and wherein said $C_{1-10}$alkylene; $C_{2-10}$alkenylene; $C_{2-10}$alkynylene, or $C_{6-12}$arylene, can be unsubstituted or substituted with one or more Z$^4$;
Q$^2$ is selected from the group consisting of $C_{1-10}$alkylene; $C_{3-6}$cycloalkylene; —OC(O)—; —NH—C (O)—; —NH—C(O)—[CR$^{13}$R$^{14}$]$_q$—; —OS(O)—; —OS(O)$_2$—; —NH—S(O)—; and —NH—S(O)$_2$;
wherein each left side of said groups is attached to L$^2$ and the right side thereof is attached to R$^{18}$;
wherein said $C_{1-10}$alkylene, optionally comprises one or more heteroatoms, said heteroatoms being each independently selected from O, S and N;

and wherein said $C_{1-10}$alkylene and said $C_{3-6}$cycloalkylene can be unsubstituted or substituted with one or more $Z^5$;
or $Q^2$ is a group of formula (ii);

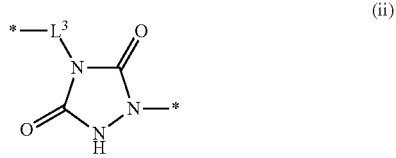

wherein the left side of the group formula (ii) with the asterisk is attached to $L^2$ and the right side thereof is attached to $R^{18}$; and wherein,
or $Q^2$-$R^{18}$ is a group of formula (iii);

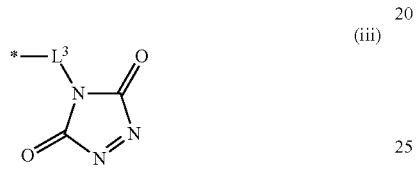

wherein the left side of the group formula (ii) is attached to $L^2$ and the right side thereof is attached to $R^{18}$; and wherein,
$L^3$ is a single bond or is selected from the group consisting of $C_{1-10}$alkylene; $C_{2-10}$alkenylene; $C_{2-10}$alkynylene; and $C_{6-12}$aryl;
wherein said $C_{1-10}$alkylene; $C_{2-10}$alkenylene; $C_{2-10}$alkynylene, or $C_{6-12}$aryl, optionally comprises one or more heteroatoms in the alkylene, alkenylene, alkynylene, or aryl moiety, said heteroatoms being each independently selected from O, S and N;
and wherein said $C_{1-10}$alkylene; $C_{2-10}$alkenylene; $C_{2-10}$alkynylene, or $C_{6-12}$aryl, can be unsubstituted or substituted with one or more $Z^6$;
$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;
$R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;
$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;
or $R^2$ and $R^3$ and $R^4$ together with the carbon atom to which they are attached can form a saturated or unsaturated 4-, 5-, 6-, 7- or 8-membered ring;
or $R^2$ and $L^1$ together with the carbon atom to which they are attached can form a saturated or unsaturated 4-, 5-, 6-, 7- or 8-membered ring;

wherein for $R^2$, $R^3$ and $R^4$, each independently; said $C_{1-20}$alkyl, $C_{2-20}$alkenyl, $C_{2-20}$alkynyl, $C_{6-12}$aryl $C_{1-6}$alkyl, heterocyclyl$C_{1-6}$alkyl; heteroaryl$C_{1-6}$alkyl, or saturated or unsaturated 4-, 5-, 6-, 7- or 8-membered ring, optionally comprises one or more heteroatoms in the alkyl, alkenyl, alkynyl, or unsaturated 4-, 5-, 6-, 7- or 8-membered ring moiety, said heteroatoms being each independently selected from O, S and N;
wherein for $R^2$, $R^3$ and $R^4$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl, heteroaryl$C_{1-6}$alkyl, or saturated or unsaturated 4-, 5-, 6-, 7- or 8-membered ring, can be unsubstituted or substituted with one or more $Z^7$;
and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;
$R^5$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl $C_{1-6}$alkyl; heterocyclyl; heteroaryl; heterocyclyl $C_{1-6}$alkyl; heteroaryl$C_{1-6}$alkyl; and a polymeric group; and a pharmaceutically active moiety;
wherein said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl$C_{1-6}$alkyl, optionally comprises one or more heteroatoms in the alkyl, alkenyl, alkynyl moiety, said heteroatoms being each independently selected from O, S and N;
wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl; can be oxidized to form at least one C=O, C=S, N=O, N=S, S=O or $S(O)_2$;
wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; heteroaryl$C_{1-6}$alkyl; and polymeric group, can be unsubstituted or substituted with one or more $Z^8$;
and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^6$ is selected from the group consisting of $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; and a pharmaceutically active moiety;

$R^7$ is selected from the group consisting of $C_{1-20}$alkyl; $C_{2-20}$alkenyl; $C_{2-20}$alkynyle; $C_{6-12}$aryl; $C_{3-8}$cycloalkyle; $C_{6-12}$aryl$C_{1-6}$alkyl; heterocyclyl; heteroaryl; heterocyclyl$C_{1-6}$alkyl; heteroaryl$C_{1-6}$alkyl; or a polymeric group; and a polymeric group; and a pharmaceutically active moiety;

or $R^6$ and $R^7$ together with the carbon atoms to which they are attached form an unsaturated 4-, 5-, 6-, 7- or 8-membered ring;

wherein for $R^6$ and $R^7$, each independently; said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl, heteroaryl$C_{1-6}$alkyl or unsaturated 4-, 5-, 6-, 7- or 8-membered ring, optionally comprises one or more heteroatoms in the alkyl, alkenyl, alkynyl, or unsaturated 4-, 5-, 6-, 7- or 8-membered ring moiety, said heteroatoms being each independently selected from O, S and N;

wherein for $R^6$ and $R^7$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$alkyl, polymeric group, or saturated or unsaturated 4-, 5-, 6-, 7- or 8-membered ring, can be unsubstituted or substituted with one or more $Z^9$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^9$ is independently selected from hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl; can be oxidized to form at least one $C=O$, $C=S$, $N=O$, $N=S$, $S=O$ or $S(O)_2$;

each $R^{10}$ is independently selected from hydrogen, $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one $C=O$, $C=S$, $N=O$, $N=S$, $S=O$ or $S(O)_2$;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl $C_{1-6}$alkyl, heterocyclyl; heteroaryl; heterocyclyl $C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one $C=O$, $C=S$, $N=O$, $N=S$, $S=O$ or $S(O)_2$;

or wherein $R^{11}$ and $R^{12}$ together with the atom to which they are attached form a 5-, 6-, or 7-membered heterocycle.

each $R^{13}$ and $R^{14}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl $C_{1-6}$alkyl, heterocyclyl; heteroaryl; heterocyclyl $C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one $C=O$, $C=S$, $N=O$, $N=S$, $S=O$ or $S(O)_2$;

or wherein $R^{13}$ and $R^{14}$ together with the atom to which they are attached form a 5-, 6-, or 7-membered heterocycle;

$R^{15}$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl $C_{1-6}$alkyl; heterocyclyl; heteroaryl; heterocyclyl $C_{1-6}$alkyl; heteroaryl$C_{1-6}$alkyl; and a polymeric group; and a pharmaceutically active moiety;

wherein said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl$C_{1-6}$alkyl, optionally comprises one or more heteroatoms in the alkyl, alkenyl, and alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl; can be oxidized to form at least one C=O, C=S, N=O, N=S, S=O or S(O)$_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; heteroaryl$C_{1-6}$alkyl; and polymeric group, can be unsubstituted or substituted with one or more $Z^{10}$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^{16}$ and $R^{17}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or S(O)$_2$;

or wherein $R^{16}$ and $R^{17}$ together with the atom to which they are attached form a 5-, 6-, or 7-membered heterocycle;

$R^{18}$ is selected from the group consisting of hydrogen, $C_{1-10}$alkyl; $C_{3-8}$cycloalkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

wherein said $C_{1-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; and heteroaryl$C_{1-6}$alkyl, optionally comprises one or more heteroatoms in the alkyl moiety, said heteroatoms being each independently selected from O, S or N;

wherein said $C_{1-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, heterocyclyl; heteroaryl; heterocyclyl$C_{1-6}$alkyl; and heteroaryl$C_{1-6}$alkyl, can be unsubstituted or substituted with one or more $Z^{11}$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

3. The compound according to statement 1 or 2, having structural formula (IA)

(IA)

wherein $R^1$, $R^2$, $R^3$, $R^4$, $R^5$, $L^1$, $Q^1$, $Z^9$ have the same meaning as defined in statement 1; and wherein each dotted line represents an optional double bond;

E is selected from N; NR$^{19}$; or CR$^{19}$; m is an integer selected from 0, 1, 2, 3 or 4;

r is an integer selected from 0, 1, 2, 3 or 4;

each R$^{19}$ is independently selected the group consisting of being not present; hydrogen, halogen; $C_{1-6}$alkyl; halo$C_{1-6}$alkyl; halo$C_{1-6}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; and a polymeric group; and a pharmaceutically active moiety; wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

4. The compound according to statement 3, wherein E is $CR^{19}$ and m is 2.

5. The compound according to any one of statements 1 to 4, having structural formula (IB)

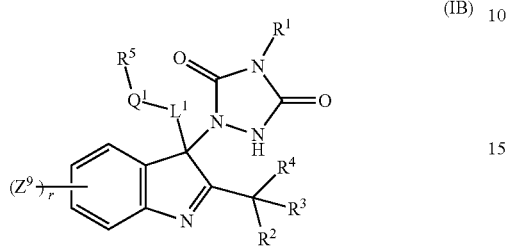

(IB)

wherein $R^1$, $R^2$, $R^3$, $R^4$, $R^5$, $L^1$, $Q^1$, $Z^9$ and r have the same meaning as defined in statement 4.

6. The compound according to any one of statements 1 to 5, wherein, $L^1$ is $C_{1-10}$alkylene; wherein said $C_{1-10}$alkylene; can be unsubstituted or substituted with one or more $Z^1$;

$Q^1$ is a single bond or is selected from the group consisting of —OC(O)—; —NH—C(O)—; —OC(O)—[$CR^{13}R^{14}$]$_q$—; and —OC(O)—[C($R^{13}$)($L^4$-O—$R^{15}$)]$_q$—[$CR^{16}R^{17}$]$_p$—O—; wherein each left side of said groups is attached to $L^1$ and the right side thereof is attached to $R^5$; and wherein, q is selected from 1; 2 or 3;

p is selected from 0; 1 or 2;

$L^4$ is a single bond; $C_{1-10}$alkylene; or $C_{2-10}$alkenylene; wherein said $C_{1-10}$alkylene; and $C_{2-10}$alkenylene; can be unsubstituted or substituted with one or more $Z^2$;

$R^1$ is selected from the group consisting of $C_{2-10}$alkyl; $C_{3-8}$cycloalkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group;

wherein said $C_{2-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; and heteroaryl$C_{1-6}$alkyl, optionally comprises one or more heteroatoms in the alkyl moiety, said heteroatoms being each independently selected from O, S or N;

wherein at least one carbon atom or heteroatom of said $C_{2-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; and heteroaryl$C_{1-6}$alkyl, can be oxidized to form at least one C=O, C=S, N=O, N=S, S=O or S(O)$_2$;

and wherein said $C_{2-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, heterocyclyl; heteroaryl; heterocyclyl$C_{1-6}$alkyl; and heteroaryl$C_{1-6}$alkyl, can be unsubstituted or substituted with one or more $Z^3$;

or $R^1$ is a group of formula (i);

(i)

wherein, $L^2$ is a single bond; $C_{1-10}$alkylene; or $C_{6-12}$arylene; wherein said $C_{1-10}$alkylene; or $C_{6-12}$arylene, can be unsubstituted or substituted with one or more $Z^4$;

$Q^2$ is selected from the group consisting of $C_{1-10}$alkylene; $C_{3-6}$cycloalkylene; —OC(O)—; —NH—C(O)—; and —NH—C(O)—[$CR^{13}R^{14}$]$_q$—; wherein each left side of said groups is attached to $L^2$ and the right side thereof is attached to $R^{18}$; wherein said $C_{1-10}$alkylene, and said $C_{3-6}$cycloalkylene can be unsubstituted or substituted with one or more $Z^5$;

or $Q^2$ is a group of formula (ii);

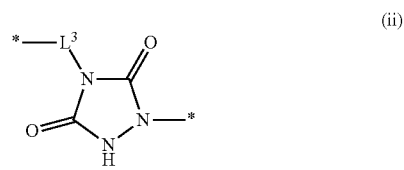

(ii)

wherein the left side of the group formula (ii) is attached to $L^2$ and the right side thereof is attached to $R^{18}$; wherein $L^3$ is a single bond or is $C_{1-10}$alkylene; wherein said $C_{1-10}$alkylene can be unsubstituted or substituted with one or more $Z^6$;

or $Q^2$-$R^{18}$ is a group of formula (iii);

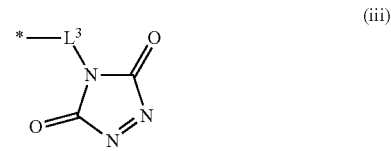

(iii)

$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group;

$R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group;

or $R^2$ and $R^3$ and $R^4$ together with the carbon atom to which they are attached form a $C_{6-12}$aryl;

and wherein for $R^2$, $R^3$ and $R^4$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl, heteroaryl$C_{1-6}$alkyl, and polymeric group, can be unsubstituted or substituted with one or more $Z^7$;

$R^5$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl $C_{1-6}$alkyl; heterocyclyl; heteroaryl; heterocyclyl $C_{1-6}$alkyl; heteroaryl$C_{1-6}$alkyl; and a polymeric group;
wherein $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heteroaryl; heterocyclyl; heterocyclyl$C_{1-6}$alkyl; heteroaryl$C_{1-6}$alkyl; and polymeric group, can be unsubstituted or substituted with one or more $Z^8$;

and wherein a carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl; can be oxidized to form a C=O, C=S, N=O, N=S, S=O or $S(O)_2$;

$R^6$ is selected from the group consisting of $C_{1-20}$alkyl; $C_{6-12}$aryl; and a polymeric group;

$R^7$ is selected from the group consisting of $C_{1-20}$alkyl; $C_{6-12}$aryl; and a polymeric group;

or $R^6$ and $R^7$ together with the carbon atoms to which they are attached form an unsaturated 5-, or 6-membered ring;

and wherein for $R^6$ and $R^7$, each independently; said $C_{1-20}$alkyl, $C_{6-12}$aryl, polymeric group, or saturated or unsaturated 5-, or 6-membered ring, can be unsubstituted or substituted with one or more $Z^9$;

$Z^1, Z^2, Z^3, Z^4, Z^5, Z^6, Z^7, Z^8, Z^9$ are each independently selected from the group consisting of halogen; $C_{1-6}$alkyl; halo$C_{1-6}$alkyl; halo$C_{1-6}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; and a polymeric group;

wherein each $R^9$ is independently selected from hydroxyl; $C_{1-20}$alkyl, $C_{6-12}$aryl, $C_{3-8}$cycloalkyl, and $C_{6-12}$aryl$C_{1-6}$alkyl;

each $R^{10}$ is independently selected from hydrogen, $C_{1-20}$alkyl, $C_{6-12}$aryl, $C_{3-8}$cycloalkyl, and $C_{6-12}$aryl$C_{1-6}$alkyl;

each $R^{11}$ and $R^{12}$ is independently selected from the group consisting of hydrogen; $C_{1-20}$alkyl, $C_{6-12}$aryl, $C_{3-8}$cycloalkyl, and $C_{6-12}$aryl$C_{1-6}$alkyl;

each $R^{13}$ and $R^{14}$ is independently selected from the group consisting of hydrogen; $C_{1-20}$alkyl, $C_{2-20}$alkenyl, $C_{6-12}$aryl, $C_{3-8}$cycloalkyl, and $C_{6-12}$aryl$C_{1-6}$alkyl;

$R^{15}$ is selected from the group consisting of hydrogen; halo; nitro; cyano; hydroxyl; $C_{1-20}$alkyl, $C_{2-20}$ alkenyl; $C_{2-20}$alkynyl; $C_{6-12}$aryl, $C_{3-8}$cycloalkyl; $C_{6-12}$aryl$C_{1-6}$alkyl; and a polymeric group; and wherein $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and polymeric group, can be unsubstituted or substituted with one or more $Z^{10}$;

each $R^{16}$ and $R^{17}$ is independently selected from the group consisting of hydrogen; $C_{1-20}$alkyl, $C_{2-20}$ alkenyl, $C_{2-20}$alkynyl, $C_{6-12}$aryl, $C_{3-8}$cycloalkyl, $C_{6-12}$aryl$C_{1-6}$alkyl;

$R^{18}$ is selected from the group consisting of hydrogen, $C_{1-10}$alkyl; $C_{3-8}$cycloalkyl; $C_{6-12}$aryl; $C_{6-12}$aryl $C_{1-6}$alkyl; and a polymeric group; and wherein said $C_{1-10}$alkyl, $C_{3-8}$cycloalkyl, $C_{6-12}$aryl, and $C_{6-12}$aryl$C_{1-6}$alkyl, can be unsubstituted or substituted with one or more $Z^{11}$;

$Z^{10}$, and $Z^{11}$ are each independently selected from the group consisting of halogen; $C_{1-6}$alkyl; halo $C_{1-6}$alkyl; halo$C_{1-6}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; and a polymeric group.

7. The compound according to any one of statements 1 to 6, wherein, $L^1$ is $C_{1-10}$alkylene; said $C_{1-10}$alkylene being unsubstituted or substituted with one or more $Z^1$;

$Q^1$ is a single bond or is selected from the group consisting of —OC(O)—; —OC(O)—$[CHR^{14}]_q$—; and —OC(O)—$[C(H)(L^4$-O—$R^{15})]_q$—$[CHR^{17}]_p$—O—; wherein each left side of said groups is attached to $L^1$ and the right side thereof is attached to $R^5$; and wherein,
q is 1 or 2;
p is 0 or 1;
$L^4$ is a single bond or $C_{1-6}$alkylene; said $C_{1-10}$alkylene being unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heteroaryl$C_{1-6}$alkyl; and a polymeric group;
wherein said $C_{2-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; and heteroaryl$C_{1-6}$alkyl, optionally comprises one or more heteroatoms in the alkyl moiety, said heteroatoms being each independently selected from O, S or N;
wherein at least one carbon atom of said $C_{2-10}$alkyl; $C_{6-12}$aryl; $C_{6-12}$aryl$C_{1-6}$alkyl; and $C_{6-12}$aryl$C_{1-6}$alkyl$C_{6-12}$aryl; can be oxidized to form at least one C=O;
and wherein said $C_{2-10}$alkyl, $C_{3-8}$cycloalkyl, $C_{6-12}$aryl, $C_{6-12}$aryl$C_{1-6}$alkyl, and $C_{6-12}$aryl$C_{1-6}$alkyl$C_{6-12}$aryl, can be unsubstituted or substituted with one or more $Z^3$;

or $R^1$ is a group of formula (i); wherein $L^2$ is a single bond; $C_{1-10}$alkylene; or $C_{6-12}$arylene; and wherein said $C_{1-10}$alkylene; or $C_{6-12}$arylene, can be unsubstituted or substituted with one or more $Z^4$;
$Q^2$ is $C_{1-10}$alkylene; $C_{3-6}$cycloalkylene; —NH—C(O)—; or —NH—C(O)—$[CR^{13}R^{14}]_q$—; wherein said $C_{1-10}$alkylene and $C_{3-6}$cycloalkylene can be unsubstituted or substituted with one or more $Z^5$;
or $Q^2$ is a group of formula (ii); wherein $L^3$ is a single bond or is $C_{1-10}$alkylene; wherein said $C_{1-10}$alkylene can be unsubstituted or substituted with one or more $Z^6$;

$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;

$R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;

or $R^2$ and $R^3$ and $R^4$ together with the carbon atom to which they are attached form a $C_{6-12}$aryl;
wherein for $R^2$, $R^3$ and $R^4$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and a polymeric group, can be unsubstituted or substituted with one or more $Z^7$;

$R^5$ is selected from the group consisting of hydrogen; halo; nitro; cyano; hydroxyl; $C_{1-20}$alkyl, $C_{2-20}$alkenyl; $C_{6-12}$aryl, $C_{3-8}$cycloalkyl; $C_{6-12}$aryl$C_{1-6}$alkyl; and a polymeric group;

wherein $C_{1-10}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and polymeric group, can be unsubstituted or substituted with one or more $Z^8$;

and wherein at least one carbon atom of said $C_{1-20}$alkyl, $C_{2-20}$alkenyl, $C_{2-20}$alkynyl, $C_{6-12}$aryl, $C_{3-8}$cycloalkyl, and $C_{6-12}$aryl$C_{1-6}$alkyl, can be oxidized to form at least one C=O;

$R^6$ and $R^7$ together with the carbon atoms to which they are attached form an unsaturated 5-, or 6-membered ring; and wherein said saturated or unsaturated 5-, or 6-membered ring can be unsubstituted or substituted with one or more $Z^9$;

$Z^1, Z^2, Z^3, Z^4, Z^5, Z^6, Z^7, Z^8, Z^9$ are each independently selected from the group consisting of halogen; $C_{1-6}$alkyl; halo$C_{1-6}$alkyl; halo$C_{1-6}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; and a polymeric group;

each $R^9$ is independently selected from hydroxyl; $C_{1-20}$alkyl, $C_{6-12}$aryl, $C_{3-8}$cycloalkyl, and $C_{6-12}$aryl$C_{1-6}$alkyl;

each $R^{10}$ is independently selected from hydrogen, $C_{1-20}$alkyl, $C_{6-12}$aryl, $C_{3-8}$cycloalkyl, and $C_{6-12}$aryl$C_{1-6}$alkyl;

each $R^{11}$ and $R^{12}$ is independently selected from the group consisting of hydrogen; $C_{1-20}$alkyl, $C_{6-12}$aryl, $C_{3-8}$cycloalkyl, and $C_{6-12}$aryl$C_{1-6}$alkyl;

each $R^{13}$ and $R^{14}$ is independently selected from the group consisting of hydrogen; $C_{1-20}$alkyl, $C_{2-20}$alkenyl, $C_{6-12}$aryl, $C_{3-8}$cycloalkyl, and $C_{6-12}$aryl$C_{1-6}$alkyl;

$R^{15}$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-6}$alkyl; or a polymeric group; and wherein $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and polymeric group, can be unsubstituted or substituted with one or more $Z^{10}$;

each $R^{16}$ and $R^{17}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, and $C_{6-12}$aryl$C_{1-6}$alkyl;

$R^{18}$ is selected from the group consisting of hydrogen, $C_{1-10}$alkyl; $C_{3-8}$cycloalkyl; $C_{6-12}$aryl; $C_{6-12}$aryl$C_{1-6}$alkyl; and a polymeric group; and wherein said $C_{1-10}$alkyl, $C_{3-8}$cycloalkyl, $C_{6-12}$aryl, and $C_{6-12}$aryl$C_{1-6}$alkyl, can be unsubstituted or substituted with one or more $Z^{11}$;

$Z^{10}$, and $Z^{11}$ are each independently selected from the group consisting of halogen; $C_{1-6}$alkyl; halo$C_{1-6}$alkyl; halo$C_{1-6}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; and a polymeric group.

8. The compound according to any one of statements 1 to 7, having structural formula (IC)

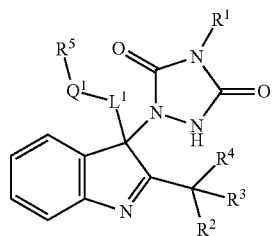

(IC)

wherein
$L^1$ is $C_{1-10}$alkylene; said $C_{1-10}$alkylene being unsubstituted or substituted with one or more $Z^1$;

$Q^1$ is a single bond or is selected from the group consisting of —OC(O)—; —OC(O)—[$CHR^{14}$]$_q$—; and —OC(O)—[C(H)($L^4$-O—$R^{15}$)]$_q$—[$CHR^{17}$]$_p$—O—; wherein each left side of said groups is attached to $L^1$ and the right side thereof is attached to $R^5$; and wherein, q is 1; p is 0 or 1; and $L^4$ is $C_{1-6}$alkylene; said $C_{1-10}$alkylene being unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl $C_{6-12}$aryl; heteroaryl$C_{1-6}$alkyl; and a polymeric group; wherein said $C_{2-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; and heteroaryl$C_{1-6}$alkyl, optionally comprises one or more heteroatoms in the alkyl moiety, said heteroatoms being each independently selected from O, S or N;

wherein at least one carbon atom of said $C_{2-10}$alkyl; $C_{6-12}$aryl; $C_{6-12}$aryl$C_{1-6}$alkyl; and $C_{6-12}$aryl$C_{1-6}$alkyl$C_{6-12}$aryl; can be oxidized to form at least one C=O;

and wherein said $C_{2-10}$alkyl, $C_{3-8}$cycloalkyl, $C_{6-12}$aryl, $C_{6-12}$aryl$C_{1-6}$alkyl, and $C_{6-12}$aryl$C_{1-6}$alkyl$C_{6-12}$aryl, can be unsubstituted or substituted with one or more $Z^3$;

or $R^1$ is -$L^2$-$Q^2$-$R^{18}$; wherein
$L^2$ is a single bond; $C_{1-10}$alkylene; or $C_{6-12}$arylene; and wherein said $C_{1-10}$alkylene; or $C_{6-12}$arylene, can be unsubstituted or substituted with one or more $Z^4$;

$Q^2$ is $C_{1-10}$alkylene; $C_{3-6}$cycloalkylene; —NH—C(O)—; or —NH—C(O)—[$CR^{13}R^{14}$]$_q$—; wherein said $C_{1-10}$alkylene, and said $C_{3-6}$cycloalkylene; can be unsubstituted or substituted with one or more $Z^5$;

or $Q^2$ is a group of formula (ii); wherein $L^3$ is a single bond or is $C_{1-10}$alkylene; wherein said $C_{1-10}$alkylene can be unsubstituted or substituted with one or more $Z^6$;

$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;

$R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;

or $R^2$ and $R^3$ and $R^4$ together with the carbon atom to which they are attached can form a $C_{6-12}$aryl;

wherein for $R^2$, $R^3$ and $R^4$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and a polymeric group, can be unsubstituted or substituted with one or more $Z^7$;

$R^5$ is selected from the group consisting of hydrogen; halo; nitro; cyano; hydroxyl; $C_{1-20}$alkyl, $C_{2-20}$alkenyl; $C_{6-12}$aryl, $C_{3-8}$cycloalkyl; $C_{6-12}$aryl$C_{1-6}$alkyl; and a polymeric group;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and polymeric group, can be unsubstituted or substituted with one or more $Z^8$;

and wherein at least one carbon atom of said $C_{1-20}$alkyl, $C_{2-20}$alkenyl, $C_{2-20}$alkynyl, $C_{6-12}$aryl, $C_{3-8}$cycloalkyl, and $C_{6-12}$aryl$C_{1-6}$alkyl, can be oxidized to form at least one C=O;

$Z^1$, $Z^2$, $Z^3$, $Z^4$, $Z^5$, $Z^6$, $Z^7$, and $Z^8$, are each independently selected from the group consisting of halogen; $C_{1-6}$alkyl; halo$C_{1-6}$alkyl; halo$C_{1-6}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; and a polymeric group;

each $R^9$ is independently selected from the group consisting of hydroxyl; $C_{1-20}$alkyl, $C_{6-12}$aryl, $C_{3-8}$cycloalkyl, and $C_{6-12}$aryl$C_{1-6}$alkyl;

each $R^{10}$ is independently selected from the group consisting of hydrogen, $C_{1-20}$alkyl, $C_{6-12}$aryl, $C_{3-8}$cycloalkyl, and $C_{6-12}$aryl$C_{1-6}$alkyl;

each $R^{11}$ and $R^{12}$ is independently selected from the group consisting of hydrogen; $C_{1-20}$alkyl, $C_{6-12}$aryl, $C_{3-8}$cycloalkyl, and $C_{6-12}$aryl$C_{1-6}$alkyl;

each $R^{13}$ and $R^{14}$ is independently selected from the group consisting of hydrogen; $C_{1-20}$alkyl, $C_{2-20}$alkenyl, $C_{6-12}$aryl, $C_{3-8}$cycloalkyl, and $C_{6-12}$aryl $C_{1-6}$alkyl;

$R^{15}$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-6}$alkyl; and a polymeric group; and wherein $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and polymeric group, can be unsubstituted or substituted with one or more $Z^{10}$;

each $R^{16}$ and $R^{17}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, and $C_{6-12}$aryl$C_{1-6}$alkyl;

$R^{18}$ is selected from the group consisting of hydrogen, $C_{1-10}$alkyl; $C_{3-8}$cycloalkyl; $C_{6-12}$aryl; $C_{6-12}$aryl$C_{1-6}$alkyl; and a polymeric group; and wherein said $C_{1-10}$alkyl, $C_{3-8}$cycloalkyl, $C_{6-12}$aryl, and $C_{6-12}$aryl$C_{1-6}$alkyl, can be unsubstituted or substituted with one or more $Z^{11}$;

$Z^{10}$, and $Z^{11}$ are each independently selected from the group consisting of halogen; $C_{1-6}$alkyl; halo$C_{1-6}$alkyl; halo$C_{1-6}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; and a polymeric group.

9. The compound according to any one of statements 1 to 8, wherein $R^5$ is a polymeric group which can be unsubstituted or substituted with one or more $Z^8$; wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

10. The compound according to any one of statements 1 to 9, wherein said compound is a polymer and $R^1$ is a polymeric group which can be unsubstituted or substituted with one or more $Z^3$; wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

11. The compound according to any one of statements 1 to 10, wherein $R^1$ is a group of formula (i), and $R^{18}$ is a polymeric group which can be unsubstituted or substituted with one or more $Z^{11}$; wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

12. A process for the preparation of a compound according to any one of statements 1 to 11, and 20 to 35, comprising the step of contacting at least one compound of formula (II) with at least one compound of formula (III), thereby obtaining a compound of formula (I), wherein $R^1$, $R^2$, $R^3$, $R^4$, $R^5$, $L^1$, $Q^1$, $Z^9$ have the same meaning as defined in any one of statement 1 to

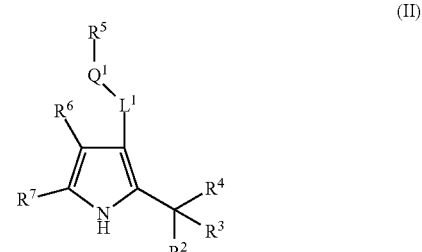

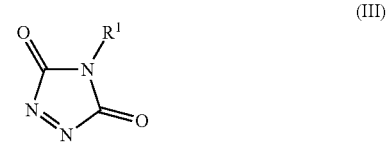

-continued

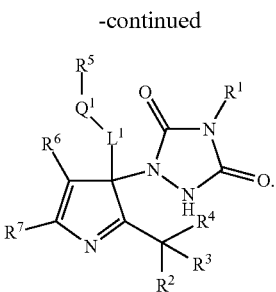
(I)

In some embodiments, with respect to the pyrrole of formula (II) both the C-2 and C-3 positions need to be substituted (to block irreversible aromatic substitution), and the carbon attached to the C-2-position should not have any attached protons, in order to avoid imine-enamine tautomery;

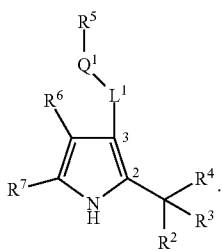
(II)

13. Use of a compound according to any one of statements 1 to 11, and 20 to 35, in polymers, membranes, adhesives, foams, sealants, molded articles, films, extruded articles, fibers, elastomers, polymer based additives, pharmaceutical and biomedical products, varnishes, paints, coatings, inks; composite material organic LEDs, organic semiconductors, conducting organic polymers, or 3D printed articles.

14. An article comprising a compound according to any one of statements 1 to 11, and 20 to 35.

15. A self-healing material comprising a compound according to any one of statements 1 to 11, and 20 to 35.

16. A process for reversible formation of a compound according to any one of statements 1 to 11, and 20 to 35, the process comprising the steps of contacting a compound of formula (II) with a compound of formula (III) at a temperature of at most 29° C. thereby forming a compound of formula (I), and subsequently releasing at least part of said of compound of formula (III) and at least part of said compound of formula (II) by submitting said compound of formula (I) to a temperature of at least 30° C.

17. A process for reshaping and/or repairing an article comprising a compound according to any one of statements 1 to 11, and 20 to 35, or an article according to statement 14, comprising the step of thermally treating the compound of formula (I) at a temperature of at least 30° C.

18. Use of a compound according to any one of statements 1 to 11, as a precursor for a compound of formula (III).

19. Remendable materials comprising a compound according to any one of statements 1 to 11, and 20 to 35. Said materials offer increased durability, safety, and cost efficiency for many applications.

20. Polyurethane obtained by contacting a compound according to any one of statements 1 to 11, and 20 to 35, with at least one isocyanate and with at least one polyol.

21. The compound according to any one of statements 1 to 4, wherein at least one of $R^1$, $R^2$, $R^3$, $R^4$, $R^5$, $R^6$ or $R^7$ is a polymeric group, said polymeric group being selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

22. The compound according to any one of statements 1 to 5, wherein at least one of $R^1$, $R^2$, $R^3$, $R^4$, $R^5$, or $Z^9$ is a polymeric group, said polymeric group being selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

23. The compound according to any one of statements 1 to 6, wherein at least one of $R^1$, $R^2$, $R^3$, $R^4$, or $R^5$ is a polymeric group, said polymeric group being selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

24. The compound according to any one of statements 1 to 4, wherein said compound is a polymer of (meth)acrylate, wherein at least one of $R^1$, $R^2$, $R^3$, $R^4$, $R^5$, $R^6$ or $R^7$ is a polymeric group, selected from the group comprising poly(methyl methacrylate); polyacrylate; polymethacrylate; copolymer of acrylate, methacrylate and/or styrene; poly(isobornyl acrylate); polyacrylonitrile; and/or block, comb and/or star copolymers of the polymeric group.

25. The compound according to any one of statements 1 to 5, wherein said compound is a polymer of (meth)acrylate, wherein at least one of $R^1$, $R^2$, $R^3$, $R^4$, $R^5$, $Z^9$ is a polymeric group, selected from the group comprising poly(methyl methacrylate); polyacrylate; polymethacrylate; copolymer of acrylate, methacrylate and/or styrene; poly(isobornyl acrylate); polyacrylonitrile; and/or block, comb and/or star copolymers of the polymeric group.

26. The compound according to any one of statements 1 to 6, wherein said compound is a polymer of (meth)acrylate, wherein at least one of $R^1$, $R^2$, $R^3$, $R^4$, $R^5$ is a polymeric group, selected from the group comprising poly(methyl methacrylate); polyacrylate; polymethacrylate; copolymer of acrylate, methacrylate and/or styrene; poly(isobornyl acrylate); polyacrylonitrile; and/or block, comb and/or star copolymers of the polymeric group.

27. The compound according to any one of statements 1 to 4, wherein said compound is a polymer of styrene wherein at least one of $R^1$, $R^2$, $R^3$, $R^4$, $R^5$, $R^6$ or $R^7$ is a polymeric group, said polymeric group being selected from the group comprising polystyrene; copolymer of acrylate, methacrylate and/or styrene; acrylonitrile butadiene styrene (ABS); styrene-butadiene rubber (SBR); and/or block, comb and/or star copolymers of the polymeric group.

28. The compound according to any one of statements 1 to 5, wherein said compound is a polymer of styrene wherein at least one of $R^1$, $R^2$, $R^3$, $R^4$, $R^5$, $Z^9$ is a polymeric group, said polymeric group being selected from the group comprising polystyrene; copolymer of acrylate, methacrylate and/or styrene; acrylonitrile butadiene styrene (ABS); styrene-butadiene rubber (SBR); and/or block, comb and/or star copolymers of the polymeric group.

29. The compound according to any one of statements 1 to 6, wherein said compound is a polymer of styrene wherein at least one of $R^1$, $R^2$, $R^3$, $R^4$, and $R^5$ is a polymeric group, said polymeric group being selected from the group comprising polystyrene; copolymer of acrylate, methacrylate and/or styrene; acrylonitrile butadiene styrene (ABS); styrene-butadiene rubber (SBR); and/or block, comb and/or star copolymers of the polymeric group.

30. The compound according to any one of statements 1 to 4, wherein said compound is a polymer of isobornyl acrylate, wherein at least one of $R^1$, $R^2$, $R^3$, $R^4$, $R^5$, $R^6$ or $R^7$ is a polymeric group selected from poly(isobornyl acrylate); and/or block, comb and/or star copolymers of the polymeric group.

31. The compound according to any one of statements 1 to 5, wherein said compound is a polymer of isobornyl acrylate, wherein at least one of $R^1$, $R^2$, $R^3$, $R^4$, $R^5$, $Z^9$ is a polymeric group selected from poly(isobornyl acrylate); and/or block, comb and/or star copolymers of the polymeric group.

32. The compound according to any one of statements 1 to 6, wherein said compound is a polymer of isobornyl acrylate, wherein at least one of $R^1$, $R^2$, $R^3$, $R^4$, $R^5$, is a polymeric group selected from poly(isobornyl acrylate); and/or block, comb and/or star copolymers of the polymeric group.

33. The compound according to any one of statements 1 to 4, wherein said compound is a polymer of urethane, having structural formula (I), wherein at least one of $R^1$, $R^2$, $R^3$, $R^4$, $R^5$, $R^6$ or $R^7$ is a polyurethane.

34. The compound according to any one of statements 1 to 5, wherein said compound is a polymer of urethane, having structural formula (I), wherein at least one of $R^1$, $R^2$, $R^3$, $R^4$, $R^5$, $Z^9$ is a polyurethane.

35. The compound according to any one of statements 1 to 6, wherein said compound is a polymer of urethane, having structural formula (I), wherein at least one of $R^1$, $R^2$, $R^3$, $R^4$, $R^5$, is a polyurethane.

36. Use of a compound according to any one of statements 1 to 11, and 20 to 35, to prepare a self-healing material.

37. Use of a compound according to any one of statements 1 to 11, and 20 to 35, to prepare a coating composition.

38. Use of a coating composition according to statements 37, for coating a substrate.

39. Use of a compound according to any one of statements 1 to 11 as an in situ precursor of triazolinedione for selective functionalization of enes, dienes, aryl and heteroaryl systems via the ene reaction, Diels-Alder reaction, and electrophilic aromatic substitution reaction of said reagent.

40. The process according to statement 12, wherein said process is reversible.

41. The process according to statement 12 or 40, wherein said step of contacting the at least one compound of formula (II) with a compound of formula (III) is performed at a temperature of at most 29° C.

42. The process according to any of statements, 12, 40, 41, further comprising the step of (a) submitting said compound of formula (I) to a temperature of at least 30° C. preferably at least 40° C., for example at least 60° C., preferably at least 80° C., thereby forming a composition comprising at least part of said compound of formula (II) and at least part of said compound of formula (III).

43. The process according to statement 42, wherein after step (a) the process also comprises the step of cooling said composition to a temperature of at most 29° C.

According to an embodiment, the present invention provides compounds of formula (I), (IA), (IB), (IC); and any subgroup thereof wherein, $L^1$ is selected from $C_{1-10}$alkylene; $C_{2-10}$alkenylene; or $C_{2-10}$alkynylene; or $L^1$ and $R^2$ together with the carbon atoms to which they are attached form a saturated or unsaturated 4-, 5-, 6-, 7- or 8-membered ring, preferably a saturated or unsaturated 5-, or 6-membered ring; preferably $L^1$ is selected from $C_{1-10}$alkylene; $C_{2-10}$alkenylene; or $C_{2-10}$alkynylene; more preferably $L^1$ is selected from $C_{1-10}$alkylene; and $C_{2-10}$alkenylene; yet more preferably, $L^1$ is $C_{1-10}$alkylene; for example $L^1$ is $C_{1-6}$alkylene; for example $L^1$ is $C_{1-6}$alkylene;

wherein said $C_{1-10}$alkylene; $C_{2-10}$alkenylene; $C_{2-10}$alkynylene, or saturated or unsaturated 4-, 5-, 6-, 7- or 8-membered ring, optionally comprises one or more heteroatoms in the alkylene, alkenylene, alkynylene, or saturated or unsaturated 4-, 5-, 6-, 7- or 8-membered ring moiety, said heteroatoms being each independently selected from O, S and N; preferably wherein said $C_{1-10}$alkylene; $C_{2-10}$alkenylene; $C_{2-10}$alkynylene, optionally comprises one or more, for example 1, 2 or 3 heteroatoms in the alkylene, alkenylene, alkynylene, said heteroatoms being each independently selected from O, S and N; preferably wherein said $C_{1-10}$alkylene; and $C_{2-10}$alkenylene; optionally comprises one or more, for example 1, 2 or 3 heteroatoms in the alkylene, and alkenylene, said heteroatoms being each independently selected from O, and N; preferably wherein said $C_{1-10}$alkylene, for example $C_{1-6}$alkylene, $C_{1-6}$alkylene, optionally comprises one or more, for example 1, 2 or 3 heteroatoms being each independently selected from O, and N;

preferably $L^1$ is selected from the group consisting of $C_{1-10}$alkylene; $C_{2-10}$alkenylene; $C_{2-10}$alkynylene; $C_{1-10}$alkyleneoxy; $C_{2-10}$alkenyleneoxy; $C_{2-10}$alkynyleneoxy; $C_{1-10}$alkyleneoxy$C_{1-10}$alkylene; $C_{2-10}$alkenyleneoxy$C_{2-10}$alkenylene; $C_{2-10}$alkynyleneoxy$C_{2-10}$alkynylene; mono- or di-$C_{1-10}$alkyleneamino; mono- or di-$C_{2-10}$alkenyleneamino; mono- or di-$C_{2-10}$alkynyleneamino; mono- or di-$C_{1-10}$alkyleneamino$C_{1-10}$alkylene; mono- or di-$C_{2-10}$alkenyleneamino$C_{2-10}$alkenylene; mono- or di-$C_{2-10}$alkynyleneamino$C_{2-10}$alkynylene; $C_{1-10}$alkylenethio; $C_{2-10}$alkenylenethio; $C_{2-10}$alkynylenethio; $C_{1-10}$alkylenethio$C_{1-10}$alkylene; $C_{2-10}$alkenylenethio$C_{2-10}$alkenylene; $C_{2-10}$alkynylenethio$C_{2-10}$alkynylene; more preferably $L^1$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneoxy$C_{1-10}$alkylene; $C_{2-10}$alkenyleneoxy$C_{2-10}$alkenylene;

mono- or di-$C_{1-10}$alkyleneamino; mono- or di-$C_{2-10}$alkenyleneamino; mono- or di-$C_{1-10}$alkyleneamino$C_{1-10}$alkylene; mono- or di-$C_{2-10}$alkenyleneamino$C_{2-10}$alkenylene; more preferably $L^1$ is selected from the group consisting of $C_{1-10}$alkylene; $C_{1-10}$alkyleneoxy; $C_{1-10}$alkyleneoxy$C_{1-10}$alkylene; mono- or di-$C_{1-10}$alkyleneamino; and mono- or di-$C_{1-10}$alkyleneamino$C_{1-10}$alkylene;

and wherein said $C_{1-10}$alkylene; $C_{2-10}$alkenylene; $C_{2-10}$alkynylene, or saturated or unsaturated 4-, 5-, 6-, 7- or 8-membered ring, can be unsubstituted or substituted with one or more $Z^1$; preferably wherein said $C_{1-10}$alkylene; $C_{2-10}$alkenylene; $C_{2-10}$alkynylene, can be unsubstituted or substituted with one or more $Z^1$; preferably wherein said $C_{1-10}$alkylene; and $C_{2-10}$alkenylene; can be unsubstituted or substituted with one or more $Z^1$; preferably wherein said $C_{1-10}$alkylene, for example $C_{1-6}$alkylene, for example $C_{1-6}$alkylene, can be unsubstituted or substituted with one or more $Z^1$;

preferably $L^1$ is selected from the group consisting of $C_{1-10}$alkylene; $C_{2-10}$alkenylene; $C_{2-10}$alkynylene; $C_{1-10}$alkyleneoxy; $C_{2-10}$alkenyleneoxy; $C_{2-10}$alkynyleneoxy; $C_{1-5}$alkyleneoxy$C_{0-5}$alkylene; $C_{2-5}$alkenyleneoxy$C_{0-5}$alkenylene; $C_{2-5}$alkynyleneoxy$C_{0-5}$alkynylene; $C_{1-10}$alkyleneamino; $C_{2-10}$alkenyleneamino; $C_{2-10}$alkynyleneamino; $C_{1-5}$alkyleneamino$C_{0-5}$alkylene; $C_{2-5}$alkenyleneamino$C_{0-5}$alkenylene; $C_{2-5}$alkynyleneamino$C_{0-5}$alkynylene; $C_{1-10}$alkylenethio; $C_{2-10}$alkenylenethio; $C_{2-10}$alkynylenethio; $C_{1-5}$alkylenethio$C_{0-5}$alkylene; $C_{2-5}$alkenylenethio$C_{0-5}$alkenylene; $C_{2-5}$alkynylenethio$C_{0-5}$alkynylene; each group being unsubstituted or substituted with one or more $Z^1$; more preferably $L^1$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^1$; more preferably $L^1$ is selected from the group consisting of $C_{1-10}$alkylene; $C_{1-10}$alkyleneoxy; and $C_{1-10}$alkyleneamino; each group being unsubstituted or substituted with one or more $Z^1$;

$Q^1$ is a single bond or is selected from the group consisting of —OC(O)—; —NH—C(O)—; —OS(O)—; —OS(O)$_2$—; —NH—S(O)—; —NH—S(O)$_2$—; —OC(O)—[$CR^{13}R^{14}$]$_q$—; and —OC(O)—[$C(R^{13})(L^4$-O—$R^{15})$]$_q$—[$CR^{16}R^{17}$]$_p$—O—; wherein each left side of said groups is attached to $L^1$ and the right side thereof is attached to $R^5$; and wherein, preferably $Q^1$ is a single bond or is selected from the group consisting of —OC(O)—; —NH—C(O)—; —OC(O)—[$CR^{13}R^{14}$]$_q$—; and —OC(O)—[$C(R^{13})(L^4$-O—$R^{15})$]$_q$—[$CR^{16}R^{17}$]$_p$—O—; preferably $Q^1$ is a single bond or is selected from the group consisting of —OC(O)—; —OC(O)—[$CR^{13}R^{14}$]$_q$—; and —OC(O)—[$C(R^{13})(L^4$-O—$R^{15})$]$_q$—[$CR^{16}R^{17}$]$_p$—O—; preferably $Q^1$ is selected from the group consisting of —OC(O)—; —OC(O)—[$CR^{13}R^{14}$]$_q$—; and —OC(O)—[$C(R^{13})(L^4$-O—$R^{15})$]$_p$—[$CR^{16}R^{17}$]$_p$—O—; wherein q is an integer selected from 1; 2 or 3; preferably 1 or 2; for example 1;

p is an integer selected from 0; 1 or 2; preferably 0 or 1; for example 1;

$L^4$ is a single bond or is selected from the group consisting of $C_{1-10}$alkylene; $C_{2-10}$alkenylene; and $C_{2-10}$alkynylene; preferably $L^4$ is a single bond or is selected from the group consisting of $C_{1-10}$alkylene; and $C_{2-10}$alkenylene; preferably $L^4$ is a single bond or is $C_{1-10}$alkylene; preferably $L^4$ is $C_{1-10}$alkylene; for example $C_{1-8}$alkylene, for example $C_{1-6}$alkylene, for example $C_{1-4}$alkylene, wherein said $C_{1-10}$alkylene; $C_{2-10}$alkenylene; and $C_{2-10}$alkynylene, optionally comprises one or more heteroatoms in the alkylene, alkenylene, alkynylene moiety, said heteroatoms being each independently selected from O, S and N; preferably wherein said $C_{1-10}$alkylene; $C_{2-10}$alkenylene; optionally comprises one or more, for example 1, 2 or 3 heteroatoms in the alkylene, alkenylene, said heteroatoms being each independently selected from O, S and N; preferably wherein said $C_{1-10}$alkylene; optionally comprises one or more, for example 1, 2 or 3 heteroatoms, said heteroatoms being each independently selected from O, and N; preferably wherein said $C_{1-10}$alkylene, for example $C_{1-8}$alkylene, $C_{1-6}$alkylene, optionally comprises one or more, for example 1, 2 or 3 heteroatoms being each independently selected from O, and N;

and wherein said $C_{1-10}$alkylene; $C_{2-10}$alkenylene; $C_{2-10}$alkynylene, can be unsubstituted or substituted with one or more $Z^2$; preferably wherein said $C_{1-10}$alkylene; and $C_{2-10}$alkenylene; can be unsubstituted or substituted with one or more $Z^2$; preferably wherein said $C_{1-10}$alkylene; for example $C_{1-8}$alkylene, for example $C_{1-6}$alkylene, can be unsubstituted or substituted with one or more $Z^2$;

preferably $L^4$ is selected from the group consisting of $C_{1-10}$alkylene; $C_{2-10}$alkenylene; $C_{2-10}$alkynylene; $C_{1-10}$alkyleneoxy; $C_{2-10}$alkenyleneoxy; $C_{2-10}$alkynyleneoxy; $C_{1-5}$alkyleneoxy$C_{0-5}$alkylene; $C_{2-5}$alkenyleneoxy$C_{0-5}$alkenylene; $C_{2-5}$alkynyleneoxy$C_{0-5}$alkynylene; $C_{1-10}$alkyleneamino; $C_{2-10}$alkenyleneamino; $C_{2-10}$alkynyleneamino; $C_{1-5}$alkyleneamino$C_{0-5}$alkylene; $C_{2-5}$alkenyleneamino$C_{0-5}$alkenylene; $C_{2-5}$alkynyleneamino$C_{0-5}$alkynylene; $C_{1-10}$alkylenethio; $C_{2-10}$alkenylenethio; $C_{2-10}$alkynylenethio; $C_{1-5}$alkylenethio$C_{0-5}$alkylene; $C_{2-5}$alkenylenethio$C_{0-5}$alkenylene; $C_{2-5}$alkynylenethio$C_{0-5}$alkynylene; each group being unsubstituted or substituted with one or more $Z^2$; more preferably $L^4$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^2$; more preferably $L^4$ is selected from the group consisting of $C_{1-10}$alkylene; $C_{1-10}$alkyleneoxy; and $C_{1-10}$alkyleneamino; each group being unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; preferably $R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heteroaryl$C_{1-6}$alkyl; and a polymeric group; preferably $R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; and a polymeric group; preferably $R^1$ is selected from the group consisting of $C_{2-10}$alkyl; $C_{6-12}$aryl; $C_{6-12}$aryl$C_{1-6}$alkyl$C_{6-12}$aryl; and a polymeric group; preferably $R^1$ is $C_{6-12}$aryl; preferably $R^1$ is $C_{2-10}$alkyl; preferably $R^1$ is $C_{6-12}$aryl$C_{1-6}$alkyl$C_{6-12}$aryl; preferably $R^1$ is a polymeric group;

wherein said $C_{2-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; heteroaryl$C_{1-6}$alkyl, optionally comprises one or more heteroatoms in the alkyl moiety, said heteroatoms being each independently selected from O, S or N; preferably wherein said $C_{2-10}$alkyl, $C_{6-12}$aryl$C_{1-6}$alkyl, $C_{6-12}$aryl$C_{1-6}$alkyl$C_{6-12}$aryl, optionally comprises one or more heteroatoms in the alkyl moiety, said heteroatoms being each independently selected from O, S or N; preferably wherein said $C_{2-10}$alkyl, $C_{6-12}$aryl$C_{1-6}$alkyl, $C_{6-12}$aryl$C_{1-6}$alkyl$C_{6-12}$aryl, optionally comprises 1, 2 or 3 heteroatoms in the alkyl moiety, said heteroatoms being each independently selected from O, or N; preferably wherein said $C_{2-10}$alkyl, $C_{6-12}$aryl$C_{1-6}$alkyl, $C_{6-12}$aryl$C_{1-6}$alkyl$C_{6-12}$aryl, optionally comprises 1, 2 or 3 N in the alkyl moiety; wherein at least one carbon atom or heteroatom of said $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; and heteroaryl$C_{1-6}$alkyl, can be oxidized to form at least one C=O, C=S, N=O, N=S, S=O or S(O)$_2$; preferably wherein at least one carbon atom of said $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; can be oxidized to form at least one C=O, C=S; preferably wherein at least one carbon atom of said $C_{2-10}$alkyl; $C_{6-12}$aryl; $C_{6-12}$aryl$C_{1-6}$alkyl$C_{6-12}$aryl; can be oxidized to form at least one C=O;

wherein said $C_{2-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, heterocyclyl; heteroaryl; heterocyclyl$C_{1-6}$alkyl; and heteroaryl$C_{1-6}$alkyl, can be unsubstituted or substituted with one or more $Z^3$; preferably wherein said $C_{2-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, can be unsubstituted or substituted with one or more $Z^3$; preferably wherein said $C_{2-10}$alkyl, $C_{6-12}$aryl, $C_{6-12}$aryl$C_{1-6}$alkyl, $C_{6-12}$aryl$C_{1-6}$alkyl$C_{6-12}$aryl, can be unsubstituted or substituted with one or more, for example 1, 2, or 3 $Z^3$; and wherein for $R^1$ said polymeric group is selected from the group comprising polyethylene oxide; polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

preferably $R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; a polymeric group; $C_{1-6}$alkyloxy$C_{1-6}$alkyl; mono- or di-$C_{1-6}$alkylamino$C_{1-6}$alkyl; $C_{1-6}$alkylthio$C_{1-6}$alkyl; $C_{6-12}$aryl$C_{1-6}$alkyloxy$C_{6-12}$aryl; heterocyclyloxy$C_{1-6}$alkyl; heteroaryloxy$C_{1-6}$alkyl; $C_{6-12}$aryloxy$C_{1-6}$alkyl$C_{6-12}$aryl; mono- or di-$C_{6-12}$arylamino$C_{1-6}$alkyl$C_{6-12}$aryl; mono- or di-$C_{6-12}$aryl$C_{1-6}$alkylamino$C_{6-12}$aryl; mono- or diheterocyclylamino$C_{1-6}$alkyl; mono- or di-heteroarylamino$C_{1-6}$alkyl; $C_{6-12}$aryl$C_{1-6}$alkylthio$C_{6-12}$aryl; $C_{6-12}$arylthio$C_{1-6}$alkyl$C_{6-12}$aryl; heterocyclylthio$C_{1-6}$alkyl; heteroarylthio$C_{1-6}$alkyl; each group being unsubstituted or substituted with one or more $Z^3$; wherein at least one carbon atom or heteroatom of each of said group can be oxidized to form at least one C=O, C=S, N=O, N=S, S=O or S(O)$_2$;

preferably $R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; a polymeric group; $C_{1-6}$alkyloxy$C_{1-6}$alkyl; mono- or di-$C_{1-6}$alkylamino$C_{1-6}$alkyl; $C_{6-12}$aryl$C_{1-6}$alkyloxy$C_{6-12}$aryl; $C_{6-12}$aryloxy$C_{1-6}$alkyl$C_{6-12}$aryl; mono- or di-$C_{6-12}$arylamino$C_{1-6}$alkyl$C_{6-12}$aryl; mono- or di-$C_{6-12}$aryl$C_{1-6}$alkylamino$C_{6-12}$aryl; each group being unsubstituted or substituted with one or more $Z^3$; wherein at least one carbon atom of each of said group can be oxidized to form at least one C=O;

or $R^1$ is a group of formula -$L^2$-$Q^2$-$R^{18}$ wherein wherein, $L^2$ is a single bond or is selected from the group consisting of $C_{1-10}$alkylene; $C_{2-10}$alkenylene; $C_{2-10}$alkynylene; and $C_{6-12}$arylene; each group being optionally comprising one or more heteroatoms in the alkylene, alkenylene, alkynylene, or arylene moiety, said heteroatoms being each independently selected from O, S and N; and each group being unsubstituted or substituted with one or more $Z^4$; preferably $L^2$ is a single bond or is selected from the group consisting of $C_{1-10}$alkylene; and $C_{6-12}$arylene; each group being optionally comprising one or more O or N in the alkylene, or arylene moiety; and each group being unsubstituted or substituted with one or more $Z^4$; preferably $L^2$ is $C_{1-10}$alkylene; or $C_{6-12}$arylene; each being unsubstituted or substituted with one or more $Z^4$; preferably $L^2$ is $C_{1-10}$alkylene unsubstituted or substituted with one or more $Z^4$; preferably $L^2$ is $C_{6-12}$arylene unsubstituted or substituted with one or more $Z^4$;

preferably $L^2$ is selected from the group consisting of $C_{1-10}$alkylene; $C_{2-10}$alkenylene; $C_{2-10}$alkynylene; $C_{6-12}$arylene; $C_{1-10}$alkyleneoxy; $C_{2-10}$alkenyleneoxy; $C_{2-10}$alkynyleneoxy; $C_{1-5}$alkyleneoxy$C_{0-5}$alkylene; $C_{2-5}$alkenyleneoxy$C_{0-5}$alkylene; $C_{2-5}$alkynyleneoxy$C_{0-5}$alkylene; $C_{1-10}$alkyleneamino; $C_{2-10}$alkenyleneamino; $C_{2-10}$alkynyleneamino; $C_{1-5}$alkyleneamino$C_{0-5}$alkylene; $C_{2-5}$alkenyleneamino$C_{0-5}$alkylene; $C_{2-5}$alkynyleneamino$C_{0-5}$alkynylene; $C_{1-10}$alkylenethio; $C_{2-10}$alkenylenethio; $C_{2-10}$alkynylenethio; $C_{1-5}$alkylenethio$C_{0-5}$alkylene; $C_{2-5}$alkenylenethio$C_{0-5}$alkenylene; $C_{2-5}$alkynylenethio$C_{0-5}$alkynylene; each group being unsubstituted or substituted with one or more $Z^6$; more preferably $L^2$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^4$; more preferably $L^2$ is selected from the group consisting of $C_{1-10}$alkylene; $C_{1-10}$alkyleneoxy; and $C_{1-10}$alkyleneamino; each group being unsubstituted or substituted with one or more $Z^4$;

$Q^2$ is selected from the group consisting of $C_{1-10}$alkylene; $C_{3-6}$cycloalkylene; —OC(O)—; —NH—C(O)—; —NH—C(O)—[CR$^{13}$R$^{14}$]$_q$—; —OS(O)—; —OS(O)—; —OS(O)$_2$—; —NH—S(O)—; and —NH—S(O)$_2$; wherein each left side of said groups is attached to $L^2$ and the right side thereof is attached to $R^{18}$; preferably $Q^2$ is selected from the group consisting of $C_{1-10}$alkylene; —OC(O)—; —NH—C(O)—; —NH—C(O)—[CR$^{13}$R$^{14}$]$_q$—; preferably $Q^2$ is selected from the group consisting of $C_{1-10}$alkylene; —OC(O)—; —NH—C(O)—;

wherein said $C_{1-10}$alkylene, optionally comprises one or more heteroatoms, said heteroatoms being each independently selected from O, S and N;

and wherein said $C_{1-10}$alkylene and said $C_{3-6}$cycloalkylene can be unsubstituted or substituted with one or more $Z^5$;
preferably $Q^2$ is selected from the group consisting of $C_{1-10}$alkylene; $C_{3-6}$cycloalkylene; —OC(O)—; —NH—C(O)—; —NH—C(O)—[CR$^{13}$R$^{14}$]$_q$—; —OS(O)—; —OS(O)$_2$—; —NH—S(O)—; —NH—S(O)$_2$; $C_{1-10}$alkyleneoxy; $C_{1-5}$alkyleneoxyC$_{0-5}$alkylene; $C_{1-10}$alkyleneamino; $C_{1-5}$alkyleneaminoC$_{0-5}$alkylene; $C_{1-10}$alkylenethio; and $C_{1-5}$alkylenethioC$_{0-5}$alkylene; each group being unsubstituted or substituted with one or more $Z^5$; preferably $Q^2$ is selected from the group consisting of $C_{1-10}$alkylene; —OC(O)—; —NH—C(O)—; —NH—C(O)—[CR$^{13}$R$^{14}$]$_q$—; $C_{1-10}$alkyleneoxy; $C_{1-10}$alkyleneamino; each group being unsubstituted or substituted with one or more $Z^5$; preferably $Q^2$ is selected from the group consisting of $C_{1-10}$alkylene; —OC(O)—; —NH—C(O)—; each group being unsubstituted or substituted with one or more $Z^5$;
or $Q^2$ is a group of formula (ii);

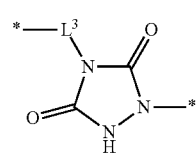

(ii)

wherein the left side of the group formula (ii) is attached to $L^2$ and the right side thereof is attached to $R^{18}$; and wherein, or $Q^2$-$R^{18}$ is a group of formula (iii);

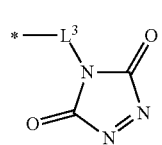

(iii)

wherein the left side of the group formula (ii) is attached to $L^2$ and the right side thereof is attached to $R^{18}$; and wherein, $L^3$ is a single bond or is selected from the group consisting of $C_{1-10}$alkylene; $C_{2-10}$alkenylene; $C_{2-10}$alkynylene; and $C_{6-12}$arylene; each group being optionally comprising one or more heteroatoms in the alkylene, alkenylene, alkynylene, or arylene moiety, said heteroatoms being each independently selected from O, S and N; and each group being unsubstituted or substituted with one or more $Z^6$; preferably $L^3$ is a single bond or is selected from the group consisting of $C_{1-10}$alkylene; and $C_{6-12}$arylene; each group optionally comprising one or more O or N in the alkylene, or arylene moiety; and each group being unsubstituted or substituted with one or more $Z^6$; preferably $L^3$ is $C_{1-10}$alkylene; or $C_{6-12}$arylene; each being unsubstituted or substituted with one or more $Z^6$; preferably $L^3$ is $C_{1-10}$alkylene unsubstituted or substituted with one or more $Z^6$; preferably $L^3$ is $C_{6-12}$arylene unsubstituted or substituted with one or more $Z^6$;
preferably $L^3$ is selected from the group consisting of $C_{1-10}$alkylene; $C_{2-10}$alkenylene; $C_{2-10}$alkynylene; $C_{6-12}$arylene; $C_{1-10}$alkyleneoxy; $C_{2-10}$alkenyleneoxy; $C_{2-10}$alkynyleneoxy; $C_{1-5}$alkyleneoxyC$_{0-5}$alkylene; $C_{2-5}$alkenyleneoxyC$_{0-5}$alkenylene; $C_{2-5}$alkynyleneoxyC$_{0-5}$alkynylene; $C_{1-10}$alkyleneamino; $C_{2-10}$alkenyleneamino; $C_{2-10}$alkynyleneamino; $C_{1-5}$alkyleneaminoC$_{0-5}$alkylene; $C_{2-5}$alkenyleneaminoC$_{0-5}$alkenylene; $C_{2-5}$alkynyleneaminoC$_{0-5}$alkynylene; $C_{1-10}$alkylenethio; $C_{2-10}$alkenylenethio; $C_{2-10}$alkynylenethio; $C_{1-5}$alkylenethioC$_{0-5}$alkylene; $C_{2-5}$alkenylenethioC$_{0-5}$alkenylene; $C_{2-5}$alkynylenethioC$_{0-5}$alkynylene; each group being unsubstituted or substituted with one or more $Z^6$; more preferably $L^3$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^6$; more preferably $L^3$ is selected from the group consisting of $C_{1-10}$alkylene; $C_{1-10}$alkyleneoxy; and $C_{1-10}$alkyleneamino; each group being unsubstituted or substituted with one or more $Z^6$;

$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$arylC$_{1-6}$alkyl; $C_{6-12}$arylC$_{1-6}$alkyl $C_{6-12}$aryl; heterocyclyl; heteroaryl; heterocyclylC$_{1-6}$alkyl; heteroarylC$_{1-6}$alkyl; and a polymeric group; each group being unsubstituted or substituted with one or more $Z^7$; and each group optionally comprises one or more O, S or N in the alkyl, alkenyl, alkynyl moiety; preferably $R^2$ is selected from the group consisting of halo; $C_{1-20}$alkyl; $C_{2-20}$alkenyl; $C_{6-12}$aryl; $C_{3-8}$cycloalkyl; $C_{6-12}$arylC$_{1-6}$alkyl; $C_{6-12}$aryl$C_{1-6}$alkylC$_{6-12}$aryl; heterocyclyl; heteroaryl; heterocyclylC$_{1-6}$alkyl; heteroarylC$_{1-6}$alkyl; and a polymeric group; each group being unsubstituted or substituted with one or more $Z^7$; and each group optionally comprises one or more O, or N in the alkyl, alkenyl moiety; preferably $R^2$ is selected from the group consisting of halo; $C_{1-20}$alkyl; $C_{2-20}$alkenyl; $C_{6-12}$aryl; $C_{3-8}$cycloalkyl; $C_{6-12}$arylC$_{1-6}$alkyl; and a polymeric group; each group being unsubstituted or substituted with one or more $Z^7$ and each group optionally comprises one or more O, or N in the alkyl moiety; preferably $R^2$ is selected from the group consisting of halo; $C_{1-20}$alkyl; $C_{6-12}$aryl; $C_{6-12}$arylC$_{1-6}$alkyl; and a polymeric group; each group being unsubstituted or substituted with one or more $Z^7$; and each group optionally comprises one or more O or N in the alkyl moiety;

preferably $R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$arylC$_{1-6}$alkyl; $C_{6-12}$arylC$_{1-6}$alkylC$_{6-12}$aryl; heterocyclyl; heteroaryl; heterocyclylC$_{1-6}$alkyl; heteroarylC$_{1-6}$alkyl; and a polymeric group; $C_{1-20}$alkyloxy; $C_{2-20}$alkenyloxy; $C_{2-20}$alkynyloxy; $C_{3-8}$cycloalkyloxy; $C_{6-12}$arylC$_{1-6}$alkyloxy; $C_{6-12}$aryloxyC$_{1-6}$alkyl; $C_{6-12}$arylC$_{1-6}$alkylC$_{6-12}$aryloxy; $C_{6-12}$aryloxyC$_{1-6}$alkylC$_{6-12}$aryl; heterocyclylC$_{1-6}$alkyloxy; heteroarylC$_{1-6}$alkyloxy; $C_{1-20}$alkylamino; $C_{2-20}$alkenylamino; $C_{2-20}$alkynylamino; $C_{3-8}$cycloalkylamino; $C_{6-12}$arylC$_{1-6}$alkylamino; $C_{6-12}$arylaminoC$_{1-6}$alkyl; $C_{6-12}$arylC$_{1-6}$alkylC$_{6-12}$arylamino; $C_{6-12}$arylaminoC$_{1-6}$alkylC$_{6-12}$aryl; heterocyclylC$_{1-6}$alkylamino; heteroarylC$_{1-6}$alkylamino; each group being unsubstituted or substituted with one or more $Z^7$; and each group optionally comprises one or more O, S or N in the alkyl, alkenyl, alkynyl moiety; preferably $R^2$ is selected from the group consisting of halo; $C_{1-20}$alkyl; $C_{2-20}$alkenyl; $C_{6-12}$aryl; $C_{3-8}$cycloalkyl; $C_{6-12}$arylC$_{1-6}$alkyl; $C_{6-12}$aryl$C_{1-6}$alkylC$_{6-12}$aryl; heterocyclyl; heteroaryl; heterocyclylC$_{1-6}$alkyl; heteroarylC$_{1-6}$alkyl; $C_{1-20}$alkyloxy; $C_{2-20}$alkenyloxy; $C_{3-8}$cycloalkyloxy; $C_{6-12}$arylC$_{1-6}$alkyloxy; $C_{1-20}$alkylamino; and a polymeric group;

each group being unsubstituted or substituted with one or more $Z^7$; preferably $R^2$ is selected from the group consisting of halo; $C_{1-20}$alkyl; $C_{2-20}$alkenyl; $C_{6-12}$aryl; $C_{3-8}$cycloalkyl; $C_{6-12}$arylC$_{1-6}$alkyl; and a polymeric group; each group being unsubstituted or substituted with one or more $Z^7$; preferably $R^2$ is selected from the group consisting of halo; $C_{1-20}$alkyl;

$C_{6-12}$aryl; $C_{6-12}$aryl$C_{1-6}$alkyl; and a polymeric group; each group being unsubstituted or substituted with one or more $Z^7$ $R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl $C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, S or N in the alkyl, alkenyl, alkynyl moiety; preferably $R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, or N in the alkyl, alkenyl moiety; preferably $R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$ and each group optionally comprises one or more O, or N in the alkyl moiety; preferably $R^3$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$; and each group optionally comprises one or more O or N in the alkyl moiety; Preferably $R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{2-20}$alkynyloxy; $C_{3-8}$cycloalkyloxy; $C_{6-12}$aryl$C_{1-6}$alkyloxy; $C_{6-12}$aryloxy$C_{1-6}$alkyl; $C_{6-12}$aryl$C_{1-6}$alkyl $C_{6-12}$aryloxy; $C_{6-12}$aryloxy$C_{1-6}$alkyl$C_{6-12}$aryl; heterocyclyl$C_{1-6}$alkyloxy; heteroaryl$C_{1-6}$alkyloxy; $C_{1-20}$alkylamino; $C_{2-20}$alkenylamino; $C_{2-20}$alkynylamino; $C_{3-8}$cycloalkylamino; $C_{6-12}$aryl$C_{1-6}$alkylamino; $C_{6-12}$arylamino$C_{1-6}$alkyl; $C_{6-12}$aryl$C_{1-6}$alkyl$C_{6-12}$arylamino; $C_{6-12}$aryamino$C_{1-6}$alkyl$C_{6-12}$aryl; heterocyclyl$C_{1-6}$alkylamino; heteroaryl$C_{1-6}$alkylamino; and a polymeric group; each group being unsubstituted or substituted with one or more $Z^7$; preferably $R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; preferably $R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$; preferably $R^3$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl $C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, S or N in the alkyl, alkenyl, alkynyl moiety; preferably $R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, or N in the alkyl, alkenyl moiety; preferably $R^4$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$; and each group optionally comprises one or more O or N in the alkyl moiety; preferably $R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{2-20}$alkynyloxy; $C_{3-8}$cycloalkyloxy; $C_{6-12}$aryl$C_{1-6}$alkyloxy; $C_{6-12}$aryloxy$C_{1-6}$alkyl; $C_{6-12}$aryl$C_{1-6}$alkyl$C_{6-12}$aryloxy; $C_{6-12}$aryloxy$C_{1-6}$alkyl$C_{6-12}$aryl; heterocyclyl$C_{1-6}$alkyloxy; heteroaryl$C_{1-6}$alkyloxy; $C_{1-20}$alkylamino; $C_{2-20}$alkenylamino; $C_{2-20}$alkynylamino; $C_{3-8}$cycloalkylamino; $C_{6-12}$aryl$C_{1-6}$alkylamino; $C_{6-12}$arylamino$C_{1-6}$alkyl; $C_{6-12}$aryl$C_{1-6}$alkyl$C_{6-12}$arylamino; $C_{6-12}$aryamino$C_{1-6}$alkyl$C_{6-12}$aryl; heterocyclyl$C_{1-6}$alkylamino; heteroaryl$C_{1-6}$alkylamino; and a polymeric group; each group being unsubstituted or substituted with one or more $Z^7$; preferably $R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; preferably $R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$; preferably $R^4$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$;

or $R^2$ and $R^3$ and $R^4$ together with the carbon atom to which they are attached can form a saturated or unsaturated 4-, 5-, 6-, 7- or 8-membered ring; preferably a saturated or unsaturated 5-, 6-, 7-membered ring; for example a saturated or unsaturated 5-, or 6-membered ring for example a phenyl ring;

or $R^2$ and $L^1$ together with the carbon atom to which they are attached can form a saturated or unsaturated 4-, 5-, 6-, 7- or 8-membered ring; preferably a saturated or unsaturated 5-, 6-, 7-membered ring; for example a saturated or unsaturated 5-, or 6-membered ring;

and wherein for each of $R^2$ and $R^3$ and $R^4$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^5$ is selected from the group consisting of hydrogen, halo; nitro; cyano; hydroxyl; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^8$; and each group optionally comprises one or more O, S or N in the alkyl, alkenyl, alkynyl moiety; wherein at least one carbon atom or heteroatom of said group can be oxidized to form at least one C=O, C=S, N=O, N=S, S=O or $S(O)_2$; preferably $R^5$ is selected from the group consisting of halo; hydroxyl, hydrogen, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^8$; and each group optionally comprises one or more O, or N in the alkyl, alkenyl moiety; wherein at least one carbon atom or heteroatom of said group can be oxidized to form at least one C=O, S=O or $S(O)_2$; preferably $R^5$ is selected from the group consisting of hydrogen, hydroxyl, halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^8$ and each group optionally comprises one or more O, or N in the alkyl moiety; wherein at least one carbon atom of said group can be oxidized to form at least one C=O; preferably $R^5$ is selected from the group consisting of halo; hydrogen, hydroxyl, $C_{1-20}$alkyl; $C_{6-12}$aryl; $C_{6-12}$aryl$C_{1-6}$alkyl; and a polymeric group; each group being unsubstituted or substituted with one or more $Z^8$; and each group optionally comprises one or more O or N in the alkyl moiety; wherein at least one carbon atom of said group can be oxidized to form at least one C=O;

preferably $R^5$ is selected from the group consisting of halo; hydrogen, hydroxyl; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; $C_{1-20}$alkyloxy; $C_{2-20}$alkenyloxy; $C_{2-20}$alkynyloxy; $C_{3-8}$cycloalkyloxy; $C_{6-12}$aryl$C_{1-6}$alkyloxy; $C_{6-12}$aryloxy$C_{1-6}$alkyl; heterocyclyl$C_{1-6}$alkyloxy; heteroaryl$C_{1-6}$alkyloxy; $C_{1-20}$alkylamino; $C_{2-20}$alkenylamino; $C_{2-20}$alkynylamino; $C_{3-8}$cycloalkylamino; $C_{6-12}$aryl$C_{1-6}$alkylamino; $C_{6-12}$arylamino$C_{1-6}$alkyl; heterocyclyl$C_{1-6}$alkylamino; heteroaryl$C_{1-6}$alkylamino; each group being unsubstituted or substituted with one or more $Z^8$; wherein at least one carbon atom or heteroatom of said group can be oxidized to form at least one C=O, C=S, N=O, N=S, S=O or $S(O)_2$; preferably $R^5$ is selected from the group consisting of halo; hydrogen, hydroxyl, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{3-8}$cycloalkyloxy; $C_{6-12}$aryl$C_{1-6}$alkyloxy; $C_{1-20}$alkylamino; and a polymeric group; each group being unsubstituted or substituted with one or more $Z^8$; wherein at least one carbon atom or heteroatom of said group can be oxidized to form at least one C=O, S=O or $S(O)_2$; preferably $R^5$ is selected from the group consisting of hydrogen; hydroxyl; halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^8$; wherein at least one carbon atom of said group can be oxidized to form at least one C=O; preferably $R^5$ is selected from the group consisting of hydrogen, hydroxyl; halo; $C_{1-20}$alkyl; $C_{6-12}$aryl; $C_{6-12}$aryl$C_{1-6}$alkyl; and a polymeric group; each group being unsubstituted or substituted with one or more $Z^8$; wherein at least one carbon atom of said group can be oxidized to form at least one C=O;

and wherein for $R^5$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly (methyl methacrylate); methacrylate and/or styrene; poly (isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^6$ is selected from the group consisting of $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^9$; and each group optionally comprises one or more O, S or N in the alkyl, alkenyl, alkynyl moiety; preferably $R^6$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^9$; and each group optionally comprises one or more O, or N in the alkyl, alkenyl moiety; preferably $R^6$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^9$ and each group optionally comprises one or more O, or N in the alkyl moiety; preferably $R^6$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;

preferably $R^6$ is selected from the group consisting of $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; $C_{1-20}$alkyloxy; $C_{2-20}$alkenyloxy; $C_{2-20}$alkynyloxy; $C_{3-8}$cycloalkyloxy; $C_{6-12}$aryl$C_{1-6}$alkyloxy; $C_{6-12}$aryloxy $C_{1-6}$alkyl; heterocyclyl$C_{1-6}$alkyloxy; heteroaryl$C_{1-6}$alkyloxy; $C_{1-20}$alkylamino; $C_{2-20}$alkenylamino; $C_{2-20}$alkynylamino; $C_{3-8}$cycloalkylamino; $C_{6-12}$aryl$C_{1-6}$alkylamino; $C_{6-12}$arylamino$C_{1-6}$alkyl; heterocyclyl$C_{1-6}$alkylamino; heteroaryl$C_{1-6}$alkylamino; each group being unsubstituted or substituted with one or more $Z^9$; preferably $R^6$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{3-8}$cycloalkyloxy; $C_{6-12}$aryl$C_{1-6}$alkyloxy; $C_{1-20}$alkylamino; and a polymeric group; each group being unsubstituted or substituted with one or more $Z^9$; preferably $R^6$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^8$; preferably $R^6$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;

$R^7$ is selected from the group consisting of $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^9$; and each group optionally comprises one or more O, S or N in the alkyl, alkenyl, alkynyl moiety; preferably $R^7$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^9$; and each group optionally comprises one or more O, or N in the alkyl, alkenyl moiety; preferably $R^7$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^9$ and each group optionally comprises one or more O, or N in the alkyl moiety; preferably $R^7$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;

preferably $R^7$ is selected from the group consisting of nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; $C_{1-20}$alkyloxy; $C_{2-20}$alkenyloxy; $C_{2-20}$alkynyloxy; $C_{3-8}$cycloalkyloxy; $C_{6-12}$aryl$C_{1-6}$alkyloxy; $C_{6-12}$aryloxy$C_{1-6}$ alkyl; heterocyclyl$C_{1-6}$alkyloxy; heteroaryl$C_{1-6}$ alkyloxy; $C_{1-20}$alkylamino; $C_{2-20}$alkenylamino; $C_{2-20}$alkynylamino; $C_{3-8}$cycloalkylamino; $C_{6-12}$aryl$C_{1-6}$alkylamino; $C_{6-12}$arylamino$C_{1-6}$alkyl; heterocyclyl$C_{1-6}$alkylamino; heteroaryl$C_{1-6}$alkylamino; each group being unsubstituted or substituted with one or more $Z^9$;

preferably $R^7$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{3-8}$cycloalkyloxy; $C_{6-12}$aryl$C_{1-6}$alkyloxy; $C_{1-20}$alkylamino; and a polymeric group; each group being unsubstituted or substituted with one or more $Z^9$; preferably $R^7$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^8$; preferably $R^7$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;

or $R^6$ and $R^7$ together with the carbon atoms to which they are attached form an unsaturated 4-, 5-, 6-, 7- or 8-membered ring; preferably an unsaturated 5-, 6-membered ring; preferably an unsaturated 6-membered ring; preferably an unsaturated 6-carbon atoms ring; which can be unsubstituted or substituted with one or more $Z^9$;

and wherein for each of $R^6$ and $R^7$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^9$ is independently selected from the group consisting of hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or $S(O)_2$; preferably wherein each $R^9$ is independently selected from the group consisting of hydroxyl; $C_{1-10}$alkyl, $C_{2-10}$alkenyl, $C_{6-12}$aryl, $C_{6-12}$aryl $C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^9$ is independently selected from the group consisting of hydroxyl; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{10}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or S(O)$_2$; preferably wherein each $R^{10}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{10}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or S(O)$_2$; preferably wherein each $R^{11}$ and $R^{12}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{11}$ and $R^{12}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein $R^{11}$ and $R^{12}$ together with the atom to which they are attached form a 5-, 6-, or 7-membered heterocycle;

each $R^{13}$ and $R^{14}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or S(O)$_2$; preferably wherein each $R^{13}$ and $R^{14}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{13}$ and $R^{14}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein $R^{13}$ and $R^{14}$ together with the atom to which they are attached form a 5-, 6-, or 7-membered heterocycle;

$R^{15}$ is selected from the group consisting of hydrogen, halo; nitro; cyano; hydroxyl; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^{10}$; and each group optionally comprises one or more O, S or N in the alkyl, alkenyl, alkynyl moiety; wherein at least one carbon atom or heteroatom of said group can be oxidized to form at least one C=O, C=S, N=O, N=S, S=O or S(O)$_2$; preferably $R^{15}$ is selected from the group consisting of halo; hydroxyl, hydrogen, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^{10}$; and each group optionally comprises one or more O, or N in the alkyl, alkenyl moiety; wherein at least one carbon atom or heteroatom of said group can be oxidized to form at least one C=O, S=O or S(O)$_2$; preferably $R^{15}$ is selected from the group consisting of hydrogen, hydroxyl, halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^{10}$ and each group optionally comprises one or more O, or N in the alkyl moiety; wherein at least one carbon atom of said group can be oxidized to form at least one C=O; preferably $R^{15}$ is selected from the group consisting of halo; hydrogen, hydroxyl, $C_{1-20}$alkyl; $C_{6-12}$aryl; $C_{6-12}$aryl$C_{1-6}$alkyl; and a polymeric group; each group being unsubstituted or substituted with one or more $Z^{10}$; and each group optionally comprises one or more O or N in the alkyl moiety; wherein at least one carbon atom of said group can be oxidized to form at least one C=O;

preferably $R^{15}$ is selected from the group consisting of halo; hydrogen, hydroxyl; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; $C_{1-20}$alkyloxy; $C_{2-20}$alkenyloxy; $C_{2-20}$alkynyloxy; $C_{3-8}$cycloalkyloxy; $C_{6-12}$aryl$C_{1-6}$alkyloxy; $C_{6-12}$aryloxy$C_{1-6}$alkyl; heterocyclyl$C_{1-6}$alkyloxy; heteroaryl$C_{1-6}$alkyloxy; $C_{1-20}$alkylamino; $C_{2-20}$alkenylamino; $C_{2-20}$alkynylamino; $C_{3-8}$cycloalkylamino; $C_{6-12}$aryl$C_{1-6}$alkylamino; $C_{6-12}$arylamino$C_{1-6}$alkyl; heterocyclyl$C_{1-6}$alkylamino; heteroaryl$C_{1-6}$alkylamino; each group being unsubstituted or substituted with one or more $Z^{10}$; wherein at least one carbon atom or heteroatom of said group can be oxidized to form at least one C=O, C=S, N=O, N=S, S=O or S(O)$_2$; preferably $R^{15}$ is selected from the group consisting of halo; hydrogen, hydroxyl, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclylC$_{1-6}$alkyl; heteroarylC$_{1-6}$alkyl; C$_{1-20}$alkyloxy; C$_{2-20}$alkenyloxy; C$_{3-8}$cycloalkyloxy; C$_{6-12}$arylC$_{1-6}$alkyloxy; C$_{1-20}$alkylamino; and a polymeric group; each group being unsubstituted or substituted with one or more Z$^{10}$; wherein at least one carbon atom or heteroatom of said group can be oxidized to form at least one C=O, S=O or S(O)$_2$; preferably R$^{15}$ is selected from the group consisting of hydrogen; hydroxyl; halo; C$_{1-20}$alkyl; C$_{2-20}$alkenyl; C$_{6-12}$aryl; C$_{3-8}$cycloalkyl; C$_{6-12}$arylC$_{1-6}$alkyl; and a polymeric group; each group being unsubstituted or substituted with one or more Z$^{10}$; wherein at least one carbon atom of said group can be oxidized to form at least one C=O; preferably R$^{15}$ is selected from the group consisting of hydrogen, hydroxyl; halo; C$_{1-20}$alkyl; C$_{6-12}$aryl; C$_{6-12}$arylC$_{1-6}$alkyl; and a polymeric group; each group being unsubstituted or substituted with one or more Z$^{10}$; wherein at least one carbon atom of said group can be oxidized to form at least one C=O;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each R$^{16}$ and R$^{17}$ is independently selected from the group consisting of hydrogen; C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-6}$alkyl, heterocyclyl; heteroaryl; heterocyclylC$_{1-6}$alkyl; and heteroaryl C$_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or S(O)$_2$; preferably wherein each R$^{16}$ and R$^{17}$ is independently selected from the group consisting of hydrogen; C$_{1-10}$alkyl, C$_{2-10}$alkenyl, C$_{6-12}$aryl, C$_{6-12}$arylC$_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each R$^{16}$ and R$^{17}$ is independently selected from the group consisting of hydrogen; C$_{1-6}$alkyl, C$_{2-6}$alkenyl, C$_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein R$^{16}$ and R$^{17}$ together with the atom to which they are attached form a 5-, 6-, or 7-membered heterocycle;

R$^{18}$ is selected from the group consisting of hydrogen, C$_{1-10}$alkyl; C$_{3-8}$cycloalkyl; C$_{6-12}$aryl; C$_{6-12}$arylC$_{1-6}$alkyl; C$_{6-12}$arylC$_{1-6}$alkylC$_{6-12}$aryl; heterocyclyl; heteroaryl; heterocyclylC$_{1-6}$alkyl; heteroarylC$_{1-6}$alkyl; and a polymeric group; wherein each group can be unsubstituted or substituted with one or more Z$^{11}$; wherein each group optionally comprises one or more heteroatoms in the alkyl moiety, said heteroatoms being each independently selected from O, S or N; preferably R$^{18}$ is selected from the group consisting of hydrogen, C$_{1-10}$alkyl; C$_{6-12}$aryl; C$_{6-12}$arylC$_{1-6}$alkyl; C$_{6-12}$arylC$_{1-6}$alkylC$_{6-12}$aryl; heteroarylC$_{1-6}$alkyl; and a polymeric group; wherein each group can be unsubstituted or substituted with one or more Z$^{11}$; wherein each group optionally comprises one or more heteroatoms in the alkyl moiety, said heteroatoms being each independently selected from O, S or N; preferably R$^{18}$ is selected from the group consisting of C$_{1-10}$alkyl; C$_{6-12}$aryl; C$_{6-12}$arylC$_{1-6}$alkyl; C$_{6-12}$arylC$_{1-6}$alkylC$_{6-12}$aryl; and a polymeric group; wherein each group can be unsubstituted or substituted with one or more Z$^{11}$; wherein each group optionally comprises one or more heteroatoms in the alkyl moiety, said heteroatoms being each independently selected from O, S or N; preferably R$^{18}$ is selected from the group consisting of hydrogen, C$_{1-10}$alkyl; C$_{6-12}$aryl; C$_{6-12}$arylC$_{1-6}$alkylC$_{6-12}$aryl; and a polymeric group; wherein each group can be unsubstituted or substituted with one or more Z$^{11}$; wherein each group optionally comprises one or more heteroatoms in the alkyl moiety, said heteroatoms being each independently selected from O, or N; preferably R$^{18}$ is C$_{6-12}$aryl which can be unsubstituted or substituted with one or more Z$^{11}$; preferably R$^{18}$ is hydrogen or C$_{1-10}$alkyl; which can be unsubstituted or substituted with one or more Z$^{11}$; wherein the alkyl optionally comprises one or more N or O; preferably R$^{18}$ is C$_{6-12}$arylC$_{1-6}$alkylC$_{6-12}$aryl; which can be unsubstituted or substituted with one or more Z$^{11}$; wherein each group optionally comprises one or more N or S in the alkyl moiety, preferably R$^{18}$ is a polymeric group which can be unsubstituted or substituted with one or more Z$^{11}$;

and wherein for R$^{18}$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

Z$^1$, Z$^2$, Z$^3$, Z$^4$, Z$^5$, Z$^6$, Z$^7$, Z$^8$, Z$^9$, Z$^{10}$, Z$^{11}$ are each independently selected from the group consisting of halogen; C$_{1-6}$alkyl; haloC$_{1-6}$alkyl; haloC$_{1-6}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; preferably Z$^1$, Z$^2$, Z$^3$, Z$^4$, Z$^5$, Z$^6$, Z$^7$, Z$^8$, Z$^9$, Z$^{10}$, Z$^{11}$ are each independently selected from the group consisting of halogen; C$_{1-6}$alkyl; haloC$_{1-6}$alkyl; haloC$_{1-6}$alkyloxy; —OR$^{10}$; nitro; —NR$^{10}$C(O)R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; preferably Z$^1$, Z$^2$, Z$^3$, Z$^4$, Z$^5$, Z$^6$, Z$^7$, Z$^8$, Z$^9$, Z$^{10}$, Z$^{11}$ are each independently selected from the group consisting of halogen; C$_{1-6}$alkyl; halo C$_{1-6}$alkyl; haloC$_{1-6}$alkyloxy; —OR$^{10}$; nitro; —NR$^{10}$C(O)R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; preferably Z$^1$, Z$^2$, Z$^3$, Z$^4$, Z$^5$, Z$^6$, Z$^7$, Z$^8$, Z$^9$, Z$^{19}$, Z$^{11}$ are each independently selected from the group consisting of halogen; C$_{1-6}$alkyl; haloC$_{1-6}$alkyl; haloC$_{1-6}$alkyloxy; nitro; —NR$^{10}$C(O)R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; or a polymeric group;

and wherein for each of Z$^1$, Z$^2$, Z$^3$, Z$^4$, Z$^5$, Z$^6$, Z$^7$, Z$^8$, Z$^9$, Z$^{10}$, Z$^{11}$, said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

According to an embodiment, the present invention provides compounds of formula (I), (IA), (IB), (IC); and any subgroup thereof wherein, $L^1$ is selected from the group consisting of $C_{1-10}$alkylene; $C_{2-10}$alkenylene; $C_{2-10}$alkynylene; $C_{1-10}$alkyleneoxy; $C_{2-10}$alkenyleneoxy; $C_{2-10}$alkynyleneoxy; $C_{1-10}$alkyleneoxy$C_{1-10}$alkylene; $C_{2-10}$alkenyleneoxy$C_{2-10}$alkenylene; $C_{2-10}$alkynyleneoxy$C_{2-10}$alkynylene; mono- or di-$C_{1-10}$alkyleneamino; mono- or di-$C_{2-10}$alkenyleneamino; mono- or di-$C_{2-10}$alkynyleneamino; mono- or di-$C_{1-10}$alkyleneamino$C_{1-10}$alkylene; mono- or di-$C_{2-10}$alkenyleneamino$C_{2-10}$alkenylene; mono- or di-$C_{2-10}$alkynyleneamino$C_{2-10}$alkynylene; $C_{1-10}$alkylenethio; $C_{2-10}$alkenylenethio; $C_{2-10}$alkynylenethio; $C_{1-10}$alkylenethio$C_{1-10}$alkylene; $C_{2-10}$alkenylenethio$C_{2-10}$alkenylene; and $C_{2-10}$alkynylenethio$C_{2-10}$alkynylene; wherein each group can be unsubstituted or substituted with one or more $Z^1$; preferably $L^1$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneoxy$C_{1-10}$alkylene; $C_{2-10}$alkenyleneoxy$C_{2-10}$alkenylene; mono- or di-$C_{1-10}$alkyleneamino; mono- or di-$C_{2-10}$alkenyleneamino; mono- or di-$C_{1-10}$alkyleneamino$C_{1-10}$alkylene; mono- or di-$C_{2-10}$alkenyleneamino$C_{2-10}$alkenylene; more preferably $L^1$ is selected from the group consisting of $C_{1-10}$alkylene; $C_{1-10}$alkyleneoxy; $C_{1-10}$alkyleneoxy$C_{1-10}$alkylene; mono- or di-$C_{1-10}$alkyleneamino; and mono- or di-$C_{1-10}$alkyleneamino$C_{1-10}$alkylene; wherein each group can be unsubstituted or substituted with one or more $Z^1$; more preferably $L^1$ is selected from the group consisting of $C_{1-10}$alkylene; $C_{2-10}$alkenylene; $C_{2-10}$alkynylene; $C_{1-10}$alkyleneoxy; $C_{2-10}$alkenyleneoxy; $C_{2-10}$alkynyleneoxy; $C_{1-5}$alkyleneoxy$C_{0-5}$alkylene; $C_{2-5}$alkenyleneoxy$C_{0-5}$alkenylene; $C_{2-5}$alkynyleneoxy$C_{0-5}$alkynylene; $C_{1-10}$alkyleneamino; $C_{2-10}$alkenyleneamino; $C_{2-10}$alkynyleneamino; $C_{1-5}$alkyleneamino$C_{0-5}$alkylene; $C_{2-5}$alkenyleneamino$C_{0-5}$alkenylene; $C_{2-5}$alkynyleneamino$C_{0-5}$alkynylene; $C_{1-10}$alkylenethio; $C_{2-10}$alkenylenethio; $C_{2-10}$alkynylenethio; $C_{1-5}$alkylenethio$C_{0-5}$alkylene; $C_{2-5}$alkenylenethio$C_{0-5}$alkenylene; $C_{2-5}$alkynylenethio$C_{0-5}$alkynylene; each group being unsubstituted or substituted with one or more $Z^1$; more preferably $L^1$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^1$; more preferably $L^1$ is selected from the group consisting of $C_{1-10}$alkylene; $C_{1-10}$alkyleneoxy; and $C_{1-10}$alkyleneamino; each group being unsubstituted or substituted with one or more $Z^1$;

$Q^1$ is a single bond or is selected from the group consisting of —OC(O)—; —NH—C(O)—; —OS(O)—; —OS(O)$_2$—; —NH—S(O)—; —NH—S(O)$_2$—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; wherein each left side of said groups is attached to $L^1$ and the right side thereof is attached to $R^5$; and wherein, preferably $Q^1$ is a single bond or is selected from the group consisting of —OC(O)—; —NH—C(O)—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; preferably $Q^1$ is a single bond or is selected from the group consisting of —OC(O)—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; preferably $Q^1$ is selected from the group consisting of —OC(O)—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; wherein q is an integer selected from 1; 2 or 3; preferably 1 or 2; for example 1;

p is an integer selected from 0; 1 or 2; preferably 0 or 1; for example 1;

$L^4$ is selected from the group consisting of $C_{1-10}$alkylene; $C_{2-10}$alkenylene; $C_{2-10}$alkynylene; $C_{1-10}$alkyleneoxy; $C_{2-10}$alkenyleneoxy; $C_{2-10}$alkynyleneoxy; $C_{1-5}$alkyleneoxy$C_{0-5}$alkylene; $C_{2-5}$alkenyleneoxy$C_{0-5}$alkenylene; $C_{2-5}$alkynyleneoxy$C_{0-5}$alkynylene; $C_{1-10}$alkyleneamino; $C_{2-10}$alkenyleneamino; $C_{2-10}$alkynyleneamino; $C_{1-5}$alkyleneamino$C_{0-5}$alkylene; $C_{2-5}$alkenyleneamino$C_{0-5}$alkenylene; $C_{2-5}$alkynyleneamino$C_{0-5}$alkynylene; $C_{1-10}$alkylenethio; $C_{2-10}$alkenylenethio; $C_{2-10}$alkynylenethio; $C_{1-5}$alkylenethio$C_{0-5}$alkylene; $C_{2-5}$alkenylenethio$C_{0-5}$alkenylene; $C_{2-5}$alkynylenethio$C_{0-5}$alkynylene; each group being unsubstituted or substituted with one or more $Z^2$; more preferably $L^4$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^2$; more preferably $L^4$ is selected from the group consisting of $C_{1-10}$alkylene; $C_{1-10}$alkyleneoxy; and $C_{1-10}$alkyleneamino; each group being unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; a polymeric group; $C_{1-5}$alkyloxy$C_{1-5}$alkyl; mono- or di-$C_{1-5}$alkylamino$C_{1-5}$alkyl; $C_{1-5}$alkylthio$C_{1-5}$alkyl; $C_{6-12}$aryl$C_{1-6}$alkyloxy$C_{6-12}$aryl; heterocyclyloxy$C_{1-6}$alkyl; heteroaryloxy$C_{1-6}$alkyl; $C_{6-12}$aryloxy$C_{1-6}$alkyl$C_{6-12}$aryl; mono- or di-$C_{6-12}$arylamino$C_{1-6}$alkyl$C_{6-12}$aryl; mono- or di-$C_{6-12}$aryl$C_{1-6}$alkylamino$C_{6-12}$aryl; mono- or diheterocyclylamino$C_{1-6}$alkyl; mono- or di-heteroarylamino$C_{1-6}$alkyl; $C_{6-12}$aryl$C_{1-6}$alkylthio$C_{6-12}$aryl; $C_{6-12}$arylthio$C_{1-6}$alkyl$C_{6-12}$aryl; heterocyclylthio$C_{1-6}$alkyl; heteroarylthio$C_{1-6}$alkyl; each group being unsubstituted or substituted with one or more $Z^3$; wherein at least one carbon atom or heteroatom of each of said group can be oxidized to form at least one C=O, C=S, N=O, N=S, S=O or S(O)$_2$; preferably $R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; a polymeric group; $C_{1-5}$alkyloxy$C_{1-5}$alkyl; mono- or di-$C_{1-5}$alkylamino$C_{1-5}$alkyl; $C_{6-12}$aryl$C_{1-6}$alkyloxyC$_{6-12}$aryl; C$_{6-12}$aryloxyC$_{1-6}$alkylC$_{6-12}$aryl; mono- or di-C$_{6-12}$arylaminoC$_{1-6}$alkylC$_{6-12}$aryl; mono- or di-C$_{6-12}$arylC$_{1-6}$alkylaminoC$_{6-12}$aryl; each group being unsubstituted or substituted with one or more Z$^3$; wherein at least one carbon atom of each of said group can be oxidized to form at least one C=O;

and wherein for R$^1$ said polymeric group is selected from the group comprising polyethylene oxide; polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

or R$^1$ is a group of formula -L$^2$-Q$^2$-R$^{18}$ wherein wherein,

L$^2$ is selected from the group consisting of C$_{1-10}$alkylene; C$_{2-10}$alkenylene; C$_{2-10}$alkynylene; C$_{6-12}$arylene; C$_{1-10}$alkyleneoxy; C$_{2-10}$alkenyleneoxy; C$_{2-10}$alkynyleneoxy; C$_{1-5}$alkyleneoxyC$_{0-5}$alkylene; C$_{2-5}$alkenyleneoxyC$_{0-5}$alkenylene; C$_{2-5}$alkynyleneoxyC$_{0-5}$alkynylene; C$_{1-10}$alkyleneamino; C$_{2-10}$alkenyleneamino; C$_{2-10}$alkynyleneamino; C$_{1-5}$alkyleneaminoC$_{0-5}$alkylene; C$_{2-5}$alkenyleneaminoC$_{0-5}$alkenylene; C$_{2-5}$alkynyleneaminoC$_{0-5}$alkynylene; C$_{1-10}$alkylenethio; C$_{2-10}$alkenylenethio; C$_{2-10}$alkynylenethio; C$_{1-5}$alkylenethioC$_{0-5}$alkylene; C$_{2-5}$alkenylenethioC$_{0-5}$alkenylene; C$_{2-5}$alkynylenethioC$_{0-5}$alkynylene; each group being unsubstituted or substituted with one or more Z$^6$; more preferably L$^2$ is selected from the group consisting of C$_{1-10}$alkylene; C$_{2-10}$alkenylene; C$_{1-10}$alkyleneoxy; C$_{2-10}$alkenyleneoxy; C$_{1-10}$alkyleneamino; C$_{2-10}$alkenyleneamino; each group being unsubstituted or substituted with one or more Z$^4$; more preferably L$^2$ is selected from the group consisting of C$_{1-10}$alkylene; C$_{1-10}$alkyleneoxy; and C$_{1-10}$alkyleneamino; each group being unsubstituted or substituted with one or more Z$^4$;

Q$^2$ is selected from the group consisting of C$_{1-10}$alkylene; C$_{3-6}$cycloalkylene; —OC(O)—; —NH—C(O)—; —NH—C(O)—[CR$^{13}$R$^{14}$]$_q$—; —OS(O)—; —OS(O)$_2$—; —NH—S(O)—; —NH—S(O)$_2$; C$_{1-10}$alkyleneoxy; C$_{1-5}$alkyleneoxyC$_{0-5}$alkylene; C$_{1-10}$alkyleneamino; C$_{1-5}$alkyleneaminoC$_{0-5}$alkylene; C$_{1-10}$alkylenethio; and C$_{1-5}$alkylenethioC$_{0-5}$alkylene; each group being unsubstituted or substituted with one or more Z$^5$; preferably Q$^2$ is selected from the group consisting of C$_{1-10}$alkylene; —OC(O)—; —NH—C(O)—; —NH—C(O)—[CR$^{13}$R$^{14}$]$_q$—; C$_{1-10}$alkyleneoxy; C$_{1-10}$alkyleneamino; each group being unsubstituted or substituted with one or more Z$^5$; preferably Q$^2$ is selected from the group consisting of C$_{1-10}$alkylene; —OC(O)—; —NH—C(O)—; each group being unsubstituted or substituted with one or more Z$^5$;

or Q$^2$ is a group of formula (ii);

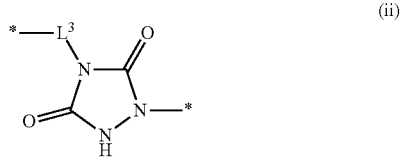

or Q$^2$-R$^{18}$ is a group of formula (iii);

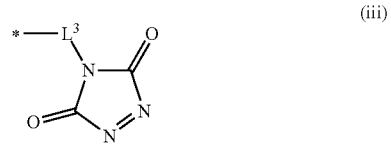

L$^3$ is a single bond or is selected from the group consisting of C$_{1-10}$alkylene; C$_{2-10}$alkenylene; C$_{2-10}$alkynylene; C$_{6-12}$arylene; C$_{1-10}$alkyleneoxy; C$_{2-10}$alkenyleneoxy; C$_{2-10}$alkynyleneoxy; C$_{1-5}$alkyleneoxyC$_{0-5}$alkylene; C$_{2-5}$alkenyleneoxyC$_{0-5}$alkenylene; C$_{2-5}$alkynyleneoxyC$_{0-5}$alkynylene; C$_{1-10}$alkyleneamino; C$_{2-10}$alkenyleneamino; C$_{2-10}$alkynyleneamino; C$_{1-5}$alkyleneaminoC$_{0-5}$alkylene; C$_{2-5}$alkenyleneaminoC$_{0-5}$alkenylene; C$_{2-5}$alkynyleneaminoC$_{0-5}$alkynylene; C$_{1-10}$alkylenethio; C$_{2-10}$alkenylenethio; C$_{2-10}$alkynylenethio; C$_{1-5}$alkylenethioC$_{0-5}$alkylene; C$_{2-5}$alkenylenethioC$_{0-5}$alkenylene; C$_{2-5}$alkynylenethioC$_{0-5}$alkynylene; each group being unsubstituted or substituted with one or more Z$^6$; more preferably L$^3$ is selected from the group consisting of C$_{1-10}$alkylene; C$_{2-10}$alkenylene; C$_{1-10}$alkyleneoxy; C$_{2-10}$alkenyleneoxy; C$_{1-10}$alkyleneamino; C$_{2-10}$alkenyleneamino; each group being unsubstituted or substituted with one or more Z$^6$; more preferably L$^3$ is selected from the group consisting of C$_{1-10}$alkylene; C$_{1-10}$alkyleneoxy; and C$_{1-10}$alkyleneamino; each group being unsubstituted or substituted with one or more Z$^6$;

R$^2$ is selected from the group consisting of halo; nitro; cyano; C$_{1-20}$alkyl; C$_{2-20}$alkenyl; C$_{2-20}$alkynyl; C$_{6-12}$aryl; C$_{3-8}$cycloalkyl; C$_{6-12}$arylC$_{1-6}$alkyl; C$_{6-12}$arylC$_{1-6}$alkyl C$_{6-12}$aryl; heterocyclyl; heteroaryl; heterocyclylC$_{1-6}$alkyl; heteroarylC$_{1-6}$alkyl; and a polymeric group; C$_{1-20}$alkyloxy; C$_{2-20}$alkenyloxy; C$_{2-20}$alkynyloxy; C$_{3-8}$cycloalkyloxy; C$_{6-12}$arylC$_{1-6}$alkyloxy; C$_{6-12}$aryloxyC$_{1-6}$alkyl; C$_{6-12}$aryl C$_{1-6}$alkylC$_{6-12}$aryloxy; C$_{6-12}$aryloxyC$_{1-6}$alkylC$_{6-12}$ aryl; heterocyclylC$_{1-6}$alkyloxy; heteroarylC$_{1-6}$alkyloxy; C$_{1-20}$alkylamino; C$_{2-20}$alkenylamino; C$_{2-20}$alkynylamino; C$_{3-8}$cycloalkylamino; C$_{6-12}$arylC$_{1-6}$alkylamino; C$_{6-12}$arylaminoC$_{1-6}$alkyl; C$_{6-12}$arylC$_{1-6}$alkylC$_{6-12}$arylamino; C$_{6-12}$aryaminoC$_{1-6}$alkylC$_{6-12}$aryl; heterocyclylC$_{1-6}$alkylamino; heteroarylC$_{1-6}$alkylamino; each group being unsubstituted or substituted with one or more Z$^7$; and each group optionally comprises one or more O, S or N in the alkyl, alkenyl, alkynyl moiety; preferably R$^2$ is selected from the group consisting of halo; C$_{1-20}$alkyl; C$_{2-20}$alkenyl;

$C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{3-8}$cycloalkyloxy; $C_{6-12}$aryl$C_{1-6}$alkyloxy; $C_{1-20}$alkylamino; and a polymeric group; each group being unsubstituted or substituted with one or more $Z^7$; preferably $R^2$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$; preferably $R^2$ is selected from the group consisting of halo; $C_{1-20}$alkyl; $C_{6-12}$aryl; $C_{6-12}$aryl$C_{1-6}$alkyl; and a polymeric group; each group being unsubstituted or substituted with one or more $Z^7$ $R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{2-20}$alkynyloxy; $C_{3-8}$cycloalkyloxy; $C_{6-12}$aryl$C_{1-6}$alkyloxy; $C_{6-12}$aryloxy$C_{1-6}$alkyl; $C_{6-12}$aryl$C_{1-6}$alkyl$C_{6-12}$aryloxy; $C_{6-12}$aryloxy$C_{1-6}$alkyl$C_{6-12}$aryl; heterocyclyl$C_{1-6}$alkyloxy; heteroaryl$C_{1-6}$alkyloxy; $C_{1-20}$alkylamino; $C_{2-20}$alkenylamino; $C_{2-20}$alkynylamino; $C_{3-8}$cycloalkylamino; $C_{6-12}$aryl$C_{1-6}$alkylamino; $C_{6-12}$arylamino$C_{1-6}$alkyl; $C_{6-12}$aryl$C_{1-6}$alkyl$C_{6-12}$arylamino; $C_{6-12}$aryamino$C_{1-6}$alkyl$C_{6-12}$aryl; heterocyclyl$C_{1-6}$alkylamino; heteroaryl$C_{1-6}$alkylamino; and a polymeric group; each group being unsubstituted or substituted with one or more $Z^7$; preferably $R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; preferably $R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$; preferably $R^3$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{2-20}$alkynyloxy; $C_{3-8}$cycloalkyloxy; $C_{6-12}$aryl$C_{1-6}$alkyloxy; $C_{6-12}$aryloxy$C_{1-6}$alkyl; $C_{6-12}$aryl$C_{1-6}$alkyl$C_{6-12}$aryloxy; $C_{6-12}$aryloxy$C_{1-6}$alkyl$C_{6-12}$aryl; heterocyclyl$C_{1-6}$alkyloxy; heteroaryl$C_{1-6}$alkyloxy; $C_{1-20}$alkylamino; $C_{2-20}$alkenylamino; $C_{2-20}$alkynylamino; $C_{3-8}$cycloalkylamino; $C_{6-12}$aryl$C_{1-6}$alkylamino; $C_{6-12}$arylamino$C_{1-6}$alkyl; $C_{6-12}$aryl$C_{1-6}$alkyl$C_{6-12}$arylamino; $C_{6-12}$aryamino$C_{1-6}$alkyl$C_{6-12}$aryl; heterocyclyl$C_{1-6}$alkylamino; heteroaryl$C_{1-6}$alkylamino; and a polymeric group; each group being unsubstituted or substituted with one or more $Z^7$; preferably $R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; preferably $R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$; preferably $R^4$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$;

or $R^2$ and $R^3$ and $R^4$ together with the carbon atom to which they are attached can form a saturated or unsaturated 4-, 5-, 6-, 7- or 8-membered ring; preferably a saturated or unsaturated 5-, 6-, 7-membered ring; for example a saturated or unsaturated 5-, or 6-membered ring for example a phenyl ring;

and wherein for each of $R^2$ and $R^3$ and $R^4$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^5$ is selected from the group consisting of halo; hydrogen, hydroxyl; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; $C_{1-20}$alkyloxy; $C_{2-20}$alkenyloxy; $C_{2-20}$alkynyloxy; $C_{3-8}$cycloalkyloxy; $C_{6-12}$aryl$C_{1-6}$alkyloxy; $C_{6-12}$aryloxy$C_{1-6}$alkyl; heterocyclyl$C_{1-6}$alkyloxy; heteroaryl$C_{1-6}$alkyloxy; $C_{1-20}$alkylamino; $C_{2-20}$alkenylamino; $C_{2-20}$alkynylamino; $C_{3-8}$cycloalkylamino; $C_{6-12}$aryl$C_{1-6}$alkylamino; $C_{6-12}$arylamino$C_{1-6}$alkyl; heterocyclyl$C_{1-6}$alkylamino; heteroaryl$C_{1-6}$alkylamino; each group being unsubstituted or substituted with one or more $Z^8$; wherein at least one carbon atom or heteroatom of said group can be oxidized to form at least one C=O, C=S, N=O, N=S, S=O or $S(O)_2$; preferably $R^5$ is selected from the group consisting of halo; hydrogen, hydroxyl, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{3-8}$cycloalkyloxy; $C_{6-12}$aryl$C_{1-6}$alkyloxy; $C_{1-20}$alkylamino; and a polymeric group; each group being unsubstituted or substituted with one or more $Z^8$; wherein at least one carbon atom or heteroatom of said group can be oxidized to form at least one C=O, S=O or S(O)$_2$; preferably R$^5$ is selected from the group consisting of hydrogen; hydroxyl; halo; C$_{1-20}$alkyl; C$_{2-20}$alkenyl; C$_{6-12}$aryl; C$_{3-8}$cycloalkyl; C$_{6-12}$arylC$_{1-6}$alkyl; and a polymeric group; each group being unsubstituted or substituted with one or more Z$^8$; wherein at least one carbon atom of said group can be oxidized to form at least one C=O; preferably R$^5$ is selected from the group consisting of hydrogen, hydroxyl; halo; C$_{1-20}$alkyl; C$_{6-12}$aryl; C$_{6-12}$arylC$_{1-6}$alkyl; and a polymeric group; each group being unsubstituted or substituted with one or more Z$^8$; wherein at least one carbon atom of said group can be oxidized to form at least one C=O;

and wherein for R$^5$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

R$^6$ is selected from the group consisting of C$_{1-20}$alkyl; C$_{2-20}$alkenyl; C$_{2-20}$alkynyl; C$_{6-12}$aryl; C$_{3-8}$cycloalkyl; C$_{6-12}$arylC$_{1-6}$alkyl; heterocyclyl; heteroaryl; heterocyclylC$_{1-6}$alkyl; heteroarylC$_{1-6}$alkyl; and a polymeric group; C$_{1-20}$alkyloxy; C$_{2-20}$alkenyloxy; C$_{2-20}$alkynyloxy; C$_{3-8}$cycloalkyloxy; C$_{6-12}$arylC$_{1-6}$alkyloxy; C$_{6-12}$aryloxyC$_{1-6}$alkyl; heterocyclylC$_{1-6}$alkyloxy; heteroarylC$_{1-6}$alkyloxy; C$_{1-20}$alkylamino; C$_{2-20}$alkenylamino; C$_{2-20}$alkynylamino; C$_{3-8}$cycloalkylamino; C$_{6-12}$arylC$_{1-6}$alkylamino; C$_{6-12}$arylaminoC$_{1-6}$alkyl; heterocyclylC$_{1-6}$alkylamino; heteroarylC$_{1-6}$alkylamino; each group being unsubstituted or substituted with one or more Z$^9$; preferably R$^6$ is selected from the group consisting of C$_{1-20}$alkyl; C$_{2-20}$alkenyl; C$_{6-12}$aryl; C$_{3-8}$cycloalkyl; C$_{6-12}$arylC$_{1-6}$alkyl; heterocyclyl; heteroaryl; heterocyclylC$_{1-6}$alkyl; heteroarylC$_{1-6}$alkyl; C$_{1-20}$alkyloxy; C$_{2-20}$alkenyloxy; C$_{3-8}$cycloalkyloxy; C$_{6-12}$arylC$_{1-6}$alkyloxy; C$_{1-20}$alkylamino; and a polymeric group; each group being unsubstituted or substituted with one or more Z$^9$; preferably R$^6$ is selected from the group consisting of C$_{1-20}$alkyl; C$_{2-20}$alkenyl; C$_{6-12}$aryl; C$_{3-8}$cycloalkyl; C$_{6-12}$arylC$_{1-6}$alkyl; and a polymeric group; each group being unsubstituted or substituted with one or more Z$^8$; preferably R$^6$ is selected from the group consisting of C$_{1-20}$alkyl; C$_{6-12}$aryl; C$_{6-12}$arylC$_{1-6}$alkyl; and a polymeric group; each group being unsubstituted or substituted with one or more Z$^9$;

R$^7$ is selected from the group consisting of C$_{1-20}$alkyl; C$_{2-20}$alkenyl; C$_{2-20}$alkynyl; C$_{6-12}$aryl; C$_{3-8}$cycloalkyl; C$_{6-12}$arylC$_{1-6}$alkyl; heterocyclyl; heteroaryl; heterocyclylC$_{1-6}$alkyl; heteroarylC$_{1-6}$alkyl; and a polymeric group; C$_{1-20}$alkyloxy; C$_{2-20}$alkenyloxy; C$_{2-20}$alkynyloxy; C$_{3-8}$cycloalkyloxy; C$_{6-12}$arylC$_{1-6}$alkyloxy; C$_{6-12}$aryloxyC$_{1-6}$alkyl; heterocyclylC$_{1-6}$alkyloxy; heteroarylC$_{1-6}$alkyloxy; C$_{1-20}$alkylamino; C$_{2-20}$alkenylamino; C$_{2-20}$alkynylamino; C$_{3-8}$cycloalkylamino; C$_{6-12}$arylC$_{1-6}$alkylamino; C$_{6-12}$arylaminoC$_{1-6}$alkyl; heterocyclylC$_{1-6}$alkylamino; heteroarylC$_{1-6}$alkylamino; each group being unsubstituted or substituted with one or more Z$^9$; preferably R$^7$ is selected from the group consisting of C$_{1-20}$alkyl; C$_{2-20}$alkenyl; C$_{6-12}$aryl; C$_{3-8}$cycloalkyl; C$_{6-12}$arylC$_{1-6}$alkyl; heterocyclyl; heteroaryl; heterocyclylC$_{1-6}$alkyl; heteroarylC$_{1-6}$alkyl; C$_{1-20}$alkyloxy; C$_{2-20}$alkenyloxy; C$_{3-8}$cycloalkyloxy; C$_{6-12}$arylC$_{1-6}$alkyloxy; C$_{1-20}$alkylamino; and a polymeric group; each group being unsubstituted or substituted with one or more Z$^9$; preferably R$^7$ is selected from the group consisting of C$_{1-20}$alkyl; C$_{2-20}$alkenyl; C$_{6-12}$aryl; C$_{3-8}$cycloalkyl; C$_{6-12}$arylC$_{1-6}$alkyl; and a polymeric group; each group being unsubstituted or substituted with one or more Z$^8$; preferably R$^7$ is selected from the group consisting of C$_{1-20}$alkyl; C$_{6-12}$aryl; C$_{6-12}$arylC$_{1-6}$alkyl; and a polymeric group; each group being unsubstituted or substituted with one or more Z$^9$;

or R$^6$ and R$^7$ together with the carbon atoms to which they are attached form an unsaturated 4-, 5-, 6-, 7- or 8-membered ring; preferably an unsaturated 5-, 6-membered ring; preferably an unsaturated 6-membered ring; preferably an unsaturated 6-carbon atoms ring; which can be unsubstituted or substituted with one or more Z$^9$;

and wherein for each of R$^6$ and R$^7$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^9$ is independently selected from the group consisting of hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or $S(O)_2$; preferably wherein each $R^9$ is independently selected from the group consisting of hydroxyl; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^9$ is independently selected from the group consisting of hydroxyl; $C_{1-6}$alkyl; $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{10}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or $S(O)_2$; preferably wherein each $R^{10}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{10}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or $S(O)_2$; preferably wherein each $R^{11}$ and $R^{12}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{11}$ and $R^{12}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein $R^{11}$ and $R^{12}$ together with the atom to which they are attached form a 5-, 6-, or 7-membered heterocycle;

each $R^{13}$ and $R^{14}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or $S(O)_2$; preferably wherein each $R^{13}$ and $R^{14}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{13}$ and $R^{14}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein $R^{13}$ and $R^{14}$ together with the atom to which they are attached form a 5-, 6-, or 7-membered heterocycle;

$R^{15}$ is selected from the group consisting of halo; hydrogen, hydroxyl; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; $C_{1-20}$alkyloxy; $C_{2-20}$alkenyloxy; $C_{2-20}$alkynyloxy; $C_{3-8}$cycloalkyloxy; $C_{6-12}$aryl$C_{1-6}$alkyloxy; $C_{6-12}$aryloxy$C_{1-6}$alkyl; heterocyclyl$C_{1-6}$alkyloxy; heteroaryl$C_{1-6}$alkyloxy; $C_{1-20}$alkylamino; $C_{2-20}$alkenylamino; $C_{2-20}$alkynylamino; $C_{3-8}$cycloalkylamino; $C_{6-12}$aryl$C_{1-6}$alkylamino; $C_{6-12}$arylamino$C_{1-6}$alkyl; heterocyclyl$C_{1-6}$alkylamino; heteroaryl$C_{1-6}$alkylamino; each group being unsubstituted or substituted with one or more $Z^{10}$; wherein at least one carbon atom or heteroatom of said group can be oxidized to form at least one C=O, C=S, N=O, N=S, S=O or $S(O)_2$; preferably $R^{15}$ is selected from the group consisting of halo; hydrogen, hydroxyl, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{3-8}$cycloalkyloxy; $C_{6-12}$aryl$C_{1-6}$alkyloxy; $C_{1-20}$alkylamino; and a polymeric group; each group being unsubstituted or substituted with one or more $Z^{10}$; wherein at least one carbon atom or heteroatom of said group can be oxidized to form at least one C=O, S=O or $S(O)_2$; preferably $R^{15}$ is selected from the group consisting of hydrogen; hydroxyl; halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^{10}$; wherein at least one carbon atom of said group can be oxidized to form at least one C=O; preferably R$^{15}$ is selected from the group consisting of hydrogen, hydroxyl; halo; C$_{1-20}$alkyl; C$_{6-12}$aryl; C$_{6-12}$arylC$_{1-6}$alkyl; and a polymeric group; each group being unsubstituted or substituted with one or more Z$^{10}$; wherein at least one carbon atom of said group can be oxidized to form at least one C=O;

and wherein for R$^{15}$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each R$^{16}$ and R$^{17}$ is independently selected from the group consisting of hydrogen; C$_{1-20}$alkyl, C$_{2-20}$alkenyl, C$_{2-20}$alkynyl, C$_{6-12}$aryl, C$_{3-8}$cycloalkyl, C$_{6-12}$arylC$_{1-6}$alkyl, heterocyclyl; heteroaryl; heterocyclylC$_{1-6}$alkyl; and heteroarylC$_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or S(O)$_2$; preferably wherein each R$^{16}$ and R$^{17}$ is independently selected from the group consisting of hydrogen; C$_{1-10}$alkyl, C$_{2-10}$alkenyl, C$_{6-12}$aryl, C$_{6-12}$arylC$_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each R$^{16}$ and R$^{17}$ is independently selected from the group consisting of hydrogen; C$_{1-6}$alkyl, C$_{2-6}$alkenyl, C$_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein R$^{16}$ and R$^{17}$ together with the atom to which they are attached form a 5-, 6-, or 7-membered heterocycle;

R$^{18}$ is selected from the group consisting of hydrogen, C$_{1-10}$alkyl; C$_{3-8}$cycloalkyl; C$_{6-12}$aryl; C$_{6-12}$arylC$_{1-6}$alkyl; C$_{6-12}$arylC$_{1-6}$alkylC$_{6-12}$aryl; heterocyclyl; heteroaryl; heterocyclylC$_{1-6}$alkyl; heteroarylC$_{1-6}$alkyl; and a polymeric group; wherein each group can be unsubstituted or substituted with one or more Z$^{11}$; wherein each group optionally comprises one or more heteroatoms in the alkyl moiety, said heteroatoms being each independently selected from O, S or N; preferably R$^{18}$ is selected from the group consisting of hydrogen, C$_{1-10}$alkyl; C$_{6-12}$aryl; C$_{6-12}$arylC$_{1-6}$alkyl; C$_{6-12}$arylC$_{1-6}$alkylC$_{6-12}$aryl; heteroarylC$_{1-6}$alkyl; and a polymeric group; wherein each group can be unsubstituted or substituted with one or more Z$^{11}$; wherein each group optionally comprises one or more heteroatoms in the alkyl moiety, said heteroatoms being each independently selected from O, S or N; preferably R$^{18}$ is selected from the group consisting of C$_{1-10}$alkyl; C$_{6-12}$aryl; C$_{6-12}$arylC$_{1-6}$alkyl; C$_{6-12}$arylC$_{1-6}$alkylC$_{6-12}$aryl; and a polymeric group; wherein each group can be unsubstituted or substituted with one or more Z$^{11}$; wherein each group optionally comprises one or more heteroatoms in the alkyl moiety, said heteroatoms being each independently selected from O, or N; preferably R$^{18}$ is selected from the group consisting of hydrogen, C$_{1-10}$alkyl; C$_{6-12}$aryl; C$_{6-12}$arylC$_{1-6}$alkylC$_{6-12}$aryl; and a polymeric group; wherein each group can be unsubstituted or substituted with one or more Z$^{11}$; wherein each group optionally comprises one or more heteroatoms in the alkyl moiety, said heteroatoms being each independently selected from O, or N; preferably R$^{18}$ is C$_{6-12}$aryl which can be unsubstituted or substituted with one or more Z$^{11}$; preferably R$^{18}$ is hydrogen or C$_{1-10}$alkyl; which can be unsubstituted or substituted with one or more Z$^{11}$; wherein the alkyl optionally comprises one or more N or O; preferably R$^{18}$ is C$_{6-12}$arylC$_{1-6}$alkylC$_{6-12}$aryl; which can be unsubstituted or substituted with one or more Z$^{11}$; wherein each group optionally comprises one or more N or S in the alkyl moiety, preferably R$^{18}$ is a polymeric group which can be unsubstituted or substituted with one or more Z$^{11}$;

and wherein for R$^{18}$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

Z$^1$, Z$^2$, Z$^3$, Z$^4$, Z$^5$, Z$^6$, Z$^7$, Z$^8$, Z$^9$, Z$^{10}$, Z$^{11}$ are each independently selected from the group consisting of halogen; C$_{1-6}$alkyl; haloC$_{1-6}$alkyl; haloC$_{1-6}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; preferably Z$^1$, Z$^2$, Z$^3$, Z$^4$, Z$^5$, Z$^6$, Z$^7$, Z$^8$, Z$^9$, Z$^{10}$, Z$^{11}$ are each independently selected from the group consisting of halogen; C$_{1-6}$alkyl; haloC$_{1-6}$alkyl; haloC$_{1-6}$alkyloxy; —OR$^{10}$; nitro; —NR$^{10}$C(O)R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; preferably Z$^1$, Z$^2$, Z$^3$, Z$^4$, Z$^5$, Z$^6$, Z$^7$, Z$^8$, Z$^9$, Z$^{10}$, Z$^{11}$ are each independently selected from the group consisting of halogen; C$_{1-6}$alkyl; haloC$_{1-6}$alkyl; haloC$_{1-6}$alkyloxy; —OR$^{10}$; nitro; —NR$^{10}$C(O)R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; preferably Z$^1$, Z$^2$, Z$^3$, Z$^4$, Z$^5$, Z$^6$, Z$^7$, Z$^8$, Z$^9$, Z$^{10}$, Z$^{11}$ are each independently selected from the group consisting of halogen; C$_{1-6}$alkyl; haloC$_{1-6}$alkyl; haloC$_{1-6}$alkyloxy; nitro; —NR$^{10}$C(O)R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; or a polymeric group;

and wherein for each of Z$^1$, Z$^2$, Z$^3$, Z$^4$, Z$^5$, Z$^6$, Z$^7$, Z$^8$, Z$^9$, Z$^{10}$, Z$^{11}$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

According to an embodiment, the present invention provides compounds of formula (I), (IA), (IB), (IC); and any subgroup thereof wherein;

$L^1$ is selected from the group consisting of $C_{1-10}$alkylene; $C_{2-10}$alkenylene; and $C_{2-10}$alkynylene; wherein each group optionally comprises one or more, for example 1, 2 or 3 heteroatoms in the alkylene, alkenylene, alkynylene, said heteroatoms being each independently selected from O, S and N;

$Q^1$ is a single bond or is selected from the group consisting of —OC(O)—; —NH—C(O)—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; preferably $Q^1$ is a single bond or is selected from the group consisting of —OC(O)—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; preferably $Q^1$ is selected from the group consisting of —OC(O)—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; wherein q is an integer selected from 1 or 2; for example 1;
p is an integer selected from 0 or 1; for example 1;
$L^4$ is a single bond or is selected from the group consisting of $C_{1-10}$alkylene; and $C_{2-10}$alkenylene; preferably $L^4$ is a single bond or is $C_{1-10}$alkylene; preferably $L^4$ is $C_{1-10}$alkylene; for example $C_{1-8}$alkylene, for example $C_{1-6}$alkylene, for example $C_{1-4}$alkylene, wherein said $C_{1-10}$alkylene; $C_{2-10}$alkenylene; optionally comprises one or more, for example 1, 2 or 3 heteroatoms in the alkylene, alkenylene, said heteroatoms being each independently selected from O, S and N; preferably wherein said $C_{1-10}$alkylene; optionally comprises one or more, for example 1, 2 or 3 heteroatoms, said heteroatoms being each independently selected from O, and N; preferably wherein said $C_{1-10}$alkylene, for example $C_{1-8}$alkylene, $C_{1-6}$alkylene, optionally comprises one or more, for example 1, 2 or 3 heteroatoms being each independently selected from O, and N; and wherein said $C_{1-10}$alkylene; and $C_{2-10}$alkenylene; can be unsubstituted or substituted with one or more $Z^2$; preferably wherein said $C_{1-10}$alkylene; for example $C_{1-8}$alkylene, for example $C_{1-6}$alkylene, can be unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heteroaryl$C_{1-6}$alkyl; and a polymeric group; preferably $R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; and a polymeric group; preferably $R^1$ is selected from the group consisting of $C_{2-10}$alkyl; $C_{6-12}$aryl; $C_{6-12}$aryl$C_{1-6}$alkyl $C_{6-12}$aryl; and a polymeric group; preferably $R^1$ is $C_{6-12}$aryl; preferably $R^1$ is $C_{2-10}$alkyl; preferably $R^1$ is $C_{6-12}$aryl$C_{1-6}$alkyl$C_{6-12}$aryl; preferably $R^1$ is a polymeric group; wherein said $C_{2-10}$alkyl, $C_{6-12}$aryl$C_{1-6}$alkyl, $C_{6-12}$aryl$C_{1-6}$alkyl $C_{6-12}$aryl, optionally comprises one or more heteroatoms in the alkyl moiety, said heteroatoms being each independently selected from O, S or N; preferably wherein said $C_{2-10}$alkyl, $C_{6-12}$aryl$C_{1-6}$alkyl, $C_{6-12}$aryl$C_{1-6}$alkyl$C_{6-12}$aryl, optionally comprises 1, 2 or 3 heteroatoms in the alkyl moiety, said heteroatoms being each independently selected from O, or N; preferably wherein said $C_{2-10}$alkyl, $C_{6-12}$aryl$C_{1-6}$alkyl, $C_{6-12}$aryl$C_{1-6}$alkyl$C_{6-12}$aryl, optionally comprises 1, 2 or 3 N in the alkyl moiety; wherein at least one carbon atom of said $C_{2-10}$alkyl; $C_{6-12}$aryl; $C_{6-12}$aryl$C_{1-6}$alkyl; $C_{6-12}$aryl $C_{1-6}$alkyl$C_{6-12}$aryl; can be oxidized to form at least one C=O, C=S; preferably wherein at least one carbon atom of said $C_{2-10}$alkyl; $C_{6-12}$aryl; $C_{6-12}$aryl$C_{1-6}$alkyl$C_{6-12}$aryl; can be oxidized to form at least one C=O; wherein said $C_{2-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, can be unsubstituted or substituted with one or more $Z^3$;

or $R^1$ is a group of formula -$L^2$-$Q^2$-$R^{18}$ wherein
$L^2$ is a single bond or is selected from the group consisting of $C_{1-10}$alkylene; and $C_{6-12}$arylene;
each group being optionally comprising one or more O or N in the alkylene, or arylene moiety;
and each group being unsubstituted or substituted with one or more $Z^4$; preferably $L^2$ is $C_{1-10}$alkylene; or $C_{6-12}$arylene; each being unsubstituted or substituted with one or more $Z^4$; preferably $L^2$ is $C_{1-10}$alkylene unsubstituted or substituted with one or more $Z^4$; preferably $L^2$ is $C_{6-12}$arylene unsubstituted or substituted with one or more $Z^4$;

$Q^2$ is selected from the group consisting of $C_{1-10}$alkylene; $C_{3-6}$cycloalkylene; —OC(O)—; —NH—C(O)—; —NH—C(O)—[CR$^{13}$R$^{14}$]$_q$—; wherein said $C_{1-10}$alkylene, optionally comprises one or more heteroatoms, said heteroatoms being each independently selected from O, S and N; and wherein said $C_{1-10}$alkylene can be unsubstituted or substituted with one or more $Z^5$;

or $Q^2$ is a group of formula (ii);

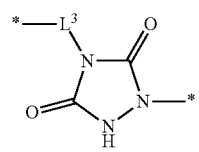

or $Q^2$-$R^{18}$ is a group of formula (iii);

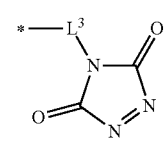

$L^3$ is a single bond or is selected from the group consisting of $C_{1-10}$alkylene; and $C_{6-12}$arylene; each group optionally comprising one or more O or N in the alkylene, or arylene moiety; and each group being unsubstituted or substituted with one or more $Z^6$; preferably $L^3$ is $C_{1-10}$alkylene; or $C_{6-12}$arylene; each being unsubstituted or substituted with one or more $Z^6$; preferably $L^3$ is $C_{1-10}$alkylene unsubstituted or substituted with one or more $Z^6$; preferably $L^3$ is $C_{6-12}$arylene unsubstituted or substituted with one or more $Z^6$;

$R^2$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, or N in the alkyl, alkenyl moiety; preferably $R^2$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$ and each group optionally comprises one or more O, or N in the alkyl moiety; preferably $R^2$ is selected from the group consisting of halo; $C_{1-20}$alkyl; $C_{6-12}$aryl; $C_{6-12}$aryl$C_{1-6}$alkyl; and a polymeric group; each group being unsubstituted or substituted with one or more $Z^7$; and each group optionally comprises one or more O or N in the alkyl moiety;

$R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, or N in the alkyl, alkenyl moiety; preferably $R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$ and each group optionally comprises one or more O, or N in the alkyl moiety; preferably $R^3$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$; and each group optionally comprises one or more O or N in the alkyl moiety;

$R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, or N in the alkyl, alkenyl moiety; preferably $R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$ and each group optionally comprises one or more O, or N in the alkyl moiety; preferably $R^4$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$; and each group optionally comprises one or more O or N in the alkyl moiety;

or $R^2$ and $R^3$ and $R^4$ together with the carbon atom to which they are attached can form saturated or unsaturated 5-, 6-, 7-membered ring; for example a saturated or unsaturated 5-, or 6-membered ring for example a phenyl ring;

or $R^2$ and $L^1$ together with the carbon atom to which they are attached can form a saturated or unsaturated 5-, 6-, 7-membered ring; for example a saturated or unsaturated 5-, or 6-membered ring;

$R^5$ is selected from the group consisting of halo; hydroxyl, hydrogen, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^8$; and each group optionally comprises one or more O, or N in the alkyl, alkenyl moiety; wherein at least one carbon atom or heteroatom of said group can be oxidized to form at least one C=O, S=O or S(O)$_2$; preferably $R^5$ is selected from the group consisting of hydrogen, hydroxyl, halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^8$ and each group optionally comprises one or more O, or N in the alkyl moiety; wherein at least one carbon atom of said group can be oxidized to form at least one C=O; preferably $R^5$ is selected from the group consisting of halo; hydrogen, hydroxyl, $C_{1-20}$alkyl; $C_{6-12}$aryl; $C_{6-12}$aryl$C_{1-6}$alkyl; and a polymeric group; each group being unsubstituted or substituted with one or more $Z^8$; and each group optionally comprises one or more O or N in the alkyl moiety; wherein at least one carbon atom of said group can be oxidized to form at least one C=O;

$R^6$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^9$; and each group optionally comprises one or more O, or N in the alkyl, alkenyl moiety; preferably $R^6$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^9$ and each group optionally comprises one or more O, or N in the alkyl moiety; preferably $R^6$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;

$R^7$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^9$; and each group optionally comprises one or more O, or N in the alkyl, alkenyl moiety; preferably $R^7$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^9$ and each group optionally comprises one or more O, or N in the alkyl moiety; preferably $R^7$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;

or $R^6$ and $R^7$ together with the carbon atoms to which they are attached form an unsaturated 5-, 6-membered ring; preferably an unsaturated 6-membered ring; preferably an unsaturated 6-carbon atoms ring; which can be unsubstituted or substituted with one or more $Z^9$;

each $R^9$ is independently selected from the group consisting of hydroxyl; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^9$ is independently selected from the group consisting of hydroxyl; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{10}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{10}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{11}$ and $R^{12}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{11}$ and $R^{12}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein $R^{11}$ and $R^{12}$ together with the atom to which they are attached form a 5-, or 6-, membered heterocycle;

each $R^{13}$ and $R^{14}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{13}$ and $R^{14}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein $R^{13}$ and $R^{14}$ together with the atom to which they are attached form a 5-, or 6-membered heterocycle;

$R^{15}$ is selected from the group consisting of halo; hydroxyl, hydrogen, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^{10}$; and each group optionally comprises one or more O, or N in the alkyl, alkenyl moiety; wherein at least one carbon atom or heteroatom of said group can be oxidized to form at least one C=O, S=O or S(O)$_2$; preferably $R^{15}$ is selected from the group consisting of hydrogen, hydroxyl, halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^{10}$ and each group optionally comprises one or more O, or N in the alkyl moiety; wherein at least one carbon atom of said group can be oxidized to form at least one C=O; preferably $R^{15}$ is selected from the group consisting of halo; hydrogen, hydroxyl, $C_{1-20}$alkyl; $C_{6-12}$aryl; $C_{6-12}$aryl$C_{1-6}$alkyl; and a polymeric group; each group being unsubstituted or substituted with one or more $Z^{10}$; and each group optionally comprises one or more O or N in the alkyl moiety; wherein at least one carbon atom of said group can be oxidized to form at least one C=O;

each $R^{16}$ and $R^{17}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{16}$ and $R^{17}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein $R^{16}$ and $R^{17}$ together with the atom to which they are attached form a 5-, or 6-membered heterocycle;

$R^{18}$ is selected from the group consisting of hydrogen, $C_{1-10}$alkyl; $C_{6-12}$aryl; $C_{6-12}$aryl$C_{1-6}$alkyl; $C_{6-12}$aryl$C_{1-6}$alkyl$C_{6-12}$aryl; heteroaryl$C_{1-6}$alkyl; and a polymeric group; wherein each group can be unsubstituted or substituted with one or more $Z^{11}$; wherein each group optionally comprises one or more heteroatoms in the alkyl moiety, said heteroatoms being each independently selected from O, S or N; preferably $R^{18}$ is selected from the group consisting of hydrogen, $C_{1-10}$alkyl; $C_{6-12}$aryl; $C_{6-12}$aryl$C_{1-6}$alkyl; $C_{6-12}$aryl$C_{1-6}$alkyl$C_{6-12}$aryl; and a polymeric group; wherein each group can be unsubstituted or substituted with one or more $Z^{11}$; wherein each group optionally comprises one or more heteroatoms in the alkyl moiety, said heteroatoms being each independently selected from O, or N; preferably $R^{18}$ is selected from the group consisting of $C_{1-10}$alkyl; $C_{6-12}$aryl; $C_{6-12}$aryl$C_{1-6}$alkyl$C_{6-12}$aryl; and a polymeric group; wherein each group can be unsubstituted or substituted with one or more $Z^{11}$; wherein each group optionally comprises one or more heteroatoms in the alkyl moiety, said heteroatoms being each independently selected from O, or N; preferably $R^{18}$ is $C_{6-12}$aryl which can be unsubstituted or substituted with one or more $Z^{11}$; preferably $R^{18}$ is hydrogen or $C_{1-10}$alkyl; which can be unsubstituted or substituted with one or more $Z^{11}$; wherein the alkyl optionally comprises one or more N or O; preferably $R^{18}$ is $C_{6-12}$aryl$C_{1-6}$alkyl$C_{6-12}$aryl; which can be unsubstituted or substituted with one or more $Z^{11}$; wherein each group optionally comprises one or more N or S in the alkyl moiety, preferably $R^{18}$ is a polymeric group which can be unsubstituted or substituted with one or more $Z^{11}$;

preferably $Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; —OR$^{10}$; nitro; —NR$^{10}$C(O)R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; preferably $Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; —OR$^{10}$; nitro; —NR$^{10}$C(O)R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; preferably $Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; nitro; —NR$^{10}$C(O)R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; or a polymeric group;

and wherein for each of $R^1$, $R^2$, $R^3$, $R^4$, $R^5$, $R^6$, $R^7$, $R^{15}$, $R^{18}$, $Z^1$, $Z^2$, $Z^3$, $Z^4$, $Z^5$, $Z^6$, $Z^7$, $Z^8$, $Z^9$, $Z^{10}$, $Z^{11}$ said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

According to an embodiment, the present invention provides compounds of formula (I), (IA), (IB), (IC); and any subgroup thereof wherein, $L^1$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneoxy$C_{1-10}$alkylene; $C_{2-10}$alkenyleneoxy$C_{2-10}$alkenylene; mono- or di-$C_{1-10}$alkyleneamino; mono- or di-$C_{2-10}$alkenyleneamino; mono- or di-$C_{1-10}$alkyleneamino$C_{1-10}$alkylene; mono- or di-$C_{2-10}$alkenyleneamino$C_{2-10}$alkenylene; more preferably $L^1$ is selected from the group consisting of $C_{1-10}$alkylene; $C_{1-10}$alkyleneoxy; $C_{1-10}$alkyleneoxy$C_{1-10}$alkylene; mono- or di-$C_{1-10}$alkyleneamino; and mono- or di-$C_{1-10}$alkyleneamino$C_{1-10}$alkylene; wherein each group can be unsubstituted or substituted with one or more $Z^1$; more preferably $L^1$ is selected from the group consisting of $C_{1-10}$alkylene; $C_{2-10}$alkenylene; $C_{2-10}$alkynylene; $C_{1-10}$alkyleneoxy; $C_{2-10}$alkenyleneoxy; $C_{2-10}$alkynyleneoxy; $C_{1-5}$alkyleneoxy$C_{0-5}$alkylene; $C_{2-5}$alkenyleneoxy$C_{0-5}$alkenylene; $C_{2-5}$alkynyleneoxy$C_{0-5}$alkynylene; $C_{1-10}$alkyleneamino; $C_{2-10}$alkenyleneamino; $C_{2-10}$alkynyleneamino; $C_{1-5}$alkyleneamino$C_{0-5}$alkylene; $C_{2-5}$alkenyleneamino$C_{0-5}$alkenylene; $C_{2-5}$alkynyleneamino$C_{0-5}$alkynylene; $C_{1-10}$alkylenethio; $C_{2-10}$alkenylenethio; $C_{2-10}$alkynylenethio; $C_{1-5}$alkylenethio$C_{0-5}$alkylene; $C_{2-5}$alkenylenethio$C_{0-5}$alkenylene; $C_{2-5}$alkynylenethio$C_{0-5}$alkynylene; each group being unsubstituted or substituted with one or more $Z^1$; more preferably $L^1$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^1$; more preferably $L^1$ is selected from the group consisting of $C_{1-10}$alkylene; $C_{1-10}$alkyleneoxy; and $C_{1-10}$alkyleneamino; each group being unsubstituted or substituted with one or more $Z^1$;

$Q^1$ is a single bond or is selected from the group consisting of —OC(O)—; —NH—C(O)—; —OC(O)—[$CR^{13}R^{14}$]$_q$—; and —OC(O)—[C($R^{13}$)($L^4$—O—$R^{15}$)]$_q$—[$CR^{16}R^{17}$]$_p$—O—; preferably $Q^1$ is a single bond or is selected from the group consisting of —OC(O)—; —OC(O)—[$CR^{13}R^{14}$]$_q$—; and —OC(O)—[C($R^{13}$)($L^4$—O—$R^{15}$)]$_q$—[$CR^{16}R^{17}$]$_p$—O—; preferably $Q^1$ is selected from the group consisting of —OC(O)—; —OC(O)—[$CR^{13}R^{14}$]$_q$—; and —OC(O)—[C($R^{13}$)($L^4$—O—$R^{15}$)]$_q$—[$CR^{16}R^{17}$]$_p$—O—; wherein
q is an integer selected from 1 or 2; for example 1;
p is an integer selected from 0 or 1; for example 1;

$L^4$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^2$; more preferably $L^4$ is selected from the group consisting of $C_{1-10}$alkylene; $C_{1-10}$alkyleneoxy; and $C_{1-10}$alkyleneamino; each group being unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; a polymeric group; $C_{1-5}$alkyloxy$C_{1-5}$alkyl; mono- or di-$C_{1-5}$alkylamino$C_{1-5}$alkyl; $C_{6-12}$aryl$C_{1-6}$alkyloxy$C_{6-12}$aryl; $C_{6-12}$aryloxy$C_{1-6}$alkyl$C_{6-12}$aryl; mono- or di-$C_{6-12}$arylamino$C_{1-6}$alkyl$C_{6-12}$aryl; mono- or di-$C_{6-12}$aryl$C_{1-6}$alkylamino$C_{6-12}$aryl; each group being unsubstituted or substituted with one or more $Z^3$; wherein at least one carbon atom of each of said group can be oxidized to form at least one C=O;

or $R^1$ is a group of formula -$L^2$-$Q^2$-$R^{18}$ wherein
wherein,
$L^2$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^4$; more preferably $L^2$ is selected from the group consisting of $C_{1-10}$alkylene; $C_{1-10}$alkyleneoxy; and $C_{1-10}$alkyleneamino; each group being unsubstituted or substituted with one or more $Z^4$;

$Q^2$ is selected from the group consisting of $C_{1-10}$alkylene; —OC(O)—; —NH—C(O)—; —NH—C(O)—[$CR^{13}R^{14}$]$_q$—; $C_{1-10}$alkyleneoxy; $C_{1-10}$alkyleneamino; each group being unsubstituted or substituted with one or more $Z^5$; preferably $Q^2$ is selected from the group consisting of $C_{1-10}$alkylene; —OC(O)—; —NH—C(O)—; each group being unsubstituted or substituted with one or more $Z^5$;
or $Q^2$ is a group of formula (ii);

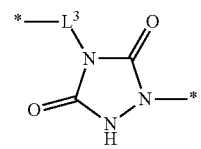

(ii)

or $Q^2$-$R^{18}$ is a group of formula (iii);

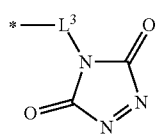

(iii)

$L^3$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^6$; more preferably $L^3$ is selected from the group consisting of $C_{1-10}$alkylene; $C_{1-10}$alkyleneoxy; and $C_{1-10}$alkyleneamino; each group being unsubstituted or substituted with one or more $Z^6$;

$R^2$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclylC$_{1-6}$alkyl; heteroarylC$_{1-6}$alkyl; C$_{1-20}$alkyloxy; C$_{2-20}$alkenyloxy; C$_{3-8}$cycloalkyloxy; C$_{6-12}$arylC$_{1-6}$alkyloxy; C$_{1-20}$alkylamino; and a polymeric group; each group being unsubstituted or substituted with one or more Z$^7$; preferably R$^2$ is selected from the group consisting of halo; C$_{1-20}$alkyl; C$_{2-20}$alkenyl; C$_{6-12}$aryl; C$_{3-8}$cycloalkyl; C$_{6-12}$arylC$_{1-6}$alkyl; and a polymeric group; each group being unsubstituted or substituted with one or more Z$^7$; preferably R$^2$ is selected from the group consisting of halo; C$_{1-20}$alkyl; C$_{6-12}$aryl; C$_{6-12}$arylC$_{1-6}$alkyl; and a polymeric group; each group being unsubstituted or substituted with one or more Z$^7$ R$^3$ is selected from the group consisting of halo; C$_{1-20}$alkyl; C$_{2-20}$alkenyl; C$_{6-12}$aryl; C$_{3-8}$cycloalkyl; C$_{6-12}$arylC$_{1-6}$alkyl; and a polymeric group; each group being unsubstituted or substituted with one or more Z$^7$; preferably R$^3$ is selected from the group consisting of halo; C$_{1-20}$alkyl; C$_{6-12}$aryl; C$_{6-12}$arylC$_{1-6}$alkyl; each group being unsubstituted or substituted with one or more Z$^7$;

R$^4$ is selected from the group consisting of halo; C$_{1-20}$alkyl; C$_{2-20}$alkenyl; C$_{6-12}$aryl; C$_{3-8}$cycloalkyl; C$_{6-12}$arylC$_{1-6}$alkyl; C$_{6-12}$arylC$_{1-6}$alkylC$_{6-12}$aryl; heterocyclyl; heteroaryl; heterocyclylC$_{1-6}$alkyl; heteroarylC$_{1-6}$alkyl; and a polymeric group; each group being unsubstituted or substituted with one or more Z$^7$; preferably R$^4$ is selected from the group consisting of halo; C$_{1-20}$alkyl; C$_{2-20}$alkenyl; C$_{6-12}$aryl; C$_{3-8}$cycloalkyl; C$_{6-12}$arylC$_{1-6}$alkyl; and a polymeric group; each group being unsubstituted or substituted with one or more Z$^7$; preferably R$^4$ is selected from the group consisting of halo; C$_{1-20}$alkyl; C$_{6-12}$aryl; C$_{6-12}$arylC$_{1-6}$alkyl; each group being unsubstituted or substituted with one or more Z$^7$;

or R$^2$ and R$^3$ and R$^4$ together with the carbon atom to which they are attached can form a saturated or unsaturated 5-, 6-, 7-membered ring; for example a saturated or unsaturated 5- or 6-membered ring for example a phenyl ring;

R$^5$ is selected from the group consisting of halo; hydrogen, hydroxyl, C$_{1-20}$alkyl; C$_{2-20}$alkenyl; C$_{6-12}$aryl; C$_{3-8}$cycloalkyl; C$_{6-12}$arylC$_{1-6}$alkyl; heterocyclyl; heteroaryl; heterocyclylC$_{1-6}$alkyl; heteroarylC$_{1-6}$alkyl; C$_{1-20}$alkyloxy; C$_{2-20}$alkenyloxy; C$_{3-8}$cycloalkyloxy; C$_{6-12}$arylC$_{1-6}$alkyloxy; C$_{1-20}$alkylamino; and a polymeric group; each group being unsubstituted or substituted with one or more Z$^8$; wherein at least one carbon atom or heteroatom of said group can be oxidized to form at least one C=O, S=O or S(O)$_2$; preferably R$^5$ is selected from the group consisting of hydrogen; hydroxyl; halo; C$_{1-20}$alkyl; C$_{2-20}$alkenyl; C$_{6-12}$aryl; C$_{3-8}$cycloalkyl; C$_{6-12}$arylC$_{1-6}$alkyl; and a polymeric group; each group being unsubstituted or substituted with one or more Z$^8$; wherein at least one carbon atom of said group can be oxidized to form at least one C=O; preferably R$^5$ is selected from the group consisting of hydrogen, hydroxyl; halo; C$_{1-20}$alkyl; C$_{6-12}$aryl; C$_{6-12}$arylC$_{1-6}$alkyl; and a polymeric group; each group being unsubstituted or substituted with one or more Z$^8$; wherein at least one carbon atom of said group can be oxidized to form at least one C=O;

R$^6$ is selected from the group consisting of C$_{1-20}$alkyl; C$_{2-20}$alkenyl; C$_{6-12}$aryl; C$_{3-8}$cycloalkyl; C$_{6-12}$arylC$_{1-6}$alkyl; heterocyclyl; heteroaryl; heterocyclylC$_{1-6}$alkyl; heteroarylC$_{1-6}$alkyl; C$_{1-20}$alkyloxy; C$_{2-20}$alkenyloxy; C$_{3-8}$cycloalkyloxy; C$_{6-12}$arylC$_{1-6}$alkyloxy; C$_{1-20}$alkylamino; and a polymeric group; each group being unsubstituted or substituted with one or more Z$^9$; preferably R$^6$ is selected from the group consisting of C$_{1-20}$alkyl; C$_{2-20}$alkenyl; C$_{6-12}$aryl; C$_{3-8}$cycloalkyl; C$_{6-12}$arylC$_{1-6}$alkyl; and a polymeric group; each group being unsubstituted or substituted with one or more Z$^8$; preferably R$^6$ is selected from the group consisting of C$_{1-20}$alkyl; C$_{6-12}$aryl; C$_{6-12}$arylC$_{1-6}$alkyl; and a polymeric group; each group being unsubstituted or substituted with one or more Z$^9$;

R$^7$ is selected from the group consisting of C$_{1-20}$alkyl; C$_{2-20}$alkenyl; C$_{6-12}$aryl; C$_{3-8}$cycloalkyl; C$_{6-12}$arylC$_{1-6}$alkyl; heterocyclyl; heteroaryl; heterocyclylC$_{1-6}$alkyl; heteroarylC$_{1-6}$alkyl; C$_{1-20}$alkyloxy; C$_{2-20}$alkenyloxy; C$_{3-8}$cycloalkyloxy; C$_{6-12}$arylC$_{1-6}$alkyloxy; C$_{1-20}$alkylamino; and a polymeric group; each group being unsubstituted or substituted with one or more Z$^9$; preferably R$^7$ is selected from the group consisting of C$_{1-20}$alkyl; C$_{2-20}$alkenyl; C$_{6-12}$aryl; C$_{3-8}$cycloalkyl; C$_{6-12}$arylC$_{1-6}$alkyl; and a polymeric group; each group being unsubstituted or substituted with one or more Z$^8$; preferably R$^7$ is selected from the group consisting of C$_{1-20}$alkyl; C$_{6-12}$aryl; C$_{6-12}$arylC$_{1-6}$alkyl; and a polymeric group; each group being unsubstituted or substituted with one or more Z$^9$;

or R$^6$ and R$^7$ together with the carbon atoms to which they are attached form unsaturated 5-, 6-membered ring; preferably an unsaturated 6-membered ring; preferably an unsaturated 6-carbon atoms ring; which can be unsubstituted or substituted with one or more Z$^9$;

R$^9$ is independently selected from the group consisting of hydroxyl; C$_{1-10}$alkyl, C$_{2-10}$alkenyl, C$_{6-12}$aryl, C$_{6-12}$aryl C$_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each R$^9$ is independently selected from the group consisting of hydroxyl; C$_{1-6}$alkyl, C$_{2-6}$alkenyl, C$_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

R$^{10}$ is independently selected from the group consisting of hydrogen; C$_{1-10}$alkyl, C$_{2-10}$alkenyl, C$_{6-12}$aryl, C$_{6-12}$aryl C$_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each R$^{10}$ is independently selected from the group consisting of hydrogen; C$_{1-6}$alkyl, C$_{2-6}$alkenyl, C$_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each R$^{11}$ and R$^{12}$ is independently selected from the group consisting of hydrogen; C$_{1-10}$alkyl, C$_{2-10}$alkenyl, C$_{6-12}$aryl, C$_{6-12}$arylC$_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each R$^{11}$ and R$^{12}$ is independently selected from the group consisting of hydrogen; C$_{1-6}$alkyl, C$_{2-6}$alkenyl, C$_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

R$^{13}$ and R$^{14}$ is independently selected from the group consisting of hydrogen; C$_{1-10}$alkyl, C$_{2-10}$alkenyl, C$_{6-12}$aryl, C$_{6-12}$arylC$_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{13}$ and $R^{14}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

$R^{15}$ is selected from the group consisting of halo; hydrogen, hydroxyl, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; $C_{1-20}$alkyloxy; $C_{2-20}$alkenyloxy; $C_{3-8}$cycloalkyloxy; $C_{6-12}$aryl$C_{1-6}$alkyloxy; $C_{1-20}$alkylamino; and a polymeric group; each group being unsubstituted or substituted with one or more $Z^{10}$; wherein at least one carbon atom or heteroatom of said group can be oxidized to form at least one C=O, S=O or $S(O)_2$; preferably $R^{15}$ is selected from the group consisting of hydrogen; hydroxyl; halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^{10}$; wherein at least one carbon atom of said group can be oxidized to form at least one C=O; preferably $R^{15}$ is selected from the group consisting of hydrogen, hydroxyl; halo; $C_{1-20}$alkyl; $C_{6-12}$aryl; $C_{6-12}$aryl$C_{1-6}$alkyl; and a polymeric group; each group being unsubstituted or substituted with one or more $Z^{10}$; wherein at least one carbon atom of said group can be oxidized to form at least one C=O;

each $R^{16}$ and $R^{17}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{16}$ and $R^{17}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

$R^{18}$ is selected from the group consisting of hydrogen, $C_{1-10}$alkyl; $C_{6-12}$aryl; $C_{6-12}$aryl$C_{1-6}$alkyl; $C_{6-12}$aryl$C_{1-6}$alkyl$C_{6-12}$aryl; heteroaryl$C_{1-6}$alkyl; and a polymeric group; wherein each group can be unsubstituted or substituted with one or more $Z^{11}$; wherein each group optionally comprises one or more heteroatoms in the alkyl moiety, said heteroatoms being each independently selected from O, S or N; preferably $R^{18}$ is selected from the group consisting of $C_{1-10}$alkyl; $C_{6-12}$aryl; $C_{6-12}$aryl$C_{1-6}$alkyl; $C_{6-12}$aryl$C_{1-6}$alkyl$C_{6-12}$aryl; and a polymeric group; wherein each group can be unsubstituted or substituted with one or more $Z^{11}$; wherein each group optionally comprises one or more heteroatoms in the alkyl moiety, said heteroatoms being each independently selected from O, or N; preferably $R^{18}$ is selected from the group consisting of hydrogen, $C_{1-10}$alkyl; $C_{6-12}$aryl; $C_{6-12}$aryl$C_{1-6}$alkyl$C_{6-12}$aryl; and a polymeric group; wherein each group can be unsubstituted or substituted with one or more $Z^{11}$; wherein each group optionally comprises one or more heteroatoms in the alkyl moiety, said heteroatoms being each independently selected from O, or N; preferably $R^{18}$ is $C_{6-12}$aryl which can be unsubstituted or substituted with one or more $Z^{11}$; preferably $R^{18}$ is hydrogen or $C_{1-10}$alkyl; which can be unsubstituted or substituted with one or more $Z^{11}$; wherein the alkyl optionally comprises one or more N or O; preferably $R^{18}$ is $C_{6-12}$aryl$C_{1-6}$ alkyl $C_{6-12}$aryl; which can be unsubstituted or substituted with one or more $Z^{11}$; wherein each group optionally comprises one or more N or S in the alkyl moiety, preferably $R^{18}$ is a polymeric group which can be unsubstituted or substituted with one or more $Z^{11}$;

$Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; —$OR^{10}$; nitro; —$NR^{10}C(O)R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; or a polymeric group; preferably $Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo $C_{1-6}$alkyloxy; —$OR^{10}$; nitro; —$NR^{10}C(O)R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; or a polymeric group; preferably $Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo $C_{1-6}$alkyl; halo$C_{1-6}$alkyloxy; nitro; —$NR^{10}C(O)R^9$; —$NR^{10}C(O)NR^{11}R^{12}$; $NR^{11}R^{12}$; cyano; —$CO_2R^{10}$; —$C(O)NR^{11}R^{12}$; or a polymeric group;

and wherein for each of $R^1$, $R^2$, $R^3$, $R^4$, $R^5$, $R^6$, $R^7$, $R^{15}$, $R^{18}$, $Z^1$, $Z^2$, $Z^3$, $Z^4$, $Z^5$, $Z^6$, $Z^7$, $Z^8$, $Z^9$, $Z^{10}$, $Z^{11}$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

According to an embodiment, the present invention provides compounds of formula (I), (IA), (IB), (IC); and any subgroup thereof wherein, $L^1$ is $C_{1-10}$alkylene; or $C_{2-10}$alkenylene; preferably, $L^1$ is $C_{1-10}$alkylene; wherein said alkylene or alkenylene optionally comprises one or more, for example 1, 2 or 3 heteroatoms in the alkylene, or alkenylene moiety said heteroatoms being each independently selected from O, S and N;

$Q^1$ is a single bond or is selected from the group consisting of —OC(O)—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; preferably $Q^1$ is selected from the group consisting of —OC(O)—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; wherein q is an integer selected from 1 or 2; for example 1;

p is an integer selected from 0 or 1; for example 1;

$L^4$ is a single bond or is $C_{1-10}$alkylene; preferably $L^4$ is $C_{1-10}$alkylene; for example $C_{1-6}$alkylene, for example $C_{1-6}$alkylene, for example $C_{1-4}$alkylene, wherein said $C_{1-10}$alkylene; optionally comprises one or more, for example 1, 2 or 3 heteroatoms in the alkylene, alkenylene, said heteroatoms being each independently selected from O, S and N; preferably wherein said $C_{1-10}$alkylene; optionally comprises one or more, for example 1, 2 or 3 heteroatoms, said heteroatoms being each independently selected from O, and N; preferably wherein said $C_{1-10}$alkylene can be unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; and a polymeric group; preferably $R^1$ is selected from the group consisting of $C_{2-10}$alkyl; $C_{6-12}$aryl; $C_{6-12}$aryl$C_{1-6}$alkyl$C_{6-12}$aryl; and a polymeric group; wherein said group optionally comprises one or more heteroatoms in the alkyl moiety, said heteroatoms being each independently selected from O, S or N; wherein at least one carbon atom of said group can be oxidized to form at least one C=O; wherein said group can be unsubstituted or substituted with one or more $Z^3$;

or $R^1$ is a group of formula -L$^2$-Q$^2$-R$^{18}$ wherein $L^2$ is $C_{1-10}$alkylene; or $C_{6-12}$arylene; each being unsubstituted or substituted with one or more $Z^4$; preferably $L^2$ is $C_{1-10}$alkylene unsubstituted or substituted with one or more $Z^4$; preferably $L^2$ is $C_{6-12}$arylene unsubstituted or substituted with one or more $Z^4$;

$Q^2$ is selected from the group consisting of $C_{1-6}$alkylene; —OC(O)—; —NH—C(O)—; —NH—C(O)—[CR$^{13}$R$^{14}$]$_q$—; wherein said $C_{1-6}$alkylene, optionally comprises one or more heteroatoms, said heteroatoms being each independently selected from O, S and N; and wherein said $C_{1-6}$alkylene can be unsubstituted or substituted with one or more $Z^5$;

or $Q^2$ is a group of formula (ii);

or $Q^2$-R$^{18}$ is a group of formula (iii);

wherein $L^3$ is $C_{1-10}$alkylene; or $C_{6-12}$arylene; each being unsubstituted or substituted with one or more $Z^6$; preferably $L^3$ is $C_{1-10}$alkylene unsubstituted or substituted with one or more $Z^6$; preferably $L^3$ is $C_{6-12}$arylene unsubstituted or substituted with one or more $Z^6$;

$R^2$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$ and each group optionally comprises one or more O, or N in the alkyl moiety; preferably $R^2$ is selected from the group consisting of halo; $C_{1-20}$alkyl; $C_{6-12}$aryl; $C_{6-12}$aryl$C_{1-6}$alkyl; and a polymeric group; each group being unsubstituted or substituted with one or more $Z^7$; and each group optionally comprises one or more O or N in the alkyl moiety;

$R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$ and each group optionally comprises one or more O, or N in the alkyl moiety; preferably $R^3$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$; and each group optionally comprises one or more O or N in the alkyl moiety;

$R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$ and each group optionally comprises one or more O, or N in the alkyl moiety; preferably $R^4$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$; and each group optionally comprises one or more O or N in the alkyl moiety;

or $R^2$ and $R^3$ and $R^4$ together with the carbon atom to which they are attached can form saturated or unsaturated 5-, 6-membered ring; for example a phenyl ring;

or $R^2$ and $L^1$ together with the carbon atom to which they are attached can form a saturated or unsaturated 5-, or 6-, membered ring;

$R^5$ is selected from the group consisting of hydrogen, hydroxyl, halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^8$ and each group optionally comprises one or more O, or N in the alkyl moiety; wherein at least one carbon atom of said group can be oxidized to form at least one C=O; preferably $R^5$ is selected from the group consisting of halo; hydrogen, hydroxyl, $C_{1-20}$alkyl; $C_{6-12}$aryl; $C_{6-12}$aryl$C_{1-6}$alkyl; and a polymeric group; each group being unsubstituted or substituted with one or more $Z^8$; and each group optionally comprises one or more O or N in the alkyl moiety; wherein at least one carbon atom of said group can be oxidized to form at least one C=O;

$R^6$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^9$ and each group optionally comprises one or more O, or N in the alkyl moiety; preferably $R^6$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;

$R^7$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^9$ and each group optionally comprises one or more O, or N in the alkyl moiety; preferably $R^7$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;

or $R^6$ and $R^7$ together with the carbon atoms to which they are attached form unsaturated 6-membered ring; preferably an unsaturated 6-carbon atoms ring; which can be unsubstituted or substituted with one or more $Z^9$;

each $R^9$ is independently selected from the group consisting of hydroxyl; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{10}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{11}$ and $R^{12}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{13}$ and $R^{14}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

$R^{15}$ is selected from the group consisting of hydrogen, hydroxyl, halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^{10}$ and each group optionally comprises one or more O, or N in the alkyl moiety; wherein at least one carbon atom of said group can be oxidized to form at least one C=O; preferably $R^{15}$ is selected from the group consisting of halo; hydrogen, hydroxyl, $C_{1-20}$alkyl; $C_{6-12}$aryl; $C_{6-12}$aryl$C_{1-6}$alkyl; and a polymeric group; each group being unsubstituted or substituted with one or more $Z^{10}$; and each group optionally comprises one or more O or N in the alkyl moiety; wherein at least one carbon atom of said group can be oxidized to form at least one C=O;

each $R^{16}$ and $R^{17}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

$R^{18}$ is selected from the group consisting of hydrogen, $C_{1-10}$alkyl; $C_{6-12}$aryl; $C_{6-12}$aryl$C_{1-6}$alkyl; $C_{6-12}$aryl$C_{1-6}$alkyl$C_{6-12}$aryl; and a polymeric group; wherein each group can be unsubstituted or substituted with one or more $Z^{11}$; wherein each group optionally comprises one or more heteroatoms in the alkyl moiety, said heteroatoms being each independently selected from O, or N; preferably $R^{18}$ is selected from the group consisting of $C_{1-10}$alkyl; $C_{6-12}$aryl; $C_{6-12}$aryl$C_{1-6}$alkyl$C_{6-12}$aryl; and a polymeric group; wherein each group can be unsubstituted or substituted with one or more $Z^{11}$; wherein each group optionally comprises one or more heteroatoms in the alkyl moiety, said heteroatoms being each independently selected from O, or N; preferably $R^{18}$ is $C_{6-12}$aryl which can be unsubstituted or substituted with one or more $Z^{11}$; preferably $R^{18}$ is hydrogen or $C_{1-10}$alkyl; which can be unsubstituted or substituted with one or more $Z^{11}$; wherein the alkyl optionally comprises one or more N or O; preferably $R^{18}$ is $C_{6-12}$aryl$C_{1-6}$alkyl $C_{6-12}$aryl; which can be unsubstituted or substituted with one or more $Z^{11}$; wherein each group optionally comprises one or more N or S in the alkyl moiety, preferably $R^{18}$ is a polymeric group which can be unsubstituted or substituted with one or more $Z^{11}$;

$Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; —$OR^{10}$; nitro; —$NR^{10}C(O)R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; or a polymeric group; preferably $Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo $C_{1-6}$alkyloxy; nitro; —$NR^{10}C(O)R^9$; —$NR^{10}C(O)NR^{11}R^{12}$; $NR^{11}R^{12}$; cyano; —$CO_2R^{10}$; —$C(O)NR^{11}R^{12}$; or a polymeric group; and wherein for each of $R^1$, $R^2$, $R^3$, $R^4$, $R^5$, $R^6$, $R^7$, $R^{15}$, $R^{18}$, $Z^1$, $Z^2$, $Z^3$, $Z^4$, $Z^5$, $Z^6$, $Z^7$, $Z^8$, $Z^9$, $Z^{10}$, $Z^{11}$ said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

According to an embodiment, the present invention provides compounds of formula (I), (IA), (IB), (IC); and any subgroup thereof wherein, $L^1$ is selected from the group consisting of $C_{1-10}$alkylene; $C_{2-10}$alkenylene; $C_{2-10}$alkynylene; $C_{1-10}$alkyleneoxy; $C_{2-10}$alkenyleneoxy; $C_{2-10}$alkynyleneoxy; $C_{1-5}$alkyleneoxy$C_{0-5}$alkylene; $C_{2-5}$alkenyleneoxy$C_{0-5}$alkenylene; $C_{2-5}$alkynyleneoxy$C_{0-5}$alkynylene; $C_{1-10}$alkyleneamino; $C_{2-10}$alkenyleneamino; $C_{2-10}$alkynyleneamino; $C_{1-5}$alkyleneamino$C_{0-5}$alkylene; $C_{2-5}$alkenyleneamino$C_{0-5}$alkenylene; $C_{2-5}$alkynyleneamino$C_{0-5}$alkynylene; $C_{1-10}$alkylenethio; $C_{2-10}$alkenylenethio; $C_{2-10}$alkynylenethio; $C_{1-5}$alkylenethio$C_{0-5}$alkylene; $C_{2-5}$alkenylenethio$C_{0-5}$alkenylene; $C_{2-5}$alkynylenethio$C_{0-5}$alkynylene; each group being unsubstituted or substituted with one or more $Z^1$; more preferably $L^1$ is selected from the group consisting of $C_{1-10}$alkylene; $C_{2-10}$alkenylene; $C_{1-10}$alkyleneoxy; $C_{2-10}$alkenyleneoxy; $C_{1-10}$alkyleneamino; $C_{2-10}$alkenyleneamino; each group being unsubstituted or substituted with one or more $Z^1$; more preferably $L^1$ is selected from the group consisting of $C_{1-10}$alkylene; $C_{1-10}$alkyleneoxy; and $C_{1-10}$alkyleneamino; each group being unsubstituted or substituted with one or more $Z^1$;

$Q^1$ is a single bond or is selected from the group consisting of —OC(O)—; —OC(O)—[$CR^{13}R^{14}$]$_q$—; and —OC(O)—[$C(R^{13})(L^4$-O—$R^{15}$)]$_q$—[$CR^{16}R^{17}$]$_p$—O—; preferably $Q^1$ is selected from the group consisting of —OC(O)—; —OC(O)—[$CR^{13}R^{14}$]$_q$—; and —OC(O)—[$C(R^{13})(L^4$-O—$R^{15}$)]$_q$—[$CR^{16}R^{17}$]$_p$—O—; wherein q is an integer selected from 1 or 2; for example 1;
p is an integer selected from 0 or 1; for example 1;
$L^4$ is selected from the group consisting of $C_{1-10}$alkylene; $C_{1-10}$alkyleneoxy; and $C_{1-10}$alkyleneamino; each group being unsubstituted or substituted with one or more $Z^2$;
$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; a polymeric group; each group being unsubstituted or substituted with one or more $Z^3$; wherein at least one carbon atom of each of said group can be oxidized to form at least one C=O;

or $R^1$ is a group of formula $-L^2-Q^2-R^{18}$ wherein
wherein,
$L^2$ is selected from the group consisting of $C_{1-10}$alkylene; $C_{1-10}$alkyleneoxy; and $C_{1-10}$alkyleneamino; each group being unsubstituted or substituted with one or more $Z^4$;
$Q^2$ is selected from the group consisting of $C_{1-10}$alkylene; —OC(O)—; —NH—C(O)—; each group being unsubstituted or substituted with one or more $Z^5$;
or $Q^2$ is a group of formula (ii);
or $Q^2-R^{18}$ is a group of formula (iii);
$L^3$ is selected from the group consisting of $C_{1-10}$alkylene; $C_{1-10}$alkyleneoxy; and $C_{1-10}$alkyleneamino; each group being unsubstituted or substituted with one or more $Z^6$;
$R^2$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$; preferably $R^2$ is selected from the group consisting of halo; $C_{1-20}$alkyl; $C_{6-12}$aryl; $C_{6-12}$aryl$C_{1-6}$alkyl; and a polymeric group; each group being unsubstituted or substituted with one or more $Z^7$
$R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$; preferably $R^3$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$;
$R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$; preferably $R^4$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$;
or $R^2$ and $R^3$ and $R^4$ together with the carbon atom to which they are attached can a phenyl ring;
$R^5$ is selected from the group consisting of hydrogen, hydroxyl; halo; $C_{1-20}$alkyl; $C_{6-12}$aryl; $C_{6-12}$aryl$C_{1-6}$alkyl; and a polymeric group; each group being unsubstituted or substituted with one or more $Z^8$; wherein at least one carbon atom of said group can be oxidized to form at least one C=O;
$R^6$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^8$; preferably $R^6$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;
$R^7$ is selected from the group consisting of $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^8$; preferably $R^7$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;
or $R^6$ and $R^7$ together with the carbon atoms to which they are attached form an unsaturated 6-carbon atoms ring; which can be unsubstituted or substituted with one or more $Z^9$;
each $R^9$ is independently selected from the group consisting of hydroxyl; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

$R^{10}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;
each $R^{11}$ and $R^{12}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;
each $R^{13}$ and $R^{14}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;
$R^{15}$ is selected from the group consisting of hydrogen; hydroxyl; halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^{10}$; wherein at least one carbon atom of said group can be oxidized to form at least one C=O; preferably $R^{15}$ is selected from the group consisting of hydrogen, hydroxyl; halo; $C_{1-20}$alkyl; $C_{6-12}$aryl; $C_{6-12}$aryl$C_{1-6}$alkyl; and a polymeric group; each group being unsubstituted or substituted with one or more $Z^{10}$; wherein at least one carbon atom of said group can be oxidized to form at least one C=O;
each $R^{16}$ and $R^{17}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;
$R^{18}$ is selected from the group consisting of $C_{1-10}$alkyl; $C_{6-12}$aryl; $C_{6-12}$aryl$C_{1-6}$alkyl; $C_{6-12}$aryl$C_{1-6}$alkyl$C_{6-12}$aryl; and a polymeric group; wherein each group can be unsubstituted or substituted with one or more $Z^{11}$; wherein each group optionally comprises one or more heteroatoms in the alkyl moiety, said heteroatoms being each independently selected from O, or N; preferably $R^{18}$ is selected from the group consisting of hydrogen, $C_{1-10}$alkyl; $C_{6-12}$aryl; $C_{6-12}$aryl$C_{1-6}$alkyl$C_{6-12}$aryl; and a polymeric group; wherein each group can be unsubstituted or substituted with one or more $Z^{11}$; wherein each group optionally comprises one or more heteroatoms in the alkyl moiety, said heteroatoms being each independently selected from O, or N; preferably $R^{18}$ is $C_{6-12}$aryl which can be unsubstituted or substituted with one or more $Z^{11}$; preferably $R^{18}$ is hydrogen or $C_{1-10}$alkyl; which can be unsubstituted or substituted with one or more $Z^{11}$; wherein the alkyl optionally comprises one or more N or O; preferably $R^{18}$ is $C_{6-12}$aryl$C_{1-6}$alkyl$C_{6-12}$aryl; which can be unsubstituted or substituted with one or more $Z^{11}$; wherein each group optionally comprises one or more N or S in the alkyl moiety, preferably $R^{18}$ is a polymeric group which can be unsubstituted or substituted with one or more $Z^{11}$;
$Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; —OR$^{10}$; nitro; —NR$^{10}$C(O)R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; or a polymeric group; preferably $Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; nitro; $-NR^{10}C(O)R^9$; $-NR^{10}C(O)NR^{11}R^{12}$; $NR^{11}R^{12}$; cyano; $-CO_2R^{10}$; $-C(O)NR^{11}R^{12}$; or a polymeric group;

and wherein for each of $R^1$, $R^2$, $R^3$, $R^4$, $R^5$, $R^6$, $R^7$, $R^{15}$, $R^{18}$, $Z^1$, $Z^2$, $Z^3$, $Z^4$, $Z^5$, $Z^6$, $Z^7$, $Z^8$, $Z^9$, $Z^{10}$, $Z^{11}$ said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

According to an embodiment, the present invention provides compounds of formula (I), (IA), (IB), (IC); and any subgroup thereof wherein, $L^1$ is $C_{1-10}$alkylene; wherein said alkylene optionally comprises one or more, for example 1 or 2 O or N heteroatoms;

$Q^1$ is selected from the group consisting of $-OC(O)-$; $-OC(O)-[CR^{13}R^{14}]_q-$; and $-OC(O)-[C(R^{13})(L^4-O-R^{15})]_q-[CR^{18}R^{17}]_p-O-$; wherein q is an integer selected from 1 or 2; for example 1; p is an integer selected from 0 or 1; for example 1;

$L^4$ is $C_{1-10}$alkylene; for example $C_{1-6}$alkylene, for example $C_{1-6}$alkylene, for example $C_{1-4}$alkylene, wherein said alkylene; optionally comprises one or more, for example 1 or 2 N or O heteroatoms; wherein said alkylene can be unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl$C_{6-12}$aryl; and a polymeric group; wherein said group optionally comprises one or more heteroatoms in the alkyl moiety, said heteroatoms being each independently selected from O, S or N; wherein at least one carbon atom of said group can be oxidized to form at least one C=O; wherein said group can be unsubstituted or substituted with one or more $Z^3$;

or $R^1$ is a group of formula -$L^2$-$Q^2$-$R^{18}$ wherein $L^2$ is $C_{1-10}$alkylene unsubstituted or substituted with one or more $Z^4$; preferably $L^2$ is $C_{6-12}$arylene unsubstituted or substituted with one or more $Z^4$;

$Q^2$ is selected from the group consisting of $C_{1-6}$alkylene; $-OC(O)-$; $-NH-C(O)-$; wherein said $C_{1-6}$alkylene, optionally comprises 1 or 2 N or O heteroatoms, and wherein said $C_{1-6}$alkylene can be unsubstituted or substituted with one or more $Z^5$;

or $Q^2$ is a group of formula (ii);

or $Q^2$-$R^{18}$ is a group of formula (iii);

wherein $L^3$ is $C_{1-10}$alkylene unsubstituted or substituted with one or more $Z^6$; preferably $L^3$ is $C_{6-12}$arylene unsubstituted or substituted with one or more $Z^6$;

$R^2$ is selected from the group consisting of halo; $C_{1-20}$alkyl; $C_{6-12}$aryl; $C_{6-12}$aryl$C_{1-6}$alkyl; and a polymeric group; each group being unsubstituted or substituted with one or more $Z^7$; and each group optionally comprises one or more O or N in the alkyl moiety;

$R^3$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$; and each group optionally comprises one or more O or N in the alkyl moiety;

$R^4$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$; and each group optionally comprises one or more O or N in the alkyl moiety;

or $R^2$ and $R^3$ and $R^4$ together with the carbon atom to which they are attached can form a phenyl ring;

$R^5$ is selected from the group consisting of halo; hydrogen, hydroxyl, $C_{1-20}$alkyl; $C_{6-12}$aryl; $C_{6-12}$aryl$C_{1-6}$alkyl; and a polymeric group; each group being unsubstituted or substituted with one or more $Z^8$; and each group optionally comprises one or more O or N in the alkyl moiety; wherein at least one carbon atom of said group can be oxidized to form at least one C=O;

$R^6$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;

$R^7$ is selected from the group consisting of $C_{1-20}$alkyl; $C_{6-12}$aryl; $C_{6-12}$aryl$C_{1-6}$alkyl; and a polymeric group; each group being unsubstituted or substituted with one or more $Z^9$;

or $R^6$ and $R^7$ together with the carbon atoms to which they are attached form unsaturated 6-carbon atoms ring; which can be unsubstituted or substituted with one or more $Z^9$;

each $R^9$ is independently selected from the group consisting of hydroxyl; $C_{1-6}$alkyl, and $C_{6-12}$aryl;

each $R^{19}$ is independently selected from the group consisting of hydrogen; $C_{1-6}$alkyl, and $C_{6-12}$aryl;

each $R^{11}$ and $R^{12}$ is independently selected from the group consisting of hydrogen; $C_{1-6}$alkyl, and $C_{6-12}$aryl;

each $R^{13}$ and $R^{14}$ is independently selected from the group consisting of hydrogen; $C_{1-6}$alkyl, and $C_{6-12}$aryl;

$R^{15}$ is selected from the group consisting of halo; hydrogen, hydroxyl, $C_{1-20}$alkyl; $C_{6-12}$aryl; $C_{6-12}$aryl$C_{1-6}$alkyl; and a polymeric group; each group being unsubstituted or substituted with one or more $Z^{10}$; and each group optionally comprises one or more O or N in the alkyl moiety; wherein at least one carbon atom of said group can be oxidized to form at least one C=O;

each $R^{16}$ and $R^{17}$ is independently selected from the group consisting of hydrogen; $C_{1-6}$alkyl, $C_{6-12}$aryl $R^{18}$ is selected from the group consisting of $C_{1-10}$alkyl; $C_{6-12}$aryl; $C_{6-12}$aryl$C_{1-6}$alkyl$C_{6-12}$aryl; and a polymeric group; wherein each group can be unsubstituted or substituted with one or more $Z^{11}$; wherein each group optionally comprises one or more heteroatoms in the alkyl moiety, said heteroatoms being each independently selected from O, or N; preferably $R^{18}$ is $C_{6-12}$aryl which can be unsubstituted or substituted with one or more $Z^{11}$; preferably $R^{18}$ is hydrogen or $C_{1-10}$alkyl; which can be unsubstituted or substituted with one or more $Z^{11}$; wherein the alkyl optionally comprises one or more N or O; preferably $R^{18}$ is $C_{6-12}$aryl$C_{1-6}$alkyl$C_{6-12}$aryl; which can be unsubstituted or substituted with one or more $Z^{11}$; wherein each group optionally comprises one or more N or S in the alkyl moiety, preferably $R^{18}$ is a polymeric group which can be unsubstituted or substituted with one or more $Z^{11}$;

$Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; nitro; —$NR^{10}C(O)R^9$; —$NR^{10}C(O)NR^{11}R^{12}$; $NR^{11}R^{12}$; cyano; —$CO_2R^{10}$; —$C(O)NR^{11}R^{12}$; or a polymeric group;

and wherein for each of $R^1$, $R^2$, $R^3$, $R^4$, $R^5$, $R^6$, $R^7$, $R^{15}$, $R^{18}$, $Z^1$, $Z^2$, $Z^3$, $Z^4$, $Z^5$, $Z^6$, $Z^7$, $Z^8$, $Z^9$, $Z^{10}$, $Z^{11}$ said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

The present invention also encompasses processes for the preparation of compounds Formula (I) and any subgroup thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds Formula (I) and the subgroups thereof can be prepared as described hereunder.

In the general schemes described below, all substituents are defined as in the general Formula (I), (IA), (IB), (IC) or any subgroups thereof, unless otherwise mentioned or indicated.

Compounds of formula (I) can be prepared as illustrated in Scheme 1 by contacting a compound of formula (II) with a compound of formula (III), thereby obtaining a compound of formula (I).

Scheme 1. wherein $R^1$, $R^2$, $R^3$, $R^4$, $R^5$, $L^1$, $Q^1$, $Z^9$ have the same meaning as defined herein

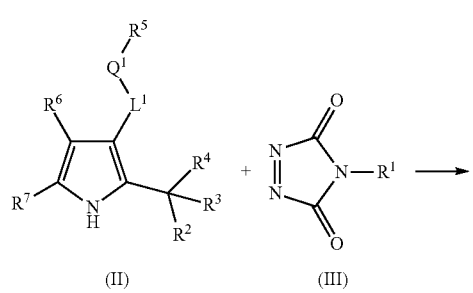

-continued

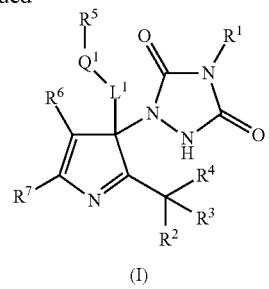

The process illustrated in Scheme 1 can take place at low temperature (<20° C.), without the need for a catalyst. Preferably, the process illustrated in Scheme 1 takes place at room temperature. In another embodiment, the process comprising the step of contacting a compound of formula (II) with a compound of formula (III) occurs at a temperature of at most 29° C., thereby forming a compound of formula (I).

In an embodiment, the step of contacting a compound of formula (II) with a compound of formula (III) is performed at equimolar conditions.

One of the advantages of this process is the intense color of triazolinedione compounds, providing a very useful visual feedback system to the progress of the process, as most of the corresponding urazoles are colorless.

The above general process is illustrated by the following more specific processes illustrated by the below Schemes, which describe the preparation of various subgroups of compounds of formula (I). The intermediates used in the preparation methods described herein are encompasses by the present invention.

Some of the intermediates of formula (II) are commercially available, others may be synthesized by procedures as set forth in the examples section.

Some of the intermediates of formula (III) are commercially available or may be synthesized by procedures such as the procedures described in Org. Synth., 1988, 50-9, 936-940; Monatsh. Chem., 2008, 139, 261-265) or as set forth in the examples section.

In an embodiment, the present invention provides a process for the preparation of intermediates of formula (III), which comprises the steps of contacting ethyl carbazate (IV, CAS number 4114-31-2), with an isocyanate of formula (V), to afford urazole of structure (VI), which is then oxidized, to afford intermediate (III) (Scheme 2).

Scheme 2: wherein $R^1$ has the same meaning as defined herein.

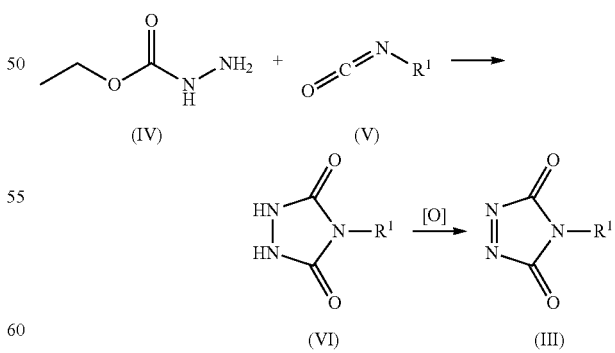

In another embodiment, the present invention provides a process for the preparation of a compound of formula (IA), according to any of the embodiments presented herein above, which comprises the step of contacting a compound of formula (VII) with a compound of formula (III), to obtain a compound of formula (IA) (scheme 3).

Scheme 3. wherein m, r, E, $R^1$, $R^2$, $R^3$, $R^4$, $R^5$, $CR^{19}$, $L^1$, $Q^1$, $Z^9$ have the same meaning as defined herin above

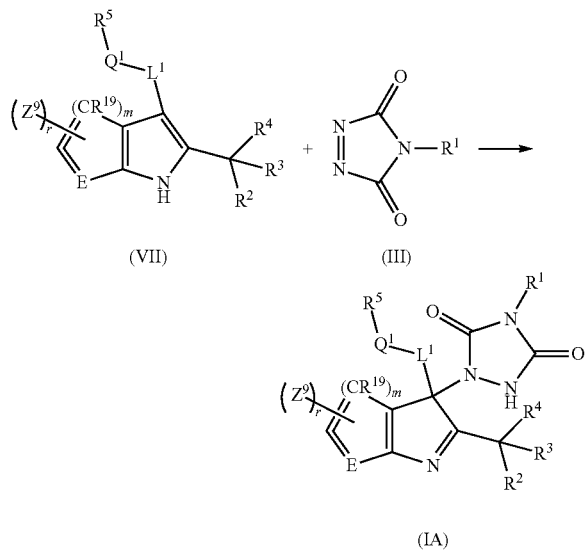

(VII)    (III)

(IA)

The process as illustrated in Scheme 3 can take place at low temperature (<20° C.), without the need for a catalyst. Preferably, the process as illustrated in Scheme 3 takes place at room temperature. In another embodiment, the contacting step occurs at a temperature of at most 29° C. In an embodiment the steps of contacting a compound of formula (VII) with a compound of formula (III) occurs at equimolar conditions Intermediates of formula (VII) may be synthesized by procedures as set forth in the examples section.

In another embodiment, the present invention provides a process for the preparation of a compound of formula (IB), according to any of the embodiments presented herein above, which comprises the step of contacting a compound of formula (IX) with a compound of formula (III), thereby obtaining a compound of formula (IB) (Scheme 4).

Scheme 4. wherein r, $R^1$, $R^2$, $R^3$, $R^4$, $R^5$, $L^1$, $Q^1$, $Z^9$ have the same meaning as defined herein above.

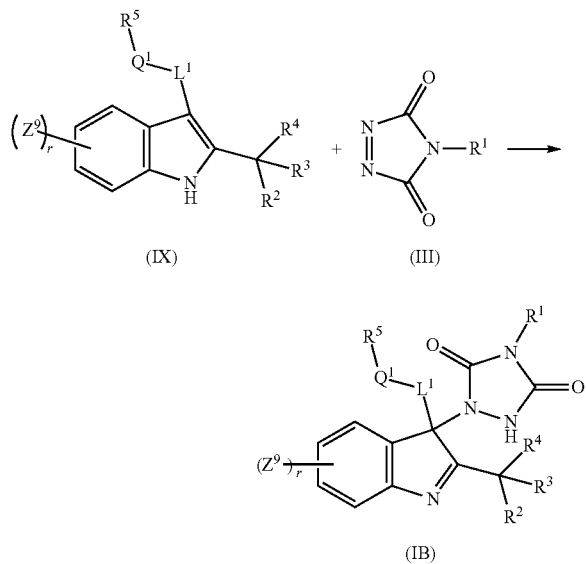

(IX)    (III)

(IB)

The process as illustrated in Scheme 4 can take place at low temperature (<20° C.), without the need for a catalyst. Preferably, the process as illustrated in Scheme 4 takes place at room temperature. In another embodiment, the contacting step occurs at a temperature of at most 29° C. In an embodiment the steps of contacting a compound of formula (IX) with a compound of formula (III) occurs at equimolar conditions Intermediates of formula (IX) are may be as set forth in the examples section.

In an embodiment, the present invention provides a process for the preparation of intermediates of formula (IX), which comprises the steps, (Scheme 5) of contacting aniline of formula (X) with a carbonyl derivative of formula (XI), to afford amide of structure (XII), which is then cyclized, to afford indole (XIII), which in turn is substituted by a compound of formula (XIV), to afford compound of formula (IX).

Scheme 5. wherein LG means a leaving group, and each LG is independently selected; and wherein r, $L^1$, $Q^1$, $R^2$, $R^3$, $R^4$, $R^5$, $Z^9$ have the same meaning as defined herein above.

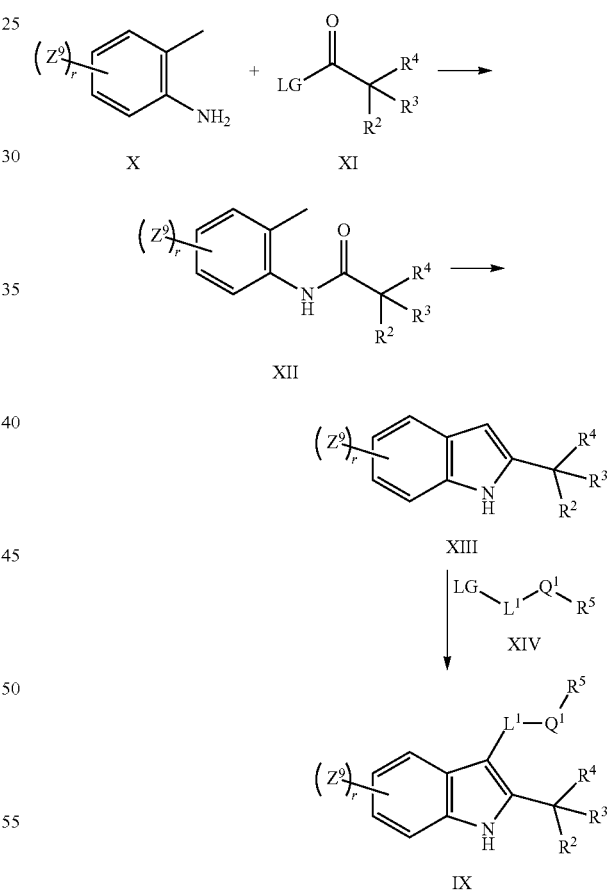

Intermediates of formula (X) are commercially available or may be synthesized by procedures known to the skilled in the art or as set forth in the examples section.

Intermediates of formula (XI) are commercially available or may be synthesized by procedures known to the skilled in the art or as set forth in the examples section.

Intermediates of formula (XII) are commercially available or may be synthesized by procedures known to the skilled in the art or as set forth in the examples section.

Intermediates of formula (XIII) are commercially available or may be synthesized by procedures known to the skilled in the art or as set forth in the examples section.

Intermediates of formula (XIV) are commercially available or may be synthesized by procedures known to the skilled in the art or as set forth in the examples section.

In another embodiment, the present invention provides a process for the preparation of a compound of formula (IC), according to any of the embodiments presented herein above, which comprises the step of contacting a compound of formula (IX) with a compound of formula (III), to obtain a compound of formula (IB) (Scheme 6)

Scheme 6. wherein $R^1$, $R^2$, $R^3$, $R^4$, $R^5$, $L^1$, $Q^1$, have the same meaning as defined herein above.

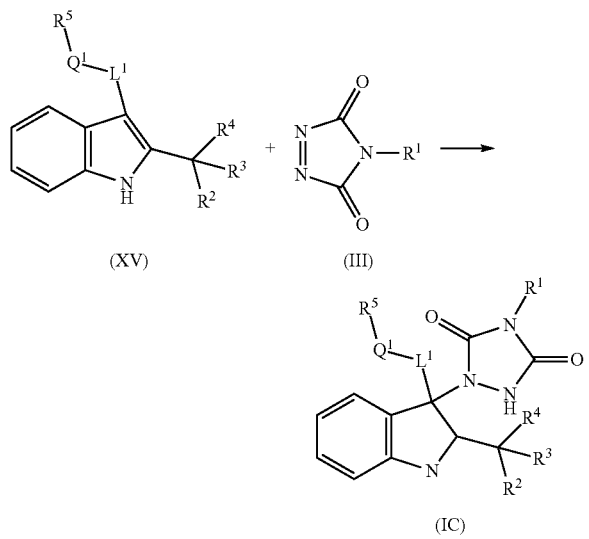

The process as illustrated in Scheme 6 can take place at low temperature (<20° C.), without the need for a catalyst. Preferably, the process as illustrated in Scheme 6 takes place at room temperature. In another embodiment, the contacting step occurs at a temperature of at most 29° C. In an embodiment the steps of contacting a compound of formula (XV) with a compound of formula (III) occurs at equimolar conditions Intermediates of formula (XV) may be synthesized as set forth in the examples section.

In an embodiment, the present invention provides a process for the preparation of intermediates of formula (XV), which comprises the steps of contacting aniline of formula (XVI) with a carbonyl derivative of formula (XI), to afford amide of structure (XVII), which is then cyclized, to afford indole (XVIII), which in turn is substituted by a compound of formula (XIV), to afford compound of formula (XIX) (Scheme 7).

Scheme 7. wherein LG means a leaving group, and each LG is independently selected; and wherein $L^1$, $Q^1$, $R^2$, $R^3$, $R^4$, $R^5$ have the same meaning as defined herein above.

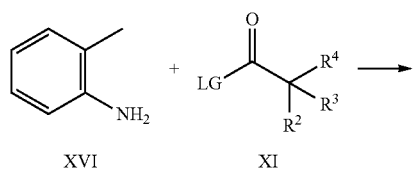

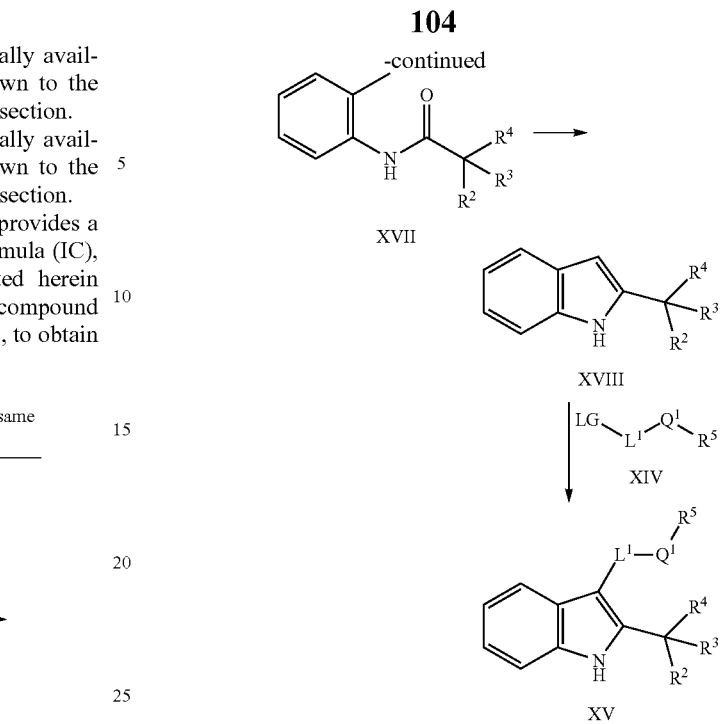

Intermediates of formula (XVI) are commercially available or may be synthesized by procedures known to the skilled in the art or as set forth in the examples section.

Intermediates of formula (XVII) are commercially available or may be synthesized by procedures known to the skilled in the art or as set forth in the examples section.

Intermediates of formula (XVIII) are commercially available or may be synthesized by procedures known to the skilled in the art or as set forth in the examples section.

The present invention also encompasses polyurethane obtained by contacting a compound of formula (I) with at least one isocyanate and with at least one polyol. In some embodiment, the compound of formula (I) comprises alcohol group, in which case the polyol can be optional.

The present invention also encompasses polyurethane obtained by contacting a compound of formula (II), (VII), (IX) or (XV) with at least one isocyanate and with at least one polyol, and then contacting the resulting product with a compound of formula (III). In some embodiment, the compound of formula (II), (VII), (IX) or (XV) can comprise one or more alcohol groups.

Suitable isocyanates for use in the preparation of polyurethane may be aromatic, cycloaliphatic, heterocyclic, araliphatic or aliphatic organic polyisocyanates. Suitable isocyanates are preferably polyisocyanates.

Suitable, polyisocyanates for use in preparing the polyurethane components comprise polyisocyanates of the type $R^y$—$(NCO)_z$ with z being at least 1 and $R^y$ being an aliphatic or aromatic group, such as hexamethylene, dicyclohexylmethane, diphenylmethane, toluene, or a similar polyisocyanate.

Non-limiting examples of suitable polyisocyanates that can be used in the present invention can be any organic polyisocyanate compound or mixture of organic polyisocyanate compounds, preferably wherein said compounds have at least two isocyanate groups. Non-limiting examples of organic polyisocyanates include diisocyanates. Non-limiting examples of organic polyisocyanates which may be used in the formulation of the present invention include aliphatic isocyanates such as hexamethylene diisocyanate; and aromatic isocyanates such as diphenylmethane diisocyanate (MDI) in the form of its 2,4', 2,2' and 4,4' isomers and mixtures thereof, the mixtures of diphenylmethane diisocyanates (MDI) and oligomers thereof, m- and p-phenylene diisocyanate, tolylene-2,4- and tolylene-2,6-diisocyanate (also known as toluene diisocyanate) in any suitable isomer mixture, chlorophenylene-2,4-diisocyanate, naphthylene-1,5-diisocyanate, diphenylene-4,4'-diisocyanate, 4,4'-diisocyanate-3,3'-dimethyl-diphenyl, 3-methyl-diphenylmethane-4,4'-diisocyanate and diphenyl ether diisocyanate; and cycloaliphatic diisocyanates such as cyclohexane-2,4- and -2,3-diisocyanate, 1-methylcyclohexyl-2,4- and -2,6-diisocyanate and mixtures thereof and bis-(isocyanatocyclohexyl)methane (e.g. 4,4'-diisocyanatodicyclohexylmethane (H12MDI)), triisocyanates such as 2,4,6-triisocyanatotoluene and 2,4,4-triisocyanatodiphenylether, isophorone diisocyanate (IPDI), butylene diisocyanate, trimethylhexamethylene diisocyanate, isocyanatomethyl-1,8-octane diisocyanate, tetramethylxylene diisocyanate (TMXDI), 1,4-cyclohexanediisocyanate (CD), and tolidine diisocyanate (TODI); any suitable mixture of these polyisocyanates.

Non-limiting examples of suitable polyols include glycols; a hydroxyl terminated polyether (polyether polyols); hydroxyl terminated polyester (polyester polyols); or mixture thereof, with one or more chain extenders, all of which are well known to those skilled in the art.

Hydroxyl terminated polyether are preferably polyether polyols derived from a diol or polyol having a total of from 2 to 15 carbon atoms, preferably an alkyl diol or glycol which is reacted with an ether comprising an alkylene oxide having from 2 to 6 carbon atoms, typically ethylene oxide or propylene oxide or mixtures thereof. For example, hydroxyl functional polyether can be produced by first reacting propylene glycol with propylene oxide followed by subsequent reaction with ethylene oxide. Useful commercial polyether polyols include poly(ethylene glycol) comprising ethylene oxide reacted with ethylene glycol, poly(propylene glycol) comprising propylene oxide reacted with propylene glycol, poly(tetramethylglycol) (PTMG) comprising water reacted with tetrahydrofuran (THF). Copolyethers can also be utilized in the current invention. Typical copolyethers include the reaction product of glycerol and ethylene oxide or glycerol and propylene oxide.

The hydroxyl terminated polyester (polyester polyols), can be produced by (1) an esterification reaction of one or more glycols with one or more dicarboxylic acids or anhydrides or (2) by transesterification reaction, i.e. the reaction of one or more glycols with esters of dicarboxylic acids. Suitable polyester also includes various lactones such as polycaprolactone typically made from caprolactone and a bifunctional initiator such as diethylene glycol. The dicarboxylic acids of the desired polyester can be aliphatic, cycloaliphatic, aromatic, or combinations thereof. Suitable dicarboxylic acids which can be used alone or in mixtures generally have a total of from 4 to 15 carbon atoms and include: succinic, glutaric, adipic, pimelic, suberic, azelaic, sebacic, dodecanedioic, isophthalic, terephthalic, cyclohexane dicarboxylic, and the like. Anhydrides of the above dicarboxylic acids such as phthalic anhydride, tetrahydrophthalic anhydride, or the like, can also be used. Adipic acid is the preferred acid. The glycols which are reacted to form a desirable polyester intermediate can be aliphatic, aromatic, or combinations thereof, and have a total of from 2 to 12 carbon atoms, and include ethylene glycol, 1,2-propanediol, 1,3-propanediol, 1,3-butanediol, 1,4-butanediol, 1,5-pentanediol, 1,6-hexanediol, 2,2-dimethyl-1,3-propanediol, 1,4-cyclohexanedimethanol, decamethylene glycol, dodecamethylene glycol, and the like. 1,4-Butanediol is the preferred glycol.

In a particular embodiment, said polyurethane can be obtained, by contacting a compound of formula (I) with a polyisocyanate such as hexamethylene diisocyanate (CAS number 822-06-0) and with a polyol such as polypropylene oxide (CAS number 25322-69-4). In another particular embodiment, said polyurethane can obtained as illustrated in Scheme 8, by contacting a compound of formula (XIX) with hexamethylene diisocyanate (XXI, CAS number 822-06-0) and with polypropylene oxide (XX, CAS number 25322-69-4), to afford a polyurethane of formula (XXII).

Scheme 8. wherein $R^1$, $R^2$, $R^3$, $R^4$, $R^5$, $R^6$, $R^7$, $L^1$, have the same meaning as defined herein above.

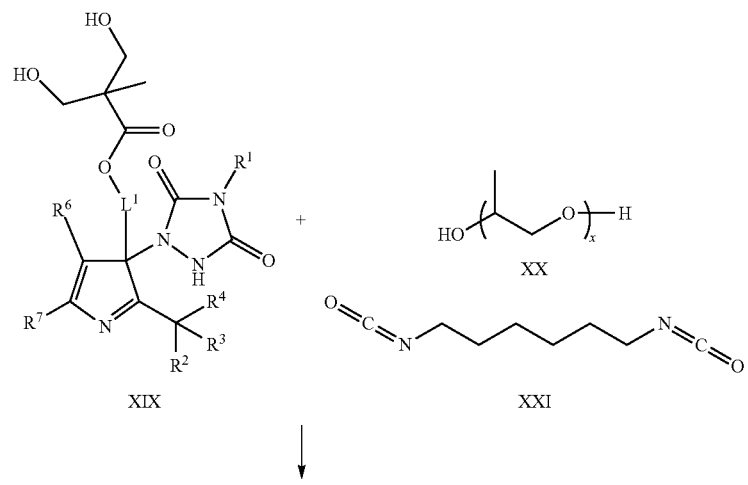

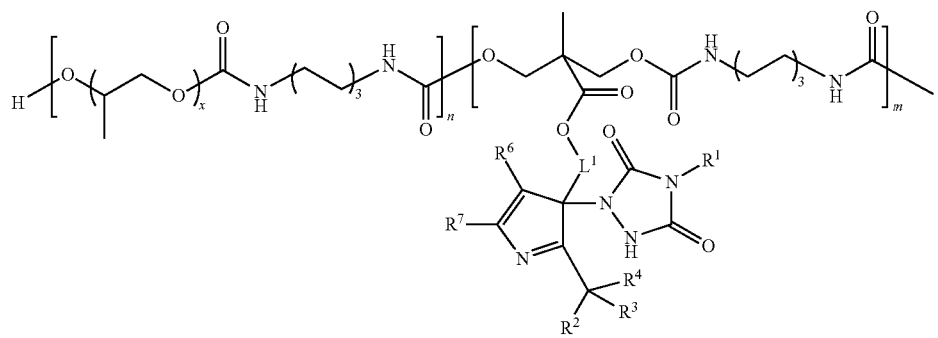

XXII

In a particular embodiment, said polyurethane can be obtained, by contacting a compound of formula (II), (VII), (IX) or (XV) with a polyisocyanate such as hexamethylene diisocyanate (CAS number 822-06-0) and with a polyol such as polypropylene oxide (CAS number 25322-69-4), and then contacting the resulting polymer with a compound of formula (III). In another particular embodiment, said polyurethane can obtained, by contacting a compound of formula (II), (VII), (IX) or (XV) with hexamethylene diisocyanate (XXI, CAS number 822-06-0) and with polypropylene oxide (XX, CAS number 25322-69-4), to afford a polyurethane which can then be contacted with a compound of formula (III). In some embodiment, the compound of formula (II), (VII), (IX) or (XV) comprises one or more alcohol group.

In another particular embodiment, said polyurethane can be obtained as illustrated in Scheme 9, by contacting a compound of formula (LV) with hexamethylene diisocyanate (XXI, CAS number 822-06-0) and with polypropylene oxide (XX, CAS number 25322-69-4), to afford a polyurethane of formula (LVI).

Scheme 9. wherein m, r, E, $CR^{19}$, $R^1$, $R^2$, $R^3$, $R^4$, $R^5$, $R^6$, $R^7$, $Z^9$, $L^1$ have the same meaning as defined herein above.

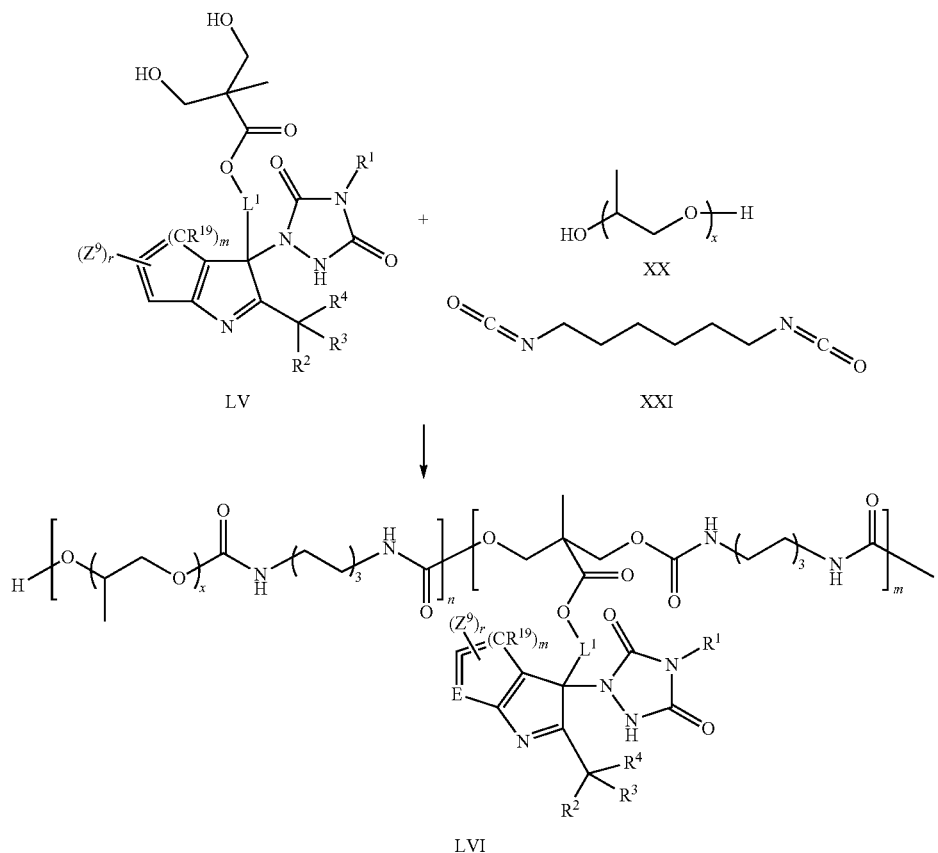

In another particular embodiment, said polyurethane can be obtained as illustrated in Scheme 10, by contacting a compound of formula (XXIII) with hexamethylene diisocyanate (XXI, CAS number 822-06-0) and with polypropylene oxide (XX, CAS number 25322-69-4), to afford a polyurethane of formula (XXIV).

Scheme 10. wherein r, $R^1$, $R^2$, $R^3$, $R^4$, $R^5$, $Z^9$, $L^1$ have the same meaning as defined herein above.

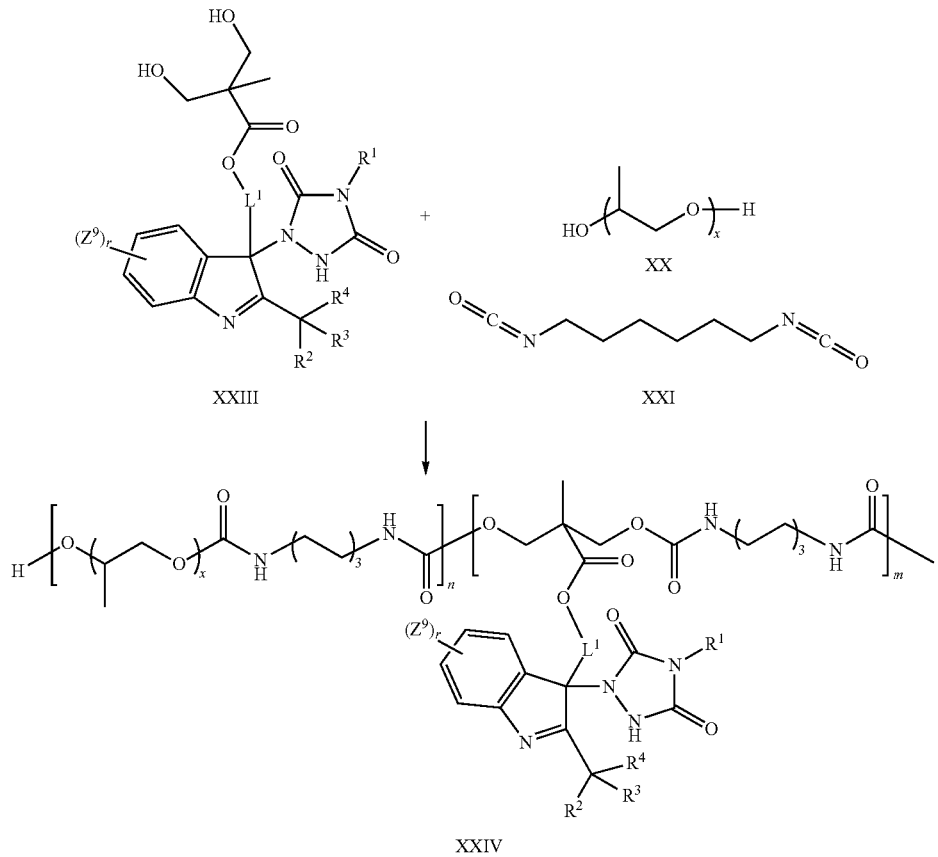

In another particular embodiment, said polyurethane can be obtained as illustrated in Scheme 11, by contacting a compound of formula (XXV) with hexamethylene diisocyanate (XXI, CAS number 822-06-0) and with polypropylene oxide (XX, CAS number 25322-69-4), to afford a polyurethane of formula (XXVI).

Scheme 11. wherein $R^1$, $R^2$, $R^3$, $R^4$, $R^5$, $L^1$ have the same meaning as defined herein above.

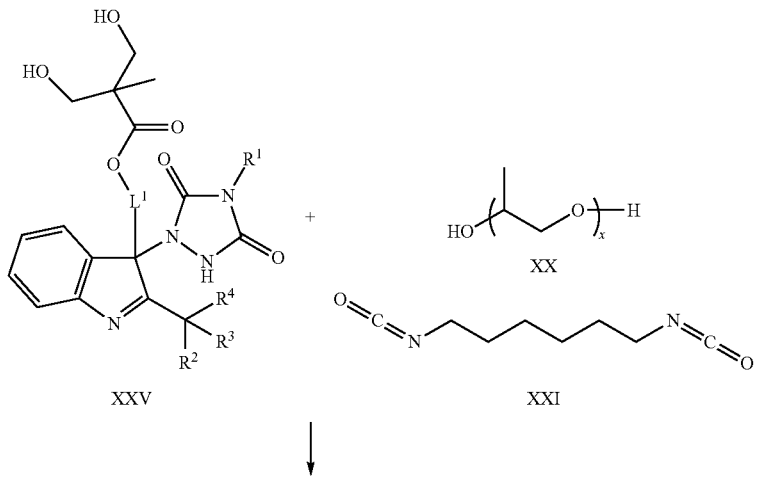

-continued

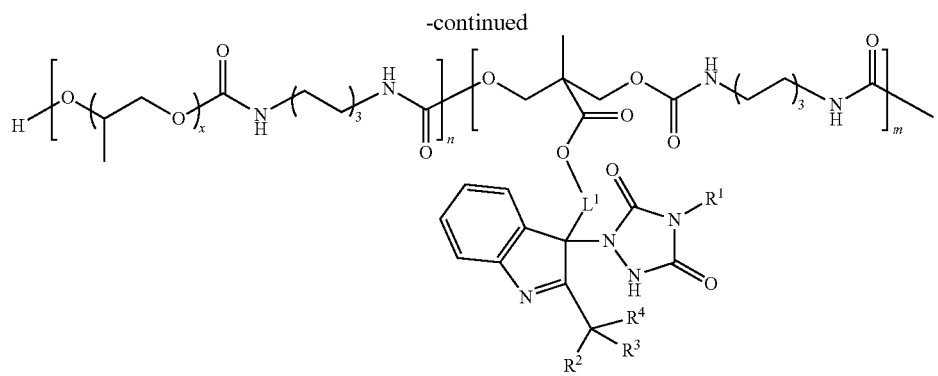

XXVI

The present invention also encompasses a polymer of (meth)acrylate obtained by contacting a compound of formula (I) with an acrylate such as methylmethacrylate (CAS number 80-62-6) and optionally in the presence of ethyl-halo-propionate.

The present invention also encompasses a polymer of an acrylate obtained by contacting a compound of formula (II), (VII), (IX) or (XV) with an acrylate such as methylmethacrylate (CAS number 80-62-6), or butyl acrylate, optionally in the presence of ethyl-halo-propionate or one or more catalysts, and then contacting the resulting product with a compound of formula (III).

In another particular embodiment, said polymer of (meth)acrylate is obtained as illustrated in Scheme 12, by contacting a compound of formula (XXVII) with methylmethacrylate (XXVIII, CAS number 80-62-6) and with ethyl-halo-propionate (XIX), to afford a polymer of (meth)acrylate of formula (XXII).

Scheme 12. wherein X is selected from Br, I or Cl, and wherein $R^1, R^2, R^3, R^4, R^5, R^6, R^7, L^1$, have the same meaning as defined herein above.

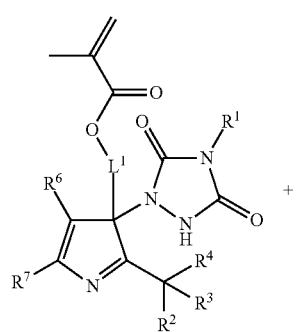

XXVII

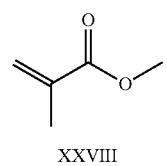

XXVIII

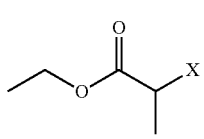

XIX

-continued

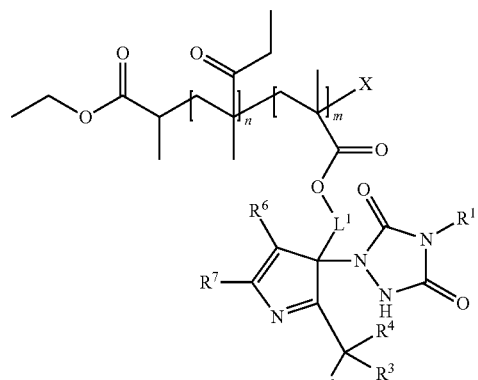

XXX

In another particular embodiment, said polymer of (meth)acrylate can be obtained as illustrated in Scheme 13, by contacting a compound of formula (LVII), with methylmethacrylate (XXVIII, CAS number 80-62-6) and with ethyl-halo-propionate (XIX), to afford a polymer of (meth)acrylate of formula (LVIII).

Scheme 13. wherein m, r, E, $CR^{19}$, $R^1, R^2, R^3, R^4, R^5, R^6, R^7, Z^9, L^1$, have the same meaning as defined herein above.

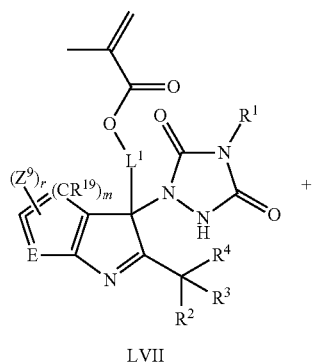

LVII

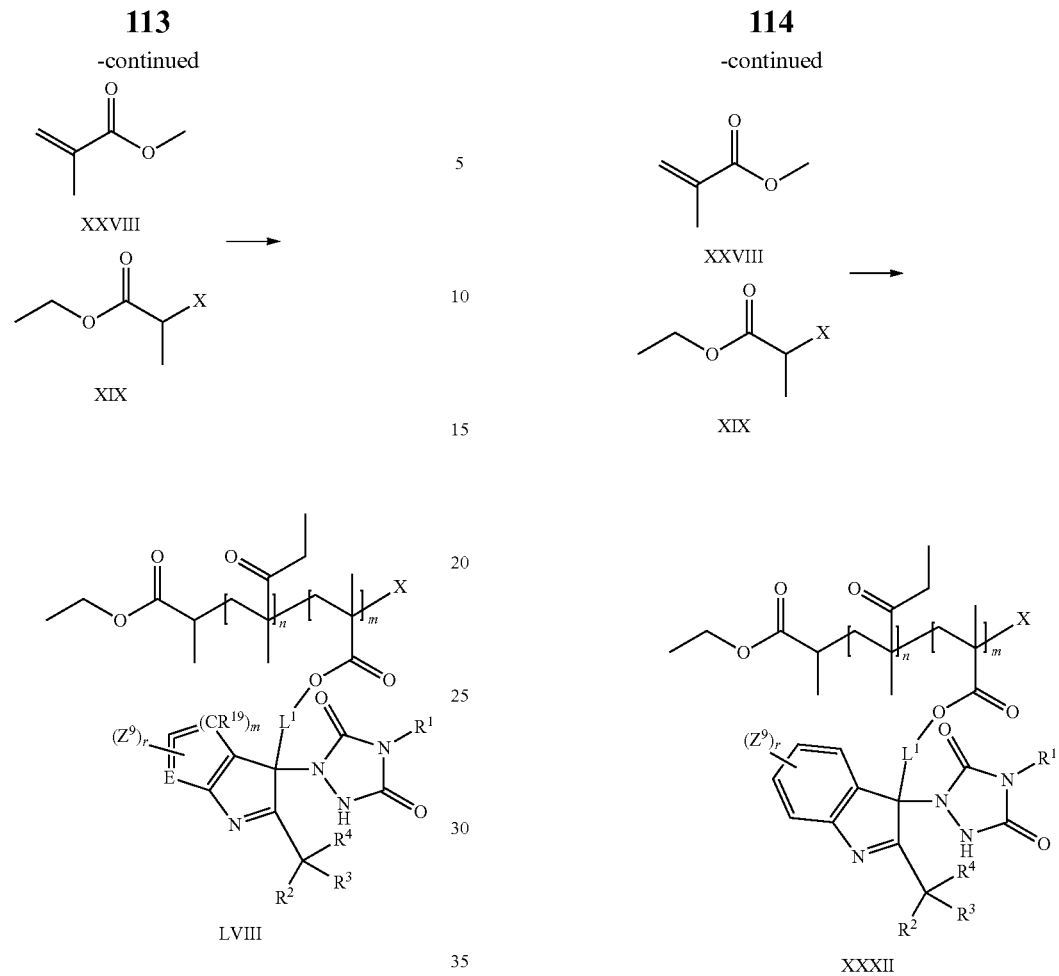

In another particular embodiment, said polymer of (meth)acrylate can be obtained as illustrated in Scheme 14, by contacting a compound of formula (XXXI), with methylmethacrylate (XXVIII, CAS number 80-62-6) and with ethyl-halo-propionate (XIX), to afford a polymer of (meth)acrylate of formula (XXX).

In another particular embodiment, said polymer of (meth)acrylate can be obtained as illustrated in Scheme 15, by contacting a compound of formula (XXXIII), with methylmethacrylate (XXVIII, CAS number 80-62-6) and with ethyl-halo-propionate (XIX), to afford a polymer of (meth)acrylate of formula (XXXIV).

Scheme 14. wherein X is selected from Br, I or Cl, and wherein r, $R^1$, $R^2$, $R^3$, $R^4$, $R^5$, $Z^9$, $L^1$, have the same meaning as defined herein above.

Scheme 15. wherein X is selected from Br, I or Cl, and wherein $R^1$, $R^2$, $R^3$, $R^4$, $R^5$, $L^1$, have the same meaning as defined herein above.

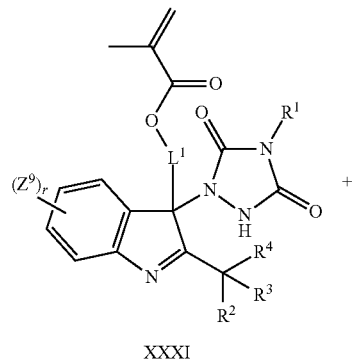

XXXI

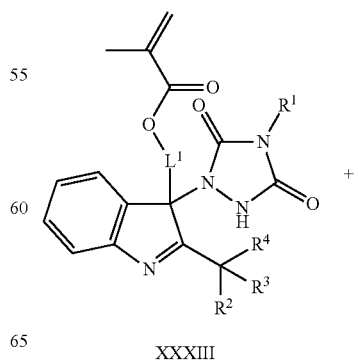

XXXIII

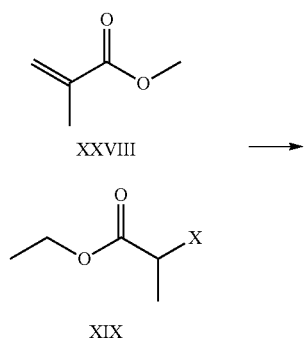

formula (XXXV), with butyl acrylate to afford a polymer of butyl acrylate. The butyl acrylate polymer can then be reacted with a compound of formula (II), (VII), (IX), or (XV).

The present invention also encompasses a polymer of isobornyl acrylate obtained by contacting a compound of formula (I) with isobornyl acrylate (CAS number 5888-33-5). In another particular embodiment, said polymer of isobornyl acrylate can be obtained as illustrated in Scheme 17, by contacting a compound of formula (XXXVII) with isobornyl acrylate (XXXVIII, CAS number 5888-33-5), to afford a polymer of isobornyl acrylate of formula (XXXIX).

Scheme 17. Wherein X is selected from Br, I or Cl, and wherein $R^1$, $R^2$, $R^3$, $R^4$, $R^5$, $R^6$, $R^7$, $L^1$, have the same meaning as defined herein above.

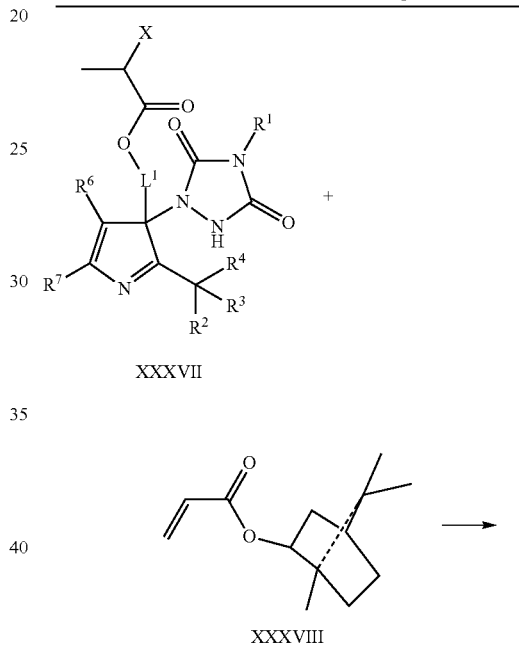

In another particular embodiment, said polymer of (meth)acrylate can be obtained as illustrated in Scheme 16, by contacting a compound of formula (XXXV), with methylmethacrylate (XXVIII, CAS number 80-62-6) to afford a polymer of (meth)acrylate of formula (XXXVI). The polymer of formula (XXXVI) can then be reacted with a compound of formula (II), (VII), (IX), or (XV).

Scheme 16. Wherein X is selected from Br, I or Cl, and wherein $L^2$, has the same meaning as defined herein above.

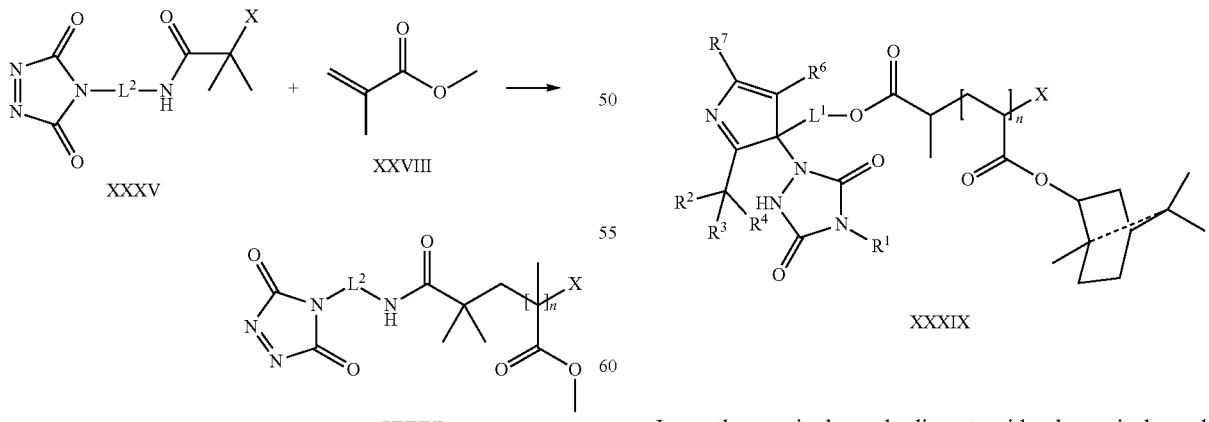

In another particular embodiment, a polymer of butyl acrylate can be obtained by contacting a compound of In another particular embodiment, said polymer isobornyl acrylate can be obtained as illustrated in Scheme 18, by contacting a compound of formula (LIX), with isobornyl acrylate (XXXVIII, CAS number 5888-33-5), to afford a polymer of isobornyl acrylate of formula (LX).

Scheme 18. wherein X is selected from Br, I or Cl, and wherein m, r, E, $CR^{19}$, $R^1$, $R^2$, $R^3$, $R^4$, $R^5$, $R^6$, $R^7$, $Z^9$, $L^1$, have the same meaning as defined herein above.

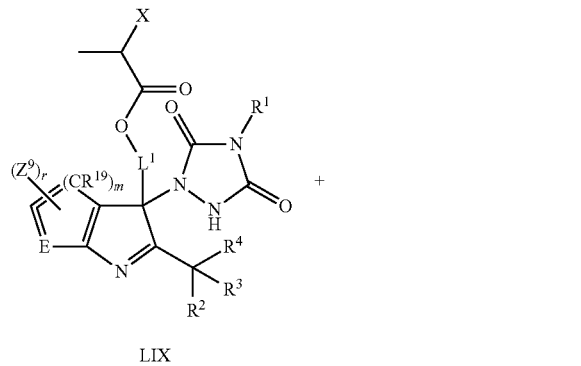

LIX

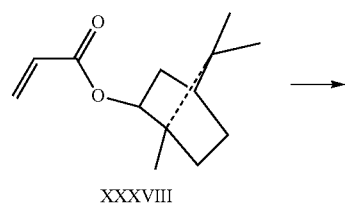

XXXVIII

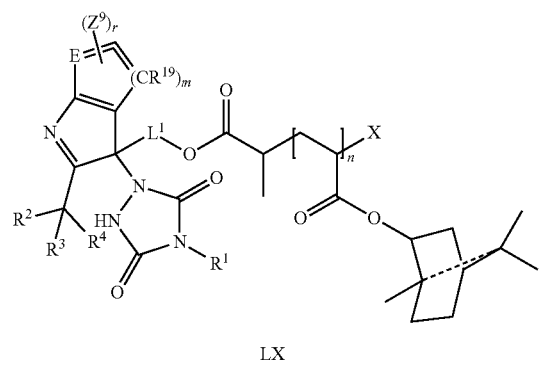

LX

In another particular embodiment, said polymer isobornyl acrylate can be obtained as illustrated in Scheme 19, by contacting a compound of formula (XL), with isobornyl acrylate (XXXVIII, CAS number 5888-33-5), to afford a polymer of isobornyl acrylate of formula (XLI).

Scheme 19. wherein X is selected from Br, I or Cl, and wherein r, $R^1$, $R^2$, $R^3$, $R^4$, $R^5$, $Z^9$, $L^1$, have the same meaning as defined herein above.

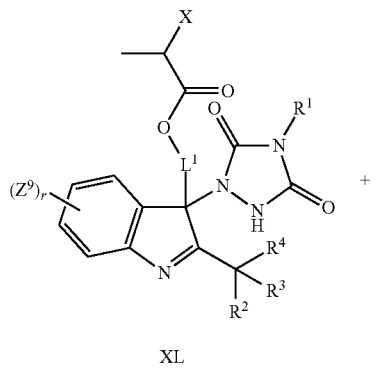

XL

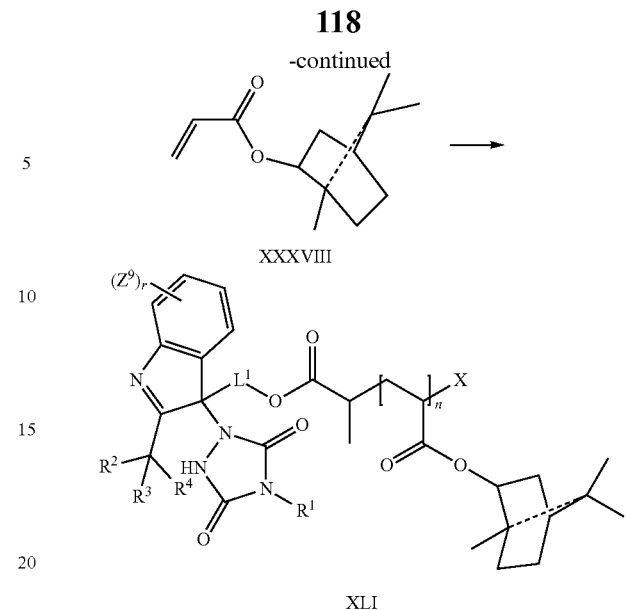

XLI

In another particular embodiment, said polymer of isobornyl acrylate can be obtained as illustrated in Scheme 20, by contacting a compound of formula (XLII), with isobornyl acrylate (XXXVIII, CAS number 5888-33-5), to afford a polymer of isobornyl acrylate of formula (XLIII).

Scheme 20. wherein X is selected from Br, I or Cl, and wherein $R^1$, $R^2$, $R^3$, $R^4$, $R^5$, $L^1$, have the same meaning as defined herein above.

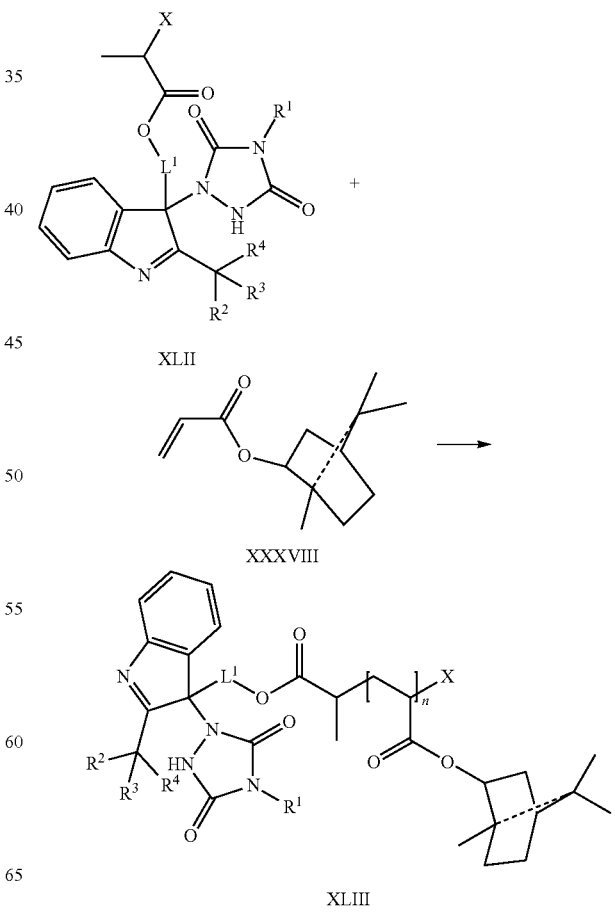

XLII

XXXVIII

XLIII

In another particular embodiment, said polymer of isobornyl acrylate can be obtained as illustrated in Scheme 21, by contacting a compound of formula (XLIV), with methylmethacrylate (XXVIII, CAS number 80-62-6) to afford a polymer of isobornyl acrylate of formula (XLV). The polymer of formula (XLV) can then be reacted with a compound of formula (II), (VII), (IX), or (XV).

Scheme 21. wherein X is selected from Br, I or Cl, and wherein $L^2$, has the same meaning as defined herein above.

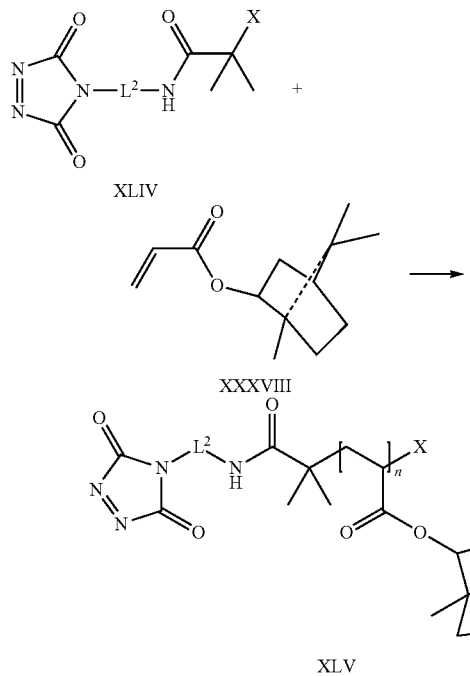

The present invention also encompasses a polymer of isobornyl acrylate obtained by contacting a compound of formula (II), (VII), (IX) or (XV) with isobornyl acrylate (CAS number 5888-33-5), and then contacting the resulting product with a compound of formula (III).

The present invention also encompasses a polymer of styrene obtained by contacting a compound of formula (I) with styrene (CAS number 100-42-5).

In another particular embodiment, said polymer of styrene can be obtained as illustrated in Scheme 22, by contacting a compound of formula (XLVI) with styrene (XLVII, CAS number 100-42-5), to afford a polymer of styrene of formula (XLVIII).

Scheme 22. wherein X is selected from Br, I or Cl, and wherein $R^1$, $R^2$, $R^3$, $R^4$, $R^5$, $R^6$, $R^7$, $L^1$, have the same meaning as defined herein above.

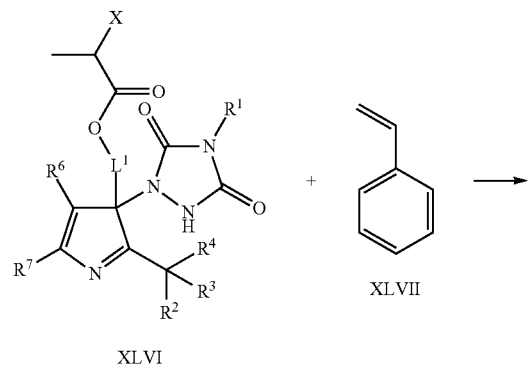

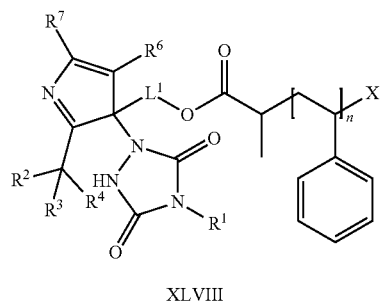

In another particular embodiment, said polymer of styrene can be obtained as illustrated in Scheme 23, by contacting a compound of formula (XLVI) with styrene (XLVII, CAS number 100-42-5), to afford a polymer of styrene of formula (XLVIII).

Scheme 23. Wherein X is selected from Br, I or Cl, and wherein m, r, E, $CR^{19}$, $R^1$, $R^2$, $R^3$, $R^4$, $R^5$, $R^6$, $R^7$, $Z^9$, $L^1$, have the same meaning as defined herein above.

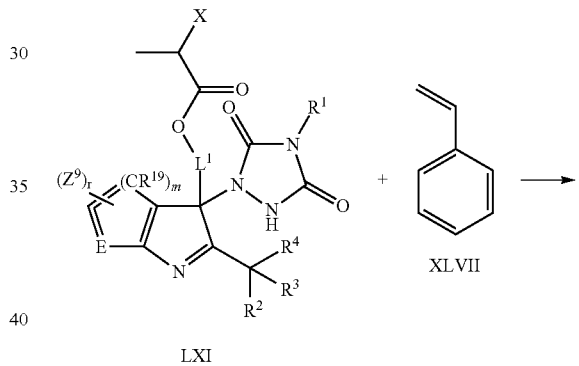

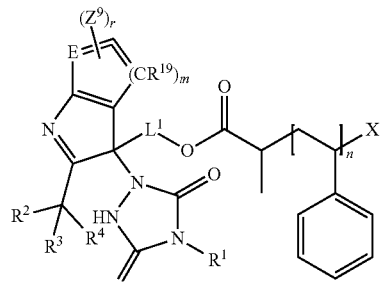

In another particular embodiment, said polymer of styrene can be obtained as illustrated in Scheme 24, by contacting a compound of formula (XLIX) with styrene (XLVII, CAS number 100-42-5), to afford a polymer of styrene of formula (L).

Scheme 24. Wherein X is selected from Br, I or Cl, and wherein r, $R^1$, $R^2$, $R^3$, $R^4$, $R^5$, $Z^9$, $L^1$, have the same meaning as defined herein above.

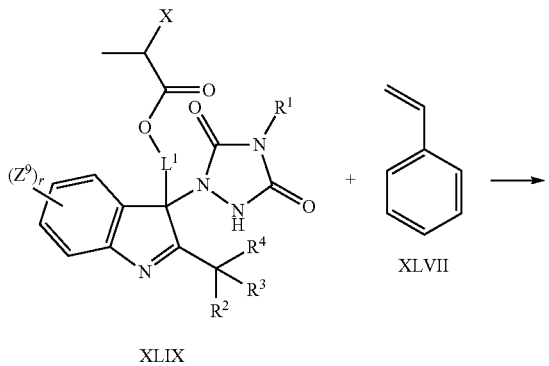

XLIX

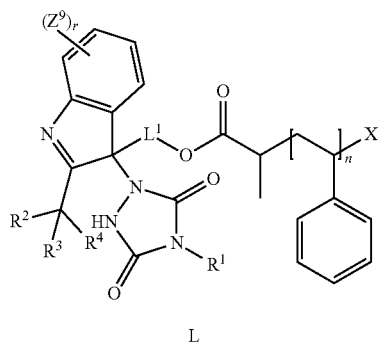

L

In another particular embodiment, said polymer of styrene can be obtained as illustrated in Scheme 25, by contacting a compound of formula (LI) with styrene (XLVII, CAS number 100-42-5), to afford a polymer of styrene of formula (LII).

Scheme 25. wherein X is selected from Br, I or Cl, and wherein $R^1$, $R^2$, $R^3$, $R^4$, $R^5$, $L^1$, have the same meaning as defined herein above.

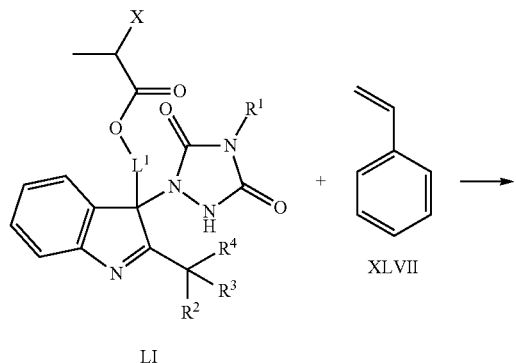

LI

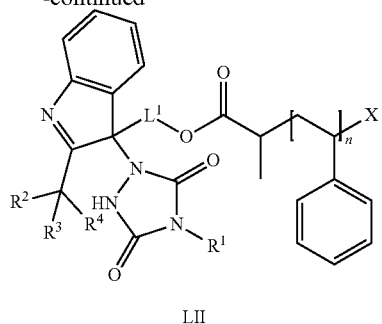

LII

In another particular embodiment, said polymer of styrene can be obtained as illustrated in Scheme 26, by contacting a compound of formula (LII) with styrene (XLVII, CAS number 100-42-5), to afford a polymer of styrene of formula (LIV). The polymer of formula (LIV) can then be reacted with a compound of formula (II), (VII), (IX), or (XV).

Scheme 26. wherein X is selected from Br, I or Cl, and wherein $L^2$, has the same meaning as defined herein above.

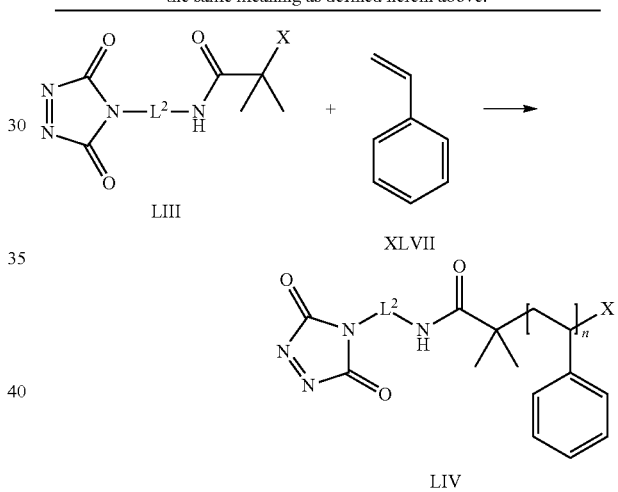

LIV

The present invention also encompasses a polymer of styrene obtained by contacting a compound of formula (II), (VII), (IX) or (XV) with styrene (CAS number 100-42-5), and then contacting the resulting product with a compound of formula (III).

The present invention also encompasses compounds of structural formula (IX),

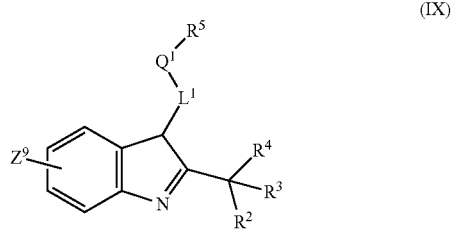

(IX)

wherein $L^1$, $Q^1$, $R^2$, $R^3$, $R^4$, $R^5$, $Z^9$ and r have the same meaning as that defined herein.

Preferably a compound of formula (IX) wherein r is an integer selected from 0, 1, 2, 4 or 4, preferably r is 0, 1 or 2, more preferably 0 or 1, yet more preferably 0;

$L^1$ is selected from $C_{1-10}$alkylene; $C_{2-10}$alkenylene; or $C_{2-10}$alkynylene; or $L^1$ and $R^2$ together with the carbon atoms to which they are attached form a saturated or unsaturated 4-, 5-, 6-, 7- or 8-membered ring, preferably a saturated or unsaturated 5-, or 6-membered ring; preferably $L^1$ is selected from $C_{1-10}$alkylene; $C_{2-10}$alkenylene; or $C_{2-10}$alkynylene; more preferably $L^1$ is selected from $C_{1-10}$alkylene; and $C_{2-10}$alkenylene; yet more preferably, $L^1$ is $C_{1-10}$alkylene; for example, $L^1$ is $C_{1-6}$alkylene; for example, $L^1$ is $C_{1-6}$alkylene;

wherein said $C_{1-10}$alkylene; $C_{2-10}$alkenylene; $C_{2-10}$alkynylene, or saturated or unsaturated 4-, 5-, 6-, 7- or 8-membered ring, optionally comprises one or more heteroatoms in the alkylene, alkenylene, alkynylene, or saturated or unsaturated 4-, 5-, 6-, 7- or 8-membered ring moiety, said heteroatoms being each independently selected from O, S and N; and wherein said $C_{1-10}$alkylene; $C_{2-10}$alkenylene; $C_{2-10}$alkynylene, or saturated or unsaturated 4-, 5-, 6-, 7- or 8-membered ring, can be unsubstituted or substituted with one or more $Z^1$;

$Q^1$ is a single bond or is selected from the group consisting of —OC(O)—; —NH—C(O)—; —OS(O)—; —OS(O)$_2$—; —NH—S(O)—; —NH—S(O)$_2$—; —OC(O)—[$CR^{13}R^{14}$]$_q$—; and —OC(O)—[C($R^{13}$)($L^4$-O—$R^{15}$)]$_q$—[$CR^{16}R^{17}$]$_p$—O—; wherein each left side of said groups is attached to $L^1$ and the right side thereof is attached to $R^5$; and wherein, preferably $Q^1$ is a single bond or is selected from the group consisting of —OC(O)—; —NH—C(O)—; —OC(O)—[$CR^{13}R^{14}$]$_q$—; and —OC(O)—[C($R^{13}$)($L^4$-O—$R^{15}$)]$_q$—[$CR^{16}R^{17}$]$_p$—O—; preferably $Q^1$ is a single bond or is selected from the group consisting of —OC(O)—; —OC(O)—[$CR^{13}R^{14}$]$_q$—; and —OC(O)—[C($R^{13}$)($L^4$-O—$R^{15}$)]$_q$—[$CR^{16}R^{17}$]$_p$—O—; preferably $Q^1$ is selected from the group consisting of —OC(O)—; —OC(O)—[$CR^{13}R^{14}$]$_q$—; and —OC(O)—[C($R^{13}$)($L^4$-O—$R^{15}$)]$_q$—[$CR^{16}R^{17}$]$_p$—O—; wherein q is an integer selected from 1; 2 or 3; preferably 1 or 2; for example 1;

p is an integer selected from 0; 1 or 2; preferably 0 or 1; for example 1;

$L^4$ is a single bond or is selected from the group consisting of $C_{1-10}$alkylene; $C_{2-10}$alkenylene; and $C_{2-10}$alkynylene; preferably $L^4$ is a single bond or is selected from the group consisting of $C_{1-10}$alkylene; and $C_{2-10}$alkenylene; preferably $L^4$ is a single bond or is $C_{1-10}$alkylene; preferably $L^4$ is $C_{1-10}$alkylene; for example $C_{1-6}$alkylene, for example $C_{1-6}$alkylene, for example $C_{1-4}$alkylene, wherein said $C_{1-10}$alkylene; $C_{2-10}$alkenylene; and $C_{2-10}$alkynylene, optionally comprises one or more heteroatoms in the alkylene, alkenylene, alkynylene moiety, said heteroatoms being each independently selected from O, S and N;

and wherein said $C_{1-10}$alkylene; $C_{2-10}$alkenylene; $C_{2-10}$alkynylene, can be unsubstituted or substituted with one or more $Z^2$; preferably wherein said $C_{1-10}$alkylene; and $C_{2-10}$alkenylene; can be unsubstituted or substituted with one or more $Z^2$; preferably wherein said $C_{1-10}$alkylene; for example $C_{1-6}$alkylene, for example $C_{1-6}$alkylene, can be unsubstituted or substituted with one or more $Z^2$;

$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl $C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, S or N in the alkyl, alkenyl, alkynyl moiety; preferably $R^2$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, or N in the alkyl, alkenyl moiety; preferably $R^2$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$ and each group optionally comprises one or more O, or N in the alkyl moiety; preferably $R^2$ is selected from the group consisting of halo; $C_{1-20}$alkyl; $C_{6-12}$aryl; $C_{6-12}$aryl$C_{1-6}$alkyl; and a polymeric group; each group being unsubstituted or substituted with one or more $Z^7$; and each group optionally comprises one or more O or N in the alkyl moiety;

$R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, S or N in the alkyl, alkenyl, alkynyl moiety; preferably $R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, or N in the alkyl, alkenyl moiety; preferably $R^3$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$ and each group optionally comprises one or more O, or N in the alkyl moiety; preferably $R^3$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$; and each group optionally comprises one or more O or N in the alkyl moiety;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl $C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, S or N in the alkyl, alkenyl, alkynyl moiety; preferably $R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; each group being unsubstituted or substituted with one or more $Z^7$; and each group optionally comprises one or more O, or N in the alkyl, alkenyl moiety; preferably $R^4$ is selected from the group consisting of halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^7$ and each group optionally comprises one or more O, or N in the alkyl moiety; preferably $R^4$ is selected from the group consisting of halo; $C_{1-20}$alkyl; $C_{6-12}$aryl; $C_{6-12}$aryl$C_{1-6}$alkyl; each group being unsubstituted or substituted with one or more $Z^7$; and each group optionally comprises one or more O or N in the alkyl moiety;

or $R^2$ and $R^3$ and $R^4$ together with the carbon atom to which they are attached can form a saturated or unsaturated 4-, 5-, 6-, 7- or 8-membered ring; preferably a saturated or unsaturated 5-, 6-, 7-membered ring; for example a saturated or unsaturated 5-, or 6-membered ring for example a phenyl ring;

or $R^2$ and $L^1$ together with the carbon atom to which they are attached can form a saturated or unsaturated 4-, 5-, 6-, 7- or 8-membered ring; preferably a saturated or unsaturated 5-, 6-, 7-membered ring; for example a saturated or unsaturated 5-, or 6-membered ring;

and wherein for each of $R^2$ and $R^3$ and $R^4$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^5$ is selected from the group consisting of hydrogen, halo; nitro; cyano; hydroxyl; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^8$; and each group optionally comprises one or more O, S or N in the alkyl, alkenyl, alkynyl moiety; wherein at least one carbon atom or heteroatom of said group can be oxidized to form at least one C=O, C=S, N=O, N=S, S=O or $S(O)_2$; preferably $R^5$ is selected from the group consisting of halo; hydroxyl, hydrogen, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^8$; and each group optionally comprises one or more O, or N in the alkyl, alkenyl moiety; wherein at least one carbon atom or heteroatom of said group can be oxidized to form at least one C=O, S=O or $S(O)_2$; preferably $R^5$ is selected from the group consisting of hydrogen, hydroxyl, halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^8$ and each group optionally comprises one or more O, or N in the alkyl moiety; wherein at least one carbon atom of said group can be oxidized to form at least one C=O; preferably $R^5$ is selected from the group consisting of halo; hydrogen, hydroxyl, $C_{1-20}$alkyl; $C_{6-12}$aryl; $C_{6-12}$aryl$C_{1-6}$alkyl; and a polymeric group; each group being unsubstituted or substituted with one or more $Z^8$; and each group optionally comprises one or more O or N in the alkyl moiety; wherein at least one carbon atom of said group can be oxidized to form at least one C=O;

and wherein for $R^5$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^9$ is independently selected from the group consisting of hydroxyl; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or $S(O)_2$; preferably wherein each $R^9$ is independently selected from the group consisting of hydroxyl; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^9$ is independently selected from the group consisting of hydroxyl; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{10}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or S(O)$_2$; preferably wherein each $R^{10}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{10}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or S(O)$_2$; preferably wherein each $R^{11}$ and $R^{12}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{11}$ and $R^{12}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein $R^{11}$ and $R^{12}$ together with the atom to which they are attached form a 5-, 6-, or 7-membered heterocycle;

each $R^{13}$ and $R^{14}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or S(O)$_2$; preferably wherein each $R^{13}$ and $R^{14}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{13}$ and $R^{14}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein $R^{13}$ and $R^{14}$ together with the atom to which they are attached form a 5-, 6-, or 7-membered heterocycle;

$R^{15}$ is selected from the group consisting of hydrogen, halo; nitro; cyano; hydroxyl; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^{10}$; and each group optionally comprises one or more O, S or N in the alkyl, alkenyl, alkynyl moiety; wherein at least one carbon atom or heteroatom of said group can be oxidized to form at least one C=O, C=S, N=O, N=S, S=O or S(O)$_2$; preferably $R^{15}$ is selected from the group consisting of halo; hydroxyl, hydrogen, $C_{1-20}$alkyl; $C_{2-20}$alkenyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; each group being unsubstituted or substituted with one or more $Z^{10}$; and each group optionally comprises one or more O, or N in the alkyl, alkenyl moiety; wherein at least one carbon atom or heteroatom of said group can be oxidized to form at least one C=O, S=O or S(O)$_2$; preferably $R^{15}$ is selected from the group consisting of hydrogen, hydroxyl, halo; $C_{1-20}$alkyl; $C_{2-20}$alkenyl; $C_{6-12}$aryl; $C_{3-8}$cycloalkyl; $C_{6-12}$aryl$C_{1-6}$alkyl; and a polymeric group; each group being unsubstituted or substituted with one or more $Z^{10}$ and each group optionally comprises one or more O, or N in the alkyl moiety; wherein at least one carbon atom of said group can be oxidized to form at least one C=O; preferably $R^{15}$ is selected from the group consisting of halo; hydrogen, hydroxyl, $C_{1-20}$alkyl; $C_{6-12}$aryl; $C_{6-12}$aryl$C_{1-6}$alkyl; and a polymeric group; each group being unsubstituted or substituted with one or more $Z^{10}$; and each group optionally comprises one or more O or N in the alkyl moiety; wherein at least one carbon atom of said group can be oxidized to form at least one C=O;

and wherein for $R^{15}$ said polymeric group is selected from the group comprising polystyrene; poly(methyl methacrylate); polyethylene oxide; polyacrylate; polymethacrylate; copolymer of acrylate, methacrylate and/or styrene; poly (isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^{16}$ and $R^{17}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; wherein each group optionally comprise one or more heteroatoms in the alkyl, alkenyl or alkynyl moiety, said heteroatoms being each independently selected from O, S and N; wherein at least one carbon atom or heteroatom of said group can be oxidized to form at least one C=O, C=S, N=O, N=S, S=O or S(O)$_2$; preferably wherein each $R^{16}$ and $R^{17}$ is independently selected from the group consisting of hydrogen; $C_{1-10}$alkyl, $C_{2-10}$alkenyl, $C_{6-12}$aryl, $C_{6-12}$aryl$C_{1-6}$alkyl; wherein each group optionally comprise one or more heteroatoms in the alkyl, alkenyl or alkynyl moiety, said heteroatoms being each independently selected from O, S and N; wherein at least one carbon atom of said group can be oxidized to form at least one C=O; preferably wherein each $R^{16}$ and $R^{17}$ is independently selected from the group consisting of hydrogen; $C_{1-6}$alkyl, $C_{2-6}$alkenyl, $C_{6-12}$aryl; wherein each group optionally comprise one or more heteroatoms in the alkyl, alkenyl or alkynyl moiety, said heteroatoms being each independently selected from O, and N; wherein at least one carbon atom of said group can be oxidized to form at least one C=O;

or wherein $R^{16}$ and $R^{17}$ together with the atom to which they are attached form a 5-, 6-, or 7-membered heterocycle;

$Z^1, Z^2, Z^7, Z^8, Z^9, Z^{10}$, are each independently selected from the group consisting of halogen; $C_{1-6}$alkyl; halo$C_{1-6}$alkyl; halo$C_{1-6}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; or a polymeric group; preferably $Z^1, Z^2, Z^7, Z^8, Z^9, Z^{10}$ are each independently selected from the group consisting of halogen; $C_{1-6}$alkyl; halo$C_{1-6}$alkyl; halo$C_{1-6}$alkyloxy; —$OR^{10}$; nitro; —$NR^{10}C(O)R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; or a polymeric group; preferably $Z^1, Z^2, Z^7, Z^8, Z^9, Z^{10}$ are each independently selected from the group consisting of halogen; $C_{1-6}$alkyl; halo$C_{1-6}$alkyl; halo$C_{1-6}$alkyloxy; —$OR^{10}$; nitro; —$NR^{10}C(O)R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; or a polymeric group; preferably $Z^1, Z^2, Z^7, Z^8, Z^9, Z^{10}$ are each independently selected from the group consisting of halogen; $C_{1-6}$alkyl; halo$C_{1-6}$alkyl; halo$C_{1-6}$alkyloxy; nitro; —$NR^{10}C(O)R^9$; —$NR^{10}C(O)NR^{11}R^{12}$; $NR^{11}R^{12}$; cyano; —$CO_2R^{10}$; —$C(O)NR^{11}R^{12}$; or a polymeric group;

and wherein for each of $Z^1, Z^2, Z^7, Z^8, Z^9, Z^{10}, Z^{11}$ said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group; preferably wherein said polymeric group is selected from the group comprising polyacrylate; polymethacrylate; polystyrene; copolymer of acrylate; poly(methyl methacrylate); methacrylate and/or styrene; poly(isobornyl acrylate); polyacrylonitrile; polyamide; polyester amide; polyurethane; ethylene propylene diene monomer (M-class) rubber (EPDM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

The present invention also encompasses a process for reshaping and/or repairing an article comprising a compound according to the first aspect of the invention, comprising the step of thermally treating the compound of formula (I) at a temperature of at least 20° C., preferably of at least 30° C.

The present invention also encompasses a process for the preparation of an extruded article comprising the step of melt extruding said compound of formula (I) according to the first aspect of the invention thereby forming a, extruded article.

The present invention also encompasses a process for the preparation of molded articles, comprising the steps of heating a compound of formula (I) according to the first aspect of the invention to obtain a molten compound and adding said molten compound into a mold thereby forming a molded article.

The present compound of formula (I) and any subgroups thereof can be used to make foams, rubbery materials and brittle materials depending on the type of polymeric group that is employed.

The present invention also encompasses the use of a compound of formula (I) in polymers, membranes, adhesives, foams, sealants, molded articles, films, extruded articles, fibers, elastomers, polymer based additives, pharmaceutical and biomedical products, varnishes, paints, coatings, inks; composite material organic LEDs, organic semiconductors, conducting organic polymers, and 3D printed articles.

The present invention also encompasses a method for formulating polymers, membranes, adhesives, foams, sealants, molded articles, films, extruded articles, fibers, elastomers, polymer based additives, pharmaceutical and biomedical products, varnishes, paints, coatings, inks; or composite material, comprising adding at least one compound of formula (I) to said polymers, membranes, adhesives, foams, sealants, molded articles, films, extruded articles, fibers, elastomers, polymer based additives, pharmaceutical and biomedical products, varnishes, paints, coatings, inks; or composite material.

The present invention also encompasses polymers, membranes, adhesives, foams, sealants, molded articles, films, extruded articles, fibers, elastomers, polymer based additives, pharmaceutical and biomedical products, varnishes, paints, coatings, inks; composite material, organic LEDs, organic semiconductors, and conducting organic polymers, 3D printed articles, comprising at least one compound of formula (I).

The present invention allows the synthesis of complex polymer architectures, which can be useful for example in coatings, membranes, films, dispersants and/or emulsifiers.

The present process can allow the coupling of at least two very different (polymer)structures that are immiscible.

The present invention is particularly suitable for preparing coatings comprising compounds according to the first aspect of the invention, wherein said preparation comprise the step of contacting a compound of formula (II) with a compound of formula (III). The invention allows the elimination UV light for curing.

The present invention is particularly suitable for functionalization of a polymer comprising the step of contacting a compound of formula (II) with a compound of formula (III).

The present invention also encompasses a method of rapid prototyping, 3D printing or fused deposition modeling comprising the step of using a compound according to the first aspect of the invention for preparing prototypes, 3D printing articles or fused deposition models.

The following examples are provided for the purpose of illustrating the present invention and by no means should be interpreted to limit the scope of the present invention.

EXAMPLES

Instrumentation

The Nuclear Magnetic Resonance spectra were recorded on a Bruker AVANCE 300 (300 MHz) and Bruker DRX500 (500 MHz) spectrometers.

Differential scanning calorimetry (DSC) analyses were performed with a TA Instruments 2920 Modulated DSC V2.6A, a helium gas flush of 25 mL minutes$^{-1}$ and a nitrogen gas flush of 19 mL minutes$^{-1}$. The samples were analyzed in TAi Tzero Hermetic Aluminium sample pans which contained 5-15 mg of the sample. Glass transition temperatures ($T_g$) were determined from inflection points in the second heating using the Universal V3.9A software from TA Instruments. Measurements were performed in a temperature range of −100-200° C. with a rate of 10 K minutes$^{-1}$.

Thermogravimetric analyses (TGA) were performed on a Mettler-Toledo TGA/SDTA 851e under nitrogen atmosphere. The sample was heated from 25 to 600° C. with a rate of 10 K minutes$^{-1}$. The thermograms were analyzed using the STARe software from Mettler-Toledo, allowing the determination of the degradation temperature ($T_{deg}$).

Size Exclusion Chromatography (SEC) was performed at 35° C. on three Polymer Standards Services GPC columns (1×GRAM Analytical 30 Å, 10 µm and 2×GRAM Analytical 1000 Å, 10 µm), placed in series. N,N-dimethylacetamide (DMA), containing 0.42 mgL$^{-1}$ lithium bromide, was used as solvent (flow of 1 mLmin$^{-1}$). The system was calibrated with standards of poly(methyl methacrylate) (PMMA) (ranging from 690 gmol$^{-1}$ to 194400 gmol$^{-1}$), with close dispersity. A Hitachi Column Oven L-7300, a Waters 2414 Refractive index Detector, a Waters 600 controller and a Waters 610 Fluid Unit were also used. The molecular weight and the dispersity were determined via Empower software.

Additional SEC analyses were performed on an Agilent (Polymer Laboratories) PLGPC 50 plus instrument, using a refraction index detector and two PLgel 5 mm MIXED-D columns (thermostated at 40° C.). Calibration was achieved using polystyrene and PMMA standards, with tetrahydrofuran as eluent, with a flow of 1 mLmin$^{-1}$. The samples were injected by means of a PL-AS RT autosampler.

The following abbreviations were use to describe different properties of the prepared polymers:

$M_n$=Number Average Molecular Weight.
$M_w$=Weight Average Molecular Weight.
Đ=Dispersity Analytical reversed phase HPLC-analyses were performed with a Phenomenex Luna $C_{18}$ (2) column (5 µm, 250 mm×4.6 mm) and a solvent gradient (0→100% acetonitrile in $H_2O$ in 15 minutes, the eluted compounds were analyzed via UV detection (λ=214 nm).

LC-MS analyses were performed on an Agilent Technologies 1100 series LC/MSD system with a diode array detector (DAD) and single quad MS detector (VL) with electrospray ionization. MW stands for Molecular Weight.

MALDI_TOF MS was performed on an Applied Biosystems Voyager De STR MALDI-TOF spectrometer equipped with 2 m linear and 3 m reflector flight tubes, and a 355 nm Blue Lion Biotech Marathon solid state laser (3.5 ns pulse). All mass spectra were obtained with an accelerating potential of 20 kV in positive ion mode and in linear and/or reflector mode. A poly(ethylene oxide) standard ($M_n$=2000 gmol$^{-1}$) was used for calibration. All data were processed using the Data Explorer 4.0.0.0 (Applied Biosystems) software package.

MALDI_TOF MS analysis of polyisobornyl acrylate (PiBA) polymers: Trans-2-[3-(4-tert-Butylphenyl)-2-methyl-2-propenylidene]malonitrile (DCTB) (20 mg·mL$^{-1}$ in tetrahydrofuran (THF) was used as a matrix, NaF$_3$Ac (1 mg·mL$^{-1}$) was used as a cationizing agent, and polymer samples were dissolved in THF (2 mg·mL$^{-1}$). Analyte solutions were prepared by mixing 10 µL of the matrix, 5 µL of the salt and 5 µL of the polymer solution. Subsequently, 0.5 µL of this mixture was spotted on the sample plate and the spots were air-dried at room temperature.

MALDI_TOF MS analysis of polystyrene (PS) polymers: Dithranol (20 mg·mL$^{-1}$ in THF) was used as a matrix, AgF$_3$Ac (1 mg·mL$^{-1}$) was used as a cationizing agent, and polymer samples were dissolved in THF (10 mg·mL$^{-1}$). Analyte solutions were prepared by mixing 5 µL of the matrix, 10 µL of the salt and 5 µL of the polymer solution. Subsequently, 0.5 µL of this mixture was spotted on the sample plate and the spots were air-dried at room temperature.

MALDI_TOF MS analysis of poly(ethylene oxide) (PEO) polymers: Dithranol (10 mg·mL$^{-1}$ in THF) was used as a matrix, NaF$_3$Ac (1 mg·mL$^{-1}$) was used as a cationizing agent, and polymer samples were dissolved in THF (10 mg·mL$^{-1}$). Analyte solutions were prepared by mixing 16 µL of the matrix, 2 µL of the salt and 2 µL of the polymer solution. Subsequently, 0.5 µL of this mixture was spotted on the sample plate and the spots were air-dried at room temperature.

Materials

Acetone (CAS: 67-64-1 Sigma-Aldrich, 99.8%), (Acetonitrile CAS 75-05-8 Fisher Chemical; 99.%99); Acryloylchloride (CAS: 814-68-6; Sigma-Aldrich, ≥97%); Aluminiumoxide (activated, basic, Brockmann I; CAS: 1344-28-1 Sigma-Aldrich); Ammonium chloride (CAS: 12125-02-9; Roth; 99%); Acetic acid (CAS: 64-19-7; Fiers; 99.8%); 2,2'-Bipyridyl (Sigma-Aldrich, ≥98%); 2,2-bis-(hydroxymethyl)propionic acid (CAS: 4767-03-7 Sigma-Aldrich, 98%); 2-bromopropionyl bromide (CAS: 563-76-8; Aldrich, 97%); n-butyllithium (CAS: 109-72-8; Sigma-Aldrich, 2.5M in hexane); butylisocyanate (CAS: 111-36-4; Sigma-Aldrich, ≥98%); celite (CAS 91053-39-3; Sigma-Aldrich); chloroform (CAS: 67-66-3 Sigma-Aldrich; 99.8%); chloroform-d (CAS: 865-49-6; Euriso-Top 99.8%); Copper Cu(0) was used as pellets (CAS: 7440-50-8; Sigma-Aldrich, ≥99.999%); copper(I)bromide (CAS: 7787-70-4; Sigma-Aldrich; 98%); copper(II)bromide (CAS: 7789-45-9; Sigma-Aldrich; 99%); 1,4-diazabicyclo[2.2.2]octane (DABCO) (CAS: 280-57-9; Sigma-Aldrich; 99%); Br$_2$ (CAS: 7726-95-6; Sigma-Aldrich; 99%); dibutyltin dilaurate (CAS: 77-58-7; TCI); dichloromethane (DCM) (CAS: 75-09-2; Sigma-Aldrich; 99.8%); Diethylether (CAS: 60-29-7; Sigma-Aldrich; 99.8%); 3,4-dihydro-2H-pyran (CAS: 110-87-2; Sigma-Aldrich, 97%); N,N-dimethylformamide (DMF) (CAS: 68-12-2 Acros Organics, 99.8%); dimethylsulfoxide (DMSO) (CAS: 67-68-5, Acros Organics, 99.7%); dimethylsulfoxide-d$_6$ (DMSO-d$_6$) (CAS: 2206-27-1, Euriso-Top, 99.8%); Ethanol (CAS: 64-17-5 Sigma-Aldrich; 99.8%); ethyl-2-bromo propionate (CAS: 535-11-5; Acros Organics, 99%); ethylacetate (CAS: 141-78-6; Sigma-Aldrich; 99.7%); ethyl carbazate (CAS: 4114-31-2; Sigma-Aldrich, 97%); n-hexane (CAS: 110-54-3 Sigma-Aldrich; 97%); trans,trans-2,4-hexadien-1,6-diol (CAS: 17102-64-6; Sigma-Aldrich, ≥97%); hexamethylene diisocyanate (CAS: 822-06-0; Fluka, ≥98); isobornylacrylate (CAS: 5888-33-5; Sigma-Aldrich technical grade); hydrochloric acid (CAS:7647-01-0; Chem-Lab, 36%); magnesium sulfate (CAS:7487-88-9; Boom); methacryloylchloride (CAS:920-46-7, Fluka, ≥97); methanesulfonyl chloride (CAS:124-63-0; Acros Organics, 99.5%); methanol (CAS: 67-56-1; Sigma-Aldrich; 99.9%); 3-methylbutyraldehyde (CAS:590-86-3; Acros Organics, 98%); 4,4'-Methylenebis (phenyl isocyanate) (CAS: 101-68-8; Sigma-Aldrich, 98%); methyl methacrylate (CAS: 80-62-6; Sigma-Aldrich, 99%); palladium on carbon (CAS: 7440-05-3; Sigma-Aldrich, 5%); polypropylene oxide ($M_n$~2000 gmol$^{-1}$) (CAS:25322-69-4 Acros Organics); potassium carbonate (CAS: 584-08-7; Roth, ≥99%); potassium hydroxide (CAS: 1310-58-3; Sigma-Aldrich, ≥90%); Silica gel 60 Å (CAS: 7631-86-9; Rocc; 99.5%); sodium bicarbonate (CAS:144-55-8; Roth; 99.5%); sodium chloride (CAS: 7647-14-5; Roth, ≥99%); sodium hydride (CAS: 7646-69-7; Sigma-Aldrich; 60%); sodium hydroxide (CAS:1310-73-2; Acros Organics; 97%); o-toluidine (CAS: 95-53-4; Sigma-Aldrich, 98%); tetrahydrofuran (THF) (CAS: 109-99-9; Sigma-Aldrich; 99.9%); toluene (CAS:108-88-3, Sigma-Aldrich, 99.9%); triethylamine (CAS:121-44-8; Acros Organics, 99%), trifluoroacetic acid (CAS: 76-05-1; Sigma-Aldrich, 99%) and trimethylacetylchloride (CAS: 3282-30-2; Sigma-Aldrich, 99%) were used as received. Solvents were purchased from Aldrich (HPLC grade) and used as received.

Styrene (Sigma-Aldrich, ≥99%), was passed over a short column of $Al_2O_3$ prior to use. Isobornyl acrylate (Sigma-Aldrich, technical grade) was purified by vacuum distillation (65° C., 1 mbar). N,N,N',N",N"-Pentamethyldiethylenetriamine (PMDETA, Acros Organics, 99+%) was distilled (85-86° C., 16 mbar) and stored at 4° C. Cu(I)Br (Sigma-Aldrich, 98%) was purified by stirring with acetic acid, then by filtering and washing with ethanol and diethylether, and finally by drying in a vacuum oven at 70° C.

Unless otherwise indicated, all parts and all percentages in the following examples, as well as throughout the specification, are parts by weight or percentages by weight respectively.

Example 1

Synthesis of 4-butyl-1-(ethoxycarbonyl) semicarbazide

A mixture of ethyl carbazate (10 g, 96.1 mmol, 1 eq) and toluene (105 mL) was placed in a three neck flask (250 mL) and cooled in an ice bath. The flask was equipped with an addition funnel, containing 10.8 mL butylisocyanate (96.1 mmol, 1 eq), a mechanical stirrer and a bulb condenser. The mixture was put under inert atmosphere and the isocyanate was added slowly under vigorous stirring. After addition the mixture was stirred at room temperature for two hours, followed by 2 hours at 90° C. After cooling the reaction to room temperature, 4-butyl-1-(ethoxycarbonyl) semicarbazide was filtered off and washed with toluene (96%).

MW.: 203.24 g/mol.

$^1$H-NMR (300 MHz, DMSO-d$_6$): δ (ppm)=0.85 (t, 3H, $CH_3$ $(CH_2)_3$), 1.22 (t, 3H, $CH_3$—$CH_2$—O), 1.27 (m, 2H, $CH_3$—$CH_2$—$CH_2$), 1.43 (m, 2H, NH—$CH_2$—$CH_2$), 3.16 (q, 2H, NH—$CH_2CH_2$), 4.15 (q, 2H, $CH_3$—$CH_2$—O), 5.22 (s, 1H, $CH_2$—NH—CO), 6.25 (s, 1H, NH—NH—CO), 6.44 (s, 1H, NH—NH—CO).

Example 2

Synthesis of 4-butyl-1,2,4-triazolidine-3,5-dione

In a 50 mL flask, 4-butyl-1-(ethoxycarbonyl) semicarbazide (12.2 g, 60.0 mmol) obtained in Example 1, was dissolved in 30 mL of an aqueous potassium hydroxide solution (4M) under inert atmosphere. This mixture was refluxed for 1.5 hour (100° C.), warm filtered, cooled to room temperature and acidified until pH 1 by adding of HCl. This mixture was cooled to room temperature to yield a white powder that was filtered off (62%).

MW.: 157.17 g/mol.

$^1$H-NMR (300 MHz, DMSO-d$_6$): δ (ppm)=0.88 (t, 3H, $CH_3$—$(CH_2)_3$), 1.25 (m, 2H, $CH_3$—$CH_2$—$CH_2$), 1.51 (m, 2H, N—$CH_2$—$CH_2$), 3.34 (t, 2H, N—$CH_2$), 10.03 (s, 2H, NH).

Example 3

Synthesis of 4-butyl-1,2,4-triazoline-3,5-dione (BuTAD or BTAD)

A mixture of 4-butyl-1,2,4-triazolidine-3,5-dione (1 g, 6.36 mmol, 1 eq) obtained in Example 2, DABCO-Br (2 g, 1.27 mmol, 0.2 eq) and dichloromethane (30 mL) was put in a flask (100 mL) under inert atmosphere, and stirred for 2 hours at room temperature. The reaction mixture was filtered off, the residue washed with dichloromethane (2×30 mL) and the filtrate was concentrated in vacuo to obtain 4-butyl-1,2,4-triazoline-3,5-dione (72%) as bright pink crystals. The temperature of the cooling batch should not exceed 50° C. due to the volatility of the obtained compound.

MW.: 155.15 g/mol.

$^1$H-NMR (300 MHz, DMSO-d$_6$): δ (ppm)=0.88 (t, 3H, $CH_3$—$(CH_2)_3$), 1.30 (m, 2H, $CH_3$—$CH_2$—$CH_2$), 1.56 (m, 2H, N—$CH_2$—$CH_2$), 3.47 (t, 2H, N—$CH_2$).

Example 4

Synthesis of 4,4'-(4,4'-diphenylmethylene)-bis-(carbethoxysemicarbazide)

A mixture of ethyl carbazate (10 g, 96.1 mmol, 1 eq) and toluene (75 mL) was placed in a three neck flask (250 mL) and cooled in an ice bath. The flask was equipped with an addition funnel, containing 12.012 g of 4,4'-Methylenebis (phenyl isocyanate) (48 mmol, 1 eq) dissolved in 50 mL of toluene, a mechanical stirrer and a bulb condenser. The mixture was put under inert atmosphere and the isocyanate was added slowly under vigorous stirring. After addition the mixture was stirred at room temperature for two hours, followed by 2 hours at 90° C. After cooling the reaction to room temperature, the desired product was filtered off as a white powder and washed with toluene (98%).

MW.: 458.27 g/mol.

$^1$H-NMR (300 MHz, DMSO-d$_6$): δ (ppm)=1.15 (t, 6H, 2×$CH_3$—$CH_2$), 3.9 (s, 2H, Ar—$CH_2$—Ar), 4.05 (q, 4H, 2×$CH_2$—$CH_3$), 7.05 (d, 4H, Ar—H), 7.35 (d, 4H, Ar—H), 7.95 (br. s, 2H, NH), 8.65 (br. s, 2H, NH), 8.9 (br. s, 2H, NH)

Example 5

Synthesis of 4,4'-(4,4'-diphenylmethylene)-bis-(urazole)

In a 50 mL flask, 4,4'-(4,4'-diphenylmethylene)-bis-(carbethoxysemicarbazide) (9.16 g, 20.0 mmol) obtained in Example 4, was dissolved in 35 mL of an aqueous potassium hydroxide solution (4M) under inert atmosphere. This mixture was refluxed for 1.5 hour (100° C.), warm filtered, cooled to room temperature and acidified until pH 1 by adding of HCl. This mixture was cooled to room temperature to yield a solid white powder that was filtered off (97%).

MW.: 366.34 g/mol.

$^1$H-NMR (300 MHz, DMSO-d$_6$): δ (ppm)=4.05 (s, 2H, Ar—CH$_2$—Ar), 7.35 (t, 8H, ArH), 10.45 (s, 4H, NH)

Example 6

Synthesis of 4,4'-(4,4'-diphenylmethylene)-bis-(1,2, 4-triazoline-3,5-dione) (MBPTAD)

A mixture of bisfunctional urazole (2 g, 5.46 mmol, 1 eq) obtained in Example 5, DABCO-Br (5 g, 3.18 mmol, 0.58 eq) and dichloromethane (30 mL) was put in a flask (100 mL) under inert atmosphere and stirred for 2 hours at room temperature. The reaction mixture was filtered off, the residue washed with dichloromethane (2×30 mL) and the filtrate was concentrated in vacuo to obtain 4,4'-(4,4'-diphenylmethylene)-bis-(1,2,4-triazoline-3,5-dione) as a white powder (83%). The temperature of the cooling batch should not exceed 50° C. due to the volatility of the obtained compound.

MW.: 362.30 g/mol.

$^1$H-NMR (300 MHz, DMSO-d$_6$): δ (ppm)=δ (ppm)=4.11 (s, 2H, C—CH$_2$—C), 7.38 (d, 4H, ArH), 7.48 (d, 4H, ArH)

Example 7

Synthesis of N-o-Tolylpivalamide

In a 500 mL flask o-toluidine (30.0 g, 0.280 mol, 1 eq) was dissolved in 240 mL dichloromethane. After addition of triethylamine (31.2 g, 0.308 mol, 1.1 eq), the solution was cooled in a water bath and trimethylacetylchloride (37.9 mL, 0.308 mol, 1.1 eq) was added dropwise. This mixture was stirred overnight under inert atmosphere. The reaction mixture was then washed with 5% aqueous HCl (360 mL), saturated sodium carbonate (360 mL) and brine (360 mL). After drying on magnesium sulfate the desired product was obtained as an ivory white powder, by removing the organic solvent under reduced pressure (98%).

MW.: 191.27 g/mol.

$^1$H-NMR (300 MHz, CDCl$_3$): δ (ppm)=1.27 (s, 9H, C(CH$_3$)$_3$), 2.19 (s, 3H, Ar CH$_3$), 6.99 (m, 1H, ArH), 7.13 (m, 3H, 2×ArH+NH), 7.80 (d, 1H, ArH).

Example 8

Synthesis of 2-tert-butyl-1H-Indole

In a one L flask, a solution of N-o-Tolylpivalamide (35 g, 0.183 mol, 1 eq) (obtained in Example 7) in dry THF (120 mL) was made under inert atmosphere. After cooling in a water bath, n-butyllithium (2.5 M in hexane, 220 mL, 0.55 mol, 3 eq) was added dropwise. The reaction mixture was stirred overnight at room temperature, after which it was cooled in an ice bath. Once the solution was cooled, saturated aqueous ammonium chloride solution (340 mL) was added slowly. The water phase was extracted with ethyl acetate (340 mL), after which the combined organic phases were dried on magnesium sulfate and concentrated in vacuo, to afford a brown solid (95%).

MW.: 173.25 g/mol.

$^1$H-NMR (500 MHz, CDCl$_3$): δ (ppm)=1.32 (s, 9H, C(CH$_3$)$_3$), 6.18 (d, 1H, t-Bu C—CH), 7.02 (m, 2H, ArH), 7.24 (d, 1H, ArH), 7.46 (d, 1H, ArH), 7.87 (br. s, 1H, NH).

$^{13}$C-NMR (125 MHz, CDCl$_3$): δ (ppm)=30.33 (CH$_3$), 31.84 (C), 96.96 (CH), 110.34 (CH), 119.60 (CH), 119.98 (CH), 121.07 (CH), 128.51 (C), 135.76 (C), 148.77 (C).

Example 9

Synthesis of 2-tert-butyl-3-isopentyl-1H-indole

A mixture of trifluoroacetic acid (3.42 g, 30 mmol, 1.5 eq), palladium (5% on activated carbon, 0.3 g) and dichloromethane (40 mL) was put under hydrogen atmosphere in a 250 mL two neck flask and cooled in an ice bath. To this mixture, a solution of 2-tert-butyl-1H-Indole (3.46 g, 20 mmol, 1 eq) (obtained in Example 8) and 3-methylbutyraldehyde (1.9 g, 22 mmol, 1.1 eq) in dichloromethane (60 mL) was added dropwise. This solution was stirred in a water bath for 5 hours, regularly flushing with hydrogen gas. With the aid of thin layer chromatography (TLC) (hexane:ethyl acetate 9:1), the reaction was followed until completion. The mixture was filtered over celite and washed with saturated aqueous sodium carbonate (100 mL). The organic phases were dried over magnesium sulfate and concentrated in vacuo to obtain the title compound as a viscous oil (99%).

MW.: 243.39 g/mol.

$^1$H-NMR (500 MHz, CDCl$_3$): δ (ppm)=0.93 (d, 6H, CH(CH$_3$)$_2$), 1.37 (s, 1H, C(CH$_3$)$_3$), 1.47 (m, 2H, i-Pr CH$_2$), 1.65 (m, 1H, CH(CH$_3$)$_2$), 2.76 (m, 2H, C—C—CH$_2$), 7.00 (m, 2H, ArH), 7.18 (d, 1H, ArH), 7.42 (d, 1H, ArH), 7.70 (br. s, 1H, NH).

$^{13}$C-NMR (125 MHz, CDCl$_3$): δ (ppm)=22.69 (CH$_3$), 23.43 (CH$_2$), 28.87 (CH), 30.59 (CH$_3$), 32.95 (C), 40.81 (CH$_2$), 110.33 (CH), 111.36 (C), 118.16 (CH), 118.94 (CH), 120.97 (CH), 129.83 (C), 134.07 (C), 141.16 (C).

Example 10

Synthesis of 2-tert-butyl-3-pentan-1-ol-1H-indole (Indole-OH)

A mixture of trifluoroacetic acid (7.91 g, 69.2 mmol, 1.5 eq), palladium (5% on activated carbon, 0.7 g) and dichloromethane (95 mL) was put under hydrogen atmosphere in a 500 mL two neck flask and cooled in an ice bath. To this mixture, a solution of 2-tert-butyl-1H-Indole (8 g, 46.2 mmol, 1 eq) (obtained in Example 8) and 3,4-dihydro-2H-pyran (4.3 g, 51.1 mmol, 1.1 eq) in dichloromethane (140 mL) was added dropwise. This solution was stirred in a water bath for 48 hours, regularly flushing with hydrogen gas. With the aid of TLC (hexane:ethyl acetate 9:1), the reaction was followed until completion. The mixture was filtered over celite and washed with saturated aqueous sodium carbonate (100 mL). The organic phases were dried over magnesium sulfate and concentrated in vacuo to obtain a yellow brown oil. Methanol was added to this oil, to afford a 10 m % dilution, followed by addition of potassium carbonate until saturation of the solution. After stirring for 15 minutes, enough water was added to double the volume. The resulting mixture was concentrated under reduced pressure, until the volume was halved. Extraction with dichloromethane (2×100 mL) followed. The obtained organic phases were collected, dried on magnesium sulfate and concentrated in vacuo to afford a yellow brown oil (99%).

MW.: 259.39 g/mol.

LC-MS (m/z): 260.2 [MH]$^+$, 282.1 [MNa]$^+$ $^1$H-NMR (500 MHz, CDCl$_3$): δ (ppm)=1.38 (s, 9H, C(CH$_3$)$_3$), 1.45 (m, 2H, CH$_2$—CH$_2$—CH$_2$), 1.59 (m, 4H, CH$_2$—CH$_2$—CH$_2$), 2.79 (t, 2H, C—C—CH$_2$), 3.59 (t, 2H, CH$_2$—OH), 7.01 (m, 2H, ArH), 7.20 (d, 1H, ArH), 7.42 (d, 1H, ArH), 7.76 (br. s, 1H, NH).
$^{13}$C-NMR (125 MHz, CDCl$_3$): δ (ppm)=25.55 (CH$_2$), 26.36 (CH$_2$), 30.60 (CH$_3$), 31.42 (CH$_2$), 32.80 (CH$_2$), 32.93 (C), 63.09 (CH$_2$), 110.28 (CH), 110.98 (C), 118.16 (CH), 118.95 (CH), 120.97 (CH), 129.79 (C), 133.98 (C), 141.31 (C).

Example 11

Synthesis of 5-(2-tert-butyl-1H-indol-3-yl)pentyl 2-bromopropanoate

In a two neck 25 mL flask a solution of Indole-OH (2 g, 7.71 mmol, 1 eq), obtained in Example 10, and dry triethylamine (1.17 g, 11.57 mmol, 1.5 eq) in dry dichloromethane (10 mL) was placed under inert atmosphere. After cooling in an ice bath, 2-bromopropionyl bromide (1.01 ml, 9.64 mmol, 1.25 eq) was added dropwise and stirred overnight at room temperature. With the aid of TLC (hexane:ethyl acetate 1:1), the reaction was followed until completion. The reaction mixture was filtered, and the filtrate was washed with water (2×10 mL) and saturated aqueous sodium carbonate (3×10 mL). After drying on magnesium sulfate the title compound was obtained by concentrating the organic solvent phase in vacuo, affording a dark brown oil (49%).
MW.: 394.35 g/mol.
$^1$H-NMR (300 MHz, CDCl3): δ (ppm)=1.39 (s, 9H, C(CH$_3$)$_3$), 1.47 (m, 2H, CH$_2$—CH$_2$—CH$_2$), 1.64 (m, 4H, CH$_2$—CH$_2$—CH$_2$), 1.75 (d, 3H, CH$_3$—CHBr), 2.79 (m, 2H, C—C—CH$_2$), 4.12 (m, 2H, CH$_2$-0), 4.30 (q, 1H, Br—CH), 7.01 (m, 2H, ArH), 7.21 (d, 1H, ArH), 7.42 (d, 1H, ArH), 7.75 (br. s, 1H, NH).

Example 12

Synthesis of 2-tert-butyl-3-pentan-1-mesylate-1H-indole

In a two neck 250 mL flask, 11.9 g of Indole-OH (45.9 mmol, 1 eq) obtained in Example 10, were dissolved in 120 mL dry THF. After addition of 9.29 g of dry triethylamine (91.8 mmol, 2 eq) this mixture was cooled in an ice bath. Then methane sulfonylchloride (5.33 mL, 68.9 mmol, 1.5 eq) was added dropwise and the mixture was stirred for 3 hours under inert atmosphere. With the aid of thin layer chromatography (TLC) (hexane:ethylacetate 1:1), the reaction was followed until completion. The mixture was washed with water (60 mL). The water phase was extracted with 60 mL THF. The combined organic phases were washed with saturated aqueous sodium carbonate (2×60 mL) and brine (60 mL). After drying over magnesium sulfate, the title compound was obtained as a black oil, after in vacuo evaporation of the solvent (80%).
MW.: 337.48 g/mol.
HRMS (m/z for [MH]$^+$): calculated: 338.1784; experimental: 338.1789.
$^1$H-NMR (300 MHz, CDCl3): δ (ppm)=1.39 (s, 9H, C(CH3)3), 1.55 (m, 6H, CH2-CH2-CH2), 2.80 (m, 2H, C—C—CH2), 2.90 (s, 3H, O—SO2-CH3), 4.17 (t, 2H, CH2-OMs), 7.01 (m, 2H, ArH), 7.21 (d, 1H, ArH), 7.41 (d, 1H, ArH), 7.80 (br. s, 1H, NH).

Example 13

Synthesis of 5-(2-tert-butyl-1H-indol-3-yl)pentyl-2, 2-bis-(hydroxymethyl)-propanoate (Indole Diol)

A mixture of 2,2-bis-(hydroxymethyl)-propionic acid (1.99 g, 14.8 mmol, 1 eq), potassium carbonate (2.25 g, 16.3 mmol, 1.1 eq) and dry DMF (15 mL) was placed in a two neck flask (50 mL) under an inert atmosphere and cooled in an ice bath. To this mixture, a solution of 2-tert-butyl-3-pentan-1-mesylate-1H-indole (5.00 g, 14.8 mmol, 1 eq) (obtained in Example 12) in dry DMF (15 mL) was added. This mixture was stirred vigorously overnight at 80° C. With the aid of TLC (hexane:ethyl acetate 1:1), the conversion of the starting product was followed. The salts were filtered off and washed with DMF, after which the filtrate was concentrated under reduced pressure. The resulting orange brown oil was diluted with 50 mL 5% triethylamine in ethyl acetate to afford a 10 m % dilution. The resulting mixture was then placed in an ultrasonic bath for 10 min. The salts were filtered off and washed with 5% triethylamine in ethyl acetate, after which the filtrate was concentrated in vacuo to obtain the title compound. This product was then purified by chromatography (gradient:hexane:ethyl acetate 4:1; hexane:ethyl acetate 1:1) to afford an orange brown oil (61%).
MW.: 375.51 g/mol.
LC-MS (m/z): 376.2 [MH]$^+$.
HRMS (m/z for [MH]$^+$): calculated: 376.2482; experimental: 376.2487.
$^1$H-NMR (500 MHz, CDCl3): δ (ppm)=1.06 (s, 3H, CO—C—CH$_3$), 1.47 (s, 9H, C(CH$_3$)$_3$), 1.53 (m, 2H, CH$_2$—CH$_2$—CH$_2$), 1.73 (m, 4H, CH$_2$—CH$_2$—CH$_2$), 2.81 (t, 2H, CH$_2$—OH), 2.88 (t, 2H, C—C—CH$_2$), 3.71 (dd, 2H, CH$_2$—OH), 3.90 (dd, 2H, CH$_2$—OH), 4.20 (t, 2H, CH$_2$—O—CO), 7.10 (m, 2H, ArH), 7.29 (d, 1H, ArH), 7.50 (d, 1H, ArH), 7.85 (br. s, 1H, NH).
$^{13}$C-NMR (125 MHz, CDCl3): δ (ppm)=17.13 (CH$_3$), 25.42 (CH$_2$), 26.38 (CH$_2$), 28.59 (CH$_2$), 30.60 (CH3), 31.16 (CH$_2$), 32.93 (C), 49.08 (C), 65.12 (CH$_2$), 68.47 (CH$_2$), 110.28 (CH), 110.72 (C), 118.11 (CH), 118.95 (CH), 120.97 (CH), 129.75 (C), 133.97 (C), 141.38 (C), 176.04 (C).

Example 14

Synthesis of 5-(2-tert-butyl-1H-indole-3-yl)pentylacrylate

In a 250 mL two neck flask, 11.9 g of Indole-OH (45.9 mmol, 1 eq) obtained in Example 10, was dissolved in 100 mL dry dichloromethane. After the addition of 5.81 g of dry triethylamine (57.4 mmol, 1.25 eq), the mixture was cooled in an ice bath. In a next step, acryloylchloride (5.20 g, 57.4 mmol, 1.25 eq) in 50 mL dry dichloromethane was added dropwise, and the mixture was stirred under inert atmosphere overnight. With the aid of TLC (hexane:ethylacetate 1:1) the reaction was followed until completion. The reaction mixture was filtrated and the filtrate sequentially partitioned with saturated aqueous sodium carbonate (50 mL), water (150 mL) and dichloromethane (50 mL). The organic phase was washed with saturated aqueous sodium carbonate (100 mL), brine (10 mL) and water (100 mL); while the aqueous phase was extracted with dichloromethane (100 mL). The combined organic phases were dried over magnesium sulfate and concentrated in vacuo to obtain the title compound as a pale yellow oil (83%).
MW.: 313.43 g/mol.
LC-MS (m/z): 314.2 [MH]$^+$.
HRMS (m/z for [MH]$^+$): calculated: 314.2115; experimental: 314.2122.
$^1$H-NMR (500 MHz, CDCl3): δ (ppm)=1.38 (s, 9H, C(CH$_3$)$_3$), 1.45 (m, 2H, CH$_2$—CH$_2$—CH$_2$), 1.63 (m, 4H, CH$_2$—CH$_2$—CH$_2$), 2.78 (t, 2H, C—C—CH$_2$), 4.09 (t, 2H, CH$_2$—O), 5.71 (dd, 1H, CO—CH—CH$_2$), 6.04 (dd, 1H, CO—CH—CH$_2$), 6.31 (dd, 1H, CO—CH—CH$_2$), 6.99 (m, 2H, ArH), 7.18 (d, 1H, ArH), 7.40 (d, 1H, ArH), 7.87 (br. s, 1H, NH).

$^{13}$C-NMR (125 MHz, CDCl3): δ (ppm)=25.52 (CH$_2$), 26.61 (CH$_2$), 28.70 (CH$_2$), 30.64 (CH$_3$), 31.34 (CH$_2$), 32.98 (C), 64.77 (CH$_2$), 110.36 (CH), 110.78 (C), 118.14 (CH), 118.95 (CH), 120.96 (CH), 128.67 (CH), 129.78 (C), 130.56 (CH2), 134.09 (C), 141.40 (C), 166.43 (C).

Example 15

Synthesis of 5-(2-tert-butyl-1H-indole-3-yl)pentylmethacrylate

In a 250 mL two neck flask, 11.9 g of Indole-OH (45.9 mmol, 1 eq) obtained in Example 10, was dissolved in 100 mL dry dichloromethane. After the addition of 5.81 g of dry triethylamine (57.4 mmol, 1.25 eq), the mixture was cooled in an ice bath. In a next step methacryloylchloride (6.00 g, 57.4 mmol, 1.25 eq) in 50 mL dry dichloromethane was added dropwise, and the mixture was stirred under inert atmosphere overnight. With the aid of TLC (hexane:ethylacetate 1:1) the reaction was followed until completion. The reaction mixture was filtrated and the filtrate sequentially partitioned with saturated aqueous sodium carbonate (50 mL), water (150 mL) and dichloromethane (50 mL). The organic phase was washed with saturated aqueous sodium carbonate solution (100 mL), brine (10 mL) and water (100 mL); while the aqueous phase was extracted with dichloromethane (100 mL). The combined organic phases were dried over magnesium sulfate and concentrated in vacuo to obtain 14.3 g (95%) of the title compound.

MW.: 327.46 g/mol.

LC-MS (m/z): 328.2 [MH]$^+$.

HRMS (m/z for [MH]$^+$): calculated: 328.2271; experimental: 328.2276.

$^1$H-NMR (500 MHz, CDCl3): δ (ppm)=1.47 (s, 9H, C(CH$_3$)$_3$), 1.55 (m, 2H, CH$_2$—CH$_2$—CH$_2$), 1.72 (m, 4H, CH$_2$—CH$_2$—CH$_2$), 1.96 (s, 3H, CO—C—CH$_3$), 2.87 (t, 2H, C—C—CH$_2$), 4.18 (t, 2H, CH$_2$—O), 5.56 (s, 1H, CO—C—CH$_2$), 6.11 (s, 1H, CO—C—CH$_2$), 7.09 (m, 2H, ArH), 7.29 (d, 1H, ArH), 7.50 (d, 1H, ArH), 7.83 (br. s, 1H, NH).

$^{13}$C-NMR (125 MHz, CDCl3): δ (ppm)=18.36 (CH$_3$), 25.49 (CH$_2$), 26.61 (CH$_2$), 28.67 (CH$_2$), 30.59 (CH$_3$), 31.26 (CH$_2$), 32.92 (C), 64.80 (CH$_2$), 110.26 (CH), 110.85 (C), 118.13 (CH), 118.97 (CH), 120.98 (CH), 125.20 (CH2), 129.75 (C), 133.95 (C), 136.55 (C), 141.31 (C), 167.57 (C).

Example 16

Synthesis of 4-nitrophenyl-1-(ethoxycarbonyl)semicarbazide

In a 50 mL two-neck flask, 4-nitrophenyl isocyanate (1 g, 6.1 mmol) was dissolved in dry toluene (15 mL). This mixture was cooled on an ice batch for 30 min. Then ethyl carbazate (0.634 g, 6.1 mmol) dissolved in dry toluene (15 mL) was added dropwise over 10 minutes. The reaction mixture was brought to room temperature and allowed to stir for 8 hours, after which it was cooled in an ice batch. The desired product was filtered off as a bright yellow powder (95%), and used without any further purification.

MW.: 268.23 g/mol.

$^1$H-NMR (300 MHz, DMSO-d$_6$): δ (ppm)=1.20 (t, 3H, CH$_3$—CH$_2$), 4.07 (q, 2H, CH$_2$—CH$_3$), 7.73 (d, 2H, ArH), 8.17 (d, 2H, ArH), 8.40 (br. s, 1H, NH), 9.04 (br. s, 1H, NH), 9.52 (br. s., 1H, NH)

Example 17

Synthesis of 4-nitrophenyl-1,2,4-triazolidine-3,5-dione

In a five mL flask, 4-nitrophenyl 1-(ethoxycarbonyl)semicarbazide (1 g, 3.7 mmol), obtained in Example 16, was dissolved in 2.5 mL of an aqueous potassium hydroxide solution (4M) under inert atmosphere. This mixture was refluxed for four hours (100° C.), warm filtered, cooled to room temperature and acidified until pH 1 with HCl. This mixture was cooled to room temperature to yield a solid white powder (95%) that was filtered off.

MW.: 222.16/mol.

$^1$H-NMR (300 MHz, DMSO-d$_6$): δ (ppm)=7.89 (d, 2H, ArH), 8.36 (d, 2H, ArH), 10.82 (br. s, 1H, NH).

Example 18

Synthesis of 4-aminophenyl-1,2,4-triazolidine-3,5-dione

In a 25 mL flask, 4-nitrophenyl-1,2,4-triazolidine-3,5-dione (0.5 g, 2.6 mmol), obtained in Example 17, was dissolved in 10 mL of methanol. A catalytic amount of palladium (5% on activated carbon) was added. Then a balloon containing hydrogen gas was placed on the reaction, this mixture was stirred vigorously for 24 hour at room temperature. The solution was filtered over a plug of celite to remove the palladium and then concentrated under reduced pressure to give the desired product (96%).

MW.: 192.17/mol.

$^1$H-NMR (300 MHz, DMSO-d$_6$): δ (ppm)=5.29 (br. s., 2H, NH2), 6.59 (d, 2H, ArH), 6.98 (d, 2H, ArH), 10.17 (br. s, 2H, NH).

Example 19

Synthesis of 2-bromo-N-[4-(3,5-dioxo-1,2,4-triazolidin-4-yl)phenyl]-2-methylpropanamide In a 25 mL flask, 4-aminophenyl-1,2,4-triazolidine-3,5-dione (1 g, 5.2 mmol), obtained in Example 18, was dissolved in 10 mL of dry pyridine. After cooling this mixture on ice, alpha-bromoisobutyryl bromide (1.20 g, 5.2 mmol, 0.65 mL) was added dropwise. The mixture was slowly brought to room temperature and stirred overnight. Then, 15 mL of water was added and the mixture was partitioned three times with ethyl acetate. The organic phase was washed once with a 1M HCl aqueous solution, and concentrated in vacuo. The product was purified by flash chromatography (gradient:ethyl acetate:MeOH:Acetic acid 95:5:1; petroleum ether 2:1), to afford 1.3 g (73%).

MW.: 341.16/mol.

$^1$H-NMR (300 MHz, DMSO-d$_6$): δ (ppm)=2.08 (s, 6H, 2×CH$_3$), 7.45 (d, 2H, ArH), 7.79 (d, 2H, ArH), 10.01 (s, 1H, NH), 10.50 (br. s, 2H, NH)

Example 20

Synthesis of 4-[(2E,4E)-2,4-hexadien-1-yloxy]-4-oxobutanoic acid

A mixture of trans,trans-2,4-hexadien-ol (2.55 g, 26 mmol), succinic anhydride (3.0 g, 30 mmol), and N,N-diisopropylethylamine (DiPEA) (3.4 g, 26 mmol) in diethyl ether (10 mL) was stirred for 2 days at ambient temperature. The solvent was removed under reduced pressure and the residue dissolved in dichloromethane and washed with aqueous solution of 5% w/w citric acid. The organic layer was dried over $MgSO_4$, filtered, and the solvent was removed under reduced pressure to afford the desired product (80%).

MW.: 327.46 g/mol.

$^1$H-NMR (500 MHz, $CDCl_3$): δ (ppm)=1.71 (d, 3H, $CH_3$—CH), 2.63 (t, 4H, $CH_2$—$CH_2$), 4.55 (d, 2H, $CH_2$-0), 5.60 (dt, 1H, —CH=CH), 5.72 (dq, 1H, —CH=CH—), 6.03 (ddq, 1H, =CH—CH=), 6.22 (dd, 1H, —CH=CH—).

Example 21

Synthesis of Polyisobornyl Acrylate-Br (PiBA-Br) Polymer 14 mL Isobornyl acrylate (66.3 mmol, 100 eq), 4.7 mL ethyl acetate (25 vol %) and 103.8 µL PMDETA (0.5 mmol, 0.75 eq) were weighed into a flask and degassed for one hour with a continuous nitrogen sparge. 47.53 mg Cu(I)Br (0.33 mmol, 0.5 eq) was added under $N_2$ atmosphere and the reaction mixture was stirred until a homogenous solution was obtained. Then, 151 µL methyl 2-bromopropionate (6.63 µmol, 1 eq), which was degassed separately, was added and the reaction mixture was placed in an oil bath at 77° C. After one hour, the reaction was stopped (18% conversion) by cooling in liquid nitrogen, addition of 200 mL cold methanol, which induced precipitation. The precipitate was filtered off and dissolved in 100 mL THF. The copper catalyst was removed by passing the reaction mixture over a column of $Al_2O_3$. After evaporating the excess solvent until a volume of 20 mL, the polymer was precipitated in 200 mL cold methanol. The polymer was filtered, washed with methanol and again dissolved in 20 mL of THF. Finally, the polymer was precipitated in 200 mL of cold methanol and dried overnight in a vacuum oven at 40° C.

$M_n$ (SEC): 2900 Da
$M_w$ (SEC): 3600 Da
polydispersity (Ð) (SEC): 1.23

Example 22

Synthesis of Polyisobornyl Acrylate-Cyclopentadiene (PiBA-Cp) Polymer

PiBA-Br (0.18 mmol) obtained in Example 21, was mixed with 89 µL tributylphosphine (0.36 mmol) and 0.162 g sodium iodide (1.08 mmol) and dissolved in dry THF (2.0 mL). The resulting solution was placed under nitrogen atmosphere. Separately, a stock solution of bis(cyclopentadienyl)nickel(II) in dry THF (0.18 mol/L) was prepared under a nitrogen atmosphere. Then 2.0 mL of the bis(cyclopentadienyl)nickel(II) solution was added to the polymer solution and this mixture was stirred overnight at room temperature. After completion of the reaction, the solution was filtrated over a short column of basic alumina, to remove the precipitated nickel(II) bromide. Then the polymer was precipitated with cold methanol, filtrated and washed thoroughly with more methanol. The resulting powder was then dissolved in chloroform and washed three times with distilled water. To obtain the PiBA-Cp, the polymer was again precipitated in cold methanol, filtrated, washed thoroughly with methanol and dried in a vacuum oven overnight at 40° C.

$M_n$ (SEC): 3500 Da
$M_w$ (SEC): 4200 Da
Ð (SEC): 1.20

Example 23

Synthesis of Polyisobornyl Acrylate-Open Diene (OD) Polymer 0.468 g (0.18 mmol) of PiBA-Br, obtained in Example 21, was dissolved in 5 mL of dry THF. Then, 0.1 g of 4-[(2E,4E)-2,4-Hexadien-1-yloxy]-4-oxobutanoic acid (HDEO) (0.36 mmol) (obtained in Example 20) and 0.054 g of 1.8 diazabicyclo(5.4.0)undec-7-ene (DBU) (0.036 mmol) were added at room temperature. The resulting mixture was stirred for five days at 50° C. under nitrogen atmosphere. The polymer was then precipitated in 25 mL cold methanol, filtrated, washed thoroughly with more methanol, and dried overnight in a vacuum oven at 40° C.

$M_n$ (SEC): 4.200 Da
$M_w$ (SEC): 4.750 Da
Ð (SEC): 1.20

Example 24

Synthesis of Indole-Polyisobornyl Acrylate Polymer (PiBA-Indole)

15 mL Isobornyl acrylate (71 mmol, 100 eq), 296.5 µL PMDETA (1.42 mmol, 2 eq) and 203.7 mg Cu(I)Br were weighed into a flask and degassed for 1 hour with a continuous nitrogen sparge. Then, a degassed solution of 280 mg 5-(2-tert-butyl-1H-indole-3-yl)pentyl-2-bromepropanoate (0.71 mmol, 1 eq) (obtained in Example 11) in five mL acetone was added, and the reaction mixture was placed in an oil bath at 50° C. After 3 hours, the reaction was stopped (12% conversion) by cooling in liquid nitrogen and addition of 200 mL cold methanol, which induced precipitation. The precipitate was filtered off and dissolved in 100 mL THF. The copper catalyst was removed by passing the reaction mixture over a column of $Al_2O_3$. After evaporating the excess solvent until a volume of 20 mL, the polymer was precipitated in 200 mL cold methanol. The polymer was filtered, washed with methanol and again dissolved in 20 mL of THF. Finally, the polymer was precipitated in 200 mL of cold methanol and dried overnight in a vacuum oven at 40° C.

$M_n$ (SEC): 1900 Da
$M_w$ (SEC): 2300 Da
Ð (SEC): 1.22

Example 25

Synthesis of Polystyrene-Br (PS-Br) Polymer

Five mL styrene (43.5 mmol, 50 eq), 5 mL toluene, Cu(0) (30 pellets), 19.43 mg Cu(II)$Br_2$ (86.9 µmol, 0.1 eq) and 63.6 µL PMDETA (0.304 mmol, 0.35 eq) were weighed into a flask and degassed for one hour with a continuous nitrogen sparge. 112.97 µL Ethyl 2-bromopropionate (0.87 mmol, 1 eq) were degassed separately in an ampoule by nitrogen sparge for one hour. After addition of the ethyl 2-bromopropionate to the reaction mixture, the flask was placed in an oil bath at 90° C. and the reaction started. After 18 hours, the reaction was stopped (82% conversion), by cooling in liquid nitrogen and addition of 100 mL cold methanol, which induced precipitation. The precipitate was filtered off and dissolved in 100 mL THF. The copper catalyst was removed by passing the reaction mixture over a column of $Al_2O_3$. After evaporating the excess solvent until a volume of 20 mL, the polymer was precipitated in 200 mL of cold methanol. The polymer was filtered, washed with methanol and again dissolved in 20 mL of THF. Finally the polymer was precipitated in 200 mL of cold methanol and dried overnight in a vacuum oven at 40° C.

$M_n$ (SEC): 4200 Da
$M_w$ (SEC): 4500 Da
Đ (SEC): 1.08

Example 26

Synthesis of Polystyrene-Cyclopentadiene (PS-Cp) Polymer

PS-Br (0.18 mmol), obtained in Example 25, was mixed with 89 µL tributylphosphine (0.36 mmol) and 0.162 g sodium iodide (1.08 mmol) and dissolved in dry THF (2.0 mL). The resulting solution was placed under nitrogen atmosphere. Separately, a stock solution of bis(cyclopentadienyl)nickel(II) in dry THF (0.18 mol/L) was prepared under a nitrogen atmosphere. Then 2.0 mL of the bis(cyclopentadienyl)nickel(II) solution was added to the polymer solution and this mixture was stirred overnight at room temperature. After completion of the reaction, the solution was filtrated over a short column of basic alumina, to remove the precipitated nickel(II) bromide. Then the polymer was precipitated with cold methanol, filtrated and washed thoroughly with more methanol. The resulting powder was then dissolved in chloroform and washed three times with distilled water. To obtain the PS-Cp, the polymer was again precipitated in cold methanol, filtrated, washed thoroughly with methanol and dried in a vacuum oven overnight at 40° C.

$M_n$ (SEC): 4000 Da
$M_w$ (SEC): 4400 Da
Đ (SEC): 1.10

Example 27

Synthesis of Polystyrene-OD Polymer (PS-OD)

0.8 g (0.18 mmol) of PS-Br, obtained in Example 25, was dissolved in 5 mL of dry THF. Then, 0.1 g of 4-[(2E,4E)-2,4-Hexadien-1-yloxy]-4-oxobutanoic acid (0.36 mmol) (obtained in Example 20) and 0.054 g of 1.8 Diazabicyclo(5.4.0)undec-7-ene (DBU) (0.036 mmol) were added at room temperature. The resulting mixture was stirred for five days at 50° C. under nitrogen atmosphere. The polymer was then precipitated in 25 mL cold methanol, filtrated, washed thoroughly with more methanol and dried overnight in a vacuum oven at 40° C.

$M_n$ (SEC): 3400 Da
$M_w$ (SEC): 3600 Da
Đ (SEC): 1.09

Example 28

Synthesis of Indole-Polystyrene Polymer (PS-Indole)

15 mL styrene (130.5 mmol, 100 eq), 10 mL toluene, Cu(0) (30 pellets), 29.14 mg Cu(II)Br$_2$ (130.49 µmol, 0.1 eq) and 95.36 µL PMDETA (0.46 mmol, 0.35 eq) were weighed into a flask and degassed for 1 hour with a continuous nitrogen sparge. A solution of 514.57 mg 5-(2-tert-butyl-1 H-indole-3-yl)pentyl-2-bromepropanoate (1.30 mmol, 1 eq) (obtained in Example 11) in five mL toluene was degassed separately in an ampoule by nitrogen sparge for one hour. After addition of 5-(2-tert-butyl-1H-indole-3-yl)pentyl-2-bromepropanoate to the reaction mixture, the flask was placed in an oil bath at 90° C. After four hours, the reaction was stopped (18% conversion) by cooling in liquid nitrogen and addition of 300 mL cold methanol, which induced precipitation. The precipitate was filtered off and dissolved in 100 mL THF. The copper catalyst was removed by passing the reaction mixture over a column of $Al_2O_3$. After evaporating the excess solvent until a volume of 20 mL, the polymer was precipitated in 200 mL of cold methanol. The polymer was filtered, washed with methanol and again dissolved in 20 mL of THF. Finally the polymer was precipitated in 200 mL of cold methanol and dried overnight in a vacuum oven at 40° C.

$M_n$ (SEC): 1400 Da
$M_w$ (SEC): 1600 Da
Đ (SEC): 1.17

Example 29

Synthesis of Indole-Poly(Methyl Methacrylate) Polymer (PMMA-Indole)

5.0 mL methyl methacrylate (46.9 mmol, 50 eq), 1.48 g 5-(2-tert-butyl-1H-indol-3-yl)pentyl 2-bromopropanoate (3.76 mmol, 4 eq) (obtained in Example 11), 9.7 mL DMF and Cu(0) (30 pellets), were weighed into a flask and degassed for one hour with a continuous nitrogen sparge. In a separate vial, a solution of 41.9 mg Cu(II)Br$_2$ (0.188 mmol, 0.2 eq), 151 µL Me$_6$TREN (0.563 mmol, 0.6 eq) and five mL DMF was degassed for one hour. The reaction was started by the addition of the Cu(II)Br$_2$ solution to the reaction mixture; the flask was then placed in an oil bath at 30° C., under inert atmosphere. After 24 hours, the reaction was stopped by cooling in liquid nitrogen. The reaction mixture was diluted in THF to double the volume, filtered over a column of $Al_2O_3$, and evaporated to a 15 mL volume. The polymer was then precipitated in 150 mL of cold methanol; filtered, washed with methanol and dried overnight in a vacuum oven at 40° C.

$M_n$ (SEC): 8.300 Da
$M_w$ (SEC): 11.000 Da
Đ (SEC): 1.32

Example 30

Synthesis of Urazole-Polystyrene Polymer 4.21 mL Styrene (36.64 mmol, 50 eq), 105.12 mg Cu(I)Br (0.73 mmol, 1 eq), and 228.90 mg 2,2'-Bipyridyl (1.47 mmol, 2 eq) were weighed into a flask and degassed for one hour with a continuous nitrogen sparge. 250 mg 2-bromo-N-[4-(3,5-dioxo-1,2,4-triazolidin-4-yl)phenyl]-2-methyl-propanamide (0.73 mmol, 1 eq), obtained in Example 19, was dissolved in one mL DMF and degassed separately in an ampule by nitrogen sparge for one hour. After addition of the 2-bromo-N-[4-(3,5-dioxo-1,2,4-triazolidin-4-yl)phenyl]-2-methylpropanamide to the reaction mixture, the flask was placed in an oil bath at 110° C. After 10 hours, the reaction was stopped (78% conversion) by cooling in liquid nitrogen and addition of 100 mL cold methanol, resulting in precipitation. The precipitate was filtered off and dissolved in 100 mL THF. The copper catalyst was removed by passing the reaction mixture over a column of $Al_2O_3$. After evaporating the excess solvent until a volume of 20 mL, the polymer was precipitated in 200 mL of cold methanol. The polymer was filtered, washed with methanol and again dissolved in 20 mL of THF. Finally the polymer was precipitated in 200 mL of cold methanol and dried overnight in a vacuum oven at 40° C.

$M_n$ (SEC): 5.200 Da
$M_w$ (SEC): 5.800 Da
Đ (SEC): 1.12

Example 31

Synthesis of Urazole-Polyisobornyl Acrylate Polymer 4.64 mL Isobornyl acrylate (21.98 mmol, 30 eq), 2 mL DMF, Cu(0) (30 pellets), 250 mg 2-bromo-N-[4-(3,5-dioxo-1,2,4-triazolidin-4-yl)phenyl]-2-methylpropanamide (0.73 mmol, 1eq) (obtained in Example 19) were weighed into a flask and degassed for one hour with a continuous nitrogen sparge. In a separate vial, 32.73 mg Cu(II)$Br_2$ (0.15 mmol, 0.2 eq), 30.6 µL $Me_6$TREN (0.15 mmol, 0.2 eq) and 1.82 mL DMF were degassed separately for one hour. The reaction was started by the addition of the Cu(II)$Br_2$ solution to the reaction mixture, the flask was placed in an oil bath at 25° C. After 72 hours, the reaction was stopped (72% conversion) by cooling in liquid nitrogen and addition of 100 mL cold methanol, which caused precipitation. The precipitate was filtered off and dissolved in 100 mL THF. The copper catalyst was removed by passing the reaction mixture over a column of $Al_2O_3$. After evaporating the excess solvent until a volume of 20 mL, the polymer was precipitated in 200 mL of cold methanol. The polymer was filtered, washed with methanol and again dissolved in 20 mL of THF. Finally the polymer was precipitated in 200 mL of cold methanol and dried overnight in a vacuum oven at 40° C.

$M_n$ (SEC): 4.400 Da
$M_w$ (SEC): 4.900 Da
Đ (SEC): 1.11

Example 32

Synthesis of Urazole-Polymethylmethacrylate Polymer 5.95 mL methylmethacrylate (55.6 mmol, 50 eq), 10 mL DMF, Cu(0) (30 pellets), 379.4 mg 2-bromo-N-[4-(3,5-dioxo-1,2,4-triazolidin-4-yl)phenyl]-2-methylpropanamide (1.11 mmol, 1 eq), obtained in Example 19, were weighed into a flask and degassed for one hour with a continuous nitrogen sparge. In a separate vial, 12.42 mg Cu(II)$Br_2$ (0.05 mmol, 0.05 eq), 44.58 µL $Me_6$TREN (0.17 mmol, 0.15 eq) and 2.58 mL DMF were degassed separately for one hour. The reaction was started by the addition of the Cu(II)$Br_2$ solution to the reaction mixture, the flask was placed in an oil bath at 25° C. After five hours, the reaction was stopped (95.1% conversion) by cooling in liquid nitrogen and addition of 150 mL cold methanol, inducing precipitation. The precipitate was filtered off and dissolved in 100 mL THF. The copper catalyst was removed by passing the reaction mixture over a column of $Al_2O_3$. After evaporating the excess solvent until a volume of 20 mL, the polymer was precipitated in 200 mL of cold methanol. The polymer was filtered, washed with methanol and again dissolved in 20 mL of THF. Finally the polymer was precipitated in 200 mL of cold methanol and dried overnight in a vacuum oven at 40° C.

$M_n$ (SEC): 15 300 Da
$M_w$ (SEC): 20 200 Da
Đ (SEC): 1.32

Example 33

Synthesis of Triazolinedione-Polystyrene Polymer (PS-TAD)

1 mmol of urazole-polystyrene polymer, obtained in Example 29, was dissolved in 5 mL of dichloromethane. Then, 0.3 mmol of DABCO-Br was added at room temperature. The solution was allowed to stir for 3 hours at room temperature. The resulting solution was filtrated and concentrated in vacuo to obtain the title compound.

Example 34

Synthesis of Triazolinedione-Polyisobornyl Acrylate Polymer (PiBA-TAD)

1 mmol of urazole-polyisobornyl acrylate polymer, obtained in Example 30, was dissolved in 5 mL of dichloromethane. Then, 0.3 mmol of DABCO-Br was added at room temperature. The solution was allowed to stir for 3 hours at room temperature. The resulting solution was filtrated and concentrated in vacuo to obtain the title compound.

Example 35

Synthesis of triazolinedione-polymethylmethacrylate polymer (PMMA-TAD)

1 mmol of urazole-polymethylmethacrylate polymer, obtained in Example 31, was dissolved in 5 mL of dichloromethane. Then, 0.3 mmol of DABCO-Br was added at room temperature. The solution was allowed to stir for 3 hours at room temperature. The resulting solution was filtrated and concentrated in vacuo to obtain the title compound.

Example 36

Synthesis of Indole-Polyurethane Polymer

A solution of 2.01 g 5-(2-tert-butyl-1H-indole-3-yl)pentyl-2,2-bis-(hydroxymethyl)-propanoate (5.36 mmol, 0.68 eq) (obtained in Example 13) in 5 mL ethyl acetate was mixed with 5.0 g polypropylene oxide (2.50 mmol, 0.32 eq) and 1.32 g of hexamethylene diisocyanate (7.86 mmol, 1 eq) in a 50 mL flask, after which 71 µL dibutyltin dilaurate were added. The mixture was stirred thoroughly and then injected between two glass plates, with a silicone spacer between the two plates. This set-up was placed for six hours in a vacuum oven at 70° C. The obtained polymer was dried in a vacuum oven overnight at 40° C. The resulting polymer contains 25% (m/m) indole-diol.

$M_n$ (SEC): 22 300 Da
$M_w$ (SEC): 68 800 Da
Ð (SEC): 3.09.
$T_g$ (DSC): −40° C.
$T_{deg}$ (TGA): 300° C.

Example 37

Synthesis of Poly(Ethylene Oxide)-OD

Poly(ethylene glycol) monomethylether (2 g, 1 mmol), 4-[(2E,4E)-2,4-hexadien-1-yloxy]-4-oxobutanoic acid (1.8 g, 9 mmol) (obtained in Example 20), and 4-dimethylamino pyridine (0.07 g, 0.6 mmol) were dissolved in 48 mL dichloromethane and the resulting mixture cooled in an ice bath. N,N-dicyclohexylcarbodiimide (1.8 g, 9 mmol), dissolved in 24 mL dichloromethane, was added dropwise to the above mixture. The resulting solution was stirred at ambient temperature for 12 h. The solution was filtered through a cotton fitted Pasteur pipette and the polymer was precipitated in cooled diethyl ether.

$M_n$ (SEC): 3300 Da
$M_w$ (SEC): 3900 Da
Ð (SEC): 1.18

Example 38

Synthesis of tris[2-(diethylamino)ethyl]amine ($Me_6TREN$)

$Me_6TREN$ was synthesized according to a procedure known in the art (Inorg. Chem, 1966, 5, 41-44).
MW.: 230.40 g/mol.

Example 39

Synthesis of poly[methylmethacrylate-co-(indole-methacrylate)] polymer (poly(MMA-co indole-MA))

5.0 mL methyl methacrylate (46.9 mmol, 40 eq), 3.84 g 5-(2-tert-butyl-1H-indole-3-yl)pentylmethacrylate (11.7 mmol, 10 eq) (obtained in Example 15), 0.991 mL ethyl-2-bromo propionate (7.63 mmol, 6.5 eq) en Co(0) (30 pellets) were mixed in a flask. In parallel, a solution containing 83.5 mg Co(II)-bromide (0.374 mmol, 0.3 eq) and 300 μL $Me_6TREN$ (1.12 mmol, 0.95 eq) (obtained in Example 38) in 18.7 mL DMF was prepared. Both solutions were degassed during one hour by passing through nitrogen gas. Then the Co(II)bromide solution was added to the methyl methacrylate solution and stirred for 24 hours at 30° C. under inert atmosphere. The reaction was stopped by cooling the mixture with liquid nitrogen. The reaction mixture was then diluted with THF to double volume, filtrated over basic aluminum oxide and concentrated in vacuo to a volume of about 20 mL. The polymer was precipitated in 200 mL cold methanol, filtrated, washed thoroughly with methanol and dried overnight in a vacuum oven at 40° C.

$M_n$ (SEC): 8900 g/mol.
$M_w$ (SEC): 16 300 g/mol.
Ð (SEC): 1.84.
$T_g$ (DSC): 91° C.
$T_{deg}$ (TGA): 270° C.

Example 40

TAD-Indole Ene-Reaction 155 mg of BTAD (1.00 mmol, 1 eq), obtained in Example 3, dissolved in 11.25 mL DMSO-$d_6$, were mixed with a solution of 376 mg of 5-(2-tert-butyl-1H-indole-3-yl)pentyl-2,2-bis-(hydroxymethyl)-propanoate (1.00 mmol, 1 eq) (obtained in Example 13) in 11.25 mL DMSO-$d_6$. The reaction was mixed at room temperature. After ten minutes, TLC analyses confirmed the reaction was completed. The slight pink color of the mixture indicated that a slight excess of BTAD was present.

Figure 1B:
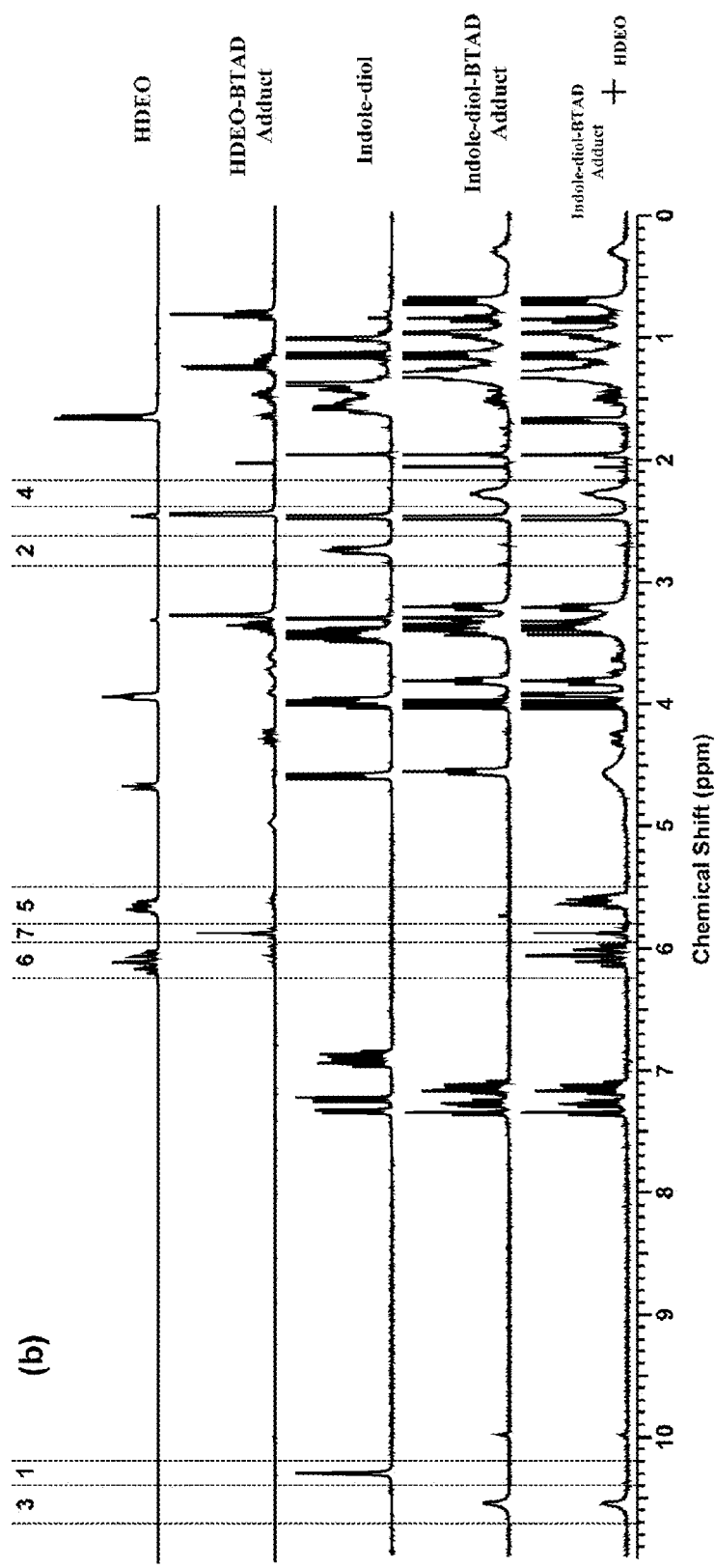
Figure 1C:
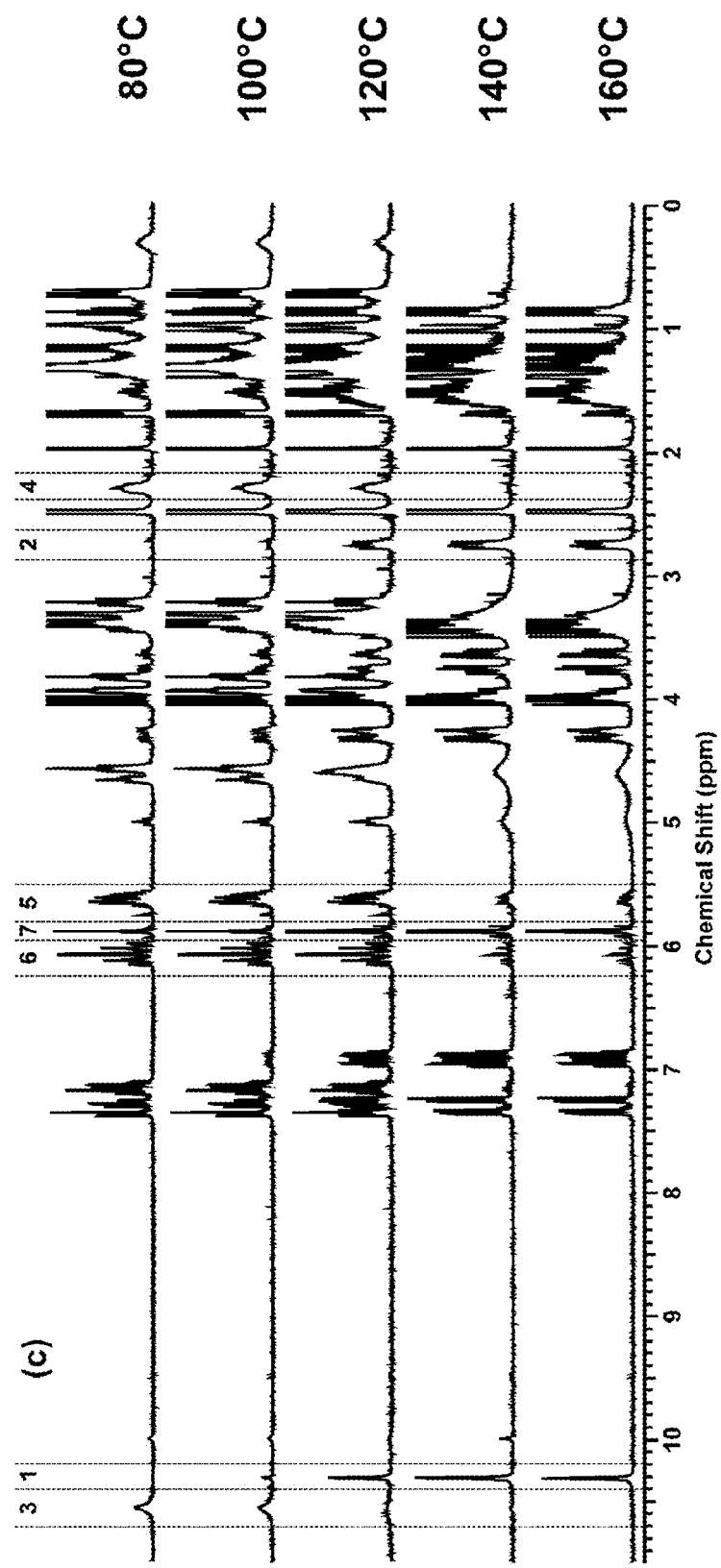

The NMR spectrum of the produced BTAD-indole adduct (FIG. 1, (b)) shows that the signal of the indole N—H group (signal 1) has been replaced by the signal of the urazole N—H group (signal 3). The chemical shift of the signal corresponding to the protons of the methylene group attached to the C-3 of the indole (signal 2) is displaced to a higher field in the ene-adduct (signal 4).

To the solution containing the BTAD-indole adduct, a solution of 108 mg 2,4-hexadien-1-ol (HDEO) (1.10 mmol, 1.1 eq) in 3 mL DMSO-$d_6$ was added. The pink color of the reaction mixture immediately disappeared. The NMR spectrum of this reaction mixture (FIG. 1, (b)) shows that the presence of HDEO has no effect over the BTAD-indole adduct (although the slight excess of BTAD present has reacted to form the corresponding HDEO-adduct (signal (7)).

After addition of HDEO, an NMR-spectrum was recorded following brief periods of heating at ever increasing temperatures. FIG. 1 (c) shows that starting from about 100° C., free 5-(2-tert-butyl-1 H-indole-3-yl)pentyl-2,2-bis-(hydroxymethyl)-propanoate can be detected (signals 1 and 2); while after heating for 15 minutes at 150° C., no more BTAD-indole adduct was detected. No side reactions or byproducts were observed (also confirmed by LC-MS analysis).

The ene-adducts of the corresponding 2-tert-butyl-3-isopentyl-1H-indole (obtained in Example 9) and the Indole-OH (obtained in Example 10), were also obtained as described herein above.

Example 41

Figure 2A:
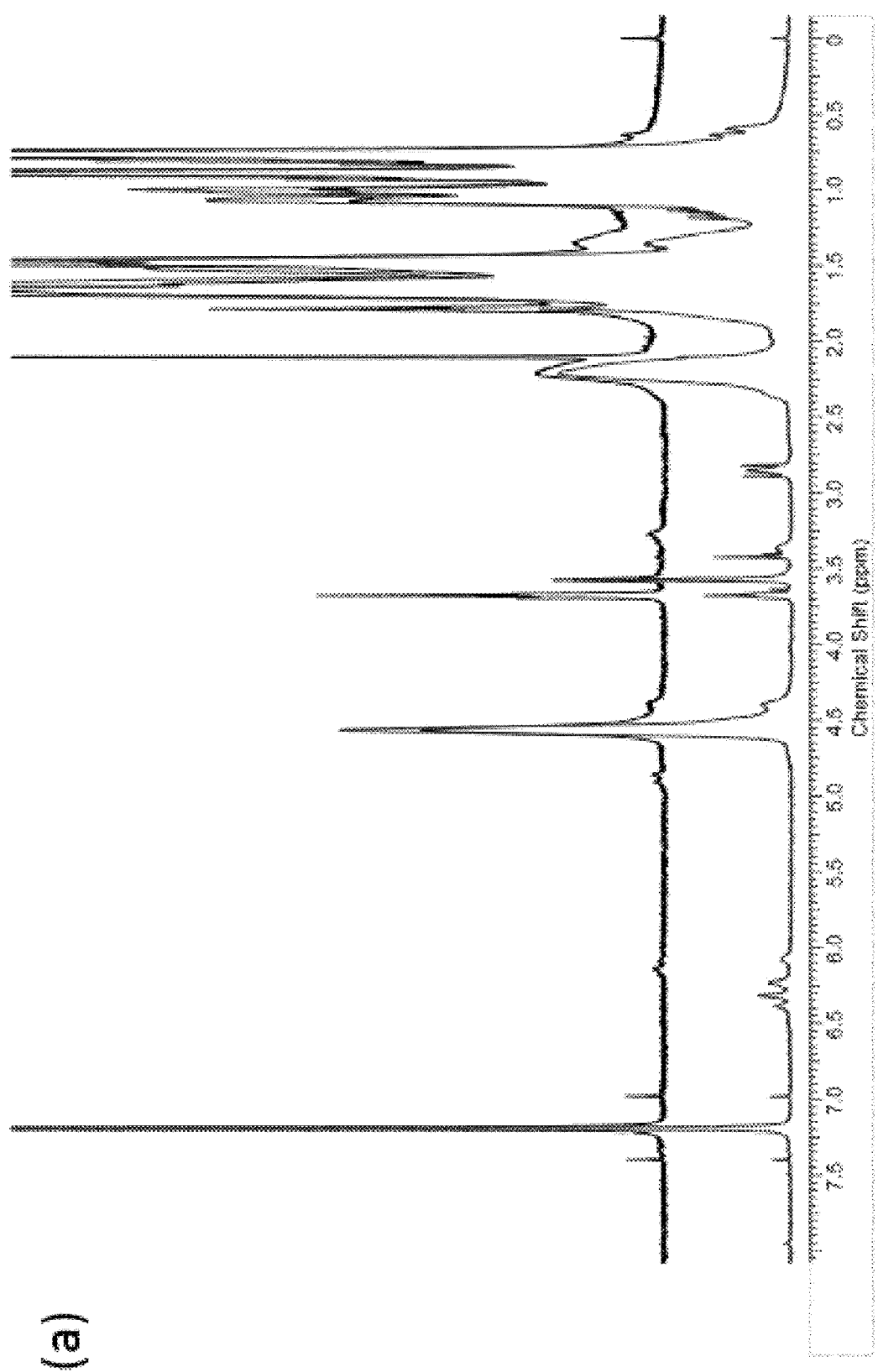
FIG. 2. Section (a) represents the superimposition of the $^1$H NMR spectra of both PiBA-Cp (bottom spectrum), and PiBA-Cp after addition of BTAD (top spectrum). Section (b) represents the MALDI spectrum of PiBA-Cp+BTAD.
Figure 2B:
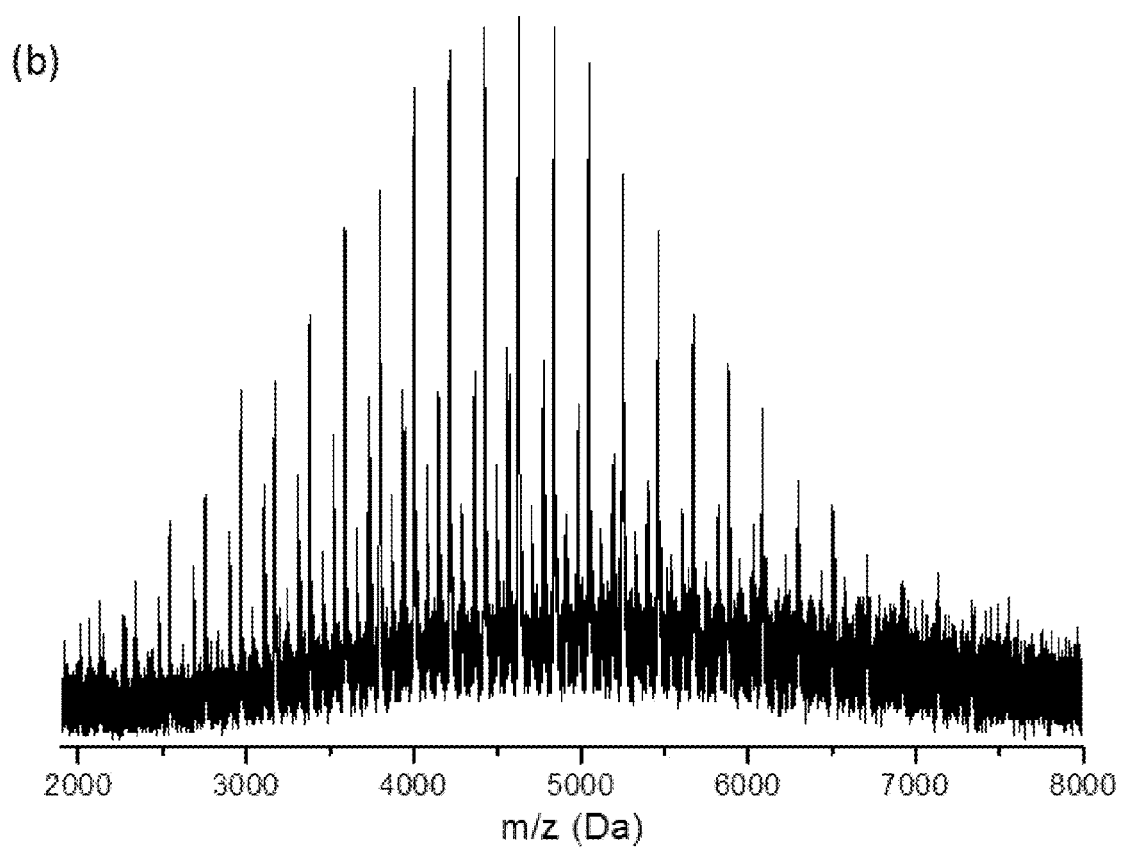

Irreversible Polymer Modification 100 mg of PiBA-Cp polymer (obtained in Example 22) was dissolved in one mL of dichloromethane. Then, 1.1 eq of BTAD, obtained in Example 3, was added at room temperature under inert atmosphere. The resulting mixture was stirred for one minute. When the red color disappeared, the resulting polymer was precipitated in 5 mL cold methanol, filtrated, washed thoroughly with methanol and dried overnight in a vacuum oven at 40° C. FIG. 2 (a) shows the superimposition of the $^1H$ NMR spectra of both PiBA-Cp (bottom spectrum), and PiBA-Cp after addition of BTAD (top spectrum), where double-bond signals of the cyclopentadiene group (~3.5 ppm) shift to a slightly lower field when this group reacts with the BTAD. FIG. 2 (b) shows the MALDI spectrum of PiBA-Cp-BTAD adduct.

PiBA-Cp:
$M_n$ (SEC): 3500 Da
$M_w$ (SEC): 4200 Da
Ð (SEC): 1.20

PiBA-Cp after Modification with BTAD
 $M_n$ (SEC): 3740 Da
 $M_w$ (SEC): 4515 Da
 Đ(SEC): 1.19

Figure 3A:
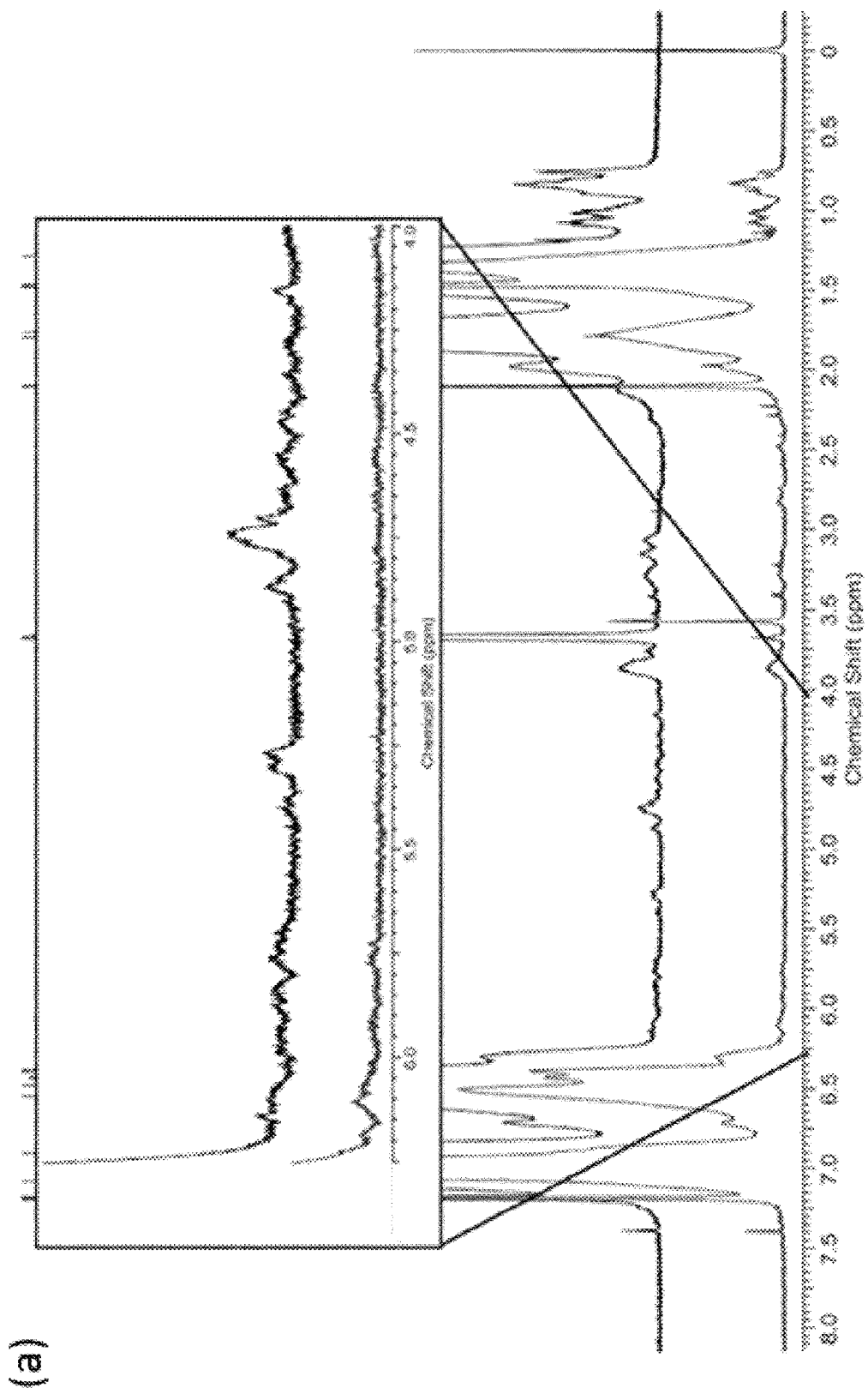
FIG. 3. Section (a) represents the superimposition of the $^1$H NMR spectra of both PS-Cp (bottom spectrum), and PS-Cp after addition of BTAD (top spectrum), plus a zoomed area of both spectra. Section (b) represents the MALDI spectrum of PS-Cp+BTAD. Section (c) represents a side-by-side comparison of a zoomed area of the theoretical MALDI spectrum of PS-Cp+BTAD (c1) and a zoomed area of the experimental MALDI spectrum of PS-Cp+BTAD (c2).
Figure 3B:
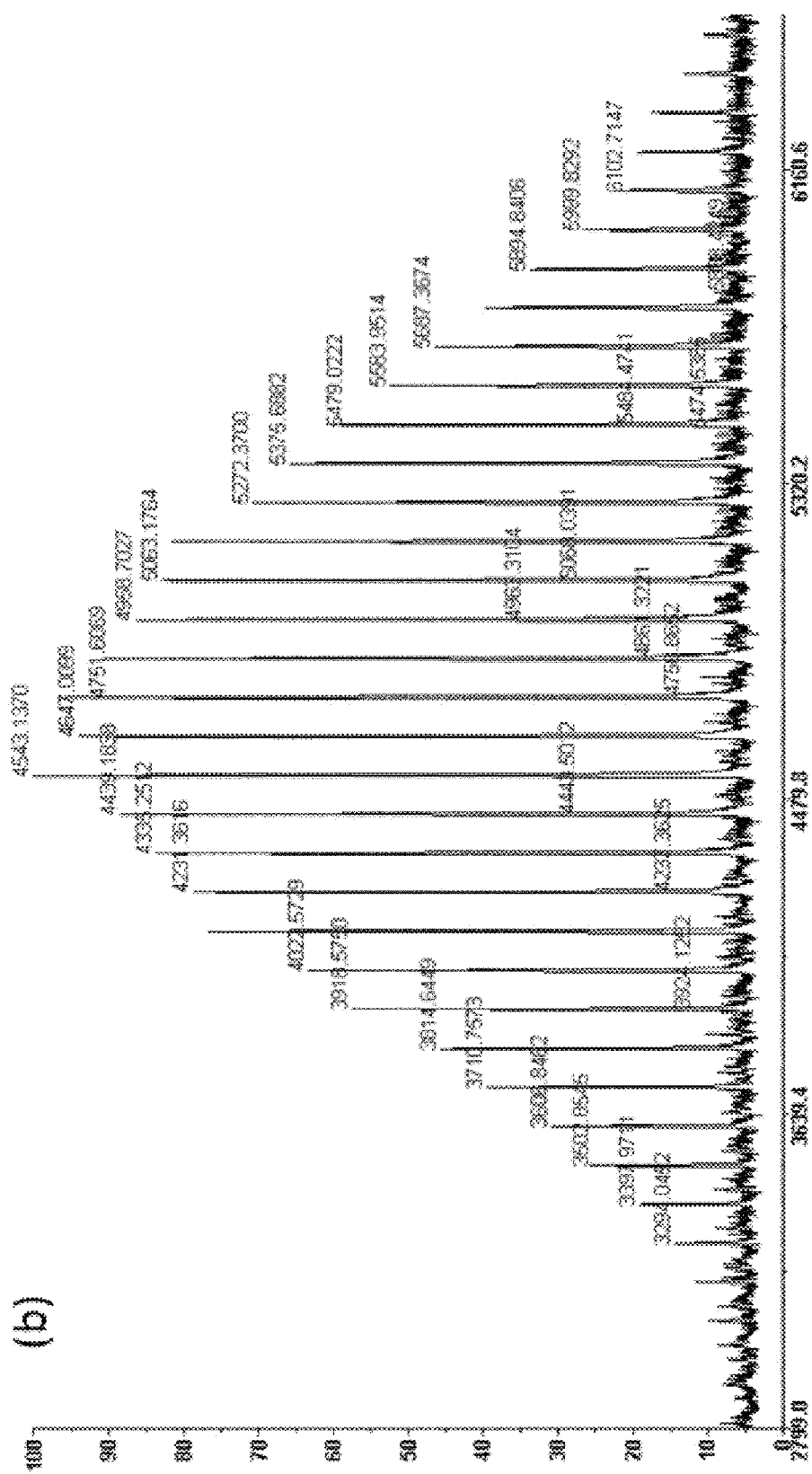
Figure 3C:
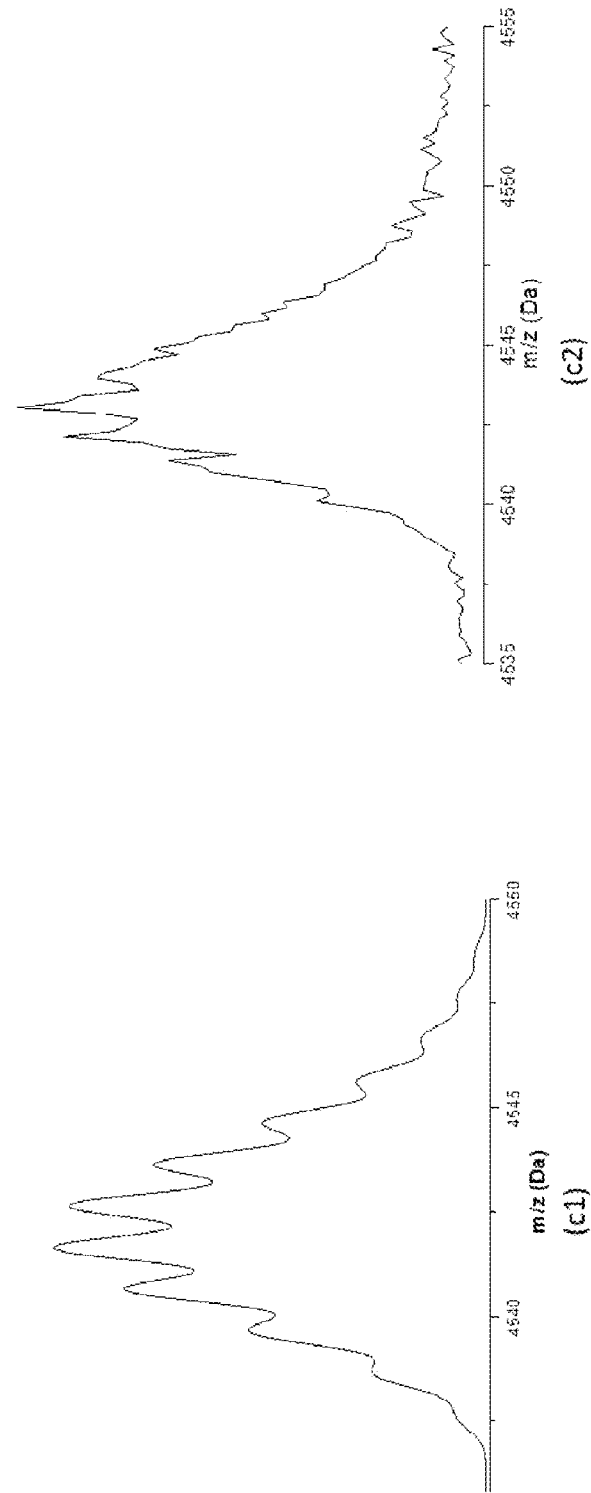

100 mg of PS-Cp polymer (obtained in Example 26) was dissolved in one mL of dichloromethane. Then, 1.1 eq of BTAD, obtained in Example 3, were added at room temperature under inert atmosphere. The resulting mixture was stirred for one minute. When the red color disappeared, the resulting polymer was precipitated in 5 mL cold methanol, filtrated, washed thoroughly with methanol and dried overnight in a vacuum oven at 40° C. FIG. 3 (a) shows the superimposition of the ¹H NMR spectra of both PS-Cp (bottom spectrum), and PS-Cp after addition of BTAD (top spectrum), together with a zoomed area of both spectra, which confirms the absence of side products for this reaction. FIG. 3 (b) shows the MALDI spectrum of PS-Cp+BTAD; while a side-by-side comparison of a zoomed area of the theoretical MALDI spectrum of PS-Cp+BTAD (FIG. 3, (c1)) and a zoomed area of the experimental MALDI spectrum of PS-Cp+BTAD (FIG. 3 (c2)) shows a good correlation between the theoretical and the experimental data.

PS-Cp:
 $M_n$ (SEC): 4000 Da
 $M_w$ (SEC): 4400 Da
 Đ(SEC): 1.10
PS-Cp after Modification with BTAD
 $M_n$ (SEC): 4500 Da
 $M_w$ (SEC): 4900 Da
 Đ(SEC): 1.08

Figure 4A:
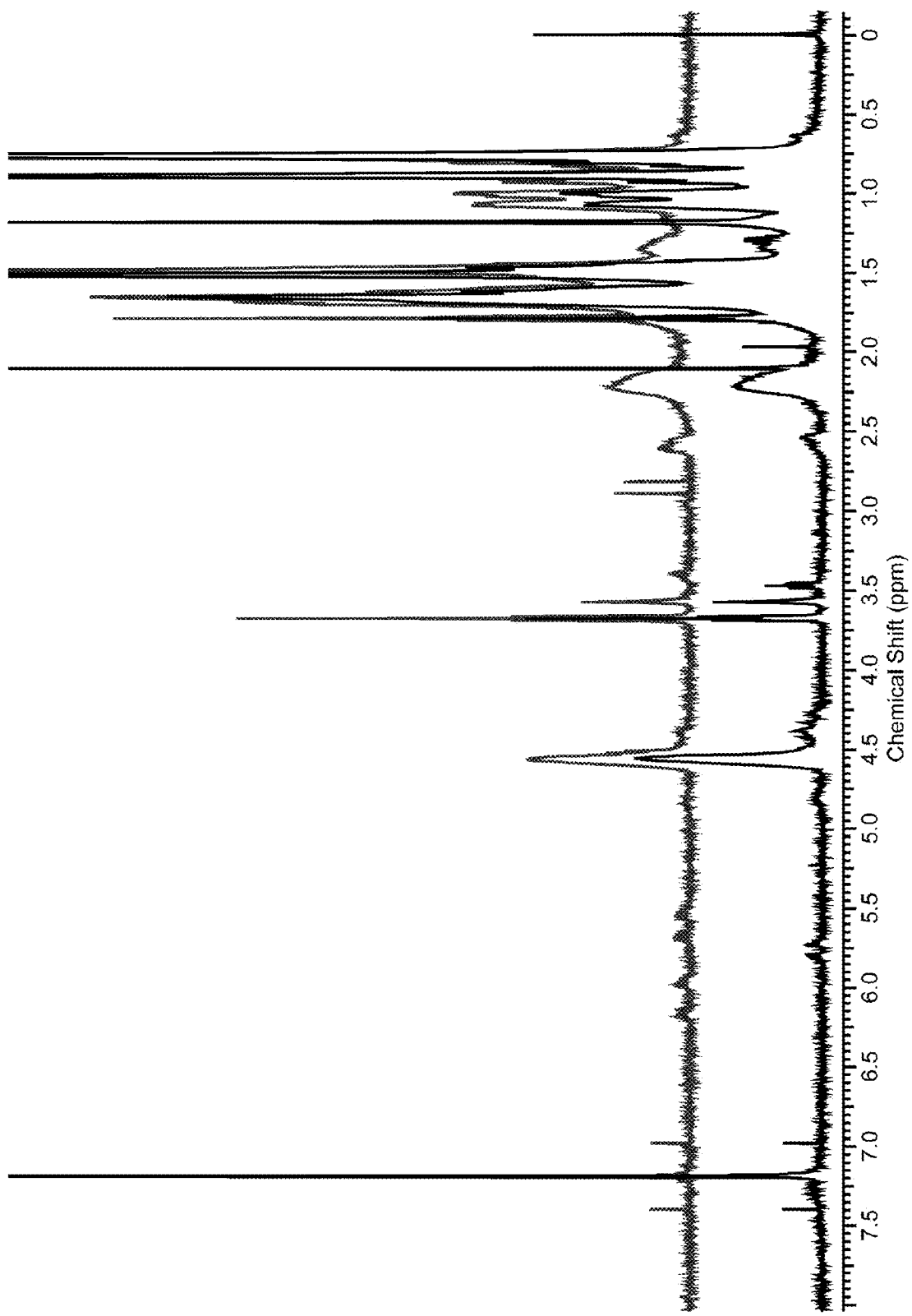
FIG. 4. Section (a) represents the superimposition of the $^1$H NMR spectra of both PiBA-OD (top spectrum), and PiBA-OD after addition of BTAD (bottom spectrum). Section (b) represents the MALDI spectrum of PiBA-OD+BTAD.
Figure 4B:
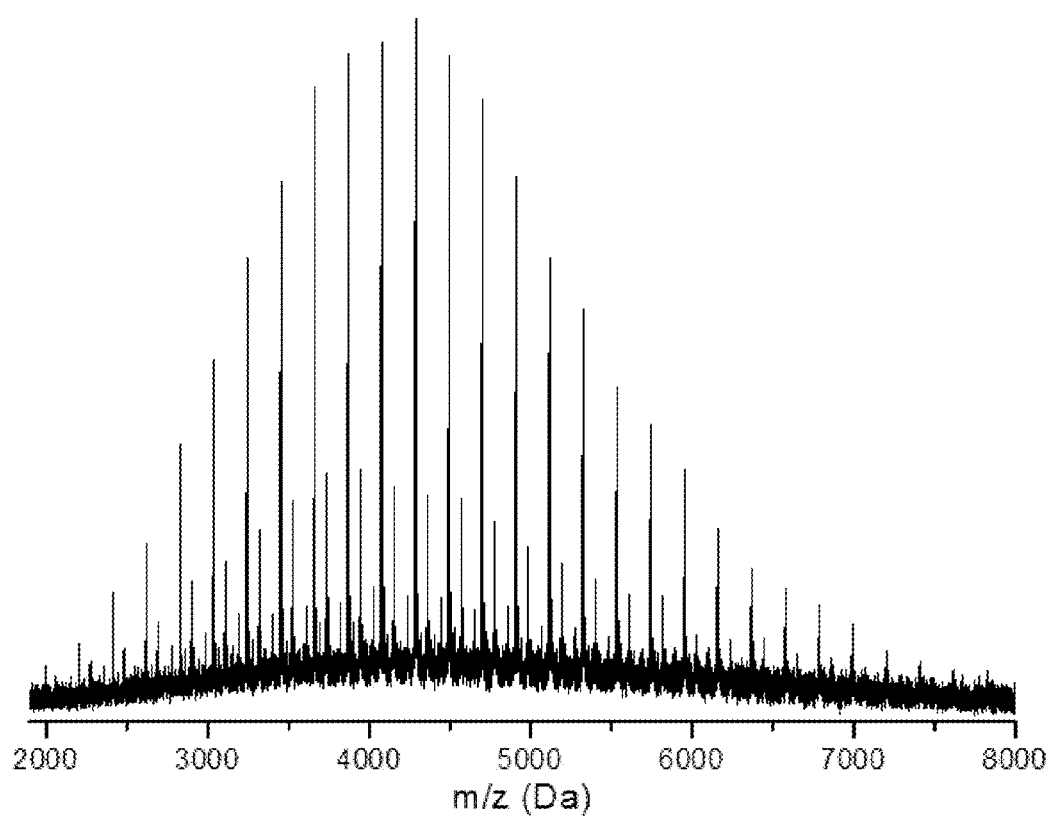

100 mg of PiBA-OD polymer (obtained in Example 23) was dissolved in one mL of dichloromethane. Then, 1.1 eq of BTAD, obtained in Example 3, were added at room temperature under inert atmosphere. The resulting mixture was stirred for one minute. When the red color disappeared, the resulting polymer was precipitated in 5 mL cold methanol, filtrated, washed thoroughly with methanol and dried overnight in a vacuum oven at 40° C. FIG. 4 (a) shows the superimposition of the ¹H NMR spectra of both PiBA-OD (top spectrum), and PiBA-OD after addition of BTAD (bottom spectrum), where the signals of both spectra are almost identical. FIG. 2 (b) shows the MALDI spectrum of PiBA-OD-BTAD adduct.

PiBA-OD:
 $M_n$ (SEC): 4200 Da
 $M_w$ (SEC): 4750 Da
 Đ(SEC): 1.20
PiBA-OD after Modification with BTAD
 $M_n$ (SEC): 5200 Da
 $M_w$ (SEC): 5900 Da
 Đ(SEC): 1.13

Figure 5A:
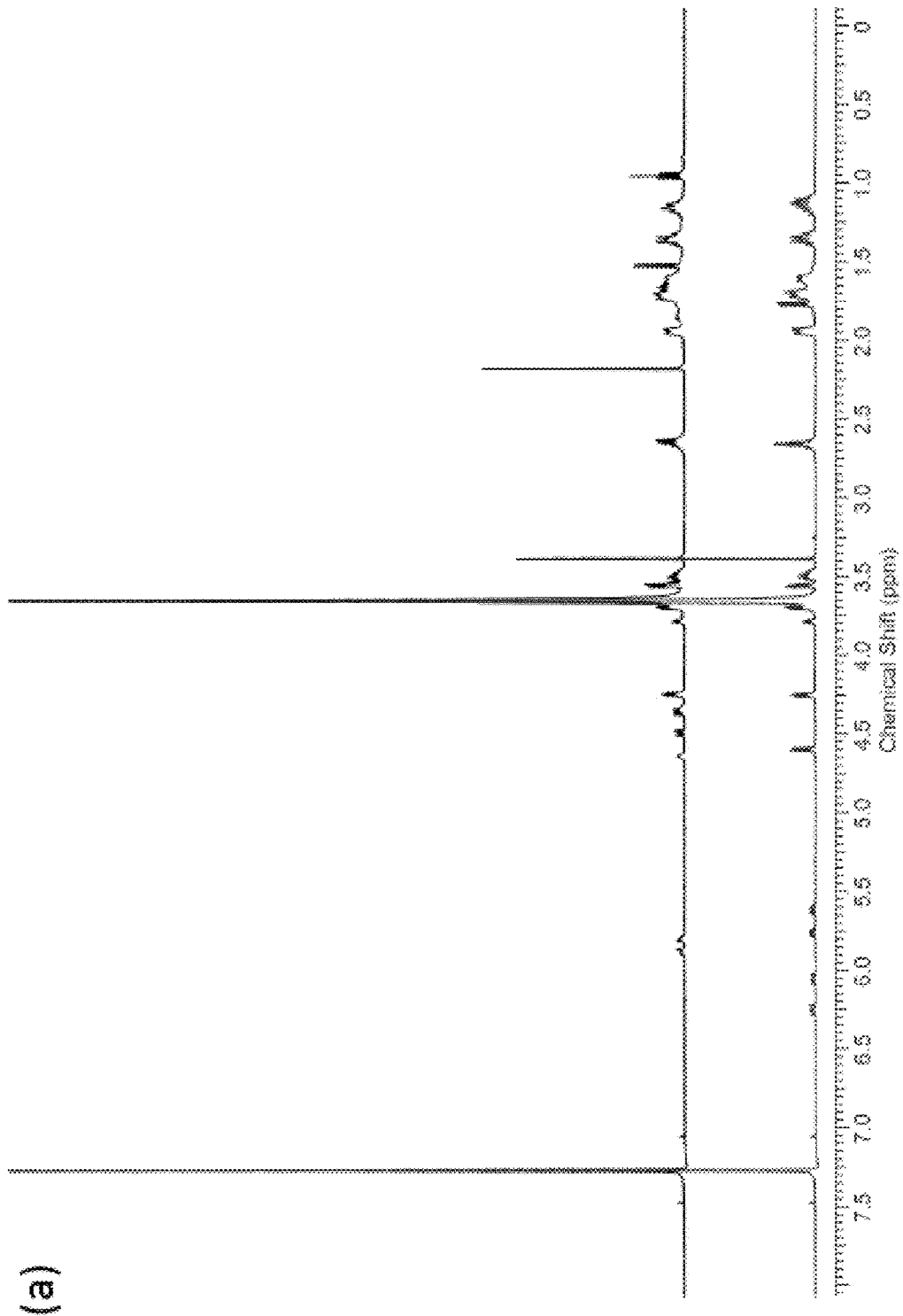
FIG. 5. Section (a) represents the superimposition of the $^1$H NMR spectra of both PEO-OD (bottom spectrum) and PEO-OD+BTAD (top spectrum). Section (b) represents a side-by-side comparison of a zoomed area of the theoretical MALDI spectrum of PEO-OD+BTAD (b1) and a zoomed area of the experimental MALDI spectrum of PEO-OD+BTAD (b2).
Figure 5B:
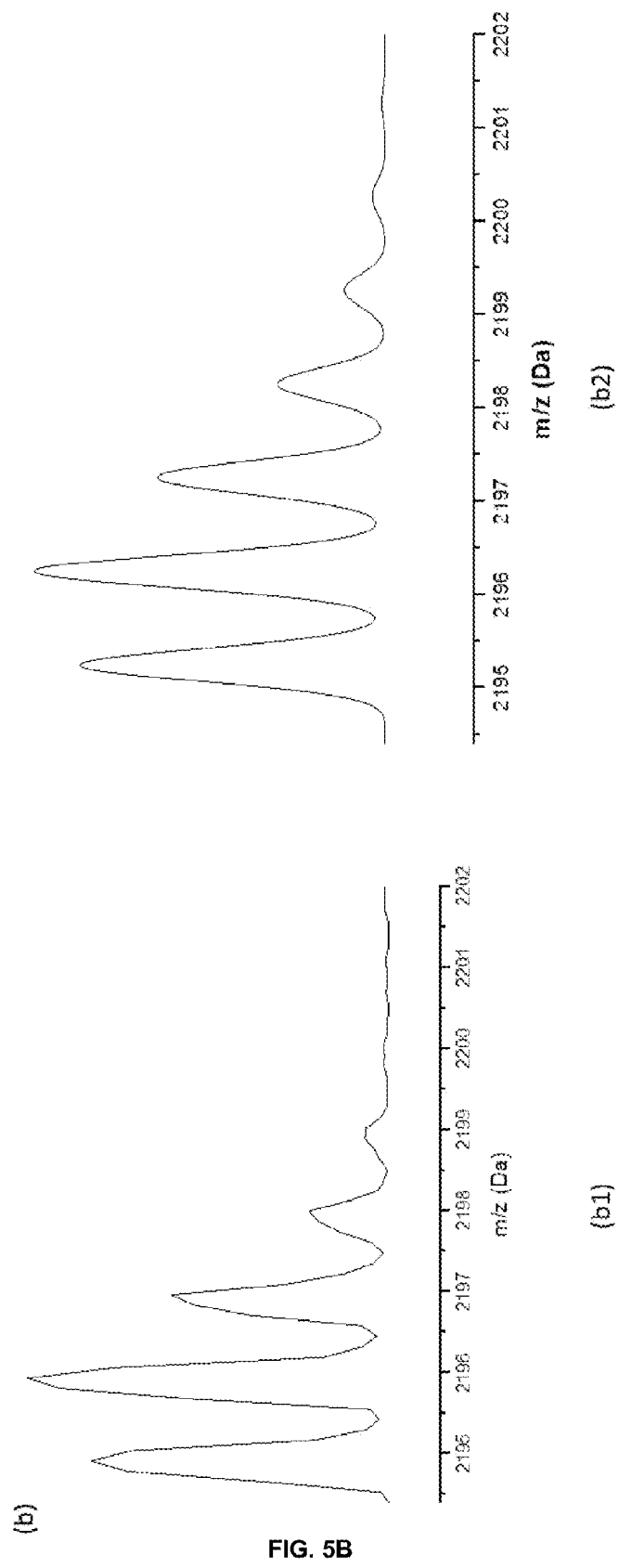

100 mg of PEO-OD polymer (obtained in Example 37) was dissolved in one mL of dichloromethane. Then, 1.1 eq of BTAD, obtained in Example 3, were added at room temperature under inert atmosphere. The resulting mixture was stirred for one minute. When the red color disappeared, the resulting polymer was precipitated in 5 mL cold methanol, filtrated, washed thoroughly with methanol and dried overnight in a vacuum oven at 40° C. FIG. 5 (a) shows the superimposition of the ¹H NMR spectra of both PEO-OD (bottom spectrum) and PEO-OD+BTAD (top spectrum), where the signals of both spectra are almost identical. FIG. 5 (b) shows a side-by-side comparison of a zoomed area of the theoretical MALDI spectrum of PEO-OD+BTAD (b1) and a zoomed area of the experimental MALDI spectrum of PEO-OD+BTAD (b2) shows a good correlation between the theoretical and the experimental data.

PEO-OD:
 $M_n$ (SEC): 3300 Da
 $M_w$ (SEC): 3900 Da
 Đ(SEC): 1.17
PEO-OD after Modification with BTAD
 $M_n$ (SEC): 3400 Da
 $M_w$ (SEC): 3900 Da
 Đ(SEC): 1.53

Example 42

Reversible Polymer Modification 1.00 g of PMMA-indole polymer (0.120 mmol, 1 eq) (obtained in Example 29) was dissolved in four mL THF. Then, 74.8 mg BTAD (0.482 mmol, 4 eq), obtained in Example 3, was added at room temperature under inert atmosphere. The resulting mixture was stirred for one hour at room temperature. When the red color disappeared, the resulting polymer was precipitated in 5 mL cold methanol, filtrated, washed thoroughly with methanol and dried overnight in a vacuum oven at 40° C.

Figure 6:
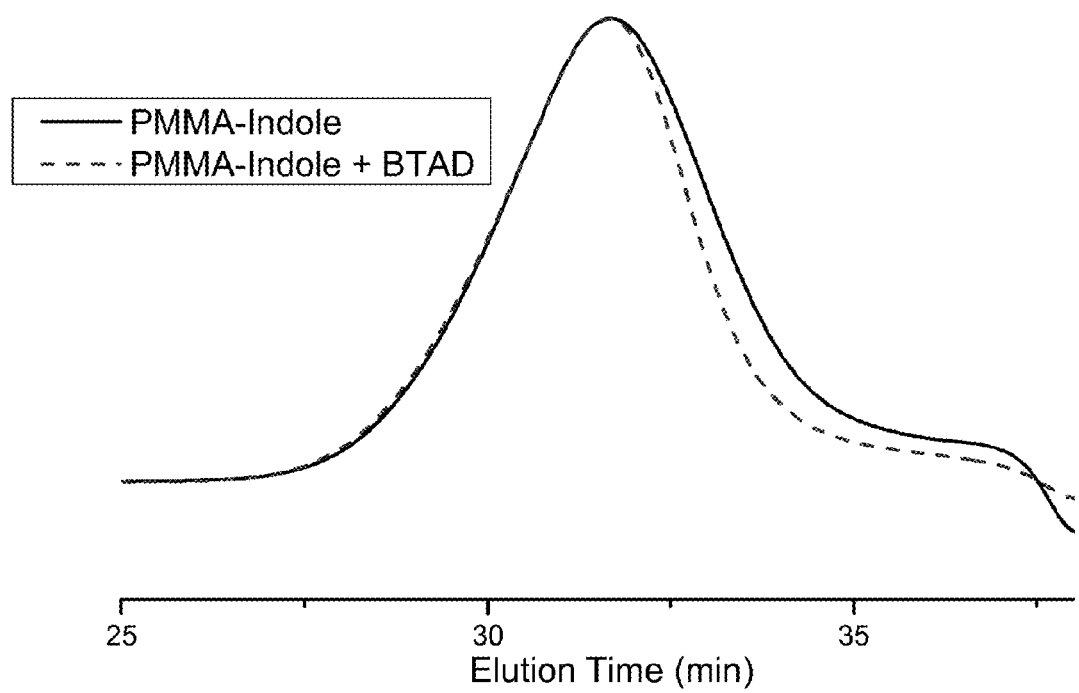
FIG. 6 represents SEC analysis of PMMA-Indole (solid line) and PMMA-Indole+BTAD (dotted line), from Example 42.

FIG. 6 shows the SEC curves of the PMMA-indole and the ene-modified polymer, since the decrease in the dispersity after modification is very small, and that there is no "shoulder" in the curve, no side reactions interfered with the adduct formation.

PMMA-Indole:
 $M_n$ (SEC): 8.300 Da
 $M_w$ (SEC): 11.000 Da
 Đ(SEC): 1.32
After Modification with BTAD:
 $M_n$ (SEC): 8.500 Da
 $M_w$ (SEC): 11.500 Da
 Đ(SEC): 1.27

Figure 7:
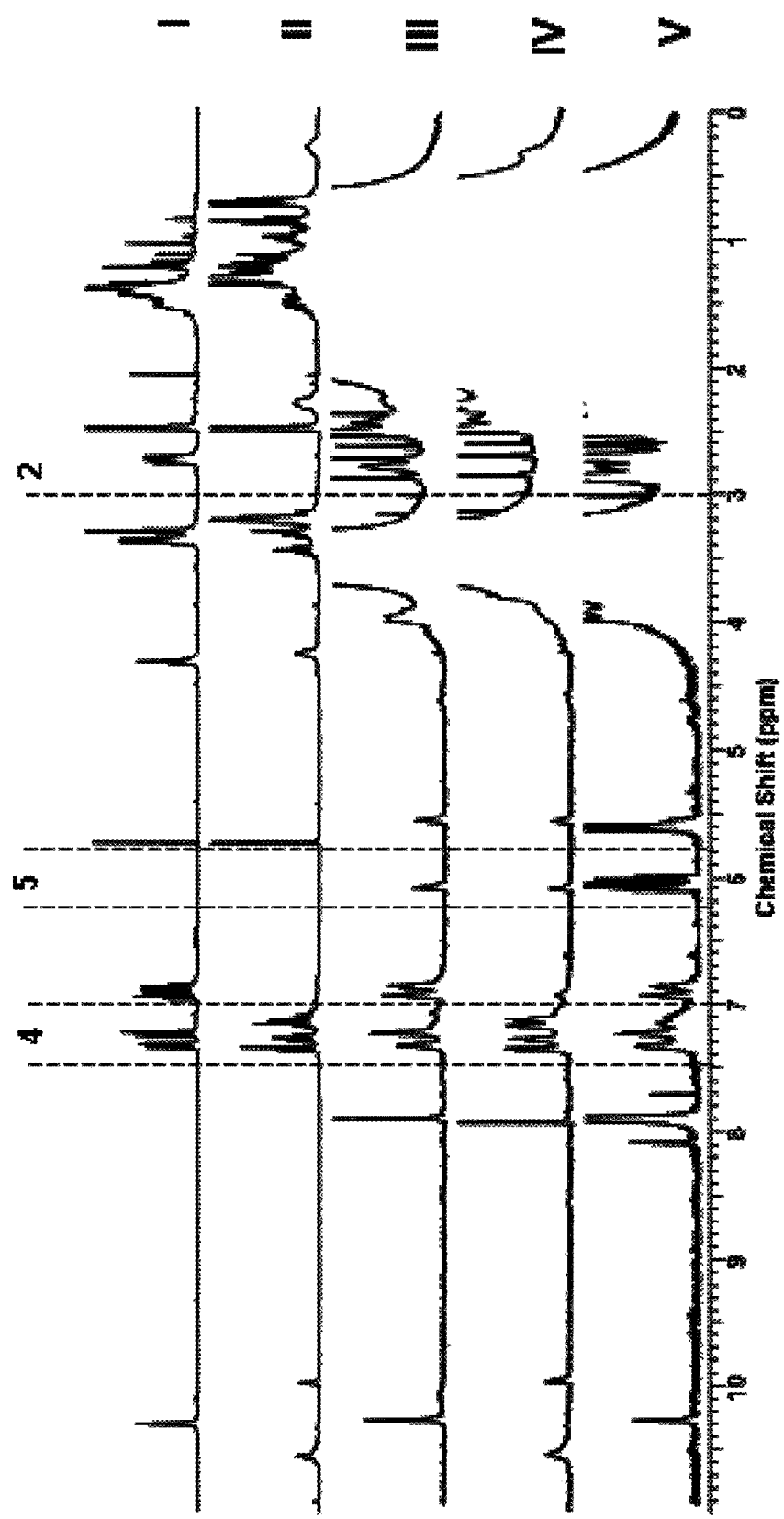
FIG. 7 represents $^1$H NMR spectra of Indole-OH (I), Indole-OH-BTAD Adduct (II) and PMMA-Indole (III), from Example 42. After reaction of BTAD with PMMA-Indole spectrum (IV) was obtained. After heating to 120° C. for 30 minutes the original spectrum (V) was obtained.

FIG. 7 (IV), shows the NMR spectrum of the ene-modified polymer. The signal for the indole N—H (signal 2) has been replaced by the signal of the urazole N—H group (signal 1). The chemical shift of the signal corresponding to the protons of the aromatic ring (signal 5) is displaced to a higher field in the ene-adduct (signal 4), showing that the ene-reaction also occurs at polymeric level.

150 mg of the ene-modified polymer (0.0181 mmol, 1 eq) and 7.09 mg HDEO (0.0723 mmol, 4 eq), were dissolved in 1.5 mL DMF and heated to 140° C. for 30 minutes. In the ¹H NMR spectrum of the resulting polymer (FIG. 7, (V)), the signals corresponding to the N—H group of the indole (signal 2), and the aromatic protons (signal 5), which were absent in the ene-modified polymer (FIG. 7, (IV)), are visible again, demonstrating the reversibility of the ene-reaction.

After Modification with BTAD:
 $M_n$ (SEC): 8.500 Da
 $M_w$ (SEC): 11.500 Da
 Đ(SEC): 1.27
After Treatment with HDEO (Heat Treatment)
 $M_n$ (SEC): 8.000 Da
 $M_w$ (SEC): 11.000 Da
 Đ(SEC): 1.30

The ene-modified polymers of the corresponding PiBA-indole polymer (obtained in Example 24) and PS-indole polymer (obtained in Example 28), were also obtained as described herein above.

Figure 8A:
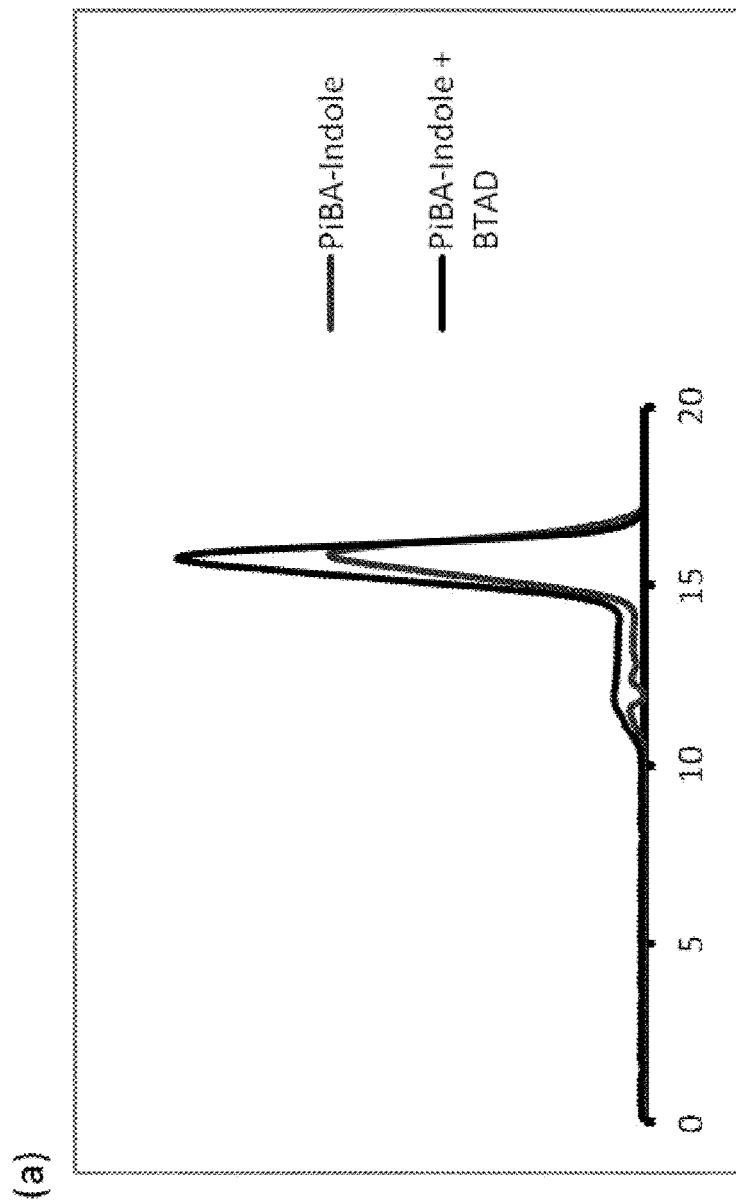
FIG. 8. Section (a) represents the SEC analysis of PiBA-Indole (smaller bottom peak) and PiBA-Indole+BTAD (larger top peak). Section (b) represents $^1$H NMR spectra of PiBA-Indole (bottom spectrum) and PiBA-Indole+BTAD (top spectrum). Section (c) represents a side-by-side comparison of the MALDI spectrum of PiBA-Indole (c1) and the MALDI spectrum of PiBA-Indole+BuTAD (c2).
Figure 8B:
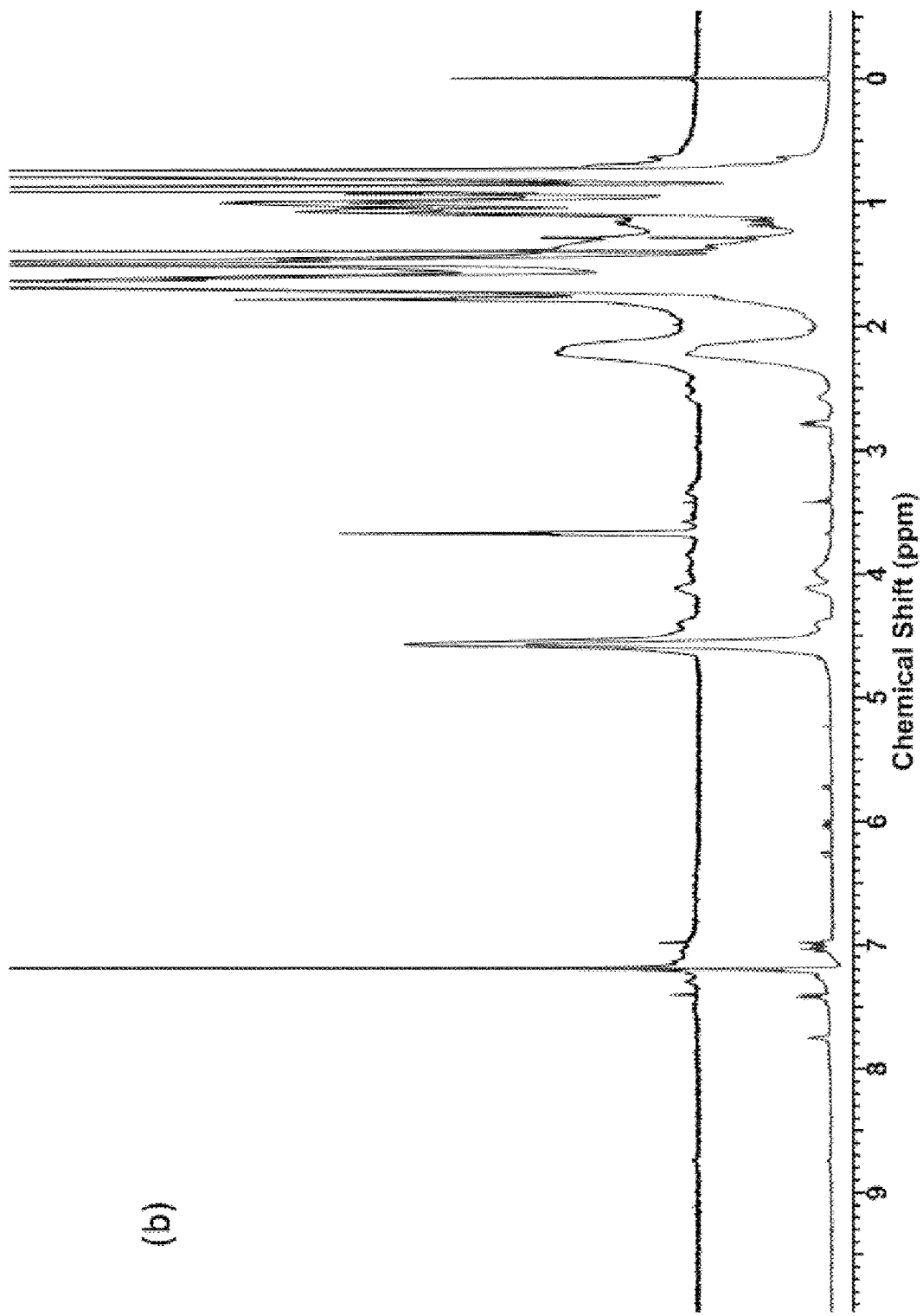
Figure 8C:
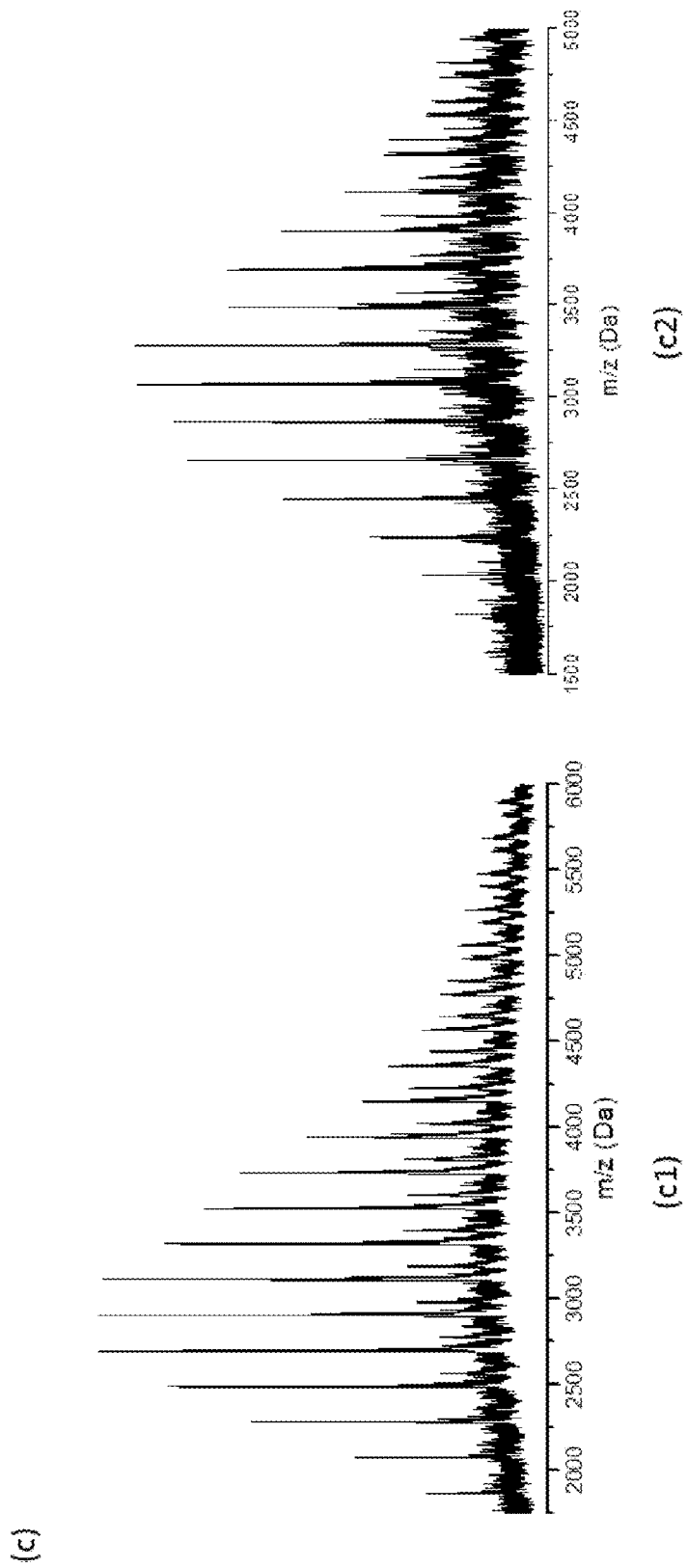

FIG. 8 (a) shows the SEC curves of the PiBA-indole smaller bottom peak) and the ene-modified polymer (PiBA-Indole+BTAD) (larger top peak), while section (b) shows the ¹H NMR spectra of PiBA-Indole (bottom spectrum) and PiBA-Indole+BTAD (top spectrum). Finally, the MALDI spectrum of PiBA-Indole (FIG. 8 (c1)) can be compared with the MALDI Spectrum of PiBA-Indole+BuTAD (FIG. 8 (c2)).

PiBA-Indole after Modification with BTAD:
$M_n$ (SEC): 3000 Da
$M_w$ (SEC): 3600 Da
Đ(SEC): 1.18

PiBA-Indole after Treatment with HDEO (Heat Treatment)
$M_n$ (SEC): 1900 Da
$M_w$ (SEC): 2300 Da
Đ(SEC): 1.22

Figure 9A:
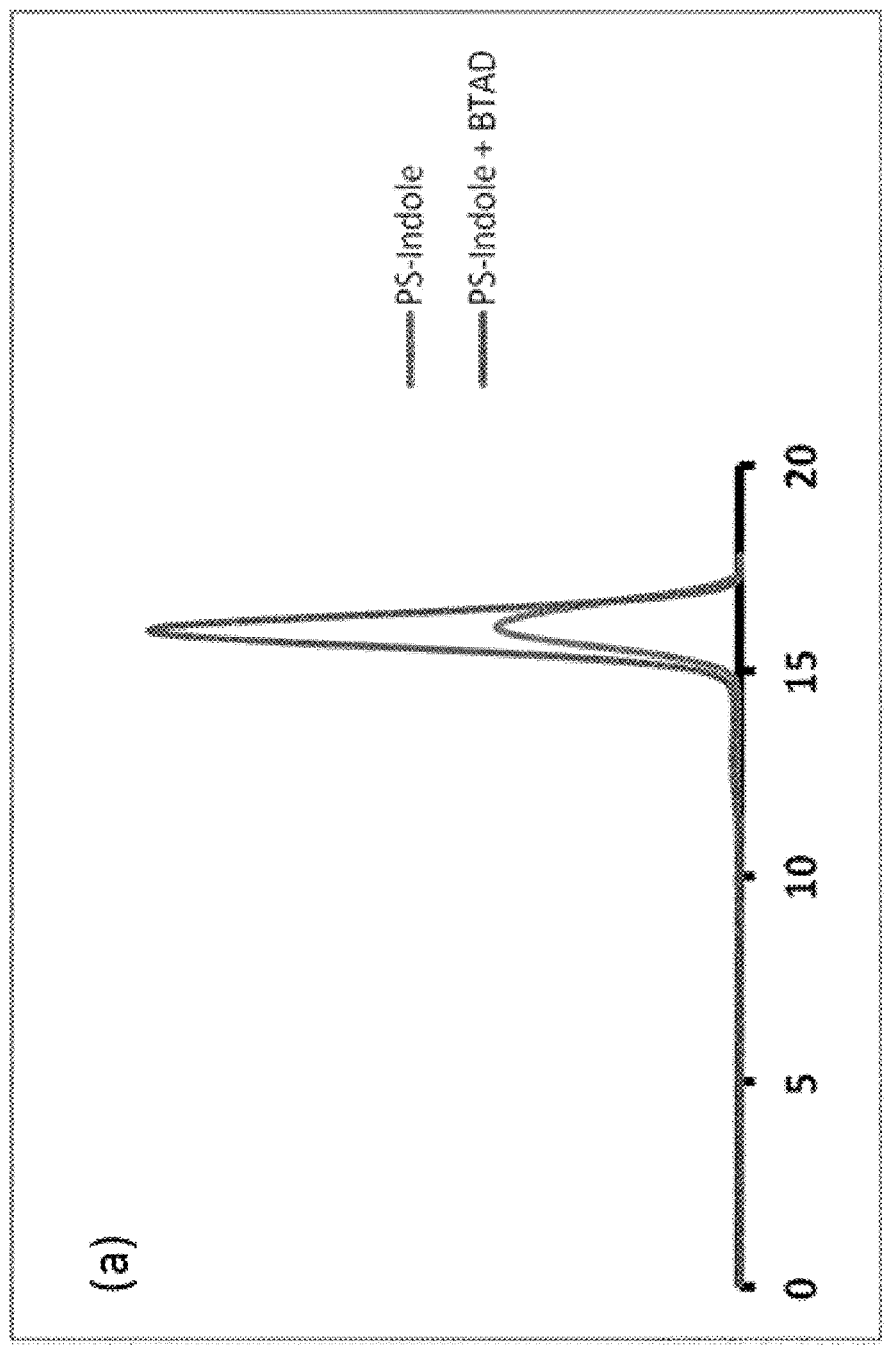
FIG. 9. Section (a) represents the SEC analysis of PS-Indole (smaller bottom peak) and PS-Indole+BTAD (larger top peak). Section (b) represents $^1$H NMR spectra of PS-Indole (bottom spectrum) and PS-Indole+BTAD (top spectrum). Section (c) represents a side-by-side comparison of the MALDI spectrum of PS-Indole (c1) and the MALDI spectrum of PS-Indole+BuTAD.
Figure 9B:
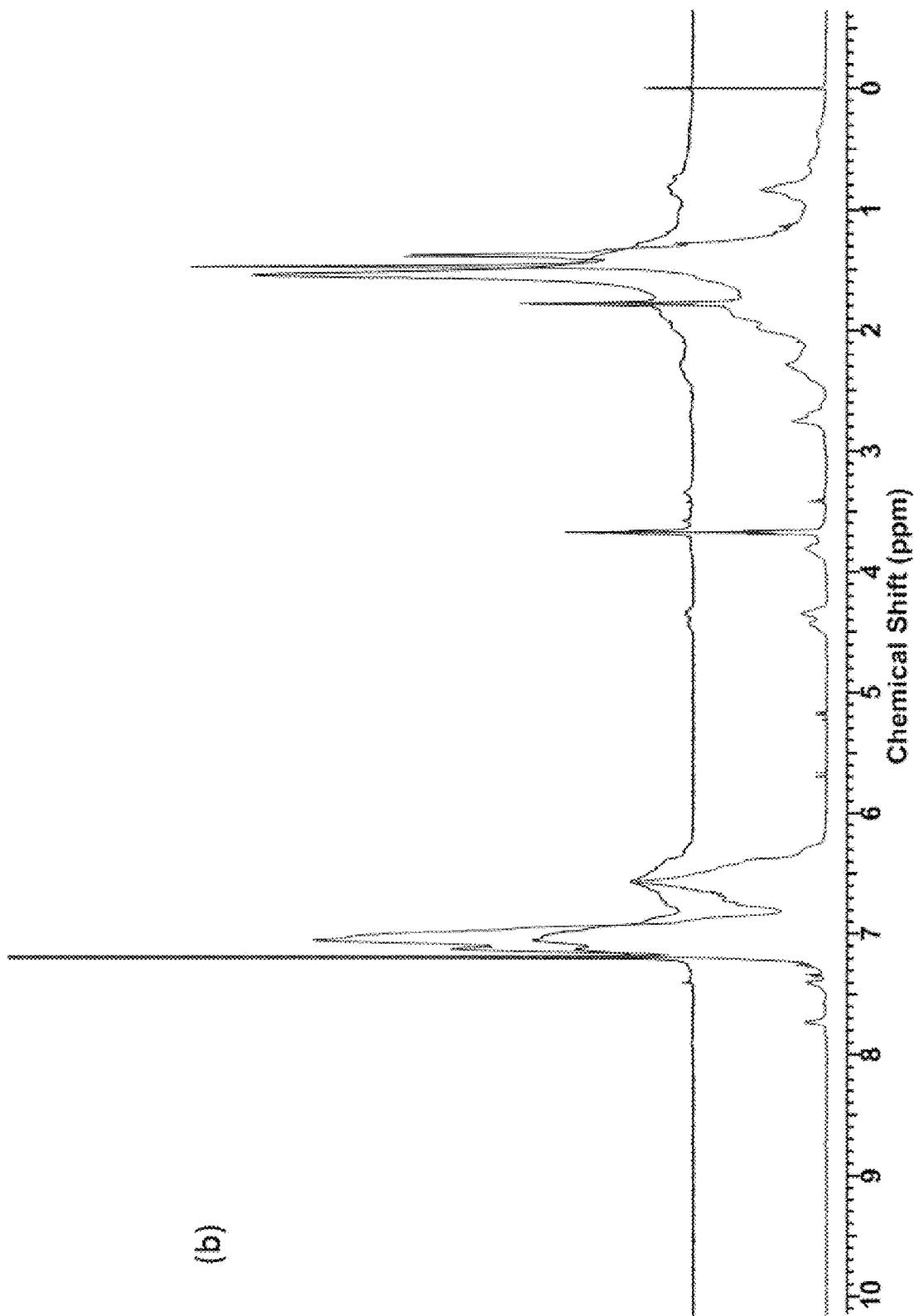
Figure 9C:
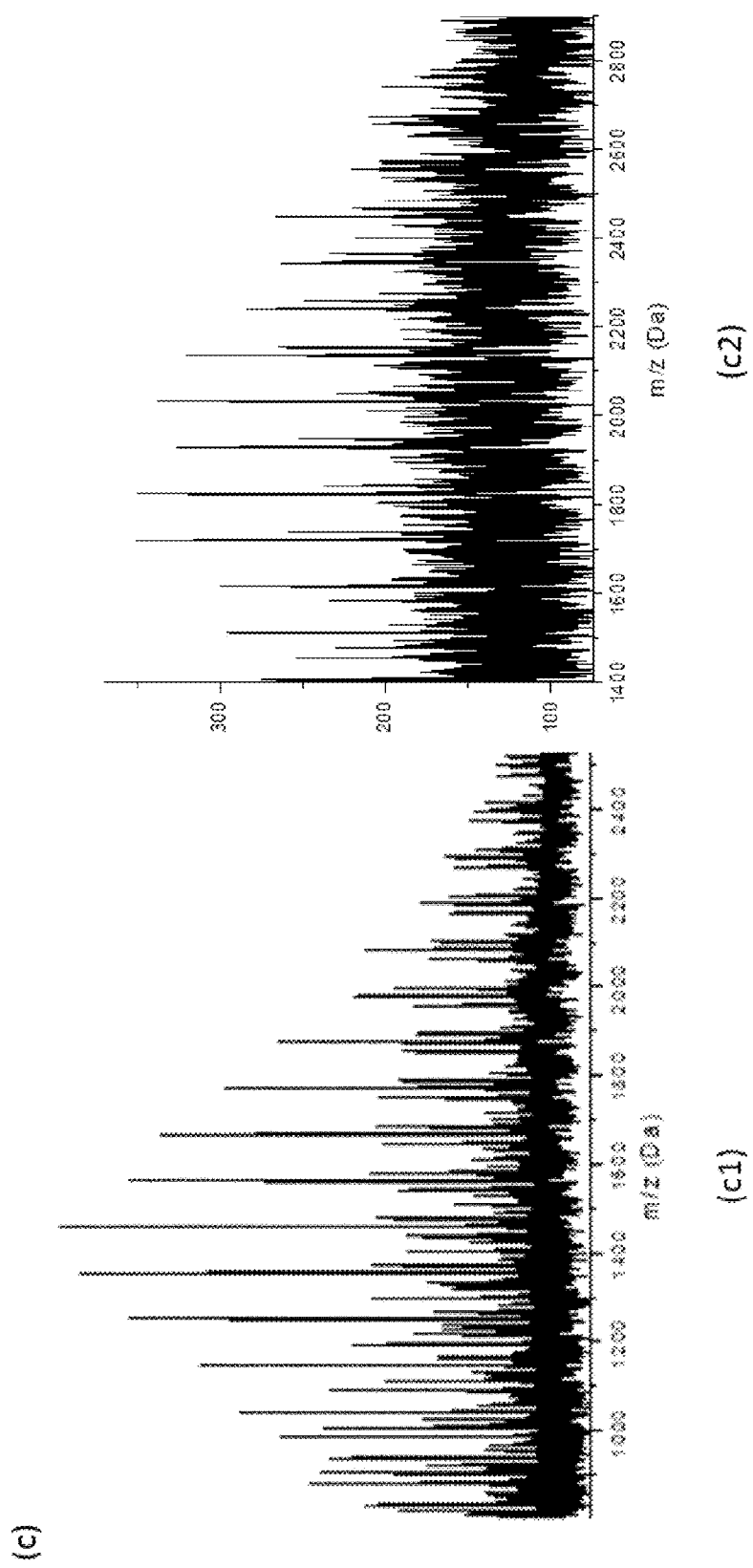

FIG. 9 (a) shows the SEC curves of the PS-indole (smaller bottom peak) and the ene-modified polymer (PS-Indole+BTAD) (larger top peak), while section (b) shows the $^1$H NMR spectra of PS-Indole (bottom spectrum) and PS-Indole+BTAD (top spectrum). Finally, the MALDI spectrum of PS-Indole (FIG. 9 (c1)) can be compared with the MALDI Spectrum of PS-Indole+BuTAD (FIG. 9 (c2)).

PS-Indole after Modification with BTAD:
$M_n$ (SEC): 2300 Da
$M_w$ (SEC): 2600 Da
Đ(SEC): 1.16

PS-Indole after Treatment with HDEO (Heat Treatment)
$M_n$ (SEC): 1400 Da
$M_w$ (SEC): 1600 Da
Đ(SEC): 1.17

Example 43

Irreversible Block Copolymer Modification 50 mg of PS-Cp polymer, obtained in Example 26, were dissolved in 0.5 mL of THF. Then, 1 eq of PiBA-TAD polymer (in 0.5 mL THF) (obtained in Example 34) was added at room temperature. The solution was stirred until the red color disappeared. The resulting block copolymer was precipitated in the appropriate solvent (cold Methanol), filtrated, washed thoroughly and dried overnight in a vacuum oven at 40° C.

50 mg of PS-Cp polymer, obtained in Example 26, were dissolved in 0.5 mL of THF. Then, 1 eq of PMMA-TAD polymer (in 0.5 mL THF) (obtained in Example 35) was added at room temperature. The solution was stirred until the red color disappeared. The resulting block copolymer was precipitated in the appropriate solvent (cold methanol), filtrated, washed thoroughly and dried overnight in a vacuum oven at 40° C.

50 mg of PS-Cp polymer, obtained in Example 26, were dissolved in 0.5 mL of THF. Then, 1 eq of PS-TAD polymer (in 0.5 mL THF) (obtained in Example 33) was added at room temperature. The solution was stirred until the red color disappeared. The resulting block copolymer was precipitated in the appropriate solvent (cold methanol), filtrated, washed thoroughly and dried overnight in a vacuum oven at 40° C.

50 mg of PS-OD polymer, obtained in Example 27, were dissolved in 0.5 mL of THF. Then, 1 eq PiBA-TAD polymer (in 0.5 mL THF) (obtained in Example 34) was added at room temperature. The solution was stirred until the red color disappeared. The resulting block copolymer was precipitated in the appropriate solvent (cold methanol), filtrated, washed thoroughly and dried overnight in a vacuum oven at 40° C.

50 mg of PS-OD polymer, obtained in Example 27, were dissolved in 0.5 mL of THF. Then, 1 eq PMMA-TAD polymer (in 0.5 mL THF) (obtained in Example 35) was added at room temperature. The solution was stirred until the red color disappeared. The resulting block copolymer was precipitated in the appropriate solvent (cold methanol), filtrated, washed thoroughly and dried overnight in a vacuum oven at 40° C.

50 mg of PS-OD polymer, obtained in Example 27, were dissolved in 0.5 mL of THF. Then, 1 eq PS-TAD polymer (in 0.5 mL THF) (obtained in Example 33) was added at room temperature. The solution was stirred until the red color disappeared. The resulting block copolymer was precipitated in the appropriate solvent (cold methanol), filtrated, washed thoroughly and dried overnight in a vacuum oven at 40° C.

Example 44

Reversible Block Copolymer Modification 50 mg of PS-indole polymer, obtained in Example 28, were dissolved in 0.5 mL of THF. Then, 1 eq PiBA-TAD polymer (in 0.5 mL THF) (obtained in Example 34) was added at room temperature. The solution was stirred until the red color disappeared. The resulting block copolymer was precipitated in the appropriate solvent (cold methanol), filtrated, washed thoroughly and dried overnight in a vacuum oven at 40° C.

The ene-modified block copolymer and HDEO, were dissolved in DMF and heated to 120° C. for hours (minutes); and the reaction mixture was then cooled to room temperature.

A similar experiment of reversible block copolymer modification is prepared by contacting PS-Indole with PS-TAD.

A similar experiment of reversible block copolymer modification is prepared by contacting PiBA-Indole with PiBA-TAD.

A similar experiment of reversible block copolymer modification is prepared by contacting PiBA-Indole with PS-TAD.

Example 45

Comparison Between Reversible and Irreversible Polymer Networks

Figure 10:
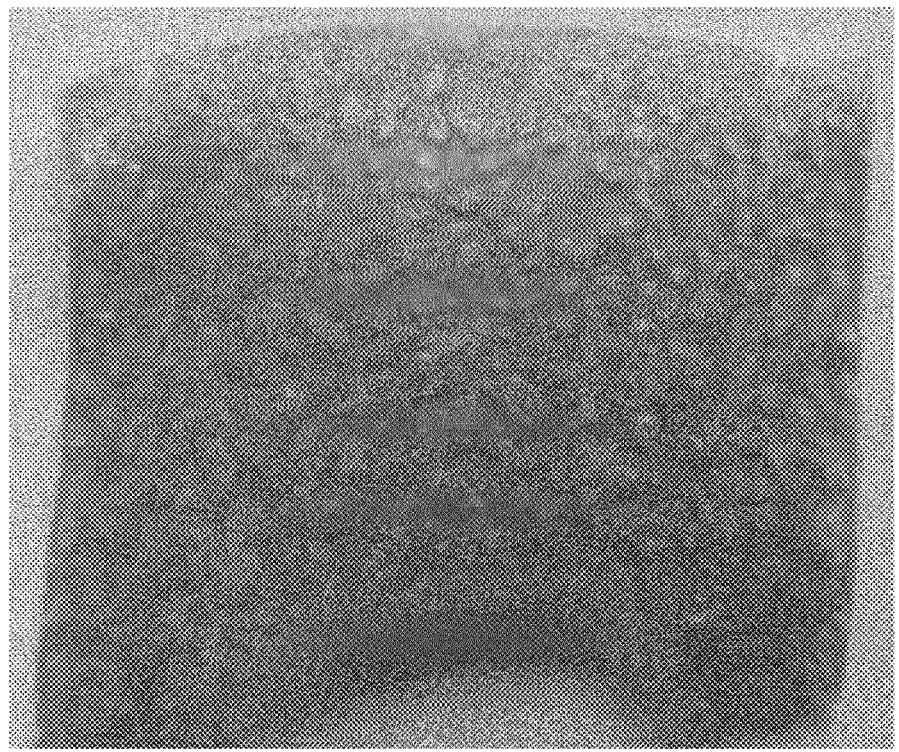
FIG. 10 is a photograph of the polyurethane-based reversible polymer network obtained in Example 45.

Reversible Polymer Network:
1.00 g of the indole-polyurethane polymer, produced in Example 36, was dissolved in 5 mL dimethylformamide; to this mixture, a solution of 58.2 mg MBPTAD (0.161 mmol, 0.25 eq) (obtained in Example 6) in 1 mL DMF, was added. Completion of the reaction was monitored by the disappearance of the red color from MBPTAF (about two minutes). Then, the resulting polymer network was dried overnight in a vacuum oven at 40° C. FIG. 10 is a photograph of the resulting polymer network.

$T_g$ (DSC): −45° C.
$T_{deg}$ (TGA): 300° C.

When this polymer material was heated to 150° C. in DMF, it became viscous, although the integrity of the network was not affected. If however HDEO (0.805 mmol, 79 mg) was added to the solution, a homogeneous solution was obtained within 10 minutes.

Figure 11:
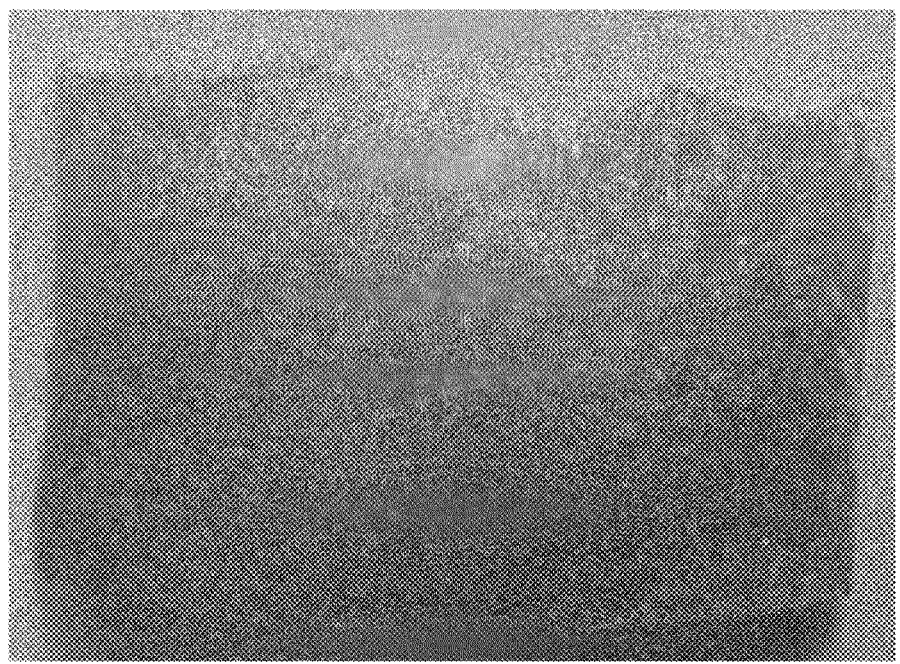
FIG. 11 is a photograph of the 2,4-hexadien-1,6-diol-based irreversible polymer network obtained in Example 45.

Irreversible Polymer Network
To a solution of 0.244 g 2,4-hexadien-1,6-diol (2.14 mmol, 0.68 eq) in 3 mL DMF, 0.194 g MBPTAD (0.536 mmol, 0.17 eq) (obtained in Example 6) were added. Completion of the reaction was monitored by the disappearance of the red color from MBPTAF (less than one minute). The resulting solution was mixed with 2.00 g polypropylene oxide (1.0 mmol, 0.32 eq) and 0.529 g hexamethylene diisocyanate (3.15 mmol, 1 eq) in a 50 mL flask. Then, 29 μL dibutyltin dilaurate was added and the mixture was stirred thoroughly. This mixture was injected between two glass plates, with a silicone spacer between the two plates. This set-up was placed in a vacuum oven at 70° C., for six hours. The resulting network was dried overnight in a vacuum oven at 40° C. FIG. 11 is a photograph of the resulting polymer network.

When this polymer material was heated to 150° C. in DMF, -no change in integrity of structure was observed When HDEO (2.68 mmol, 263 mg) was added, the network remained insoluble, even after heating to 200° C.

Example 46

Synthesis of a Reversible Network Formation Based on Poly(MMA-Co Indole-MA)

1.00 g of poly(MMA-co indole-MA), produced in Example 39, was dissolved in 4 mL THF. To this mixture, a solution of 124 mg MBPTAD (0.342 mmol, 0.25 eq) (obtained in Example 6) in 1.5 mL THF, was added. Completion of the reaction was monitored by the disappearance of the red color from MBPTAF (about three minutes). The resulting polymer network was dried overnight in a vacuum oven.
$T_g$ (DSC): 101° C.
$T_{deg}$ (TGA): 280° C.

Example 47

Direct Synthesis of a Reversible Polyurethane Network

To a solution of 0.805 g 5-(2-tert-butyl-1H-indole-3-yl)pentyl-2,2-bis-(hydroxymethyl)-propanoate (2.14 mmol, 0.68 eq) (obtained in Example 13) in 3 mL dimethylformamide, 0.194 g MBPTAD (0.536 mmol, 0.17 eq) (obtained in Example 6) were added. Completion of the reaction was monitored by the disappearance of the red color from MBPTAF (less than one minute). The resulting solution was mixed with 2.00 g polypropylene oxide (1.00 mmol, 0.32 eq) and 0.529 g hexamethylene diisocyanate (3.15 mmol, 1 eq) in a 50 mL flask. Then 29 μL dibutyltin dilaurate were added and the mixture was stirred thoroughly. This mixture was injected between two glass plates, with a silicone spacer between the two plates. This set-up was placed in a vacuum oven at 70° C., for six hours. The resulting network was dried overnight in a vacuum oven at 40° C.
$T_g$ (DSC): -49° C.
$T_{deg}$ (TGA): 300° C.

Example 48

Self-Healing of the Polymer Networks

Figure 12:
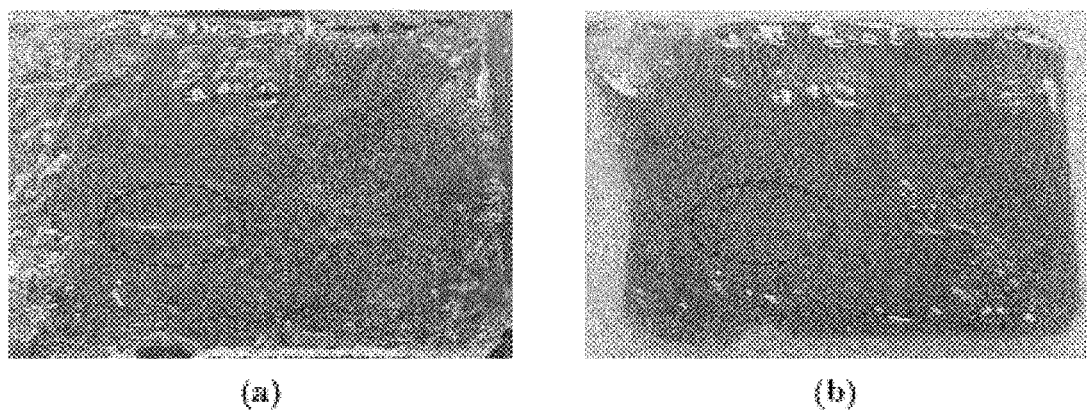
FIG. 12 shows the self-healing experiment of Example 48. Section (a) shows the scratch made in the polyurethane-based network. Section (b) shows the polyurethane-based network after thermal treatment.

With the aid of a utility knife, a one cm scratch was made in the polyurethane-base network obtained in Example 45 (FIG. 12 (a)). The material was then heated to 120° C. for an hour. After this thermal treatment, the scratch has been reduced to a small irregularity on the surface (FIG. 12 (b)). Manually applying stress perpendicularly to the direction of the cut did not reveal a weak spot at the location of the original damage, confirming the sample was fully healed.

Example 49

Workability of the Polymer Networks

Figure 13:
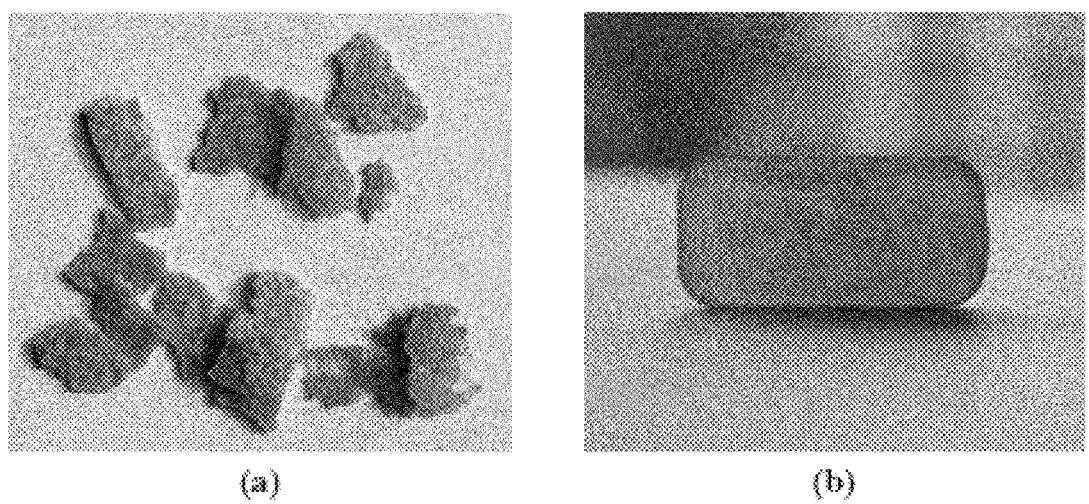
FIG. 13 shows the workability experiment of Example 49. Section (a) shows the PMMA-based network torn into pieces. Section (b) shows the PMMA-based network after thermal treatment.
Figure 14:
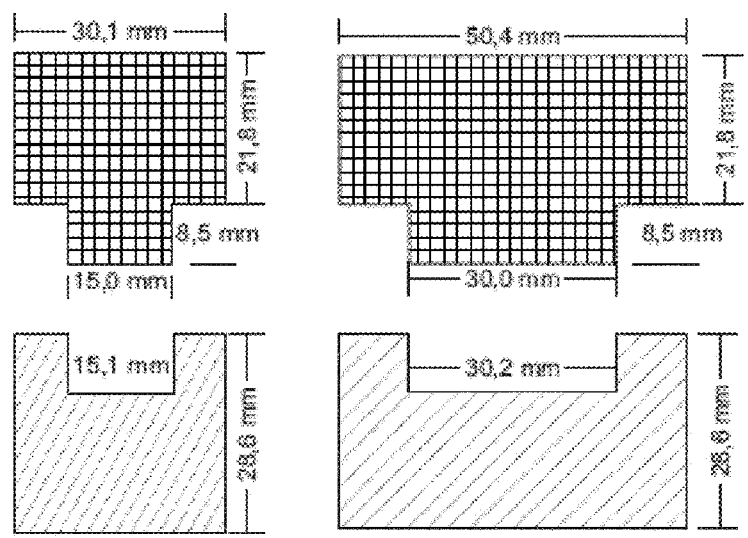
FIG. 14 shows the specifications of the mold used in Example 49.

The PMMA-based network was torn into large pieces (FIG. 13 (a)) and put into a mold (FIG. 14). After heating the material to 120° C., it was compressed for 30 minutes at the same temperature. As shown in FIG. 13 (b), a homogeneous sample was retrieved, after cooling to room temperature. However, this homogenous sample remained insoluble in DMF, leading to the conclusion that this workability can be assigned to the exchangeable TAD-indole bonds than to an irreversible degradation of MBPTAD. This tearing and reforming cycle could be repeated for multiple times, each with the identical result.

Example 50

Synthesis of 3-benzhydryl-2-phenyl-1H-indole

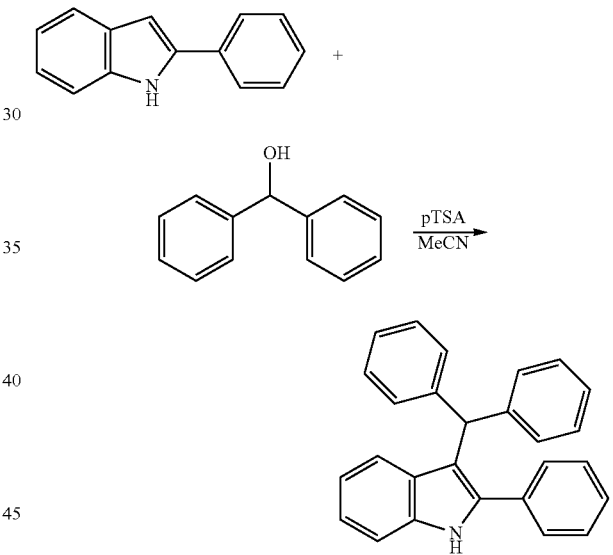

In a 100 mL flask, 2-phenyl-1H-indole (1.0 g, 5.17 mmol, 1 eq), benzhydrol (1.0 g, 7.76 mmol, 1.5 eq) and p-toluene sulfonic acid (0.20 g, 1.04 mmol, 0.2 eq) were dissolved in acetonitrile (20 mL). The reaction mixture was stirred for 2 days under inert atmosphere until 2-phenyl-1H-indole had completely reacted. The reaction mixture was then filtered, then ethyl acetate (80 mL) was added to the filtrate and the solution was washed with saturated sodium carbonate solution (2×10 mL). The organic phase was dried over magnesium sulfate, filtrated and concentrated in vacuo. By recrystallization in water:ethanol 1:2, the title product was purified as a white crystalline powder (1.51 g, 4.19 mmol, 81%).
Bruto formula: $C_{27}H_{21}N$
Molecular weight: 359.17 g mol$^{-1}$
LC-MS (m/z): 360.1 [MH]$^+$
HRMS (m/z for [MH]$^+$ calculated/experimental): 360.1747/360.1733.
RF. value (ethyl acetate:heptane 1:9): 0.23

$^1$H-NMR (300 MHz, DMSO-d$_6$): δ (ppm)=5.79 (s, 1H, Ar—CH—Ar), 6.77 (t, 1H, NH—C—CH=CH—CH), 6.91 (d, 1H, ArH), 7.03 (t, 1H, NH—C—CH=CH), 7.08-7.33 (m, 10H, ArH), 7.33-7.55 (m, 6H, ArH), 11.39 (s, 1H, NH)

$^{13}$C-NMR (125 MHz, DMSO-d$_6$): δ (ppm)=47.30 (CH), 111.42 (CH), 113.37 (C), 118.75 (CH), 120.34 (CH), 121.10 (CH), 126.05 (CH), 127.55 (C), 127.77 (CH), 128.22 (CH), 128.37 (CH), 128.66 (CH), 128.72 (CH), 132.62 (C), 135.65 (C), 136.37 (C), 143.94 (C)

Example 51

Synthesis of 3-isopentyl-2-phenyl-1H-indole

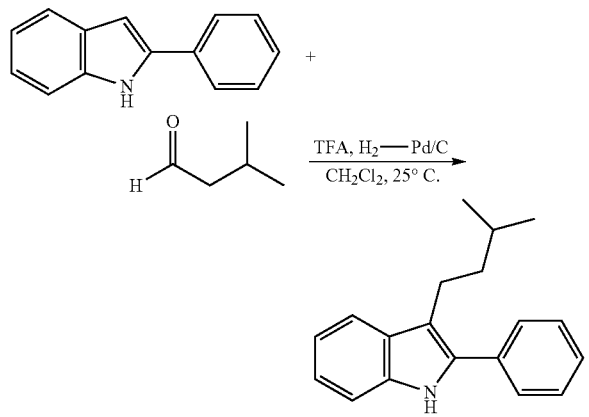

A mixture of trifluoroacetic acid (0.60 mL, 7.76 mmol, 1.5 eq), palladium (a pinch of 5% Pd on activated carbon, 0.3 g) and dichloromethane (12 mL) was put under hydrogen atmosphere in a 100 mL two neck flask and cooled in an ice bath and stirred. A solution of 2-phenyl-1H-indole (1.0 g, 5.17 mmol, 1 eq) and 0.61 mL isovaleraldehyde (5.69 mmol, 1.1 eq) in 18 mL dichloromethane was added drop wise to this mixture. The reaction mixture was vigorously stirred for 5 hours in a water bath and frequently flushed with hydrogen gas until complete reaction of the starting product. Completion of the reaction was monitored by thin layer chromatography (TLC) using as diluent ethyl acetate:heptane 1:9. The catalyst was removed from the reaction mixture by filtration over celite and thoroughly washing with dichloromethane. The obtained filtrate was washed with 30 mL saturated sodium carbonate solution and dried over magnesium sulfate. After removing the solvent in vacuo the desired product was obtained as a brown oil (1.34 g, 5.07 mmol, 96%). Bruto formula: C$_{19}$H$_{21}$N Molecular weight: 263.38 g mol$^{-1}$ LC-MS (m/z): 264.20 [MH]$^+$ HRMS (m/z for [MH]$^+$ calculated/experimental): 264.1747/264.1735.

RF value (ethyl acetate:heptane 1:9): 0.20

$^1$H-NMR (300 MHz, DMSO-d$_6$): δ (ppm)=0.92 (d, 6H, CH$_3$), 1.55 (m, 2H, i-Pr—CH$_2$), 1.62 (m, 1H, CH—(CH$_3$)$_2$), 2.84 (t, 2H, CH$_2$—CH$_2$-i-Pr), 7.00 (t, 1H, NH—C—CH=CH—CH), 7.10 (t, 1H, NH—C—CH=CH), 7.36 (m, 2H, ArH), 7.50 (m, 3H, ArH), 7.62 (m, 2H, CH$_2$—C=C—C=CH), 11.11 (s, 1H, NH)

Example 52

Synthesis of 3-methyl-2-phenyl-1H-indole

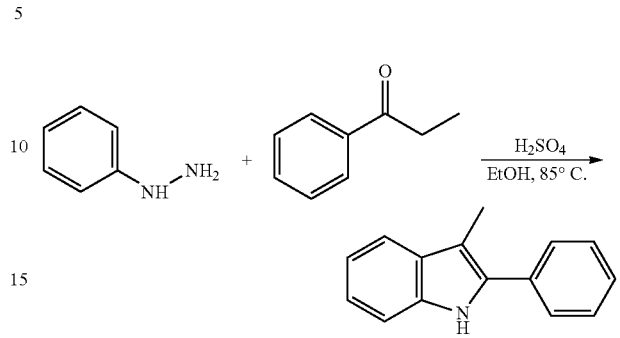

Phenyl hydrazine (2.55 mL, 0.026 mol, 1 eq), propiophenone (3.45 mL, 0.026 mol, 1 eq) and concentrated sulfuric acid (2.75 mL 0.052 mol, 2 eq) were added with 100 mL ethanol in a 250 mL two neck flask. The reaction mixture was refluxed under inert atmosphere. The progress of the reaction was monitored by thin layer chromatography (ethyl acetate:heptane 1:9). Once the hydrazine had completely reacted, but the propiophenone was still identified on TLC, an extra supply of phenyl hydrazine (0.26 mL, 2.6 mmol, 0.1 eq) was added. After completion of the reaction, the cooled solution was precipitated in a 10 fold excess of ice-water. After filtration 3-methyl-2-phenyl-1H-indole was obtained as a solid and purified by recrystallization in water:ethanol 1:2, to obtain the title compound as white needle shaped crystals (5.02 g, 0.024 mmol, 93%). Bruto formula: C$_{15}$H$_{13}$N Molecular weight: 207.28 g mol$^{-1}$ LC-MS (m/z): 208.1 [MH]$^+$ HRMS (m/z for [MH]$^+$ calculated/experimental): 208.1121/208.1113.

RF. value (ethyl acetate:heptane 1:9): 0.23

$^1$H-NMR (300 MHz, DMSO-d$_6$): δ (ppm)=2.41 (s, 3H, CH$_3$), 7.01 (t, 1H, NH—C—CH=CH—CH), 7.11 (t, 1H, NH—C—CH=CH), 7.35 (t, 2H, ArH), 7.51 (t, 3H, ArH), 7.67 (dd, 2H, ArH), 11.15 (s, 1H, NH)

$^{13}$C-NMR (125 MHz, DMSO-d$_6$): δ (ppm)=9.82 (CH$_3$), 106.74 (C), 110.99 (CH), 118.39 (CH), 118.54 (CH), 121.52 (CH), 126.94 (CH), 127.46 (CH), 128.68 (CH), 129.36 (C), 133.06 (C), 133.71 (C), 135.90 (C)

Example 53

Synthesis of 2,3-diphenyl-1H-indole

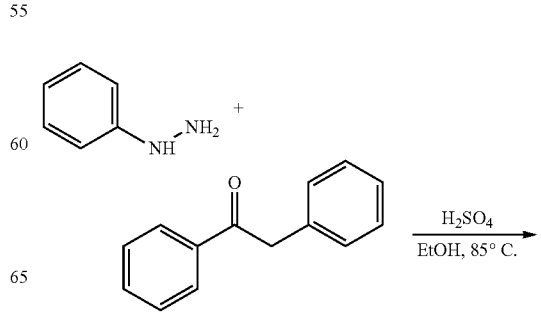

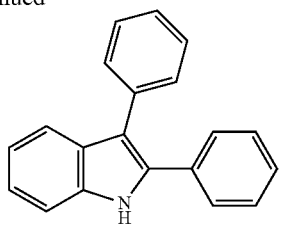

Phenyl hydrazine (10.2 mL, 0.52 mol, 1 eq), 2-phenylacetophenone (20.3 g, 0.52 mol, 1 eq) and concentrated sulfuric acid (11.0 mL, 1.04 mol, 2 eq) were added with 100 mL ethanol in a 500 mL two neck flask. The reaction mixture was refluxed overnight under inert atmosphere. Completion of the reaction was monitored by thin layer chromatography (TLC) using as diluent ethyl acetate:heptane 1:9. After cooling, the mixture was precipitated in 1.5 L ice in water and filtered. The obtained solid was recrystallized in water:ethanol (1:2) to yield 2,3-diphenyl-1H-indole as brown crystals (25.94 g, 0.096 mmol, 93%). Bruto formula: $C_{20}H_{15}N$ Molecular weight: 269.35 g mol$^{-1}$ LC-MS (m/z): 270.1 [MH]$^{+}$ RF. value (ethyl acetate:heptane 1:9): 0.30

$^1$H-NMR (300 MHz, DMSO-d$_6$): δ (ppm)=7.04 (t, 1H, NH—C—CH—CH—CH), 7.16 (t, 1H, NH—C—CH—CH), 7.25-7.44 (m, 8H, ArH) 7.45-7.51 (m, 4H, ArH), 11.56 (s, 1H, NH) $^{13}$C-NMR (125 MHz, DMSO-d$_6$): δ (ppm)=111.40 (CH), 113.21 (C), 118.48 (CH), 119.61 (CH), 121.89 (CH), 125.95 (CH), 127.38 (CH), 127.89 (C), 128.08 (CH), 128.37 (CH), 128.51 (CH), 129.66 (CH), 132.39 (C), 133.99 (C), 135.21 (C), 136.02 (C)

Example 54

Synthesis of 3-(4-nitrophenyl)-2-phenyl-1H-indole (1$^{st}$ Method)

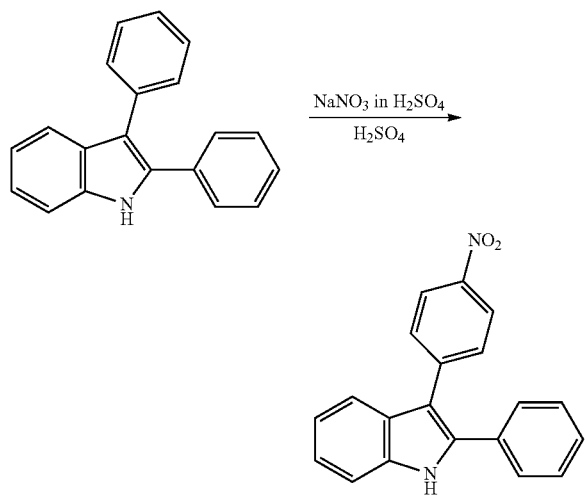

A mixture of 2,3-diphenyl-1H-indole (11.1 mmol, 1 eq, prepared as described in Example 53), in 60 mL of concentrated sulfuric acid was cooled in a salt ice bath and placed under inert atmosphere. To this mixture 0.943 g of sodium nitrate (11.1 mmol, 1 eq) in 60 mL of concentrated sulfuric acid was added. After stirring for 5 hours at room temperature, the reaction mixture was poured over ice and diluted with 200 mL of toluene. The aqueous phase was extracted repeatedly with toluene and the combined organic phases were dried over magnesium sulfate. After removing the solvent in vacuo, the residue was purified by column chromatography (ethyl acetate:heptane 1:4) and 3-(4-nitrophenyl)-2-phenyl-1H-indole was obtained as an orange solid (0.419 g, 1.33 mmol, 12%). Bruto formula: $C_{20}H_{14}N_2O_2$ Molecular weight: 314.34 g mol$^{-1}$ LC-MS (m/z): 315.1 [MH]$^{+}$ RF. value (ethyl acetate:heptane 1:4): 0.27

$^1$H-NMR (300 MHz, DMSO-d$_6$): δ (ppm)=7.13 (t, 1H, ArH), 7.23 (t, 1H, ArH), 7.33-7.54 (m, 6H, ArH), 7.55-7.81 (m, 3H, ArH), 8.12 en 8.23 (m, 2H, ArH), 11.80 en 11.88 (s, 1H, NH)

$^{13}$C-NMR (125 MHz, DMSO-d$_6$): δ (ppm)=111.15 (C), 111.88 (CH), 118.31 (CH), 120.50 (CH), 122.50 (CH), 123.90 (CH), 127.06 (C), 128.28 (CH), 128.72 (CH), 128.83 (CH), 130.21 (CH), 131.77 (C), 136.28 (C), 143.03 (C), 145.04 (C), 148.11 (C)

Example 55

Synthesis of 3-(4-nitrophenyl)-2-phenyl-1H-indole (2$^{nd}$ Method)

Step 1 Electrophilic Aromatic Nitration Reaction of 2-Phenylacetophenone

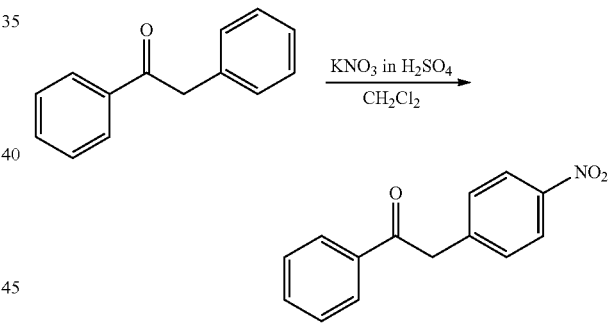

In a 100 mL flask a homogeneous solution of 5.06 g potassium nitrate (50.0 mmol, 10 eq) in 2.6 ml concentrated sulfuric acid (47.5 mmol, 9.5 eq) was prepared. The solution was placed under inert atmosphere and stirred vigorously before adding 25 mL of dichloromethane. While the mixture was being cooled in an ice bath, a solution of 2-phenylacetophenone (0.981 g, 5.00 mmol, 1 eq) in 8 mL dichloromethane was added drop wise to the vigorously stirred solution. After stirring for 24 hours at room temperature, the reaction mixture was poured in 30 mL of a 10 w % sodium sulfate solution. The organic phase was washed with 2 times 10 mL of 10 w % sodium sulfate solution, dried over magnesium sulfate and concentrated in vacuo. The obtained orange solid was a mixture of 4 products where 2-(4-nitrophenyl)-acetophenone was isolated by column chromatography (ethyl acetate:heptane 1:7) as a yellow solid (0.398 g, 1.65 mmol, 33%). Bruto formula: $C_{14}H_{11}NO_3$ Molecular weight: 241.25 g mol$^{-1}$ LC-MS (m/z): 242.2 [MH]$^{+}$ ¹H-NMR (300 MHz, CDCl₃): δ (ppm)=4.69 (s, 2H, CH₂), 7.33 (d, 1H, ArH), 7.41-7.65 (m, 5H, ArH), 7.97-8.07 (m, 2H, ArH), 8.13 (d, 1H, ArH)

Step 2 Fischer Indole Synthesis with 2-(4-nitrophenyl)-acetophenone

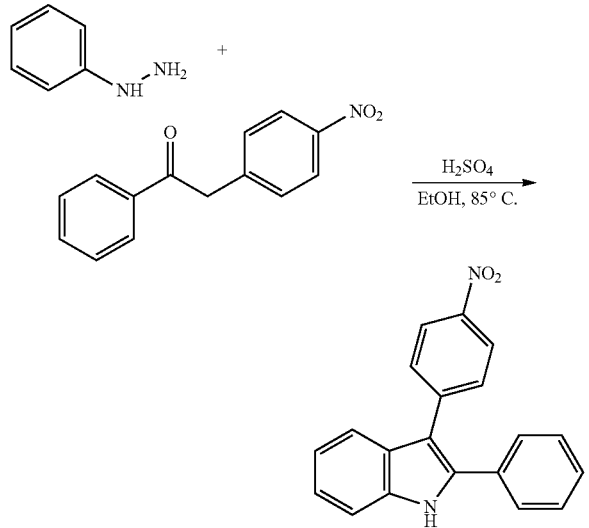

In a 50 mL two neck flask, 0.163 mL of phenyl hydrazine (1.65 mmol, 1 eq), 0.398 g of 2-(4-nitrophenyl)-acetophenone (38, 1.65 mmol, 1 eq) and 0.176 mL of concentrated sulfuric acid (3.30 mmol, 2 eq) were dissolved in 10 mL ethanol. The reaction mixture was refluxed overnight and the progress of the reaction was followed by thin layer chromatography (ethyl acetate:heptane 1:4). After cooling the reaction mixture was precipitated to obtain 3-(4-nitrophenyl)-2-phenyl-1H-indole (0.368 g, 1.17 mmol, 71%) Bruto formula: C₂₀H₁₄N₂O₂

Molecular weight: 314.34 g mol⁻¹

LC-MS (m/z): 315.1 [MH]⁺

RF. value (ethyl acetate:heptane 1:4): 0.24

Example 56

Synthesis of 5-isopropyl-3-methyl-2-phenyl-1H-indole

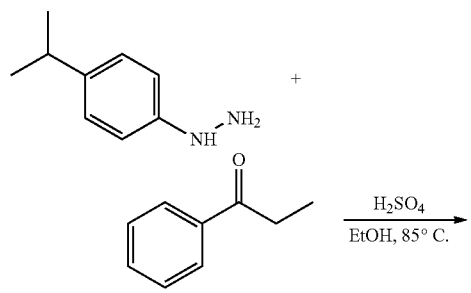

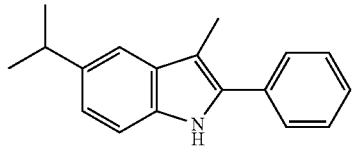

In a 100 mL two neck flask, 1.50 g of 4-isopropylphenylhydrazine (10.0 mmol, 1 eq), 1.33 mL of propiophenone (10.0 mmol, 1 eq) and 1.08 mL of concentrated sulfuric acid (20.0 mmol, 2 eq) were dissolved in 50 mL ethanol. The reaction mixture was refluxed for 3 hours under inert atmosphere. After cooling 5-isopropyl-3-methyl-2-phenyl-1H-indole was precipitated in an ice/water mixture (250 mL), filtered and dried overnight in vacuo. 2.15 g of the title product was obtained (8.62 mmol, 86%). Bruto formula: C₁₈H₁₉N Molecular weight: 249.36 g mol⁻¹

LC-MS (m/z): 250.2 [MH]⁺

HRMS (m/z for [MH]⁺ calculated/experimental): 250.1590/250.1601.

¹H-NMR (300 MHz, DMSO-d₆): δ (ppm)=1.27 (d, 6H, CH—(CH₃)₂), 2.41 (s, 3H, C═C—CH₃), 2.98 (heptaplet, 1H, CH—(CH₃)₂), 7.01 (d, 1H, ArH), 7.25-7.38 (m, 3H, ArH), 7.50 (t, 2H, ArH), 7.66 (d, 2H, ArH), 11.00 (s, 1H, NH)

¹³C-NMR (125 MHz, DMSO-d₆): δ (ppm)=9.87 (CH₃), 24.68 (CH₃), 33.67 (CH₃), 106.57 (C), 110.80 (CH), 115.12 (CH), 120.65 (CH), 126.78 (CH), 127.36 (CH), 128.63 (CH), 129.39 (C), 133.25 (C), 133.81 (C), 134.58 (C), 138.64 (C)

Example 57

Synthesis of 5-isopropyl-2,3-diphenyl-1H-indole

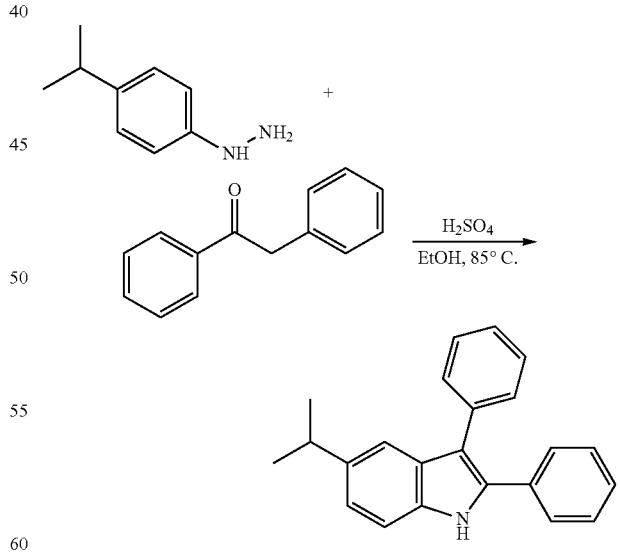

In a 50 mL two neck flask, 1.20 g of 4-isopropylphenylhydrazine (8.02 mmol, 1 eq), 1.57 g of 2-phenylacetophenone (8.02 mmol, 1 eq) and 0.86 mL of concentrated sulfuric acid (16.0 mmol, 2 eq) were dissolved in 30 mL ethanol. The reaction mixture was refluxed for 3 hours under inert atmosphere. After cooling, 5-isopropyl-2,3-diphenyl-1H-indole was precipitated in an ice/water mixture (150 mL), filtrated and dried overnight in vacuo. 2.26 g of the title product was obtained (7.26 mmol, 91%). Bruto formula: $C_{23}H_{21}N$ Molecular weight: 311.83 g mol$^{-1}$ LC-MS (m/z): 312.2 [MH]$^+$ HRMS (m/z for [MH]$^+$ calculated/experimental): 312.1747/312.1747.

$^1$H-NMR (300 MHz, DMSO-d$_6$): δ (ppm)=1.22 (d, 6H, CH$_3$), 2.94 (heptaplet, 1H, CH—(CH$_3$)$_2$), 7.08 (d, 1H, ArH), 7.22-7.48 (m, 12H, ArH), 11.42 (s, 1H, NH)

$^{13}$C-NMR (125 MHz, DMSO-d$_6$): δ (ppm)=24.58 (CH$_3$), 33.67 (CH$_3$), 111.33 (CH), 113.15 (C), 115.23 (CH), 121.00 (CH), 125.97 (CH), 127.35 (CH), 127.95 (C), 128.05 (CH), 128.44 (CH), 128.62 (CH), 129.76 (CH), 132.58 (C), 134.16 (C), 134.71 (C), 135.48 (C), 139.80 (C)

Example 58

Synthesis of Indole Containing Initiator

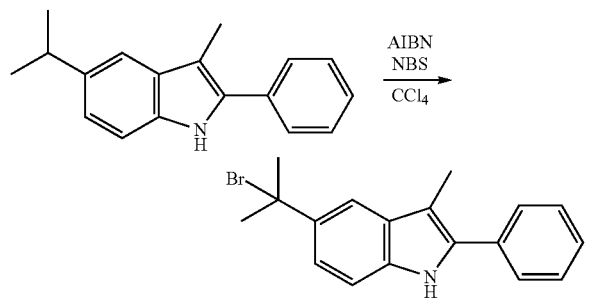

In a 100 mL two neck flask, a solution of 5-isopropyl-3-methyl-2-phenyl-1H-indole (1.20 g, 4.81 mmol, 1 eq; prepared as described in Example 56) in 20 mL tetrachloromethane was prepared. To this mixture 0.857 g of N-bromosuccinimide (NBS, 4.81 mmol, 1 eq) and 0.0790 g of azobisisobutyronitrile (AIBN, 0.481 mmol, 0.1 eq) were added. After refluxing for 7 hours, a second batch of NBS (0.357 g, 2.01 mmol, 0.4 eq) and AIBN (0.0330 g, 0.201 mmol, 0.4 eq) were added. After refluxing for 48 hours the mixture was filtered, washed with dichloromethane and concentrated in vacuo. The residue was dissolved in 20 mL ethyl acetate and extracted with water (2×10 mL). The organic phase was washed with brine (10 mL), dried over magnesium sulfate and concentrated in vacuo. The brown oil was purified by column chromatography (ethyl acetate: heptane 1:9) to obtain the indole containing initiator (0.742 g, 2.26 mmol, 47%). Bruto formula: $C_{23}H_{21}N$ Molecular weight: 328.25 g mol$^{-1}$ LC-MS (m/z): 329.0 [MH]$^+$ Example 59

Synthesis of Indole Containing Initiator

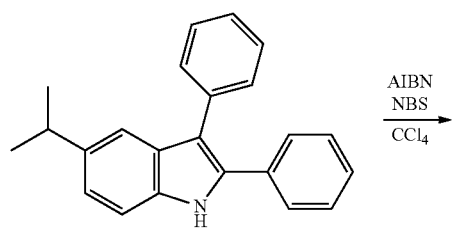

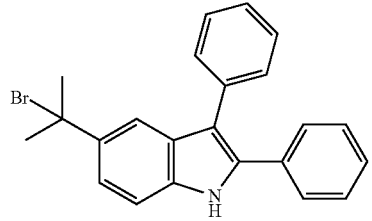

In a 100 mL two neck flask, a solution of 5-isopropyl-2,3-diphenyl-1H-indole (1.00 g, 3.21 mmol, 1 eq, prepared as described in Example 57) in 20 mL of tetrachloromethane was prepared. To this mixture, 0.571 g of N-bromosuccinimide (NBS, 3.21 mmol, 1 eq) and 0.0527 g of azobisisobutyronitrile (AIBN, 0.481 mmol, 0.1 eq) were added. After refluxing for 7 hours, a second batch of NBS (0.238 g, 1.34 mmol, 0.4 eq) and AIBN (0.321 g, 0.201 mmol, 0.4 eq) was added. After refluxing for 48 hours the mixture was filtered, washed with dichloromethane and concentrated in vacuo. The residue was dissolved in 20 mL ethyl acetate and extracted with water (2×10 mL). The organic phase was washed with brine (10 mL), dried over magnesium sulfate and concentrated in vacuo. The brown oil was purified by column chromatography (ethyl acetate:heptane 1:9) to obtain the indole containing initiator, as a white solid (0.714 g, 1.83 mmol, 57%). Bruto formula: $C_{23}H_{21}N$ Molecular weight: 390.32 g mol$^{-1}$ LC-MS (m/z): 391.2 [MH]$^+$ RF. value (ethyl acetate:heptane 1:9): 0.21

$^1$H-NMR (300 MHz, DMSO-d$_6$): δ (ppm)=1.21 (d, 6H, CH$_3$), 7.23-7.47 (m, 12H, ArH), 7.63 (s, 1H, Br(CH$_3$)$_2$C—C—CH), 11.59 (s, 1H, NH)

$^{13}$C-NMR (125 MHz, DMSO-d$_6$): δ (ppm)=23.32 (CH$_3$), 32.18 (CH$_3$), 113.13 (C), 114.83 (CH), 115.53 (CH), 117.24 (C), 126.29 (CH), 127.76 (CH), 127.82 (C), 128.13 (CH), 128.52 (CH), 128.75 (CH), 129.68 (CH), 132.07 (C), 134.74 (C), 135.23 (C), 135.29 (C), 137.37 (C)

Example 60

Synthesis of Methyl-Indole Monomer-Precursor

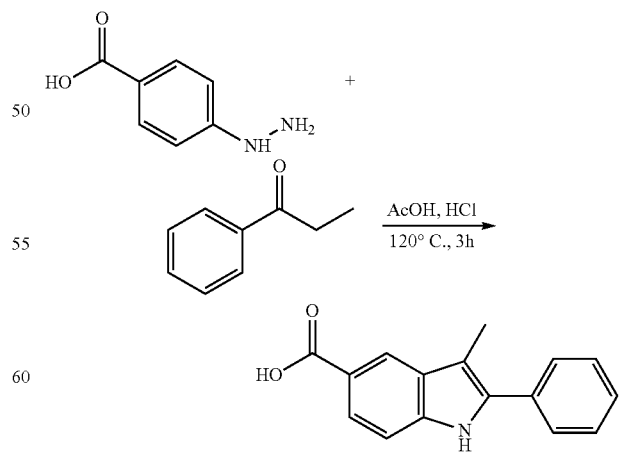

To a mixture of 1.00 g of 4-hydrazinobenzoic acid (6.57 mmol, 1 eq) and 0.87 mL of propiophenone (6.57 mmol, 1 eq) in a 250 mL two neck flask, 50 mL of concentrated sulfuric acid and 15 mL of concentrated hydrochloric acid were added. After refluxing for 3 hour, the reaction mixture was cooled to room temperature. By careful addition of deionized water (60 mL) to the mixture, the obtained precursor was precipitated. After filtration the product was dried overnight in vacuo, to obtain the precursor as a green powder (0.92 g, 3.86 mmol, 56%). Bruto formula: $C_{16}H_{13}NO_2$ Molecular weight: 251.29 g mol$^{-1}$
LC-MS (m/z): 252.1 [MH]$^+$
RF. value (ethyl acetate:heptane 1:9): 0.23
$^1$H-NMR (300 MHz, DMSO-d$_6$): δ (ppm)=2.44 (s, 3H, CH$_3$), 7.35-7.43 (m, 2H, ArH), 7.53 (t, 2H, ArH), 7.65-7.71 (m, 2H, ArH), 7.74 (d, 1H, ArH), 8.21 (s, 1H, HOOC—C—CH—C), 11.54 (s, 1H, NH), 12.40 (s, 1H, COOH)
$^{13}$C-NMR (125 MHz, DMSO-d$_6$): δ (ppm)=9.62 (CH$_3$), 108.06 (C), 110.70 (CH), 121.07 (CH), 121.13 (C), 122.85 (CH), 127.40 (CH), 127.62 (CH), 128.76 (CH), 128.88 (C), 132.45 (C), 135.27 (C), 138.38 (C), 168.37 (C).

Example 61

Synthesis of Phenyl-Indole Monomer-Precursor

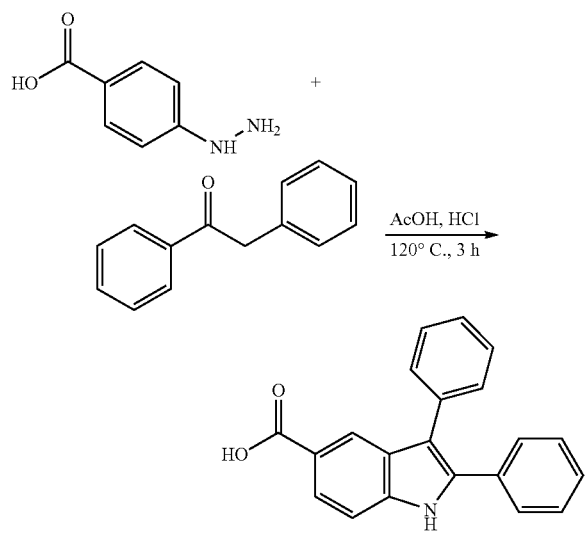

To a mixture of 3.00 g of 4-hydrazinobenzoic acid (19.7 mmol, 1 eq) and 3.87 g of 2-phenylacetophenone (19.7 mmol, 1 eq) in a 500 mL two neck flask, 200 mL of concentrated sulfuric acid and 60 mL of concentrated hydrochloric acid were added. After refluxing for 3 hour, the reaction mixture was cooled to room temperature. By careful addition of deionized water (250 mL) to the mixture, the obtained precursor was precipitated. After filtration the product was dried overnight in vacuo to obtain the precursor as a light brown powder (4.62 g, 75%) Bruto formula: $C_{21}H_{15}NO_2$ Molecular weight: 313.36 g mol$^{-1}$
LC-MS (m/z): 312.0 [M-H]$^-$
RF. value (ethyl acetate:heptane 1:9): 0.21
$^1$H-NMR (300 MHz, DMSO-d$_6$): δ (ppm)=7.28-7.54 (m, 11H, ArH), 7.80 (d, 1H, ArH), 8.13 (s, 1H, HOOC—C—CH—C), 11.94 (s, 1H, NH), 12.48 (s, 1H, COOH)
$^{13}$C-NMR (125 MHz, DMSO-d$_6$): δ (ppm)=111.28 (CH), 114.41 (C), 121.28 (CH), 122.23 (C), 123.27 (CH), 126.53 (CH), 127.71 (C), 127.90 (CH), 128.18 (CH), 128.59 (CH), 128.81 (CH), 129.82 (CH), 131.88 (C), 134.61 (C), 135.54 (C), 138.54 (C), 168.23 (C)

Example 62

Synthesis of Poly(Butyl Acrylate) with Diphenyl-Indole Initiator

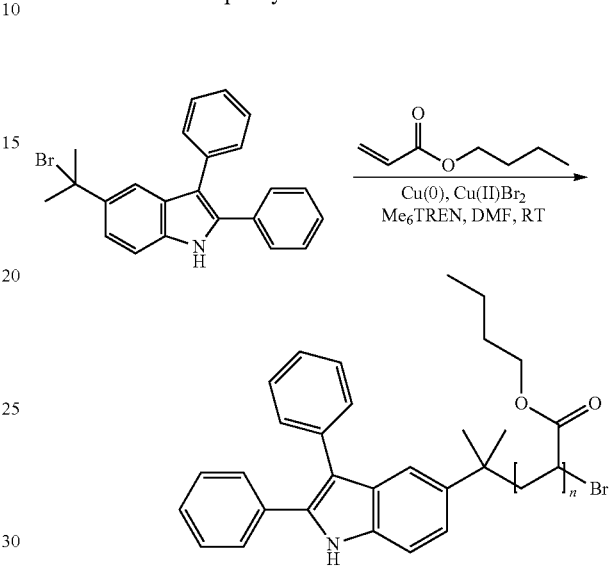

In a 10 mL flask, 0.45 mL of butyl acrylate (3.11 mmol, 50 eq) and 24.3 mg of diphenyl-indole initiator (3.76 mmol, 4 eq, prepared as described in Example 59) were dissolved in 0.3 mL of DMF. Copper (10 pellets) was then added to the mixture. In parallel, a second solution containing 0.700 mg of copper(II)bromide (0.0031 mmol, 0.05 eq) and 1.72 mg of tris[2-(dimethylamino)ethyl]amine (Me$_6$TREN) (7.5 μmol, 0.12 eq) in 0.3 mL of DMF was prepared. Both solutions were degassed with argon for 30 minutes. The copper(II)bromide solution was added to the butyl acrylate solution and the mixture was stirred for 24 hours under inert atmosphere. The polymerization was halted by exposing the solution to air and by cooling it in liquid nitrogen. After diluting with THF to double the volume, the mixture was filtrated over basis aluminum oxide and concentrated in vacuo. The polymer was dried overnight in vacuo at 40° C.

$M_n$ (SEC): 22 100 and 2 700 g mol$^{-1}$
$M_w$ (SEC): 28 800, resp. 3 000 g mol$^{-1}$
Đ (SEC): 1.30, resp. 1.11

Example 63

Synthesis of Urazole-Polybutyl Acrylate

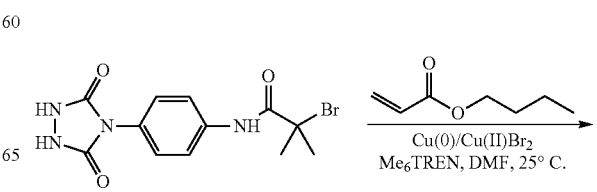

-continued

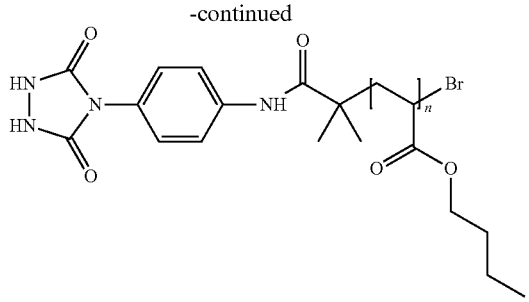

2.1 mL of butyl acrylate (14.66 mmol, 50 eq), 4 mL DMF, Cu(0) (20 pellets), 100 mg urazole-initiator (0.29 mmol, 1 eq) were weighed into a flask and degassed for 1 hour with a continuous nitrogen sparge. In a separate vial, 3.27 mg Cu(II)Br$_2$ (0.29 mmol, 0.05 eq), 8.1 mg Me$_6$TREN (0.04 mmol, 0.12 eq) and 1.22 mL DMF were degassed separately for 1 hour. The reaction was started by the addition of the Cu(II)Br$_2$/ligand-solution to the reaction mixture, the flask was placed in an oil bath at 25° C. After 22 hours, the reaction was stopped (83% conversion) by cooling in liquid nitrogen under air atmosphere and removing the copper catalyst by passing the reaction mixture over a column of Al$_2$O$_3$. After evaporating the excess solvent, the polymer was poured in a petri dish and dried overnight in a vacuum oven at 40° C.

$M_n$ (SEC): 20.0 kg/mol
$M_w$ (SEC): 27.7 kg/mol
Đ (SEC): 1.38

Example 64

Synthesis of 2-tert-butyl, 3-ethyl-1H-aza-indole

Step 1: Synthesis of N-o-pyridylpivalamide

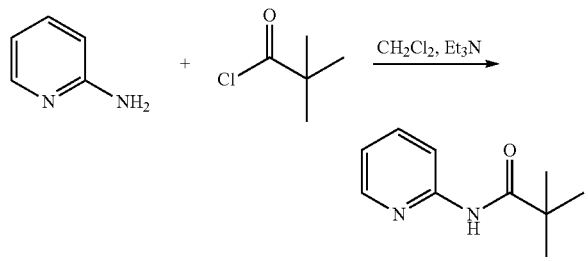

In a 100 mL flask, 2-aminopyridine (3.0 g, 0.032 mol, 1 eq) was dissolved in 35 mL of dichloromethane. After addition of triethylamine (3.6 g, 0.035 mol, 1.1 eq), the solution was cooled in a water bath and trimethylacetylchloride (4.31 mL, 0.035 mol, 1.1 eq) was added dropwise. This mixture was stirred overnight under inert atmosphere. The reaction mixture was then 2 times washed with saturated sodium carbonate solution (30 mL) and brine (30 mL). After drying on magnesium sulfate the desired product was obtained as a powder by removing the organic solvent under reduced pressure (5.2 g, 0.029 mol, 91%).

Bruto formula: C$_{10}$H$_{14}$N$_2$O.
MW.: 178.27 g/mol.
$^1$H-NMR (300 MHz, CDCl$_3$): δ (ppm)=1.23 (s, 9H, C(CH$_3$)$_3$), 6.93 (m, 1H, ArH), 7.60 (m, 1H, ArH), 8.01 (s, 1H, NH), 8.17 (m, 2H, ArH).

Step 2: Synthesis of 2-tert-butyl, 3-ethyl-1H-aza-indole

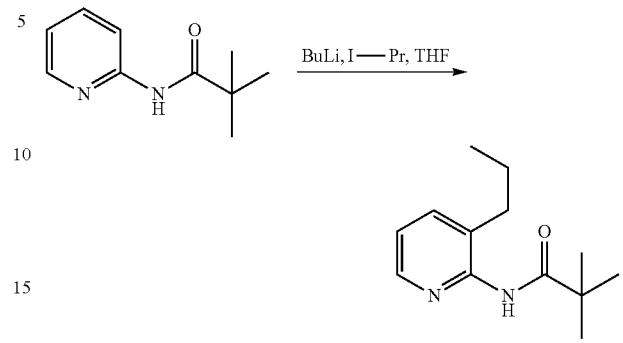

In a 50 mL flask, a solution of N-o-pyridylpivalamide (1 g, 5.6 mmol, 1 eq) in dry THF (7 mL) was prepared under inert atmosphere. After cooling to −78° C. n-butyllithium (2.5 M in hexane, 5 mL, 12.32 mmol, 2.2 eq) was added dropwise. The reaction mixture was stirred for 30 minutes at −78° C., followed by stirring for 2 hours at 10° C. The mixture was cooled to −78° C. again and a solution of 1-iodopropane (1.20 mL, 12.32 mmol) in anhydrous THF (7 mL) was added. The mixture was stirred for 2 hours at −78° C. and overnight at room temperature. The obtained mixture was directly used in the next step without purification.

Step 3: Synthesis of 2-tert-butyl, 3-ethyl-1H-aza-indole

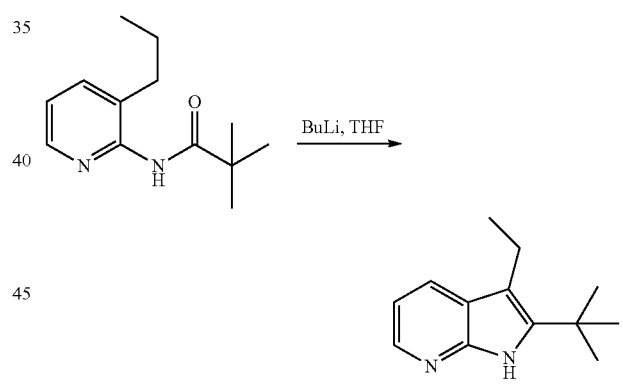

After cooling the mixture obtained in step 2 in a water bath, n-butyllithium (2.5 M in hexane, 8.16 mL, 20.4 mmol, 3 eq) was added dropwise. The reaction mixture was stirred overnight at room temperature, after which it was cooled in an ice bath. Once the solution was cooled, saturated aqueous ammonium chloride solution (40 mL) was added slowly, followed by potassium carbonate. The water phase was extracted with ethyl acetate (3×100 mL), after which the combined organic phases were dried on magnesium sulfate and concentrated in vacuo. This was purified by column chromatography (hexane:ethyl acetate:triethylamine 9:1: 0.1) to obtain the pure compound (0.225 g, 1.11 mmol, 20%). Bruto formula: C$_{13}$H$_{18}$N$_2$.

MW.: 202.30 g/mol.
$^1$H-NMR (300 MHz, CDCl$_3$): δ (ppm)=1.27 (t, 3H, CH$_2$—CH$_3$), 1.49 (s, 9H, C(CH$_3$)$_3$), 2.89 (q, 2H, CH2-CH3), 7.01 (dd, 1H, ArH), 7.81 (dd, 1H, ArH), 8.20 (dd, 1H, ArH), 8.63 (br. s, 1H, NH).

Example 65

TAD-Indole Reversible Reaction Experiments

BTAD prepared as described in Example 3 was mixed in a 1:1 ratio with solutions of different indoles in DMSO-$d_6$. The reactants were mixed at room temperature. After complete reaction, 1 equivalent of 2,4-hexadien-1-ol (HDEO) in DMSO-$d_6$ was added to the solution containing the BTAD-indole adduct. After addition of HDEO, NMR-analyses were preformed following brief periods of heating at ever increasing temperatures. Samples were taken at the indicated temperatures and the fraction of free indole was calculated from $^1$H-NMR. The results are shown in Table 1.

TABLE 1

| Temperature | Isopentyl indole Example 9 | indole-OH of example 10 | Indole diol of example 1 | Methyl indole of example 52 | phenyl indole of example 53 | nitrophenyl indole of examples 54 or 55 | Aza-Indole of example 64 |
|---|---|---|---|---|---|---|---|
| 50 | 1.40187 | 0.6135 | 0 | 0.9667 | 0.35394 | 0.57471 | — |
| 60 | 1.40187 | 0 | 1.06383 | 0 | 1.06548 | 3.45821 | — |
| 70 | 1.86916 | 0.6135 | 2.65957 | 0.75758 | 4.24723 | 12.93103 | — |
| 80 | 2.80374 | 2.45399 | 2.65957 | 1.51679 | 11.36515 | 28 | — |
| 90 | 3.27103 | 4.90798 | 3.19149 | 3.1556 | 27.58054 | 58.51648 | — |
| 100 | 8.41121 | 7.36196 | 9.04255 | 5.8952 | 60.81158 | 88.68421 | 27 |
| 110 | 15.88785 | 20.2454 | 18.08511 | 13.46578 | 86.12044 | 98.75622 | — |
| 120 | 36.91589 | 33.74233 | 42.55319 | 36.39495 | 98.39427 | 100 | 56 |
| 130 | 58.41121 | 58.89571 | 62.76596 | 70.73733 | 99.42279 | 100 | — |
| 140 | 80.37383 | 84.66258 | 89.89362 | 94.54976 | 99.42279 | 100 | 100 |
| 150 | 87.38318 | 94.47853 | 94.14894 | 98.31528 | 99.04005 | 100 | — |
| 160 | 88.31776 | 96.93252 | 96.2766 | 100 | 100 | 100 | 100 |

The invention claimed is:

1. A compound of formula (I) or a stereoisomer, enantiomer, racemic, or tautomer thereof,

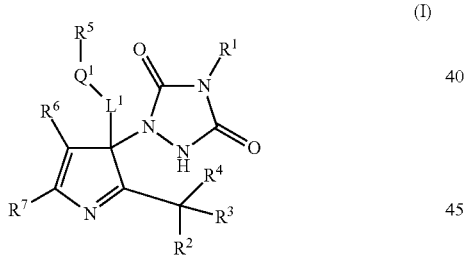

(I)

wherein, $L^1$ is selected from $C_{1-10}$alkylene; $C_{2-10}$alkenylene; or $C_{2-10}$alkynylene; or $L^1$ and $R^2$ together with the carbon atoms to which they are attached form a saturated or unsaturated 4-, 5-, 6-, 7- or 8-membered ring;

wherein said $C_{1-10}$alkylene; $C_{2-10}$alkenylene; $C_{2-10}$alkynylene, or saturated or unsaturated 4-, 5-, 6-, 7- or 8-membered ring, optionally comprises one or more heteroatoms in the alkylene, alkenylene, alkynylene, or saturated or unsaturated 4-, 5-, 6-, 7- or 8-membered ring moiety, said heteroatoms being each independently selected from O, S and N;

and wherein said $C_{1-10}$alkylene; $C_{2-10}$alkenylene; $C_{2-10}$alkynylene, or saturated or unsaturated 4-, 5-, 6-, 7- or 8-membered ring can be unsubstituted or substituted with one or more $Z^1$;

$Q^1$ is a single bond or is selected from the group consisting of —OC(O)—; —NH—C(O)—; —OS(O)—; —OS(O)$_2$—; —NH—S(O)—; —NH—S(O)$_2$—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; wherein each left side of said groups is attached to $L^1$ and the right side thereof is attached to $R^5$; and wherein, q is an integer selected from 1; 2 or 3;

p is an integer selected from 0; 1 or 2;

$L^4$ is a single bond or is selected from the group consisting of $C_{1-10}$alkylene; $C_{2-10}$alkenylene; and $C_{2-10}$alkynylene;

wherein said $C_{1-10}$alkylene; $C_{2-10}$alkenylene; and $C_{2-10}$alkynylene, optionally comprises one or more heteroatoms in the alkylene, alkenylene, alkynylene moiety, said heteroatoms being each independently selected from O, S and N;

and wherein said $C_{1-10}$alkylene; $C_{2-10}$alkenylene; $C_{2-10}$alkynylene can be unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

wherein said $C_{2-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; heteroaryl$C_{1-6}$alkyl, optionally comprises one or more heteroatoms in the alkyl moiety, said heteroatoms being each independently selected from 0, S or N;

wherein at least one carbon atom or heteroatom of said $C_{2-10}$alkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; and heteroaryl$C_{1-6}$alkyl can be oxidized to form at least one C=O, C=S, N=O, N=S, S=O or S(O)$_2$;

wherein said $C_{2-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, heterocyclyl; heteroaryl; heterocyclyl$C_{1-6}$alkyl; and heteroaryl$C_{1-6}$alkyl can be unsubstituted or substituted with one or more $Z^3$;

and wherein said polymeric group is selected from the group comprising polyethylene oxide; polyacrylate; polymethacrylate; polystyrene; copolymer of acrylate; poly(methyl methacrylate); methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group; or $R^1$ is a group of formula (i);

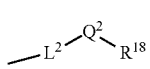
(i)

wherein, $L^2$ is a single bond or is selected from the group consisting of $C_{1-10}$alkylene; $C_{2-10}$alkenylene; $C_{2-10}$alkynylene; and $C_{6-12}$arylene;

wherein said $C_{1-10}$alkylene; $C_{2-10}$alkenylene; $C_{2-10}$alkynylene, or $C_{6-12}$arylene, optionally comprises one or more heteroatoms in the alkylene, alkenylene, alkynylene, or arylene moiety, said heteroatoms being each independently selected from O, S and N;

and wherein said $C_{1-10}$alkylene; $C_{2-10}$alkenylene; $C_{2-10}$alkynylene, or $C_{6-12}$arylene, can be unsubstituted or substituted with one or more $Z^4$;

$Q^2$ is selected from the group consisting of $C_{1-10}$alkylene; $C_{3-6}$cycloalkylene; —OC(O)—; —NH—C(O)—; —NH—C(O)—[CR$^{13}$R$^{14}$]$_q$; —OS(O)—; —OS(O)$_2$—; —NH—S(O)—; and —NH—S(O)$_2$; wherein each left side of said groups is attached to $L^2$ and the right side thereof is attached to $R^{18}$;

wherein said $C_{1-10}$alkylene, optionally comprises one or more heteroatoms, said heteroatoms being each independently selected from O, S and N;

and wherein said $C_{1-10}$alkylene and said $C_{3-6}$cycloalkylene; can be unsubstituted or substituted with one or more $Z^5$;

or $Q^2$ is a group of formula (ii);

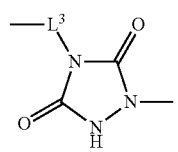
(ii)

wherein the left side of the group formula (ii) is attached to $L^2$ and the right side thereof is attached to $R^{18}$; and wherein, or $Q^2$-$R^{18}$ or is a group of formula (iii);

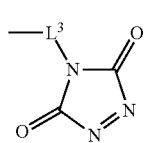
(iii)

wherein the left side of the group formula (ii) is attached to $L^2$ and the right side thereof is attached to $R^{18}$; and wherein, $L^3$ is a single bond or is selected from the group consisting of $C_{1-10}$alkylene; $C_{2-10}$alkenylene; $C_{2-10}$alkynylene; and $C_{6-12}$aryl;

wherein said $C_{1-10}$alkylene; $C_{2-10}$alkenylene; $C_{2-10}$alkynylene, or $C_{6-12}$aryl, optionally comprises one or more heteroatoms in the alkylene, alkenylene, alkynylene, or aryl moiety, said heteroatoms being each independently selected from O, S and N;

and wherein said $C_{1-10}$alkylene; $C_{2-10}$alkenylene; $C_{2-10}$alkynylene, or $C_{6-12}$aryl can be unsubstituted or substituted with one or more $Z^6$;

$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety; $R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

or $R^2$ and $R^3$ and $R^4$ together with the carbon atom to which they are attached can form a saturated or unsaturated 4-, 5-, 6-, 7- or 8-membered ring;

or $R^2$ and $L^1$ together with the carbon atom to which they are attached can form a saturated or unsaturated 4-, 5-, 6-, 7- or 8-membered ring;

wherein for $R^2$, $R^3$ and $R^4$, each independently; said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$ alkyl, or saturated or unsaturated 4-, 5-, 6-, 7- or 8-membered ring, optionally comprises one or more heteroatoms in the alkyl, alkenyl, alkynyl, or unsaturated 4-, 5-, 6-, 7- or 8-membered ring moiety, said heteroatoms being each independently selected from O, S and N;

wherein for $R^2$, $R^3$ and $R^4$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl, heteroaryl$C_{1-6}$ alkyl, or saturated or unsaturated 4-, 5-, 6-, 7- or 8-membered ring can be unsubstituted or substituted with one or more $Z^7$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^5$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-6}$ alkyl; heterocyclyl; heteroaryl; heterocyclyl$C_{1-6}$alkyl;

heteroaryl$C_{1-6}$alkyl; and a polymeric group; and a pharmaceutically active moiety;

wherein said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl$C_{1-6}$alkyl, optionally comprises one or more heteroatoms in the alkyl, alkenyl, alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; heteroaryl$C_{1-6}$alkyl; and polymeric group can be unsubstituted or substituted with one or more $Z^8$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$R^6$ is selected from the group consisting of $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; and a pharmaceutically active moiety;

$R^7$ is selected from the group consisting of $C_{1-20}$alkyl; $C_{2-20}$alkenyl; $C_{2-20}$alkynyl; $C_{6-12}$aryl; $C_{3-8}$cycloalkyl e; $C_{6-12}$aryl$C_{1-6}$alkyl; heterocyclyl; heteroaryl; heterocyclyl$C_{1-6}$alkyl; heteroaryl$C_{1-6}$alkyl; or a polymeric group; and a polymeric group; and a pharmaceutically active moiety;

or $R^6$ and $R^7$ together with the carbon atoms to which they are attached form an unsaturated 4-, 5-, 6-, 7- or 8-membered ring;

wherein for $R^6$ and $R^7$, each independently; said $C_{1-20}$alkyl, $C_{2-20}$alkenyl, $C_{2-20}$alkynyl, $C_{6-12}$aryl $C_{1-6}$alkyl, heterocyclyl$C_{1-6}$alkyl, heteroaryl$C_{1-6}$ alkyl or unsaturated 4-, 5-, 6-, 7- or 8-membered ring, optionally comprises one or more heteroatoms in the alkyl, alkenyl, alkynyl, or unsaturated 4-, 5-, 6-, 7- or 8-membered ring moiety, said heteroatoms being each independently selected from O, S and N;

wherein for $R^6$ and $R^7$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl, heteroaryl, heterocyclyl$C_{1-6}$alkyl, heteroaryl$C_{1-6}$ alkyl, polymeric group, or saturated or unsaturated 4-, 5-, 6-, 7- or 8-membered ring can be unsubstituted or substituted with one or more $Z^9$;

and wherein said polymeric group is selected from the group comprising polystyrene; poly(methyl methacrylate); polyethylene oxide; polyacrylate); polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^9$ is independently selected from hydroxyl; $C_{1-20}$alkyl, $C_{2-20}$alkenyl, $C_{2-20}$alkenyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$ alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl; can be oxidized to form at least one C=O, C=S, N=O, N=S, S=O or $S(O)_2$;

each $R^{10}$ is independently selected from hydrogen, $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$ alkyl;

wherein said $C_{1-10}$alkyl, $C_{2-20}$alkenyl, $C_{2-20}$alkynyl, $C_{6-12}$alyl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

each $R^{11}$ and $R^{12}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl $C_{1-6}$alkyl, heterocyclyl; heteroaryl; heterocyclyl$C_{1-6}$ alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

or wherein $R^{11}$ and $R^{12}$ together with the atom to which they are attached form a 5-, 6-, or 7-membered heterocycle;

each $R^{13}$ and $R^{14}$ is independently selected from the group consisting of hydrogen; $C_{1-20}$alkyl, $C_{2-20}$alkenyl, $C_{2-20}$alkynyl; $C_{6-12}$aryl; $C_{3-8}$cycloalkyl; $C_{6-12}$aryl$C_{1-6}$alkyl; heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

or wherein $R^{13}$ and $R^{14}$ together with the atom to which they are attached form a 5-, 6-, or 7-membered heterocycle;

$R^{15}$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-6}$alkyl; heterocyclyl; heteroaryl; heterocyclyl$C_{1-6}$alkyl; heteroaryl$C_{1-6}$alkyl; and a polymeric group; and a pharmaceutically active moiety;

wherein said $C_{1-20}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl$C_{1-6}$alkyl, optionally comprises one or more heteroatoms in the alkyl, alkenyl, and alkynyl moiety, said heteroatoms being each independently selected from O, S and N;

wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl $C_{1-6}$alkyl; can be oxidized to form at least one C=O, C=S, N=O, N=S, S=O or $S(O)_2$;

wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; heteroaryl$C_{1-6}$alkyl; and polymeric group can be unsubstituted or substituted with one or more $Z^{10}$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

each $R^{16}$ and $R^{17}$ is independently selected from the group consisting of hydrogen; $C_{1-20}$alkyl, $C_{2-20}$alkenyl, $C_{2-20}$alkynyl; $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl;

wherein said $C_{1-10}$alkyl, $C_{2-20}$alkenyl, $C_{2-20}$alkynyl, $C_{6-12}$aryl$C_{1-6}$alkyl, heterocyclyl$C_{1-6}$alkyl; and heteroaryl$C_{1-6}$alkyl, optionally comprise one or more heteroatoms in the alkyl, alkenyl or alkynyl moiety, said heteroatoms being each independently selected from O, S and N;

and wherein at least one carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$alkyl; can be oxidized to form at least one C=O, C=S, N=O, N=S, S=O or $S(O)_2$;

or wherein $R^{16}$ and $R^{17}$ together with the atom to which they are attached form a 5-, 6-, or 7-membered heterocycle;

$R^{18}$ is selected from the group consisting of hydrogen, $C_{1-10}$alkyl; $C_{3-8}$cycloalkyl; $C_{6-12}$aryl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group; and a pharmaceutically active moiety;

wherein said $C_{1-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; and heteroaryl$C_{1-6}$alkyl, optionally comprises one or more heteroatoms in the alkyl moiety, said heteroatoms being each independently selected from O, S or N;

wherein said $C_{1-10}$alkyl, $C_{3-8}$cycloalkyl, $C_{6-12}$aryl, $C_{6-12}$aryl$C_{1-6}$alkyl, $C_{6-12}$aryl$C_{1-6}$alkyl$C_{6-12}$aryl, heterocyclyl; heteroaryl; heterocyclyl$C_{1-6}$alkyl; and heteroaryl$C_{1-6}$alkyl can be unsubstituted or substituted with one or more $Z^{11}$;

and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group;

$Z^1$, $Z^2$, $Z^3$, $Z^4$, $Z^5$, $Z^6$, $Z^7$, $Z^8$, $Z^9$, $Z^{10}$, $Z^{11}$ are each independently selected from the group consisting of halogen; $C_{1-6}$alkyl; halo$C_{1-6}$alkyl; halo$C_{1-6}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; or a polymeric group; and wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

2. The compound according to claim 1, having structural formula (IA)

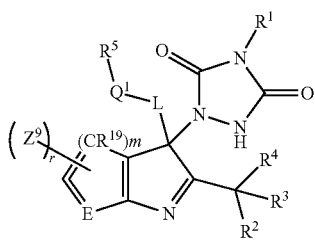

(IA)

wherein R$^1$, R$^2$, R$^3$, R$^4$, R$^5$, L$^1$, Q$^1$, Z$^9$ have the same meaning as defined in claim 1; and wherein,
each dotted line represents an optional double bond;
E is selected from N; NR$^{19}$; or CR$^{19}$; m is an integer selected from 0, 1, 2, 3 or 4;
r is an integer selected from 0, 1, 2, 3 or 4;
each R$^{19}$ is independently selected the group consisting of being not present; hydrogen, halogen; C$_{1-6}$alkyl; haloC$_{1-6}$alkyl; haloC$_{1-6}$alkyloxy; —OR$^{10}$; —SR$^{10}$; —S(O)R$^9$; —S(O)$_2$R$^9$; -SO$_2$NR$^{11}$R$^{12}$; nitro; —NR$^{10}$C(O)R$^9$; NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; and a polymeric group; and a pharmaceutically active moiety; wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

3. The compound according to claim 2, wherein E is CR$^{19}$ and m is 2.

4. The compound according to claim 3, having structural formula (IB)

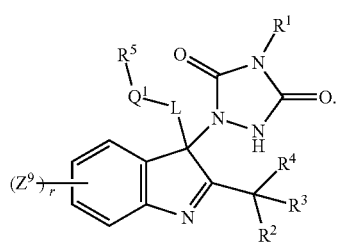

(IB)

5. The compound according to claim 1, wherein,
L$^1$ is C$_{1-10}$alkylene; wherein said C$_{1-10}$alkylene can be unsubstituted or substituted with one or more Z$^1$;
Q$^1$ is a single bond or is selected from the group consisting of —OC(O)—; —NH—C(O)—; —OC(O)—[CR$^{13}$R$^{14}$]$_q$—; and —OC(O)—[C(R$^{13}$)(L$^4$-O—R$^{15}$)]$_q$—[CR$^{16}$R$^{17}$]$_p$—O—; wherein each left side of said groups is attached to L$^1$ and the right side thereof is attached to R$^5$; and wherein,
q is selected from 1; 2 or 3;

p is selected from 0; 1 or 2;
L$^4$ is a single bond; C$_{1-10}$alkylene; or C$_{2-10}$alkenylene; wherein said C$_{1-10}$alkylene; and C$_{2-10}$alkenylene can be unsubstituted or substituted with one or more Z$^2$;
R$^1$ is selected from the group consisting of C$_{2-10}$alkyl; C$_{3-8}$cycloalkyl; C$_{6-12}$aryl; C$_{6-12}$arylC$_{1-6}$alkyl; C$_{6-12}$arylC$_{1-6}$alkylC$_{6-12}$aryl; heterocyclyl; heteroaryl; heterocyclylC$_{1-6}$alkyl; heteroarylC$_{1-6}$alkyl; and a polymeric group;
wherein said C$_{2-10}$alkyl, C$_{6-12}$arylC$_{1-6}$alkyl, C$_{6-12}$arylC$_{1-6}$alkylC$_{6-12}$aryl, heterocyclylC$_{1-6}$alkyl; and heteroarylC$_{1-6}$alkyl, optionally comprises one or more heteroatoms in the alkyl moiety, said heteroatoms being each independently selected from O, S or N;
wherein at least one carbon atom or heteroatom of said C$_{2-10}$alkyl, C$_{6-12}$arylC$_{1-6}$alkyl, C$_{6-12}$arylC$_{1-6}$alkylC$_{6-12}$aryl, heterocyclylC$_{1-6}$alkyl; and heteroarylC$_{1-6}$alkyl, can be oxidized to form at least one C=O, C=S, N=O, N=S, S=O or S(O)$_2$;
and wherein said C$_{2-10}$alkyl, C$_{3-8}$cycloalkyl, C$_{6-12}$aryl, C$_{6-12}$arylC$_{1-6}$alkyl, C$_{6-12}$arylC$_{1-6}$alkylC$_{6-12}$aryl, heterocyclyl; heteroaryl; heterocyclylC$_{1-6}$alkyl; and heteroarylC$_{1-6}$alkyl can be unsubstituted or substituted with one or more Z$^3$;
or R$^1$ is a group of formula (i);

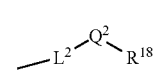

(i)

wherein,
L$^2$ is a single bond; C$_{1-10}$alkylene; or C$_{6-12}$arylene; wherein said C$_{1-10}$alkylene; or C$_{6-12}$arylene can be unsubstituted or substituted with one or more Z$^4$;
Q$^2$ is selected from the group consisting of C$_{1-10}$alkylene; —OC(O)—; —NH—C(O)—; and —NH—C(O)—[CR$^{13}$R$^{14}$]$_q$—; wherein each left side of said groups is attached to L$^2$ and the right side thereof is attached to R$^{18}$; wherein said C$_{1-10}$alkylene can be unsubstituted or substituted with one or more Z$^5$;
or Q$^2$ is a group of formula (ii);

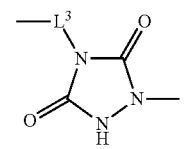

(ii)

wherein the left side of the group formula (ii) is attached to L$^2$ and the right side thereof is attached to R$^{18}$; wherein L$^3$ is a single bond or is C$_{1-10}$alkylene; wherein said C$_{1-10}$alkylene can be unsubstituted or substituted with one or more Z$^6$;
or Q$^2$-R$^{18}$ is a group of formula (iii);

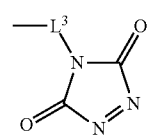

(iii)

$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group;

$R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; $C_{6-12}$aryl$C_{1-6}$alkyl$C_{6-12}$aryl; heterocyclyl; heteroaryl; heterocyclyl$C_{1-6}$alkyl; heteroaryl$C_{1-6}$alkyl; and a polymeric group;

or $R^2$ and $R^3$ and $R^4$ together with the carbon atom to which they are attached form a $C_{6-12}$aryl;

and wherein for $R^2$, $R^3$ and $R^4$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl, heteroaryl$C_{1-6}$alkyl, and polymeric group can be unsubstituted or substituted with one or more $Z^7$;

$R^5$ is selected from the group consisting of hydrogen; halo; nitro; cyano; hydroxyl; $C_{1-20}$alkyl, $C_{2-20}$alkenyl; $C_{2-20}$alkynyl; $C_{6-12}$aryl, $C_{3-8}$cycloalkyl; $C_{6-12}$aryl$C_{1-6}$ alkyl; heterocyclyl; heteroaryl; heterocyclyl$C_{1-6}$alkyl; heteroaryl$C_{1-6}$alkyl; and a polymeric group;

wherein $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; heteroaryl$C_{1-6}$alkyl; and polymeric group can be unsubstituted or substituted with one or more $Z^8$;

and wherein a carbon atom or heteroatom of said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, heterocyclyl; heteroaryl; heterocyclyl$C_{1-6}$alkyl; and heteroaryl$C_{1-6}$ alkyl; can be oxidized to form a C=O, C=S, N=O, N=S, S=O or $S(O)_2$;

$R^6$ is selected from the group consisting of $C_{1-20}$alkyl; $C_{6-12}$aryl; and a polymeric group;

$R^7$ is selected from the group consisting of $C_{1-20}$alkyl; $C_{6-12}$aryl; and a polymeric group;

or $R^6$ and $R^7$ together with the carbon atoms to which they are attached form an unsaturated 5-, or 6-membered ring;

and wherein for $R^6$ and $R^7$, each independently; said $C_{1-20}$alkyl, $C_{6-12}$aryl, polymeric group, or saturated or unsaturated 5-, or 6-membered ring can be unsubstituted or substituted with one or more $Z^9$;

$Z^1$, $Z^2$, $Z^3$, $Z^4$, $Z^5$, $Z^6$, $Z^7$, $Z^8$, $Z^9$ are each independently selected from the group consisting of halogen; $C_{1-6}$alkyl; halo$C_{1-6}$alkyl; halo$C_{1-6}$alkyloxy; —$OR^{10}$; —$S^{10}$; —$S(O)R^9$; —$S(O)_2R^9$; -$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; and a polymeric group;

wherein each $R^9$ is independently selected from hydroxyl; $C_{1-20}$alkyl, $C_{6-12}$aryl, $C_{3-8}$cycloalkyl, and $C_{6-12}$aryl$C_{1-6}$alkyl;

each $R^{10}$ is independently selected from hydrogen, $C_{1-20}$alkyl, $C_{6-12}$aryl, $C_{3-8}$cycloalkyl, and $C_{6-12}$aryl$C_{1-6}$alkyl;

each $R^{11}$ and $R^{12}$ is independently selected from the group consisting of hydrogen; $C_{1-20}$alkyl, $C_{6-12}$aryl, $C_{3-8}$cycloalkyl, and $C_{6-12}$aryl$C_{1-6}$alkyl;

each $R^{13}$ and $R^{14}$ is independently selected from the group consisting of hydrogen; $C_{1-20}$alkyl, $C_{2-20}$alkenyl, $C_{6-12}$aryl, $C_{3-8}$cycloalkyl, and $C_{6-12}$aryl$C_{1-6}$alkyl;

$R^{15}$ is selected from the group consisting of hydrogen; halo; nitro; cyano; hydroxyl; $C_{1-20}$alkenyl; $C_{2-20}$alkynyl; $C_{6-12}$aryl, $C_{3-8}$cycloalkyl; $C_{6-12}$aryl$C_{1-6}$ alkyl; and a polymeric group; and wherein $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and polymeric group can be unsubstituted or substituted with one or more $Z^{10}$;

each $R^{16}$ and $R^{17}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl;

$R^{18}$ is selected from the group consisting of hydrogen, $C_{1-10}$alkyl; $C_{3-8}$cycloalkyl; $C_{6-12}$aryl; $C_{6-12}$aryl $C_{1-6}$alkyl; and a polymeric group; and wherein said $C_{1-10}$alkyl, $C_{3-8}$cycloalkyl, $C_{6-12}$aryl, and $C_{6-12}$aryl$C_{1-6}$alkyl can be unsubstituted or substituted with one or more $Z^{11}$;

$Z^{10}$, and $Z^{11}$ are each independently selected from the group consisting of halogen; $C_{1-6}$alkyl; halo $C_{1-6}$alkyl; halo$C_{1-6}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; and a polymeric group.

6. The compound according to claim 1, wherein, $L^1$ is $C_{1-10}$alkylene; said $C_{1-10}$alkylene being unsubstituted or substituted with one or more $Z^1$;

$Q^1$ is a single bond or is selected from the group consisting of —OC(O)—; —OC(O)—[$CHR^{14}$]$_q$—; and —OC(O)—[C(H)($L^4$-O—$R^{15}$)]$_q$—[$CHR^{17}$]$_p$—O—; wherein each left side of said groups is attached to $L^1$ and the right side thereof is attached to $R^5$; and wherein, q is 1 or 2;

p is 0 or 1;

$L^4$ is a single bond or $C_{1-6}$alkylene; said $C_{1-10}$alkylene being unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl $C_{6-12}$aryl; heteroaryl$C_{1-6}$alkyl; and a polymeric group;

wherein said $C_{2-10}$alkyl, $C_{6-12}$aryl$C_{1-6}$alkyl, $C_{6-12}$aryl$C_{1-6}$alkyl$C_{6-12}$aryl, heterocyclyl$C_{1-6}$alkyl; and heteroaryl$C_{1-6}$alkyl, optionally comprises one or more heteroatoms in the alkyl moiety, said heteroatoms being each independently selected from O, S or N;

wherein at least one carbon atom of said $C_{2-10}$alkyl; $C_{6-12}$aryl; $C_{6-12}$aryl$C_{1-6}$alkyl; and $C_{6-12}$aryl$C_{1-6}$alkyl$C_{6-12}$aryl; can be oxidized to form at least one C=O;

and wherein said $C_{2-10}$alkyl, $C_{3-8}$cycloalkyl, $C_{6-12}$aryl, $C_{6-12}$aryl$C_{1-6}$alkyl, and $C_{6-12}$aryl$C_{1-6}$alkyl$C_{6-12}$aryl can be unsubstituted or substituted with one or more $Z^3$;

or $R^1$ is a group of formula (i); wherein $L^2$ is a single bond; $C_{1-10}$alkylene; or $C_{6-12}$arylene; and wherein said $C_{1-10}$alkylene or $C_{6-12}$arylene can be unsubstituted or substituted with one or more $Z^4$;

$Q^2$ is $C_{1-10}$alkylene; —NH—C(O)—; or —NH—C(O)—[$CR^{13}R^{14}$]$_q$—; wherein said $C_{1-10}$alkylene can be unsubstituted or substituted with one or more $Z^5$;

or $Q^2$ is a group of formula (ii); wherein $L^3$ is a single bond or is $C_{1-10}$alkylene; wherein said $C_{1-10}$alkylene can be unsubstituted or substituted with one or more $Z^6$;

$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;

$R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;

$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;

or $R^2$ and $R^3$ and $R^4$ together with the carbon atom to which they are attached form a $C_{6-12}$aryl;

wherein for $R^2$, $R^3$ and $R^4$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and a polymeric group can be unsubstituted or substituted with one or more $Z^7$;

$R^5$ is selected from the group consisting of hydrogen; halo; nitro; cyano; hydroxyl; $C_{1-20}$alkyl, $C_{2-20}$alkenyl; $C_{6-12}$aryl, $C_{3-8}$cycloalkyl; $C_{6-12}$aryl$C_{1-6}$alkyl; and a polymeric group;

wherein $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and polymeric group can be unsubstituted or substituted with one or more $Z^8$;

and wherein at least one carbon atom of said $C_{1-20}$alkyl, $C_{2-20}$alkenyl, $C_{2-20}$alkynyl, $C_{6-12}$aryl, $C_{3-8}$cycloalkyl, and $C_{6-12}$aryl$C_{1-6}$alkyl, can be oxidized to form at least one C=O;

$R^6$ and $R^7$ together with the carbon atoms to which they are attached form an unsaturated 5-, or 6-membered ring; and wherein said saturated or unsaturated 5-, or 6-membered ring can be unsubstituted or substituted with one or more $Z^9$;

$Z^1$, $Z^2$, $Z^3$, $Z^4$, $Z^5$, $Z^6$, $Z^7$, $Z^8$, $Z^9$ are each independently selected from the group consisting of halogen; $C_{1-6}$alkyl; halo$C_{1-6}$alkyl; halo$C_{1-6}$alkyloxy; —OR$^{10}$; —SR$^{10}$; —S(O)R$^9$; —S(O)$_2$R$^9$; -SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; and a polymeric group;

each $R^9$ is independently selected from hydroxyl; $C_{1-20}$alkyl, $C_{6-12}$aryl, $C_{3-8}$cycloalkyl, and $C_{6-12}$aryl$C_{1-6}$alkyl;

each $R^{10}$ is independently selected from hydrogen, $C_{1-20}$alkyl, $C_{6-12}$aryl, $C_{3-8}$cycloalkyl, and $C_{6-12}$aryl$C_{1-6}$alkyl;

each $R^{11}$ and $R^{12}$ is independently selected from the group consisting of hydrogen; $C_{1-20}$alkyl, $C_{6-12}$aryl, $C_{3-8}$cycloalkyl, and $C_{6-12}$aryl$C_{1-6}$alkyl;

each $R^{13}$ and $R^{14}$ is independently selected from the group consisting of hydrogen; $C_{1-20}$alkyl, $C_{2-20}$alkenyl, $C_{642}$aryl, $C_{3-8}$cycloalkyl, and $C_{6-12}$aryl$C_{1-6}$ alkyl;

$R^{15}$ is selected from the group consisting of hydrogen; halo; nitro; cyano; hydroxyl; $C_{1-20}$alkenyl; $C_{2-20}$alkynyl; $C_{6-12}$aryl, $C_{3-8}$cycloalkyl; $C_{6-12}$aryl$C_{1-6}$ alkyl; or a polymeric group; and wherein $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and polymeric group can be unsubstituted or substituted with one or more $Z^{10}$;

each $R^{16}$ and $R^{17}$ is independently selected from the group consisting of hydrogen; $C_{1-20}$alkenyl, $C_{2-20}$alkynyl, $C_{6-12}$aryl, $C_{3-8}$cycloalkyl, and $C_{6-12}$aryl$C_{1-6}$alkyl;

$R^{18}$ is selected from the group consisting of hydrogen, $C_{1-10}$alkyl; $C_{3-8}$cycloalkyl; $C_{6-12}$aryl; $C_{6-12}$aryl$C_{1-6}$ alkyl; and a polymeric group; and wherein said $C_{1-10}$alkyl, $C_{3-8}$cycloalkyl, $C_{6-12}$aryl, and $C_{6-12}$aryl$C_{1-6}$alkyl can be unsubstituted or substituted with one or more $Z^{11}$;

$Z^{10}$, and $Z^{11}$ are each independently selected from the group consisting of halogen; $C_{1-6}$alkyl; halo$C_{1-6}$alkyl; halo$C_{1-6}$alkyloxy; —OR$^{10}$; —SR$^{10}$; —S(O)R$^9$; —S(O)$_2$R$^9$; —SO$_2$NR$^{11}$R$^{12}$; nitro; —NR$^{10}$C(O)R$^9$; —NR$^{10}$S(O)$_2$R$^9$; —NR$^{10}$C(O)NR$^{11}$R$^{12}$; NR$^{11}$R$^{12}$; cyano; —CO$_2$R$^{10}$; —C(O)NR$^{11}$R$^{12}$; —C(O)R$^9$; and a polymeric group.

7. The compound according to claim 1, having structural formula (IC)

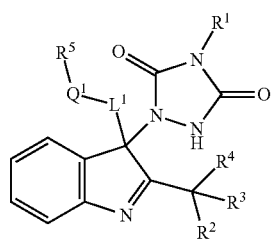

(IC)

wherein $L^1$ is $C_{1-10}$alkylene; said $C_{1-10}$alkylene being unsubstituted or substituted with one or more $Z^1$;

$Q^1$ is a single bond or is selected from the group consisting of —OC(O)—; —OC(O)—[CHR$^{14}$]$_q$—; and —OC(O)—[C(H)(L$^4$-O—R$^{15}$)]$_q$—[CHR$^{17}$]$_p$—O—; wherein each left side of said groups is attached to $L^1$ and the right side thereof is attached to R$^5$; and wherein, q is 1; p is 0 or 1; and $L^4$ is $C_{1-6}$alkylene; said $C_{1-10}$alkylene being unsubstituted or substituted with one or more $Z^2$;

$R^1$ is selected from the group consisting of $C_{2-10}$alkyl; $C_{6-12}$aryl; $C_{6-12}$aryl$C_{1-6}$alkyl; $C_{6-12}$aryl$C_{1-6}$alkyl $C_{6-12}$aryl; heteroaryl$C_{1-6}$alkyl; and a polymeric group;

wherein said $C_{6-12}$aryl$C_{1-6}$alkyl, $C_{6-12}$aryl$C_{1-6}$alkyl $C_{6-12}$aryl, heterocyclyl$C_{1-6}$alkyl; and heteroaryl $C_{1-6}$alkyl, optionally comprises one or more heteroatoms in the alkyl moiety, said heteroatoms being each independently selected from O, S or N;

wherein at least one carbon atom of said $C_{2-10}$alkyl; $C_{6-12}$aryl; $C_{6-12}$aryl$C_{1-6}$alkyl; and $C_{6-12}$aryl$C_{1-6}$alkyl$C_{6-12}$aryl; can be oxidized to form at least one C=O;

and wherein said $C_{2-10}$alkyl, $C_{3-8}$cycloalkyl, $C_{6-12}$aryl, $C_{6-12}$aryl$C_{1-6}$alkyl, and $C_{6-12}$aryl$C_{1-6}$alkyl$C_{6-12}$aryl can be unsubstituted or substituted with one or more $Z^3$;

or $R^1$ is -$L^2$-$Q^2$-$R^{18}$; wherein
  $L^2$ is a single bond; $C_{1-10}$alkylene; or $C_{6-12}$arylene; and wherein said $C_{1-10}$alkylene; or $C_{6-12}$arylene can be unsubstituted or substituted with one or more $Z^4$;
  $Q^2$ is $C_{1-10}$alkylene; —NH—C(O)—; or —NH—C(O)—[$CR^{13}R^{14}$]$_q$—; wherein said $C_{1-10}$alkylene can be unsubstituted or substituted with one or more $Z^5$;
  or $Q^2$ is a group of formula (ii); wherein $L^3$ is a single bond or is $C_{1-10}$alkylene; wherein said $C_{1-10}$alkylene can be unsubstituted or substituted with one or more $Z^6$;
$R^2$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;
$R^3$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;
$R^4$ is selected from the group consisting of halo; nitro; cyano; $C_{1-20}$alkyl; $C_{2-20}$alkenyl; $C_{2-20}$alkynyl; $C_{6-12}$aryl; $C_{3-8}$cycloalkyl; $C_{6-12}$aryl$C_{1-6}$alkyl; and a polymeric group;
or $R^2$ and $R^3$ and $R^4$ together with the carbon atom to which they are attached can form a $C_{6-12}$aryl;
  wherein for $R^2$, $R^3$ and $R^4$, each independently; said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and a polymeric group can be unsubstituted or substituted with one or more $Z^7$;
$R^5$ is selected from the group consisting of hydrogen; halo; nitro; cyano; hydroxyl; $C_{1-20}$alkyl, $C_{2-20}$alkenyl; $C_{6-12}$aryl, $C_{3-8}$cycloalkyl; $C_{6-12}$aryl$C_{1-6}$alkyl; and a polymeric group;
  wherein said $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and polymeric group can be unsubstituted or substituted with one or more $Z^8$;
  and wherein at least one carbon atom of said $C_{1-20}$alkyl, $C_{2-20}$alkenyl, $C_{2-20}$alkynyl, $C_{6-12}$aryl, $C_{3-8}$cycloalkyl, and $C_{6-12}$aryl$C_{1-6}$alkyl, can be oxidized to form at least one C=O;
$Z^1$, $Z^2$, $Z^3$, $Z^4$, $Z^5$, $Z^6$, $Z^7$, and $Z^8$, are each independently selected from the group consisting of halogen; $C_{1-6}$alkyl; halo$C_{1-6}$alkyl; halo$C_{1-6}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; and a polymeric group;
each $R^9$ is independently selected from the group consisting of hydroxyl; $C_{1-20}$alkyl, $C_{6-12}$aryl, $C_{3-8}$cycloalkyl, and $C_{6-12}$aryl$C_{1-6}$alkyl;
each $R^{10}$ is independently selected from the group consisting of hydrogen, $C_{1-20}$alkyl, $C_{6-12}$aryl, —$C_{3-8}$cycloalkyl, and $C_{6-12}$aryl$C_{1-6}$alkyl;
each $R^{11}$ and $R^{12}$ is independently selected from the group consisting of hydrogen; $C_{1-20}$alkyl, $C_{6-12}$aryl, $C_{3-8}$cycloalkyl, and $C_{6-12}$aryl$C_{1-6}$alkyl;
each $R^{13}$ and $R^{14}$ is independently selected from the group consisting of hydrogen; $C_{1-20}$alkyl, $C_{2-20}$alkenyl, $C_{6-12}$aryl, $C_{3-8}$cycloalkyl, and $C_{6-12}$aryl$C_{1-6}$alkyl;
$R^{15}$ is selected from the group consisting of hydrogen; halo; nitro; cyano; hydroxyl; $C_{1-20}$alkenyl; $C_{2-20}$alkynyl; $C_{6-12}$aryl; $C_{3-8}$cycloalkyl; $C_{6-12}$aryl$C_{1-6}$alkyl; and a polymeric group; and wherein $C_{1-20}$alkyl, $C_{2-20}$alkenyl, $C_{2-20}$alkynyl, $C_{6-12}$aryl, $C_{3-8}$cycloalkyl, $C_{6-12}$aryl$C_{1-6}$alkyl, and polymeric group can be unsubstituted or substituted with one or more $Z^{10}$;
each $R^{16}$ and $R^{17}$ is independently selected from the group consisting of hydrogen; $C_{1-20}$alkyl, $C_{2-20}$alkenyl, $C_{2-20}$alkynyl, $C_{6-12}$aryl, $C_{3-8}$cycloalkyl, and $C_{6-12}$aryl$C_{1-6}$alkyl;
$R^{18}$ is selected from the group consisting of hydrogen, $C_{1-10}$alkyl; $C_{3-8}$cycloalkyl; $C_{6-12}$aryl; $C_{6-12}$aryl$C_{1-6}$alkyl; and a polymeric group; and wherein said $C_{1-10}$alkyl, $C_{3-8}$cycloalkyl, $C_{6-12}$aryl, and $C_{6-12}$aryl$C_{1-6}$alkyl can be unsubstituted or substituted with one or more $Z^{11}$;
$Z^{10}$, and $Z^{11}$ are each independently selected from the group consisting of halogen; $C_{1-6}$alkyl; halo$C_{1-6}$alkyl; halo$C_{1-6}$alkyloxy; —$OR^{10}$; —$SR^{10}$; —$S(O)R^9$; —$S(O)_2R^9$; —$SO_2NR^{11}R^{12}$; nitro; —$NR^{10}C(O)R^9$; —$NR^{10}S(O)_2R^9$; —$NR^{10}C(O)NR^{11}R^{12}$; $NR^{11}R^{12}$; cyano; —$CO_2R^{10}$; —$C(O)NR^{11}R^{12}$; —$C(O)R^9$; and a polymeric group.

8. The compound according to claim 1, wherein $R^5$ is a polymeric group which can be unsubstituted or substituted with one or more $Z^8$; wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

9. The compound according to claim 1, wherein said compound is a polymer and $R^1$ is a polymeric group which can be unsubstituted or substituted with one or more $Z^3$; wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes; acrylonitrile butadiene styrene (ABS); styrene-butadiene rubber (SBR); polysiloxanes; and/or block, comb and/or star copolymers of the polymeric group.

10. The compound according to claim 1, wherein $R^1$ is a group of formula (i), and $R^{18}$ is a polymeric group which can be unsubstituted or substituted with one or more $Z^{11}$; wherein said polymeric group is selected from the group comprising polystyrene; poly(methyl methacrylate); polyethylene oxide; polyacrylate; polymethacrylate; copolymer of acrylate, methacrylate and/or styrene; poly(isobornyl acrylate); polyacrylonitrile; polyether; polyester; polylactic acid; polyamide; polyester amide; polyurethane; polycarbonate; poly-alpha-olefin; ethylene propylene diene monomer (M-class) rubber (EPDM); ethylene propylene rubber (EPM); hydrogenated or unhydrogenated polybutadienes;

acrylonitrile butadiene styrene (ABS); styrene-butadiene rubber (SBR); polysiloxanes; and/or block, comb and/or star copolymers of the polymeric group.

11. A process for the preparation of a compound according to claim 1, comprising the step of contacting at least one compound of formula (II) with at least one compound of formula (III), thereby obtaining a compound of formula (I);

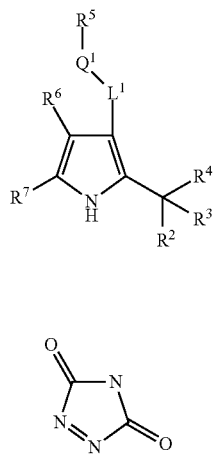
(II)
(III)

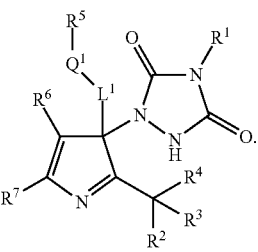
(I)

12. An in situ precursor of a triazolinedione reagent for the functionalization of enes, dienes, aryl and heteroaryl systems via the ene reactions, Diels-Alder reactions, and electrophilic aromatic substitution reactions of said reagent, wherein the in situ precursor comprises a compound according to claim 1.

13. Polymers, membranes, adhesives, foams, sealants, molded articles, films, extruded articles, fibers, elastomers, polymer based additives, pharmaceutical and biomedical products, varnishes, paints, coatings, inks, composite material, organic LEDs, organic semiconductors, conducting organic polymers, or 3D printed articles comprising a compound according to claim 1.

14. An article comprising a compound according to claim 1.

15. A process for reshaping and/or repairing an article comprising a compound according to claim 1, comprising the step of thermally treating the compound of formula (I) at a temperature of at least 30° C.

* * * * *